(12) United States Patent
Dragovich et al.

(10) Patent No.: US 10,729,738 B2
(45) Date of Patent: Aug. 4, 2020

(54) HINDERED DISULFIDE DRUG CONJUGATES

(71) Applicant: Genentech, Inc., South San Francisco, CA (US)

(72) Inventors: Peter Dragovich, South San Francisco, CA (US); Zhonghua Pei, South San Francisco, CA (US); Thomas Pillow, South San Francisco, CA (US); Jack Sadowsky, South San Francisco, CA (US); Jinhua Chen, Shanghai (CN); John Wai, Shanghai (CN)

(73) Assignee: Genentech, Inc., South San Francisco, CA (US)

( * ) Notice: Subject to any disclaimer, the term of this patent is extended or adjusted under 35 U.S.C. 154(b) by 384 days.

(21) Appl. No.: 15/293,743

(22) Filed: Oct. 14, 2016

(65) Prior Publication Data

US 2017/0112891 A1 Apr. 27, 2017

(30) Foreign Application Priority Data

Oct. 16, 2015 (WO) ................ PCT/CN2015/092084

(51) Int. Cl.
| | | |
|---|---|---|
| *A61K 38/05* | (2006.01) | |
| *A61K 47/54* | (2017.01) | |
| *A61K 47/68* | (2017.01) | |
| *A61K 47/64* | (2017.01) | |
| *A61K 47/55* | (2017.01) | |
| *A61K 31/5365* | (2006.01) | |
| *A61K 31/5517* | (2006.01) | |

(52) U.S. Cl.
CPC .......... *A61K 38/05* (2013.01); *A61K 31/5365* (2013.01); *A61K 31/5517* (2013.01); *A61K 47/542* (2017.08); *A61K 47/545* (2017.08); *A61K 47/55* (2017.08); *A61K 47/64* (2017.08); *A61K 47/643* (2017.08); *A61K 47/6803* (2017.08); *A61K 47/6849* (2017.08); *A61K 47/6851* (2017.08); *A61K 47/6855* (2017.08); *A61K 47/6867* (2017.08)

(58) Field of Classification Search
CPC .. A61K 47/64; A61K 47/643; A61K 47/6803; A61K 31/5365; A61K 31/5517
See application file for complete search history.

(56) References Cited

U.S. PATENT DOCUMENTS

| | | |
|---|---|---|
| 5,122,368 A | 6/1992 | Greenfield et al. |
| 5,208,020 A | 5/1993 | Chari et al. |
| 5,416,064 A | 5/1995 | Chari et al. |
| 6,441,163 B1 | 8/2002 | Chari et al. |
| 6,630,579 B2 | 10/2003 | Chari et al. |
| 7,223,837 B2 | 5/2007 | De Groot et al. |
| 7,521,541 B2 | 4/2009 | Eigenbrot et al. |
| 8,142,784 B2 | 3/2012 | Ebens, Jr. et al. |
| 8,389,697 B2 | 3/2013 | Beria et al. |
| 8,470,984 B2 | 6/2013 | Caruso et al. |
| 8,742,076 B2 | 6/2014 | Cohen et al. |
| 8,900,589 B2 | 12/2014 | Beria et al. |
| 10,058,613 B2 * | 8/2018 | Dragovich ......... C07K 16/2803 |
| 2004/0039176 A1 | 2/2004 | Widdison |
| 2007/0060534 A1 | 3/2007 | Matteucci et al. |
| 2016/0074527 A1 * | 3/2016 | Flygare .............. A61K 47/6889 424/181.1 |
| 2016/0074528 A1 | 3/2016 | Flygare et al. |

FOREIGN PATENT DOCUMENTS

| | | |
|---|---|---|
| WO | 199802446 A1 | 1/1998 |
| WO | 2003068144 A2 | 8/2003 |
| WO | 2004016801 A2 | 2/2004 |
| WO | 2009099741 A1 | 8/2009 |
| WO | 2010009124 A2 | 1/2010 |
| WO | 2013055987 A1 | 4/2013 |
| WO | 2014011518 A1 | 1/2014 |
| WO | 2014068443 A1 | 5/2014 |
| WO | 2014159981 A2 | 10/2014 |
| WO | 2015023355 A1 | 2/2015 |
| WO | 2015095212 A1 | 6/2015 |
| WO | 2015110935 A1 | 7/2015 |
| WO | 2016040825 A1 | 3/2016 |
| WO | 2016044560 A1 | 3/2016 |

OTHER PUBLICATIONS

Supplemental information for Pillow et al (Chemical Science, vol. 8, pp. 366-370, ePub Aug. 22, 2016) (Year: 2016).*
Torchlin et al Advanced Drug Delivery Reviews, 2008, vol. 60, pp. 548-558) (Year: 2008).*
Kratz (Journal of Controlled Release, 2008, vol. 132, pp. 171-183) (Year: 2008).*
Flygare et al., "Antibody-Drug Conjugates for the Treatment of Cancer", Chem. Biol. Drug Design, 2013, vol. 81, pp. 113-121.
Giddens et al., "Analogues of DNA minor groove cross-linking agents incorporating aminoCBI, an amino derivative of the duocarmycins: Synthesis, cytotoxicity, and potential as payloads for antibody-drug conjugates", Bioorganic & Medicinal Chemistry, 2016, vol. 24, pp. 6075-6081.

(Continued)

*Primary Examiner* — Karen A. Canella
(74) *Attorney, Agent, or Firm* — Viksnins Harris Padys Malen LLP

(57) ABSTRACT

The invention relates generally to disulfide drug conjugates wherein a linker comprising a sulfur-bearing carbon atom substituted with at least one hydrocarbyl or substituted hydrocarbyl is conjugated by a disulfide bond to a cysteine sulfur atom of a targeting carrier, and wherein the linker is further conjugated to a drug moiety. The invention further relates to activated linker-drug conjugates suitable for conjugation to a targeting carrier by a disulfide bond. The invention further relates to methods for preparing hindered disulfide drug conjugates.

22 Claims, 29 Drawing Sheets

Specification includes a Sequence Listing.

(56) References Cited

OTHER PUBLICATIONS

Pillow et al., "Site-Specific Trastuzumab Maytansinoid Antibody-Drug Conjugates with Improved Therapeutic Activity through Linker and Antibody Engineering", J. Med. Chem., 2014, vol. 57, No. 19, pp. 7890-7899.
Pillow et al., "Decoupling stability and release in disulfide bonds with antibody-small molecule conjugates", Chemical Science, 2017, vol. 8. pp. 366-370.
Zhang et al., "Linker Immolation Determines Cell Killing Activity of Disulfide-Linked Pyrrolobenzodiazepine Antibody-Drug Conjugates", ACS Medicinal Chemistry Letters, 2016, vol. 7, No. 11, pp. 988-993.
Zhang et al., "Chemical Structure and Concentration of Intratumor Catabolites Determine Efficacy of Antibody Drug conjugates", Drug Metabolism and Disposition, 2016, vol. 44, No. 9, pp. 1517-1523.
International Search Report and Written Opinion for Application No. PCT/IB2016/056186, dated Jan. 18, 2017, 16 pages.

\* cited by examiner

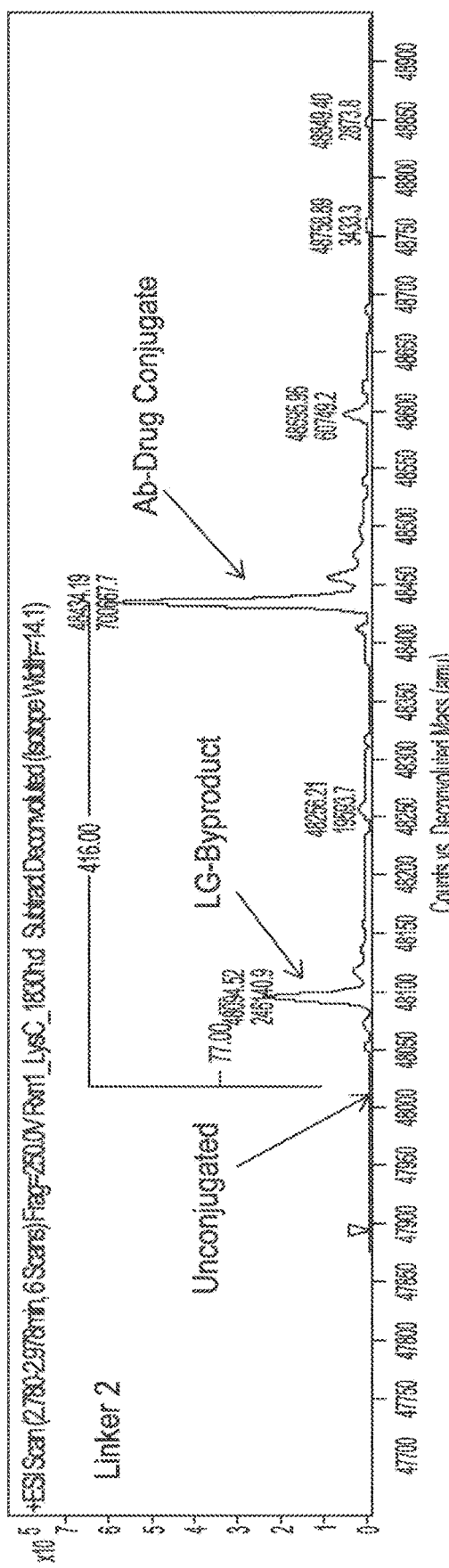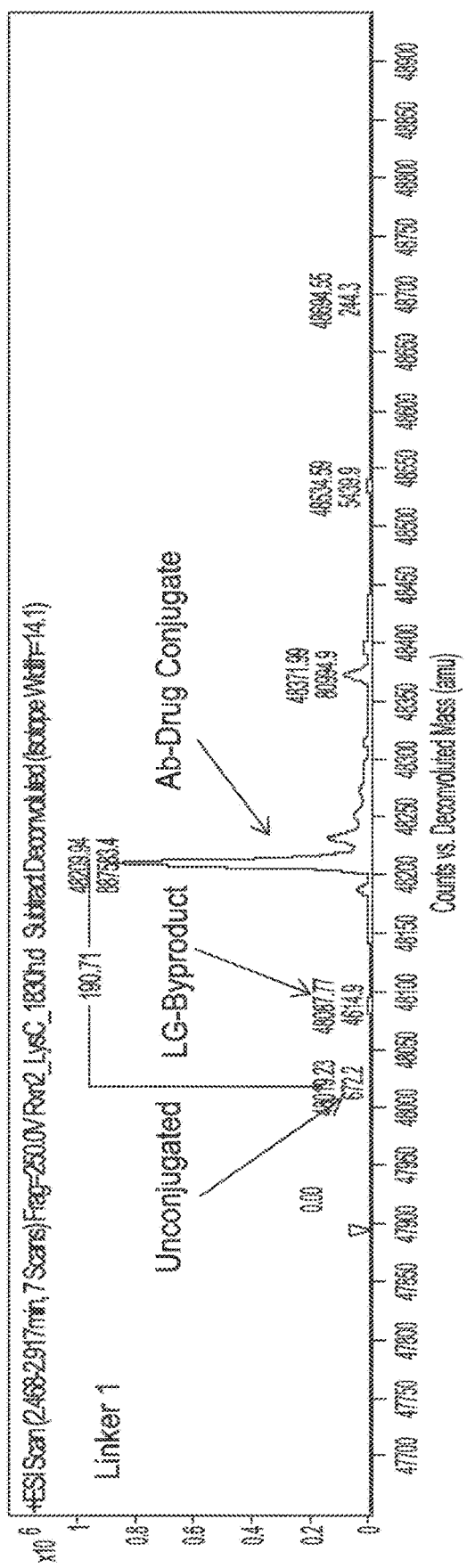
FIG. 3A
FIG. 3B

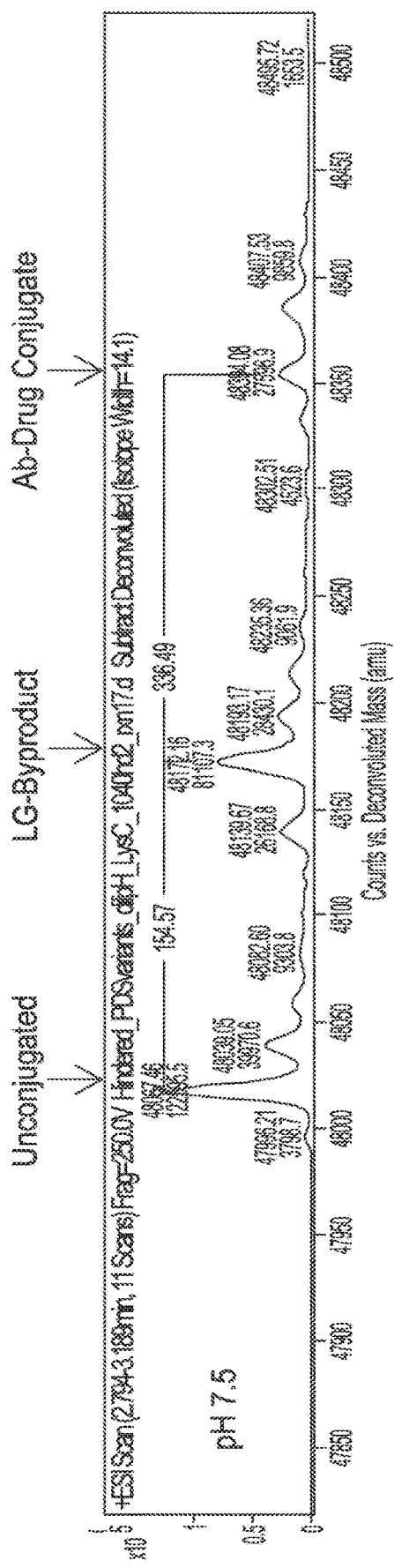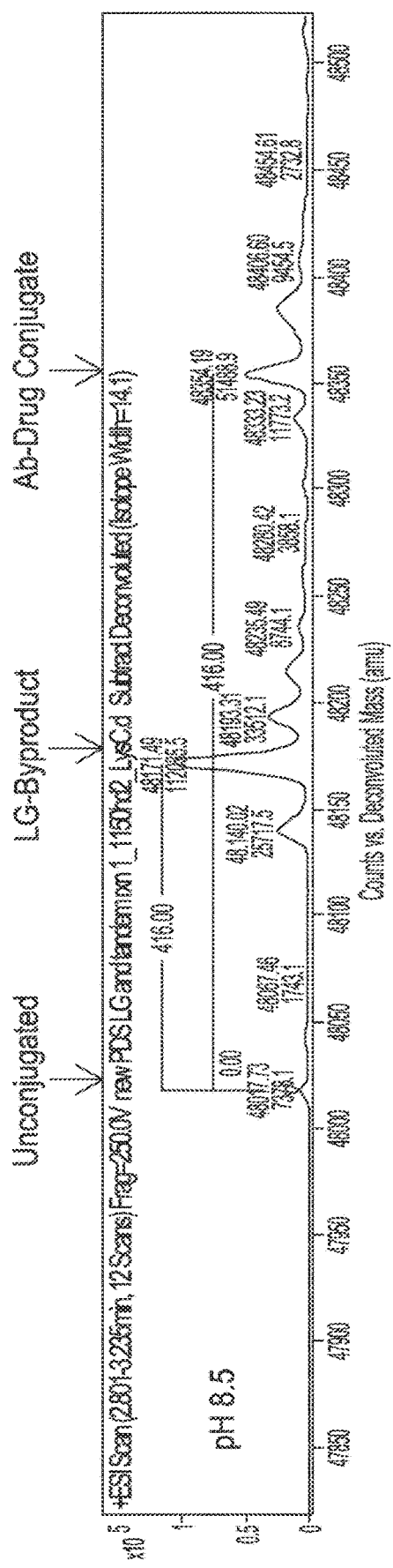
FIG. 4C
FIG. 4D

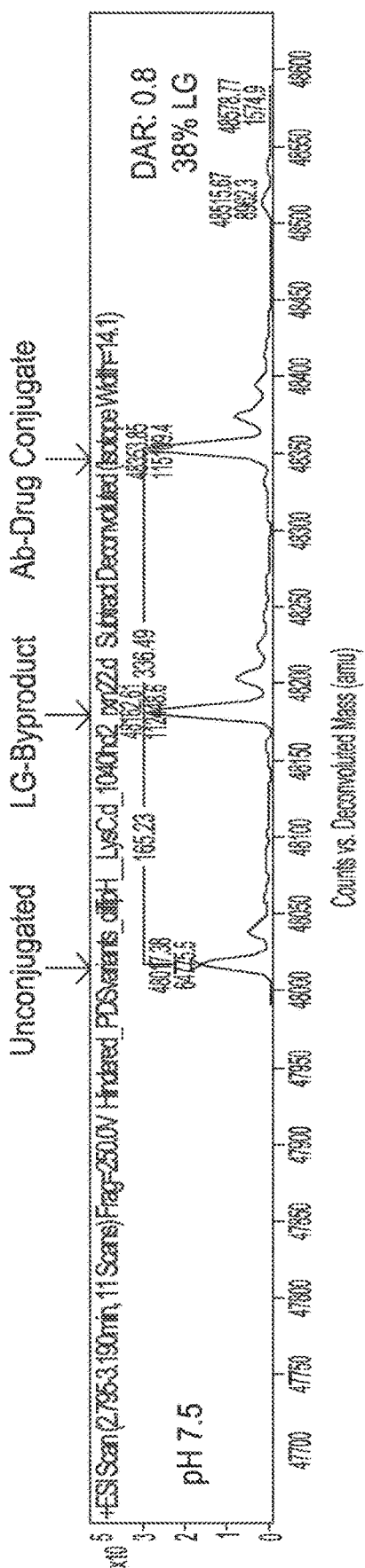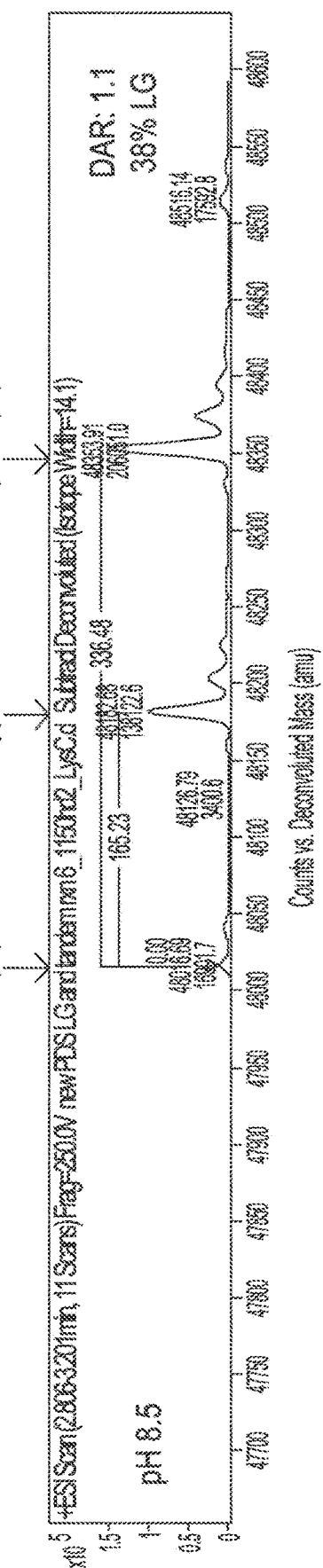

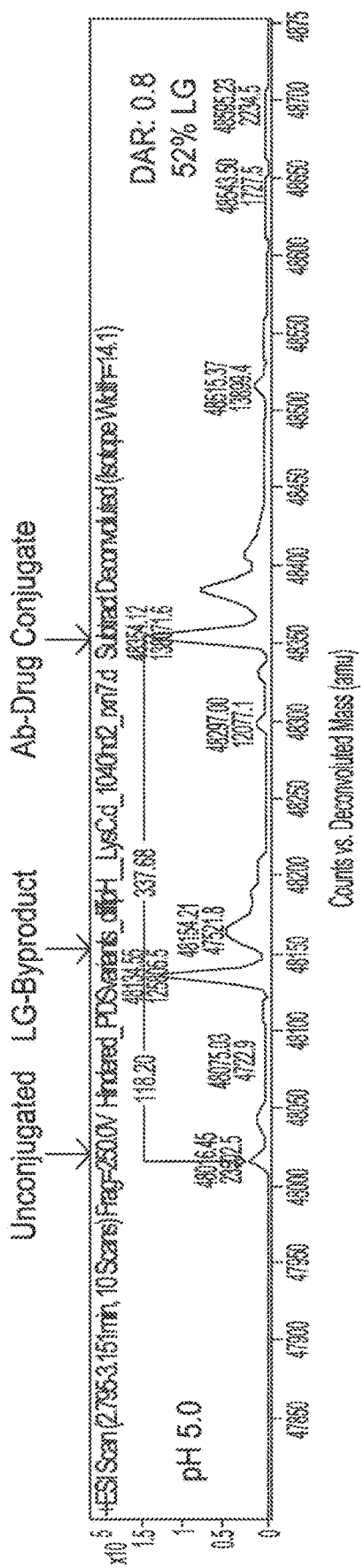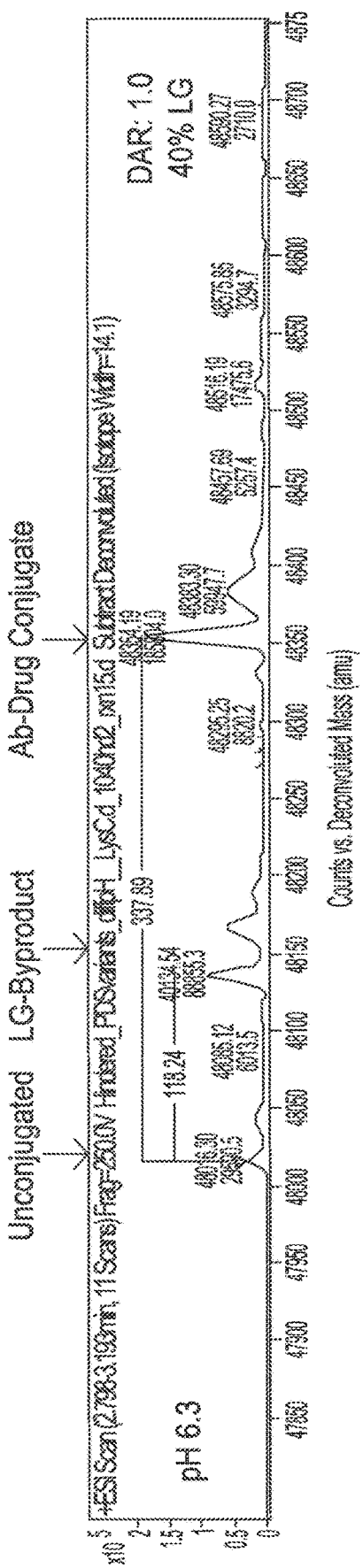
FIG. 7A
FIG. 7B

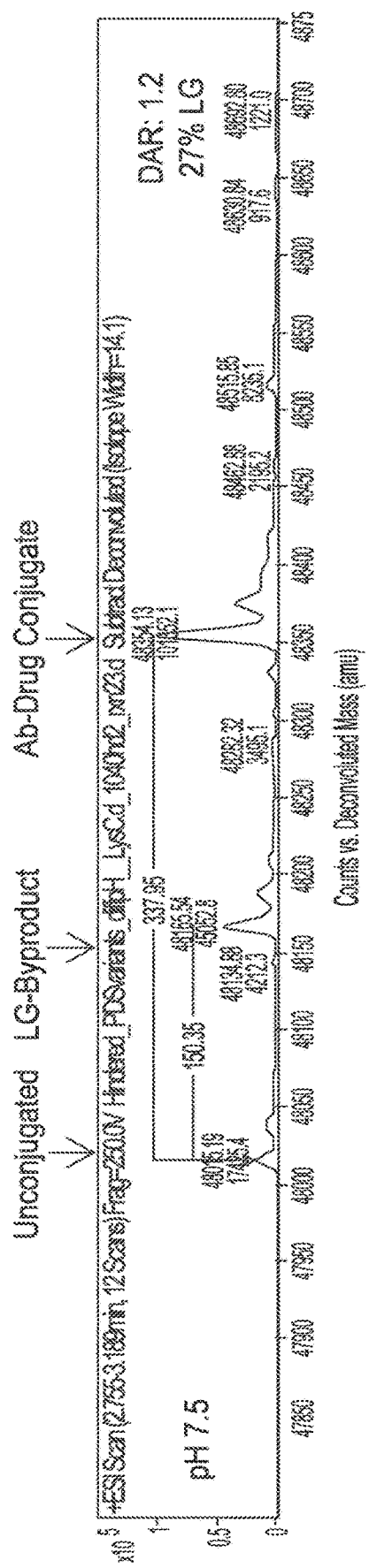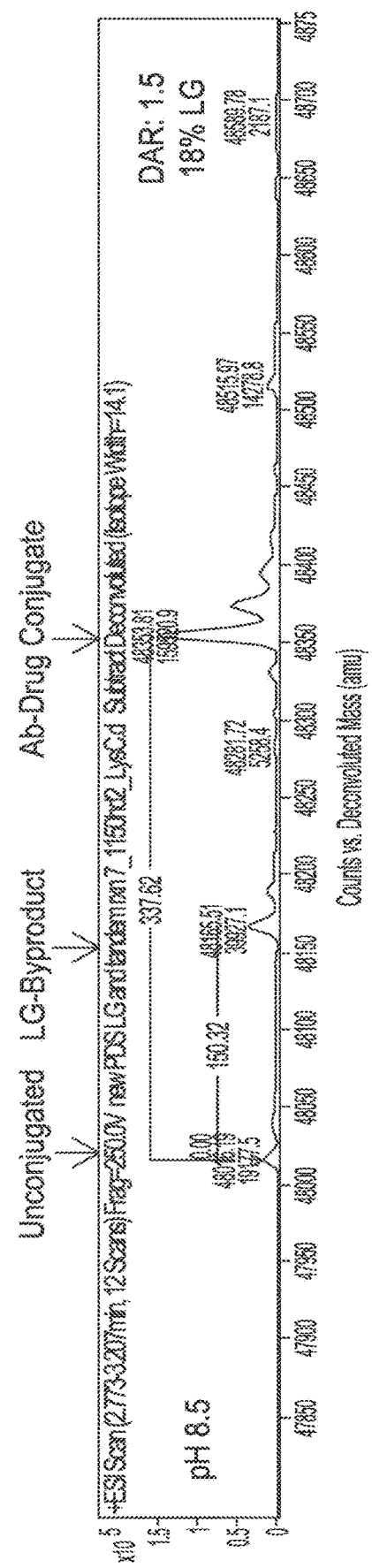
FIG. 7C
FIG. 7D

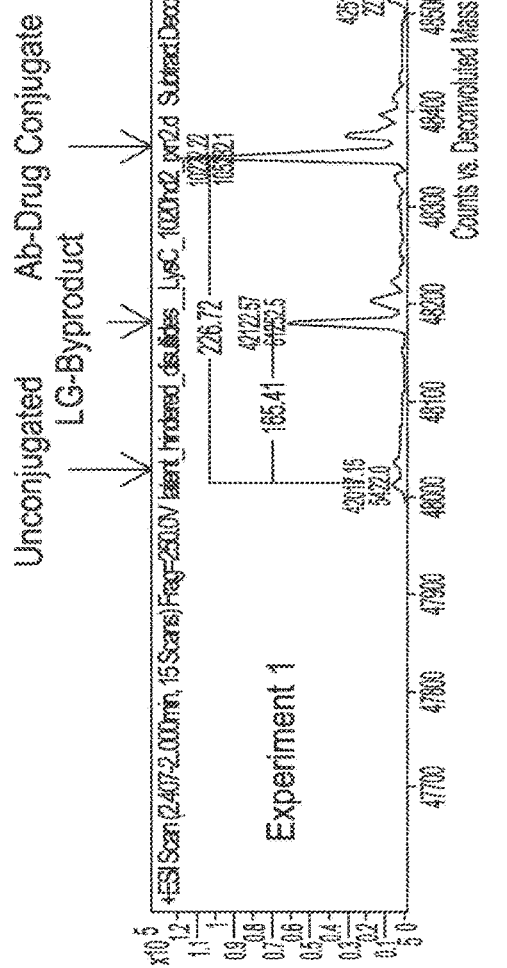
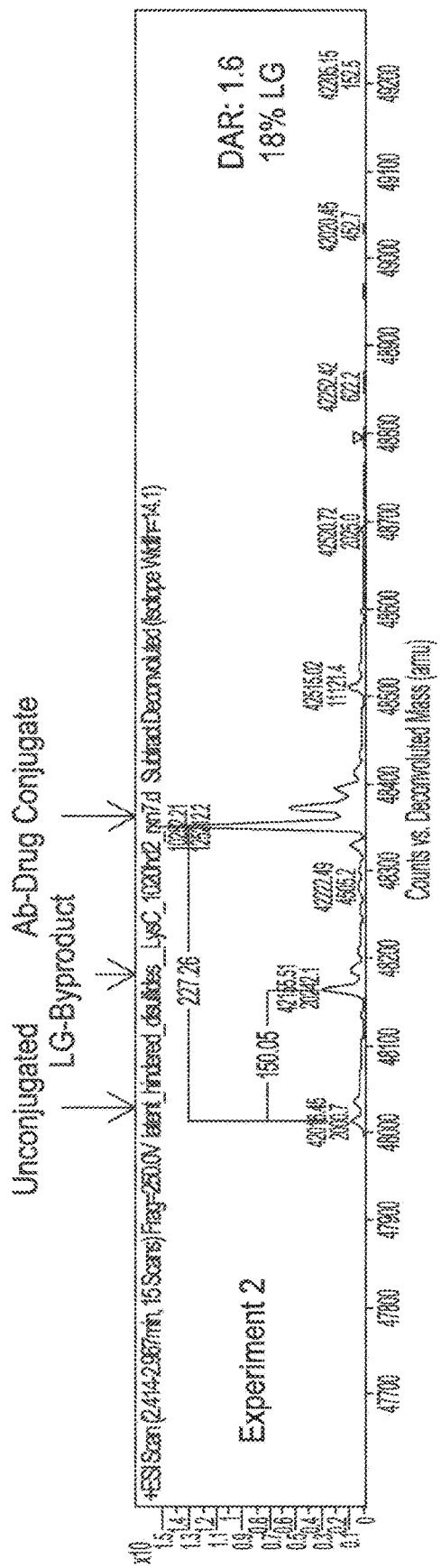
FIG. 8A
FIG. 8B

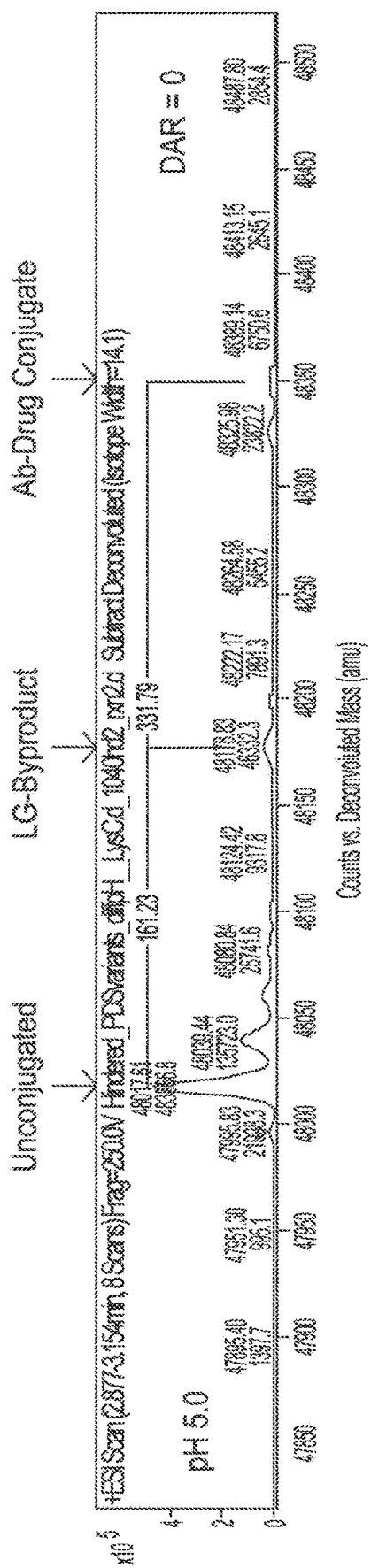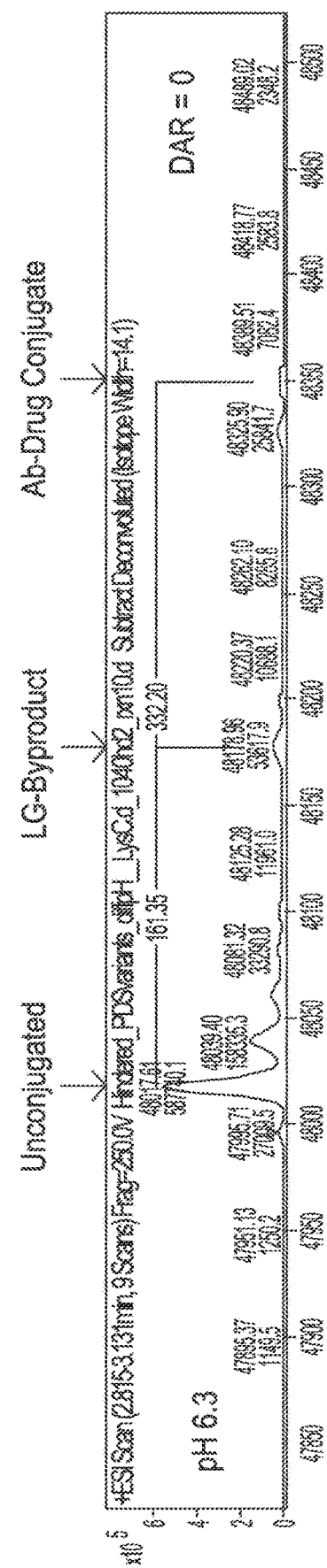
FIG. 9A
FIG. 9B

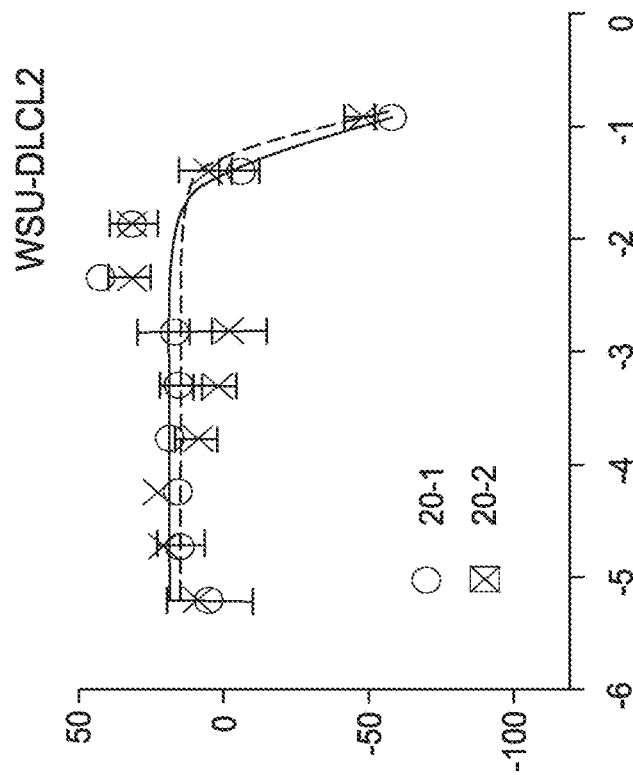
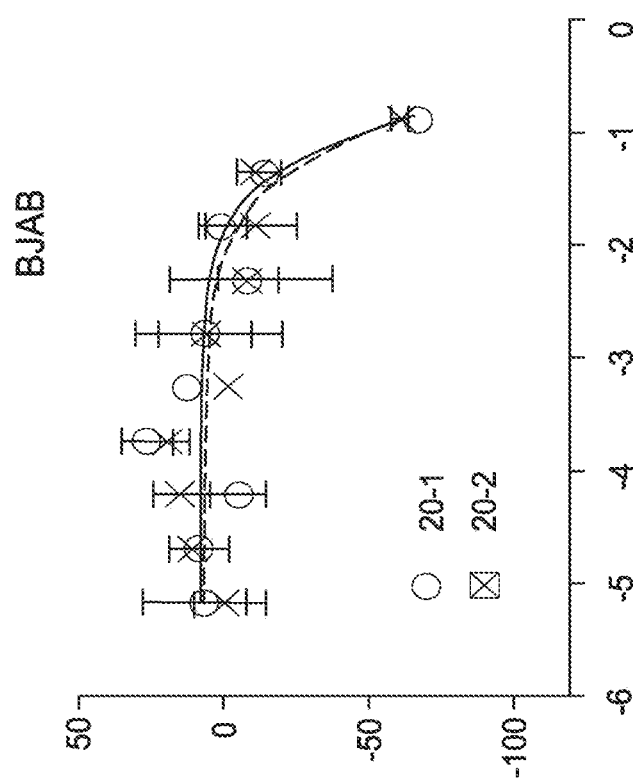
FIG. 11D
FIG. 11C

HINDERED DISULFIDE DRUG CONJUGATES

CROSS-REFERENCE TO RELATED APPLICATION

This application claims priority benefit of International Application Serial No. PCT/CN2015/092084 filed on Oct. 16, 2015, which is incorporated herein in its entirety.

SEQUENCE LISTING

The instant application contains a Sequence Listing which has been submitted electronically in ASCII format and is hereby incorporated by reference in its entirety. Said ASCII copy, created on Dec. 6, 2016, is named P33072-US-01.txt and is 503 bytes in size.

FIELD OF THE DISCLOSURE

The field of the disclosure relates generally to methods of preparing conjugates comprising a selective carrier, a hindered linker, and a drug moiety wherein the linker is conjugated to the selective carrier by a disulfide bond.

BACKGROUND

Conjugates comprising a selective carrier-linker-drug structure (e.g., an antibody-drug conjugate, or ADC), are attractive selective chemo-therapeutic molecules, as they combine ideal properties of selectivity to a target cell and cytotoxic drugs. Selective carriers include proteins, peptides and antibodies. By directing potent cytotoxic drugs to a target cell, the desired therapeutic effect may be enhanced in the target cell while minimizing the effect on non-targeted cells. Successful selective carrier-linker-drug conjugate development for a given target cell depends, among other factors, on optimization of carrier selection, linker stability in the bloodstream, sufficient linker immolation in the cell for release of an effective amount of the drug, cytotoxic drug potency and mode of linker-drug conjugation to the antibody. More particularly, effective carrier-drug conjugates are characterized by at least one or more of the following: (i) a carrier-drug conjugate formation method wherein the antibody retains sufficient specificity to a target and wherein the drug efficacy is maintained; (ii) carrier-drug conjugate stability sufficient to limit drug release in the blood; (iii) sufficient cell membrane transport efficiency (endocytosis) to achieve a therapeutic intracellular carrier-drug conjugate concentration; (iv) sufficient intracellular drug release from the carrier-drug conjugate sufficient to achieve a therapeutic drug concentration; and (v) drug cytotoxicity in nanomolar or sub-nanomolar amounts.

Problematically, effective blood stream stability and effective intracellular drug release from the carrier-drug conjugates are typically coupled and inversely related for selective carrier-drug conjugates known in the art such that conjugates that exhibit blood stability also exhibit poor intracellular drug release.

A need therefore exists for efficacious selective carrier-linker-drug conjugates that are stable in the bloodstream and that provide for effective intracellular drug release.

SUMMARY

In some embodiments, the disclosure relates to a linker-drug conjugate compound of structure (I):

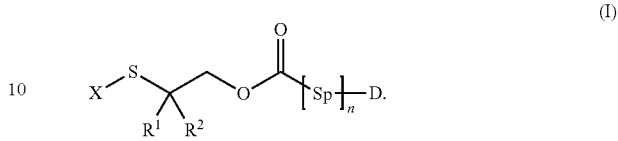

X is a leaving group. The leaving group, X, and the sulfur atom, S, are bound via a disulfide bond. $R^1$ and $R^2$ are independently selected from H and $C_{1-3}$ alkyl, wherein only one of $R^1$ and $R^2$ can be H, or $R^1$ and $R^2$ together with the carbon atom to which they are bound form a three- to six-membered ring optionally comprising an oxygen heteroatom. Sp is an optional immolating spacer wherein n is 0 or 1 and D is a drug moiety.

In some other embodiments, the disclosure relates to a disulfide conjugate compound of structure (II):

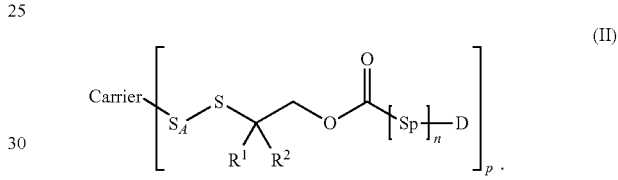

The carrier comprises a cysteine sulfur atom, $S_A$. p is 1, 2, 3, 4, 5, 6, 7, or 8. $R^1$ and $R^2$ are independently selected from H and $C_{1-3}$ alkyl, wherein only one of $R^1$ and $R^2$ can be H, or $R^1$ and $R^2$ together with the carbon atom to which they are bound form a three- to six-membered ring optionally comprising an oxygen heteroatom. Sp is an optional spacer wherein n is 0 or 1 and D is a drug moiety.

In some other embodiments, the disclosure relates to a method of preparing a disulfide conjugate compound of structure (II):

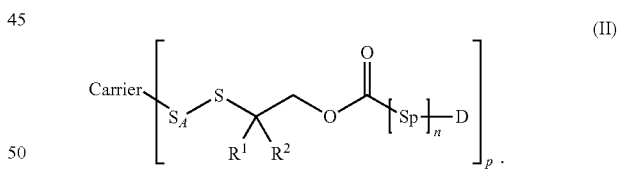

The method comprises forming a reaction mixture comprising (i) a solvent system comprising water, (ii) a carrier comprising at least one cysteine having a sulfhydryl moiety having a sulfur atom $S_A$ capable of bonding to a linker sulfur atom to form the disulfide bond, and (iii) a stoichiometric excess of a linker-drug conjugate compound of structure (I):

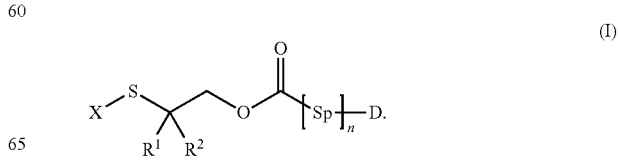

X is a leaving group; the leaving group and the linker are bound via disulfide bond; each $R^1$ and $R^2$ are independently selected from H and $C_{1-3}$ alkyl, wherein only one of $R^1$ and $R^2$ can be H, or $R^1$ and $R^2$ together with the carbon atom to which they are bound form a three- to six-membered ring optionally comprising an oxygen heteroatom; Sp is an optional spacer wherein n is 0 or 1; and D is a drug moiety. The reaction mixture is reacted to form a product mixture comprising the disulfide conjugate compound of structure (II) wherein p is 1, 2, 3, 4, 5, 6, 7 or 8, and wherein the average value of p for a plurality of formed disulfide conjugate compounds in the product mixture is from about 1 to about 5, from about 1.5 to about 3, from about 1.5 to about 2.5, from about 1.7 to about 2.3, from about 1.8 to about 2.2, or about 2.

In some other embodiments, the disclosure relates to a pharmaceutical composition comprising the disulfide conjugate compound as described elsewhere herein and a pharmaceutically acceptable diluent, carrier or excipient. In some other aspects, the disclosure relates to a method of treating cancer comprising administering to a patient the pharmaceutical composition.

In some other embodiments, the disclosure relates to an antibody-drug conjugate compound as described elsewhere herein for use in a method for treating cancer.

In some other embodiments, the disclosure relates to a method of making an antibody-drug conjugate compound as described elsewhere herein, the method comprising reacting an antibody with a linker-drug compound of Formula (I) as described elsewhere herein.

In some other embodiments, the disclosure relates to an article of manufacture comprising a pharmaceutical composition as described elsewhere herein, a container, and a package insert or label indicating that the pharmaceutical composition can be used to treat cancer.

BRIEF DESCRIPTION OF THE DRAWINGS

FIGS. 3A and 3B are LC/MS ESI scans depicting the purity by area percent for a reaction product mixture comprising an antibody-linker-drug conjugate having the antibody bound to a linker by a disulfide bond and formed by reacting one or more CD22 LC K149C antibody cysteine thiol groups with a leaving group-S-linker-drug component wherein the leaving group was methylsulfonate. FIG. 3A depicts the results for Linker 1 and FIG. 3B depicts the results for Linker 2 (as further discussed in example 5, below).

FIGS. 4A to 4D are LC/MS ESI scans depicting the purity by area percent for a reaction product mixture formed at varying pH and comprising an antibody-linker-probe conjugate having the antibody bound to a linker by a disulfide bond and formed by reacting one or more CD22 LC K149C antibody cysteine thiol groups with a leaving group-S-linker-drug component wherein the leaving group was 5-nitropyridine and the linker carbon atom bearing the sulfur atom was hindered with two methyl groups. FIGS. 4A to 4D depict the LC/MS ESI results for the antibody probe conjugates formed in pH 5.0, 6.3, 7.5 and 8.5 buffers, respectively (as further discussed in example 6, below).

FIGS. 5A to 5D depict the LC/MS ESI results for antibody-probe conjugates formed in pH 5.0, 6.3, 7.5 and 8.5 buffers, respectively (as further discussed in example 7, below).

FIGS. 6A to 6D are LC/MS ESI scans depicting the purity by area percent for a reaction product mixture formed at varying pH and comprising an antibody-linker-probe conjugate having the antibody bound to a linker by a disulfide bond and formed by reacting one or more CD22 LC K149C antibody cysteine thiol groups with a leaving group-S-linker-probe component wherein the leaving group was

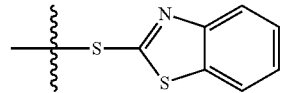 [SMILES: *Sc1nc2ccccc2s1]

and the linker carbon atom bearing the sulfur atom was hindered with two methyl groups. FIGS. 6A to 6D depict the LC/MS ESI results for antibody-probe conjugates formed in pH 5.0, 6.3, 7.5 and 8.5 buffers, respectively (as further discussed in example 8, below).

FIGS. 7A to 7D are LC/MS ESI scans depicting the purity by area percent for a reaction product mixture formed at varying pH and comprising an antibody-linker-probe conjugate having the antibody bound to a linker by a disulfide bond and formed by reacting one or more CD22 LC K149C antibody cysteine thiol groups with a leaving group-S-linker-probe component wherein the leaving group was:

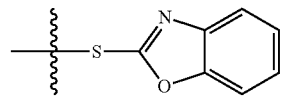 [SMILES: *Sc1nc2ccccc2o1]

and the linker carbon atom bearing the sulfur atom was hindered with two methyl groups. FIGS. 7A to 7D depict the LC/MS ESI results for antibody-probe conjugates formed in pH 5.0, 6.3, 7.5 and 8.5 buffers, respectively (as further discussed in example 9, below).

FIGS. 8A to 8D are LC/MS ESI scans depicting the purity by area percent for four reaction product mixtures formed at pH 8.5 and comprising an antibody-linker-probe conjugate having the antibody bound to a linker by a disulfide bond and formed by reacting one or more CD22 LC K149C antibody cysteine thiol groups with different leaving group-S-linker-probe component wherein the leaving groups were as follows

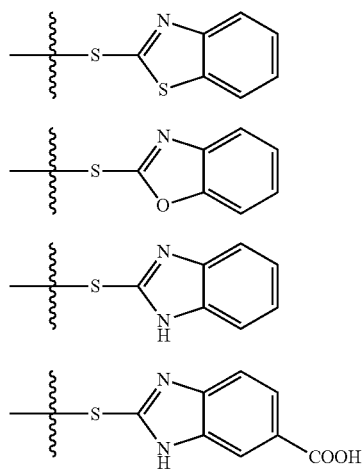

Figure 8C:
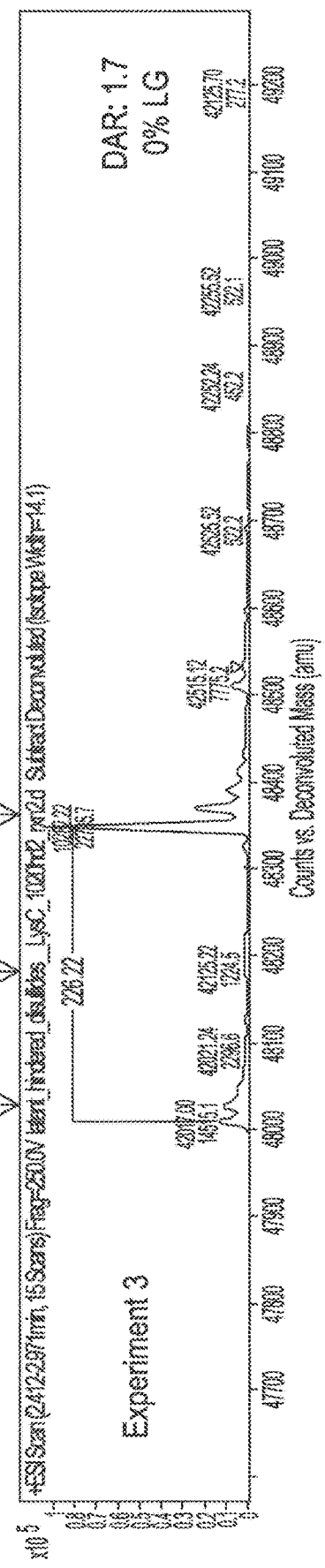
Figure 8D:
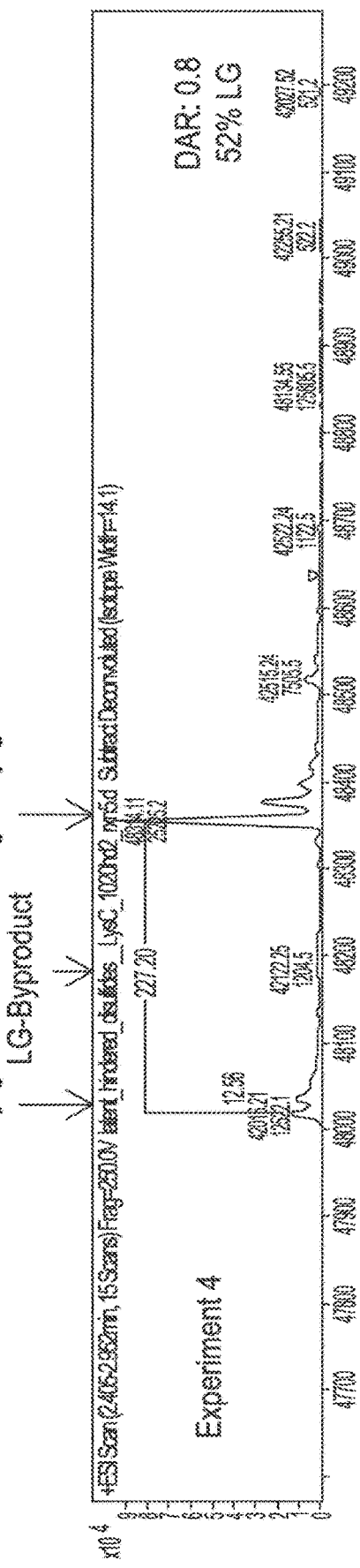
Figure 9C:
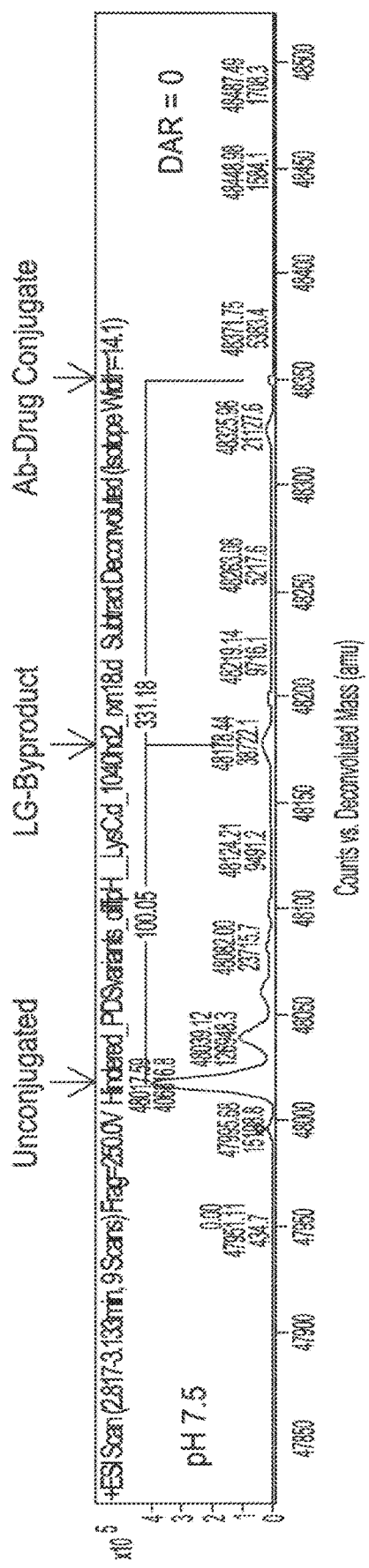
Figure 9D:
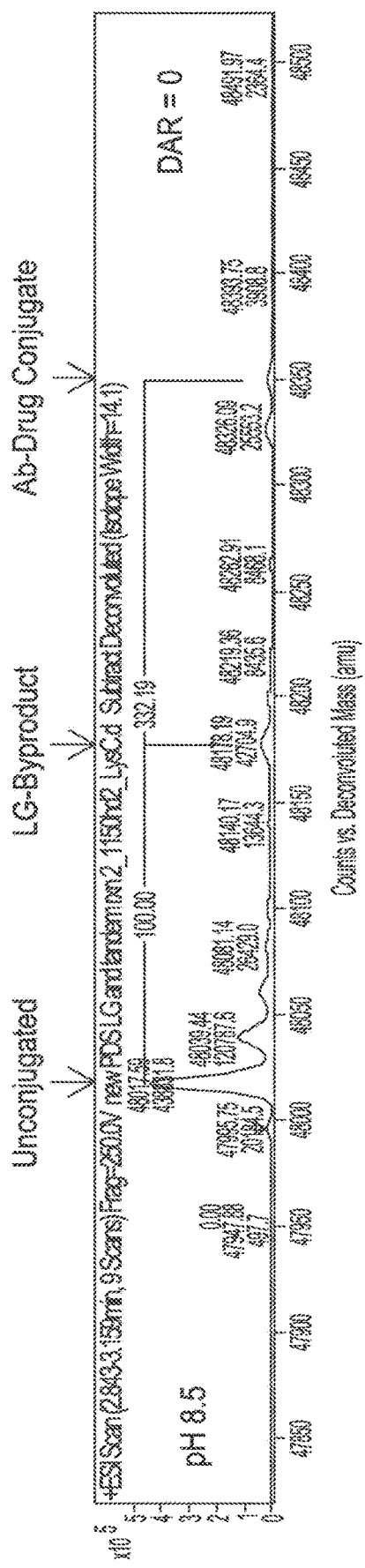

FIG. 8D and the carbon atom bearing the sulfur atom for each linker was hindered with two methyl groups (as further discussed in example 10, below).

FIGS. 9A to 9D are LC/MS ESI scans depicting the purity by area percent for four reaction product mixtures formed at varying pH and comprising an ADC having the antibody bound to a linker by a disulfide bond and formed by reacting one or more CD22 LC K149C antibody cysteine thiol groups with a leaving group-S-linker-drug component wherein the leaving group was, 5-nitropyridine, the linker carbon atom bearing the sulfur atom was hindered with two methyl groups, and the drug was a maytansinoid. FIGS. 9A to 9D depict the LC/MS ESI results for antibody-linker-probe conjugates formed in pH 5.0, 6.3, 7.5 and 8.5 buffers, respectively (as further discussed in example 11, below).

Figure 10A:
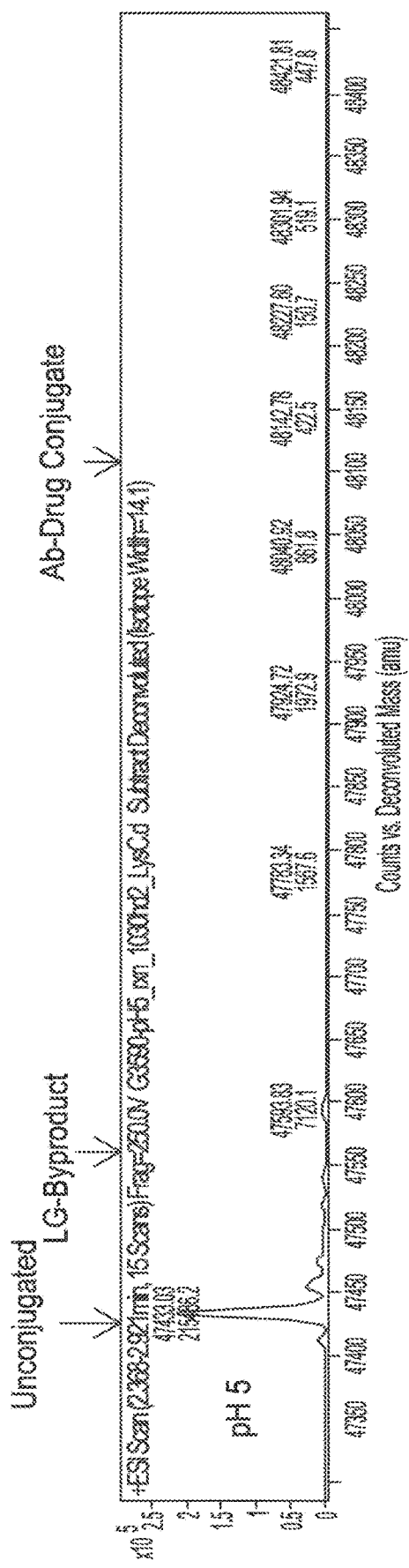
Figure 10B:
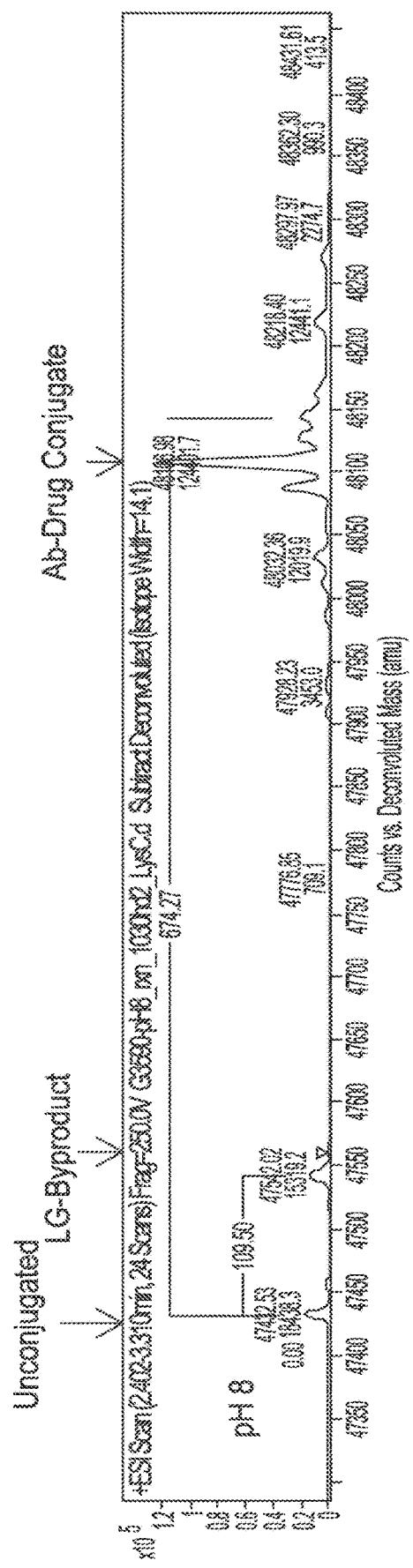

FIGS. 10A and 10B are LC/MS ESI scans depicting the purity by area percent for a reaction product mixture formed at pH 5 and pH 8, respectively, and comprising an antibody-probe conjugate having the antibody bound to a linker by a disulfide bond and formed by reacting one or more anti-HER2 4D5 HC A118C antibody cysteine thiol groups with a leaving group-S-linker-probe component wherein the leaving group was pyridine and the linker carbon atom bearing the sulfur atom was hindered with a methyl group (as further discussed in example 13, below).

Figure 11B:
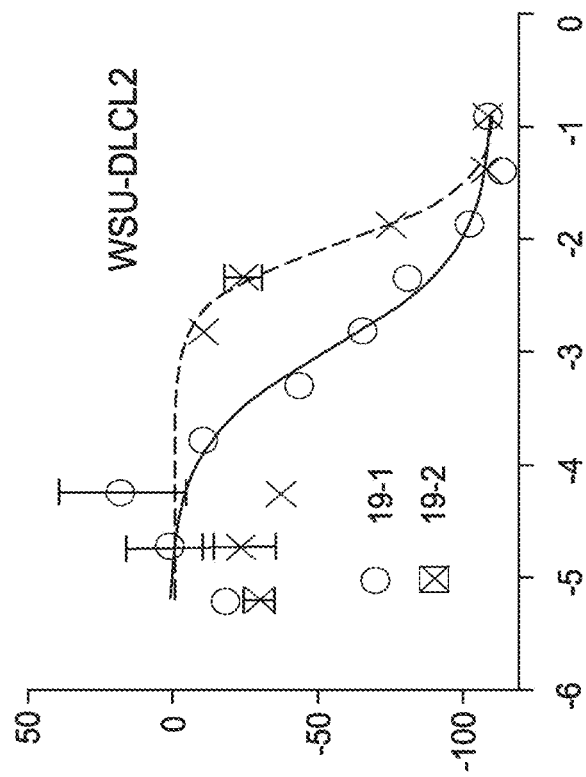
Figure 11A:
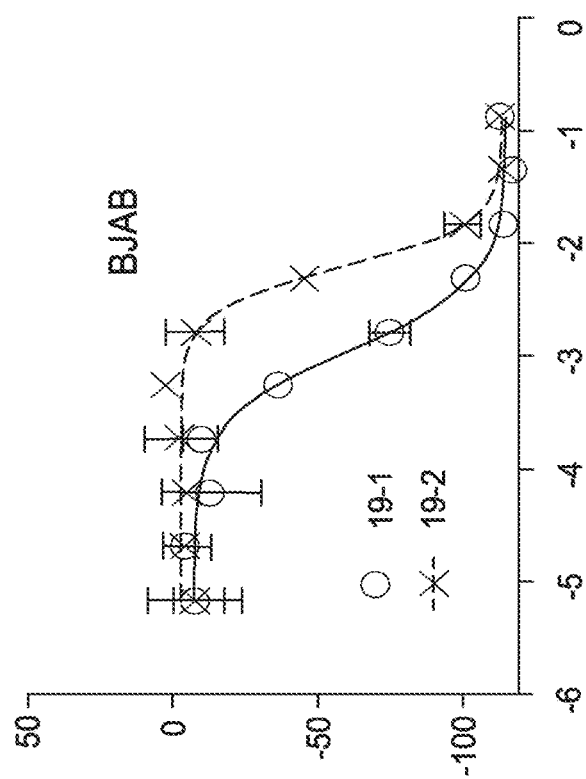
Figure 11F:
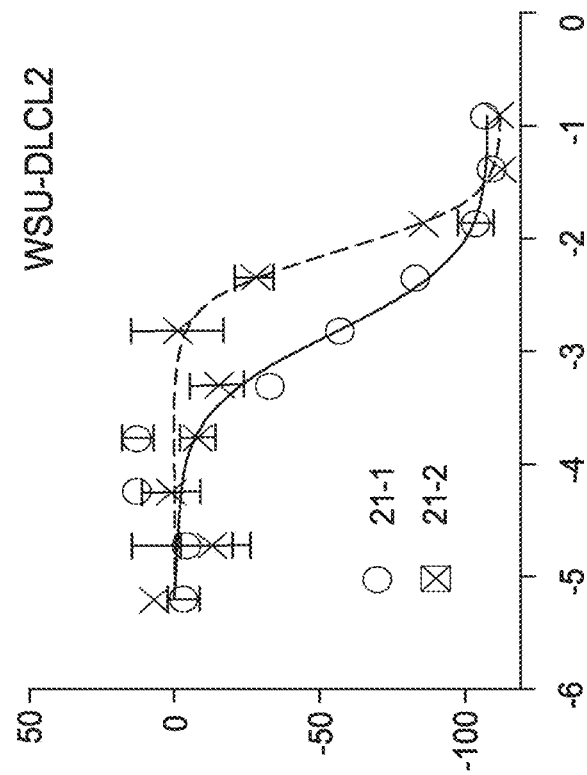
Figure 11E:
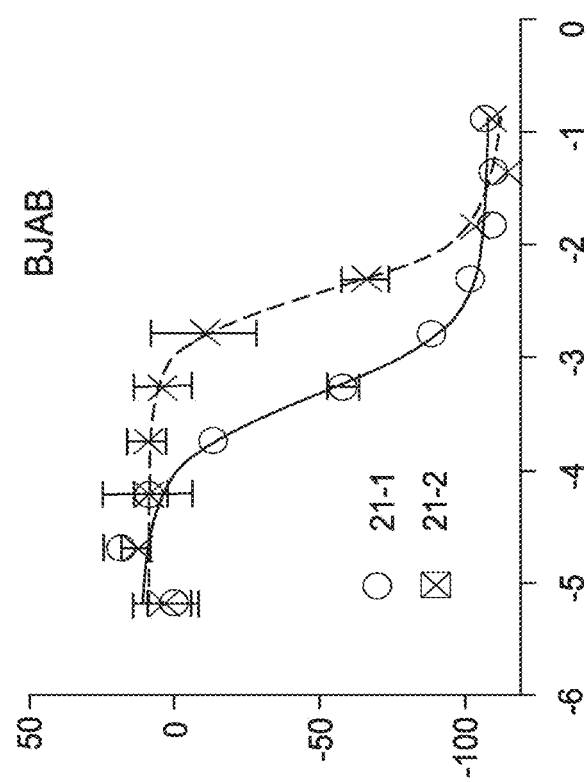

FIGS. 11A to 11F depict % Cell Viability versus Log Concentration [μM] for compounds designated as "19-1", "19-2", "20-1", "20-2", "21-1" and "21-2". Compound 19-1 was PBD dimer anti-CD22 ADC comprising a methyl-hindered disulfide linker and was evaluated against CD22-expressing BJAB and WSU-DLCL2 cell lines (FIGS. 11A and 11B). Compound 19-2 was a PBD dimer anti-NaPi ADC comprising a methyl-hindered disulfide linker and was evaluated against CD22-expressing BJAB and WSU-DLCL2 cell lines (FIGS. 11A and 11B). Compound 20-1 was a PBD dimer anti-CD22 ADC comprising a cyclopropyl-hindered disulfide linker and was evaluated against CD22-expressing BJAB and WSU-DLCL2 cell lines (FIGS. 11C and 11D). Compound 20-2 was a PBD dimer anti-NaPi ADC comprising a cyclopropyl-hindered disulfide linker and was evaluated against CD22-expressing BJAB and WSU-DLCL2 cell lines (FIGS. 11C and 11D). Compound 21-1 was PBD dimer anti-CD22 ADC comprising a cyclobutyl-hindered disulfide linker and was evaluated against CD22-expressing BJAB and WSU-DLCL2 cell lines (FIGS. 11E and 11F). Compound 21-2 was a PBD dimer anti-NaPi ADC comprising a cyclobutyl-hindered disulfide linker and was evaluated against CD22-expressing BJAB and WSU-DLCL2 cell lines (FIGS. 11E and 11F).

Figure 13A:
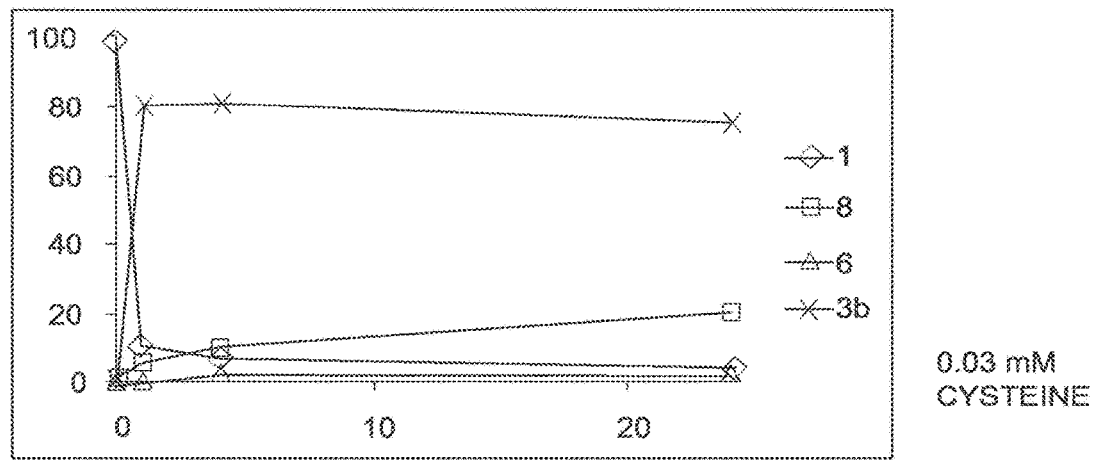
Figure 13B:
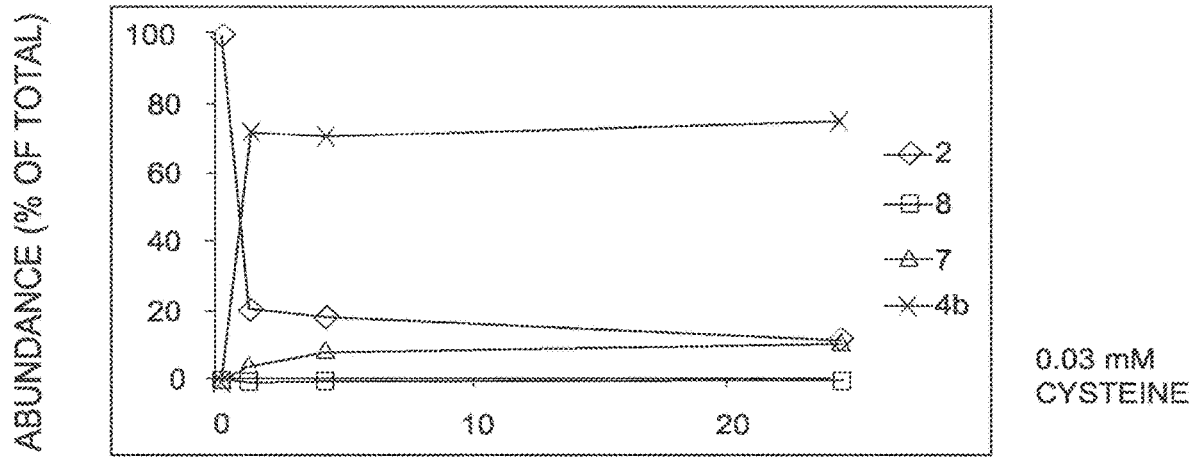
Figure 13C:
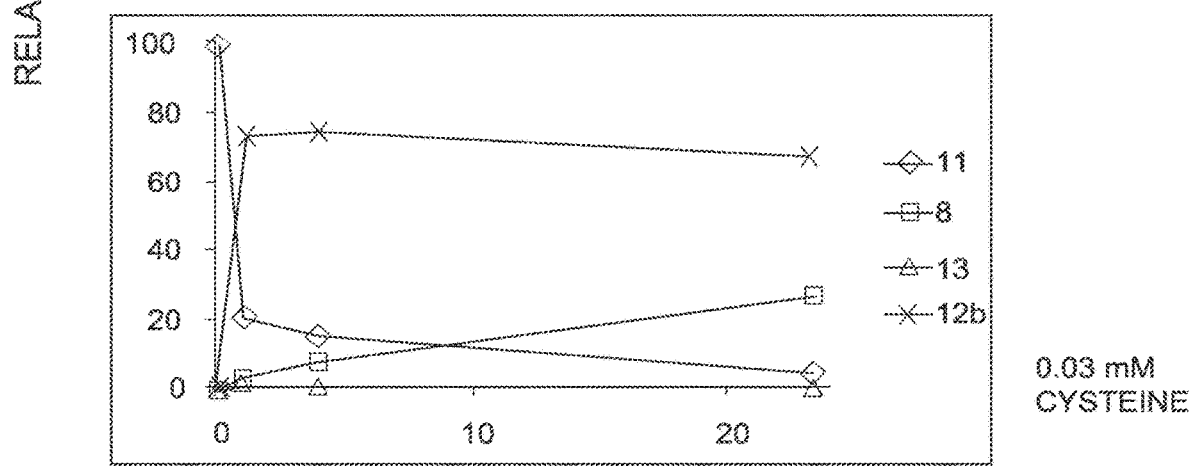
Figure 14A:
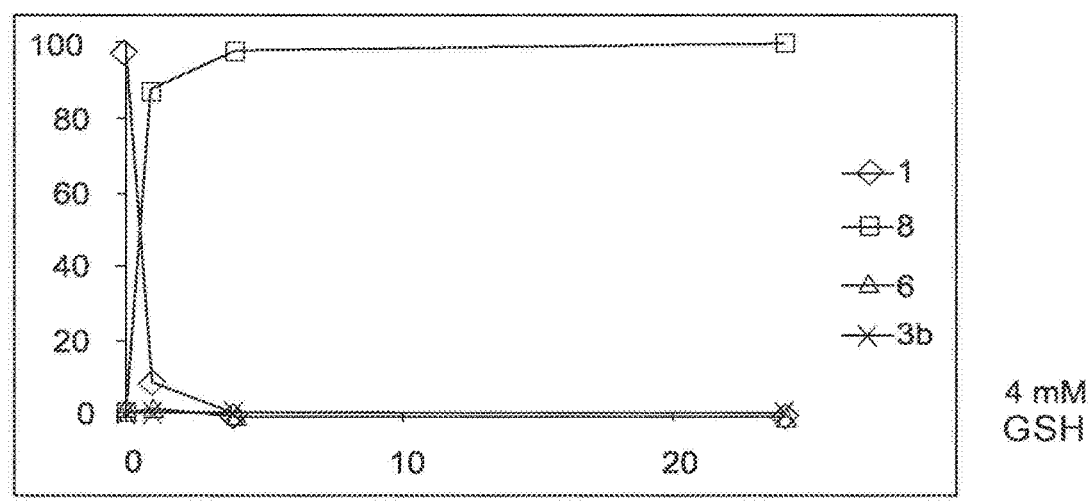
Figure 14B:
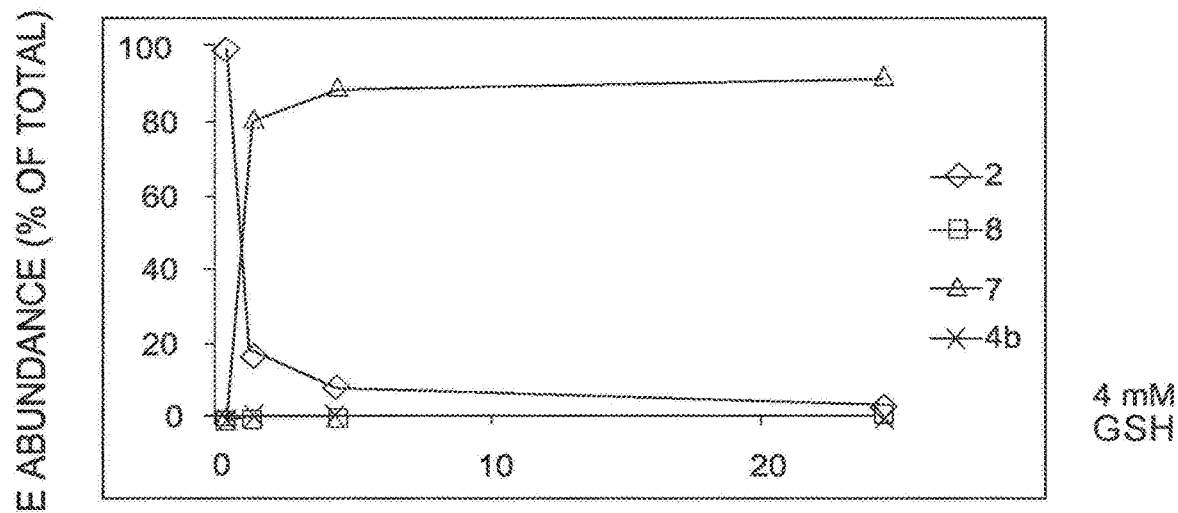
Figure 14C:
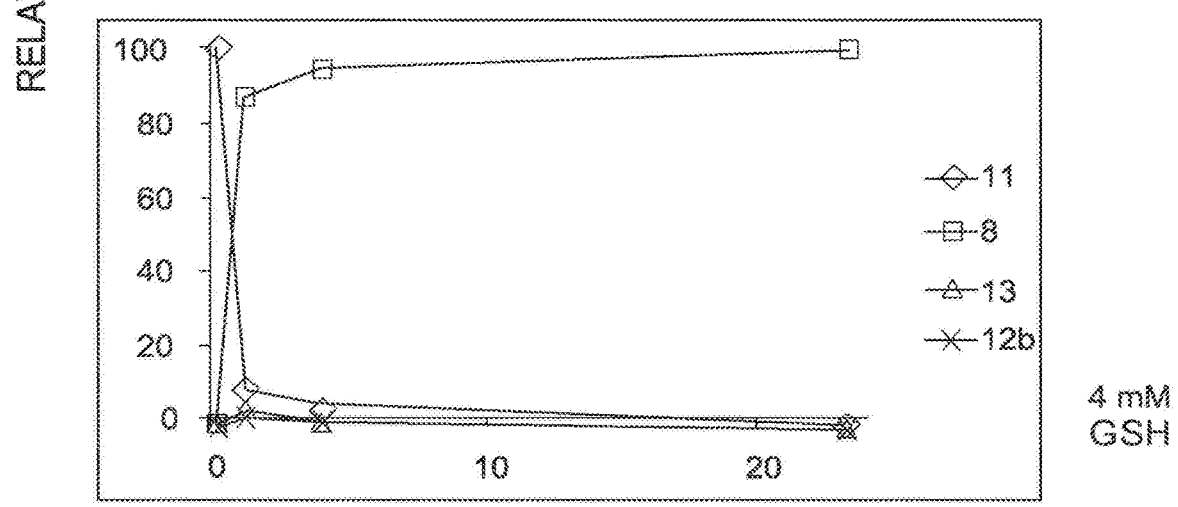
Figure 15A:
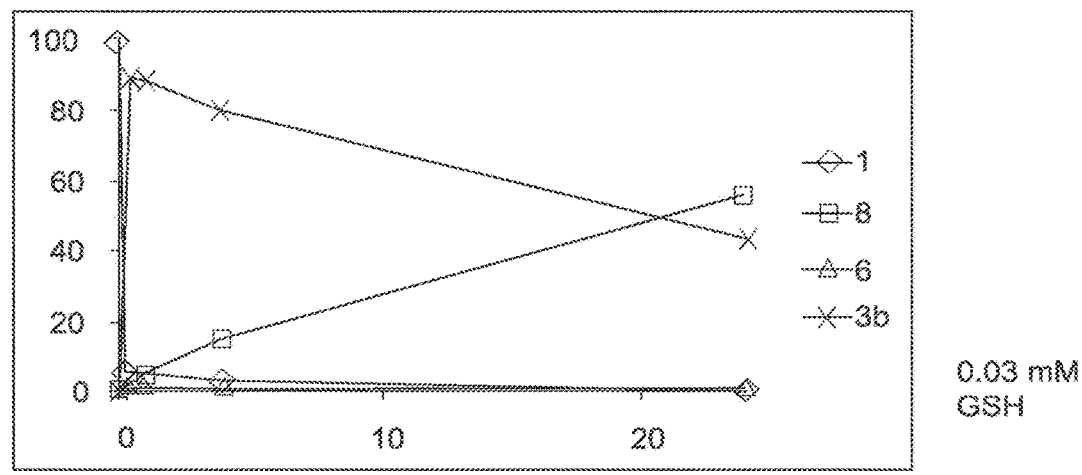
Figure 15B:
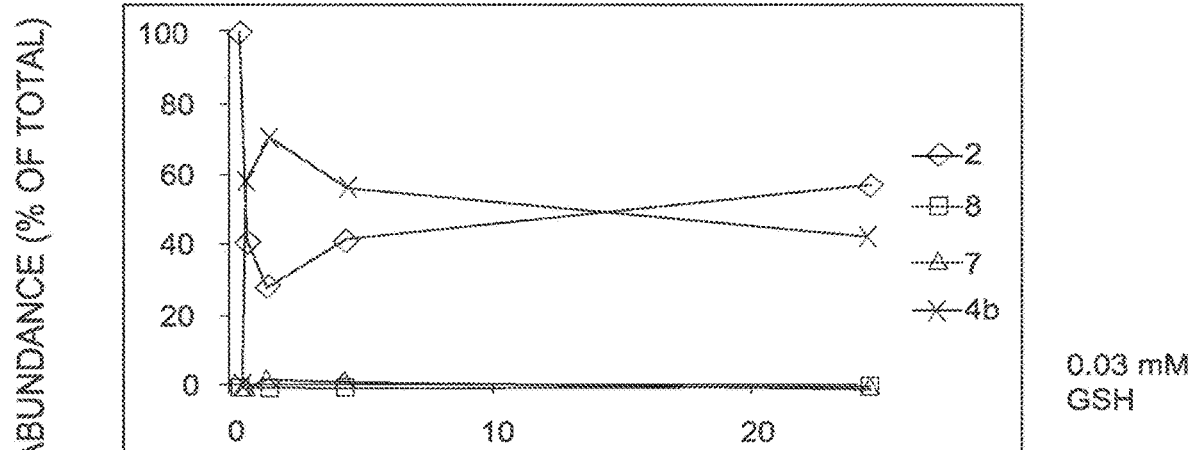
Figure 15C:
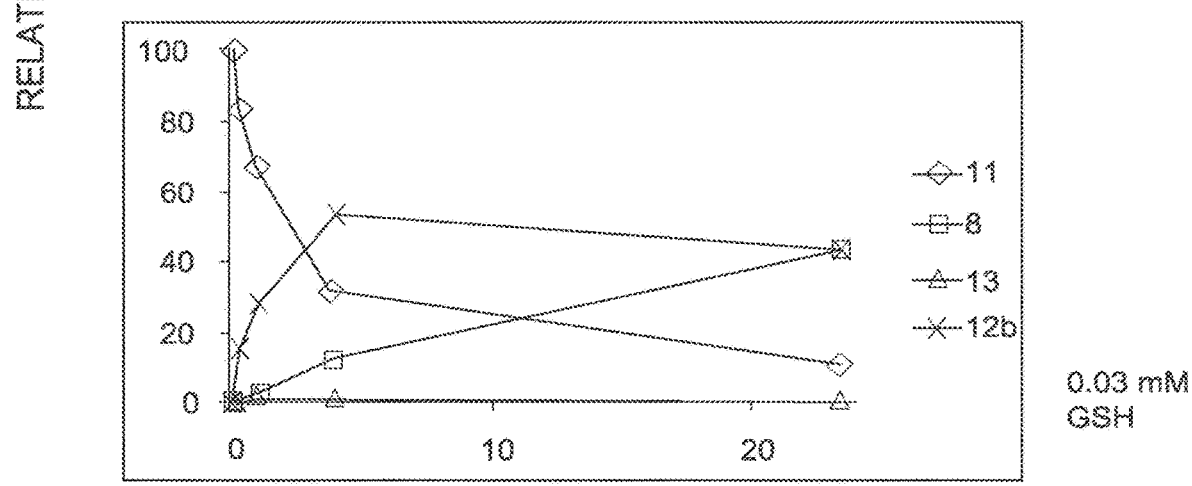

FIGS. 12A to 12C, 13A to 13C, 14A to 14C, and 15A to 15C depict relative abundance of disulfide cleavage and immolation products over time. Products were monitored by LC/MS from incubations of drug analog 1 (a PBD dimer having a methyl-hindered disulfide linker and designated as "1" in FIGS. 12A, 13A, 14A and 15A), drug analog 2 (a PBD dimer having a cyclopropyl-hindered disulfide linker and designated as "2" in FIGS. 12B, 13B, 14B and 15B), and drug analog 11 (a PBD dimer having a cyclobutyl-hindered disulfide linker and designated as "11" in FIGS. 12C, 13C, 14C and 15C). Incubations were done at pH 7.0 and 37° C. in the presence of: 0.2 mM cysteine (FIGS. 12A, 12B and 12C); 0.03 mM cysteine (FIGS. 13A, 13B and 13C); 4 mM glutathione (FIGS. 14A, 14B and 14C); and 0.03 mM glutathione (FIGS. 15A, 15B and 15C). In FIGS. 12A to 12C, 13A to 13C, 14A to 14C, and 15A to 15C, the PBD dimer payload is designated as "8". In FIGS. 12A, 13A, 14A and 15A, compounds 3a and 3b (designated as "3a" and "3b", respectively) refer to drug analog 1 (having a methyl-hindered disulfide) conjugated to cysteine (compound 3a) and glutathione (compound 3b) via a disulfide bond. In FIGS. 12B, 13B, 14B and 15B compounds 4a and 4b (designated as "4a" and "4b", respectively) refer to drug analog 2 (having a cyclopropyl-hindered disulfide) conjugated to cysteine (compound 4a) and glutathione (compound 4b) via a disulfide bond. In FIGS. 12C, 13C, 14C and 15C, compounds 12a and 12b (designated as "12a" and "12b", respectively) refer to drug analog 11 (having a cyclobutyl-hindered disulfide) conjugated to cysteine (compound 12a) and glutathione (compound 12b) (cyclobutyl) via a disulfide bond. In FIGS. 12A, 13A, 14A and 15A, compound 6 (designated as "6") refers to a disulfide reduction/immolation product of compounds 3a and 3b. In FIGS. 12B, 13B, 14B and 15B, compound 7 (designated as "7") refers to a disulfide reduction/immolation product of compounds 4a and 4b. In FIGS. 12C, 13C, 14C and 15C, compound 13 (designated as "13") refers to a disulfide reduction/immolation product of compounds 12a and 12b.

Figure 16:
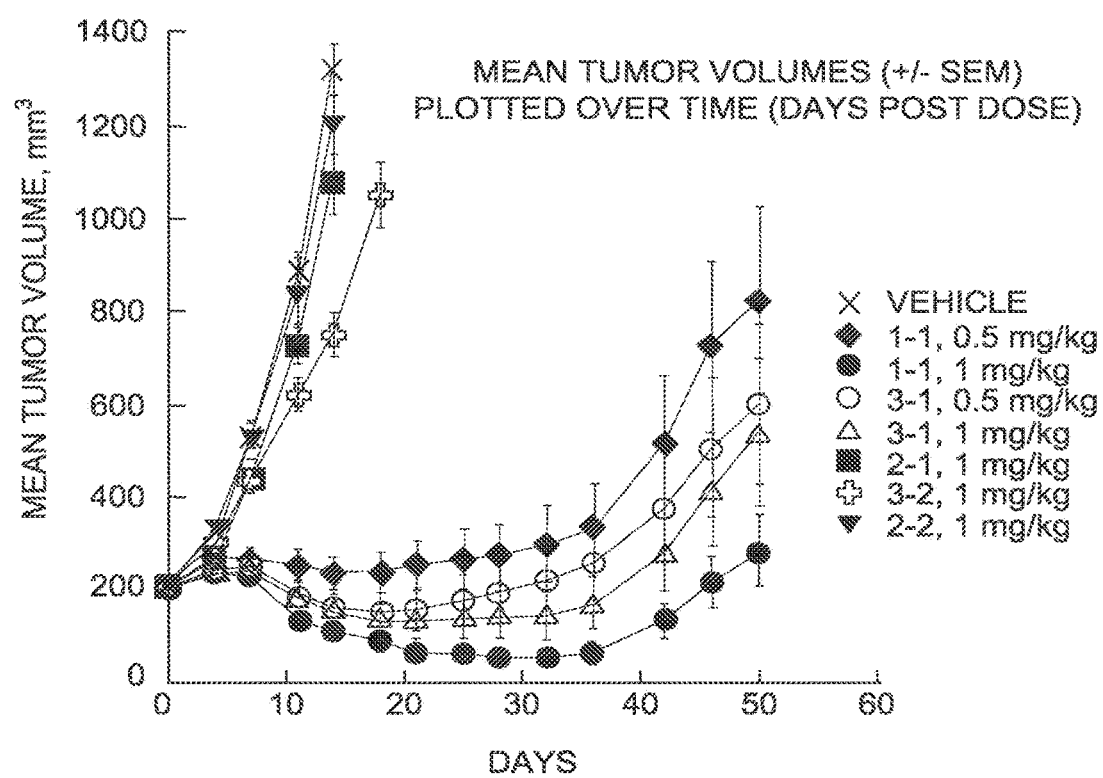

FIG. 16 depicts the anti-tumor effects in mean tumor volume (mm$^3$) versus post-dose time (days) of disulfide-linked PBD ADCs in mice bearing human B-cell lymphoma WSU-DLCL2 xenografts for compounds designated as "1-1", "2-1", "3-1", "2-2" and "3-2". Compound 1-1 was an anti-CD22 PBD dimer ADC having a disulfide linker hindered with a methyl moiety. Compound 2-1 was an anti-CD22 PBD dimer ADC having a disulfide linker hindered with a cyclopropyl moiety. Compound 3-1 was an anti-CD22 PBD dimer ADC having a disulfide linker hindered with a cyclobutyl moiety. Compound 2-2 was a non-target control anti-NaPi PBD dimer ADC having a disulfide linker hindered with a cyclopropyl moiety. Compound 3-2 was a non-target control anti-NaPi PBD dimer ADC having a disulfide linker hindered with a cyclobutyl moiety.

Figure 17:
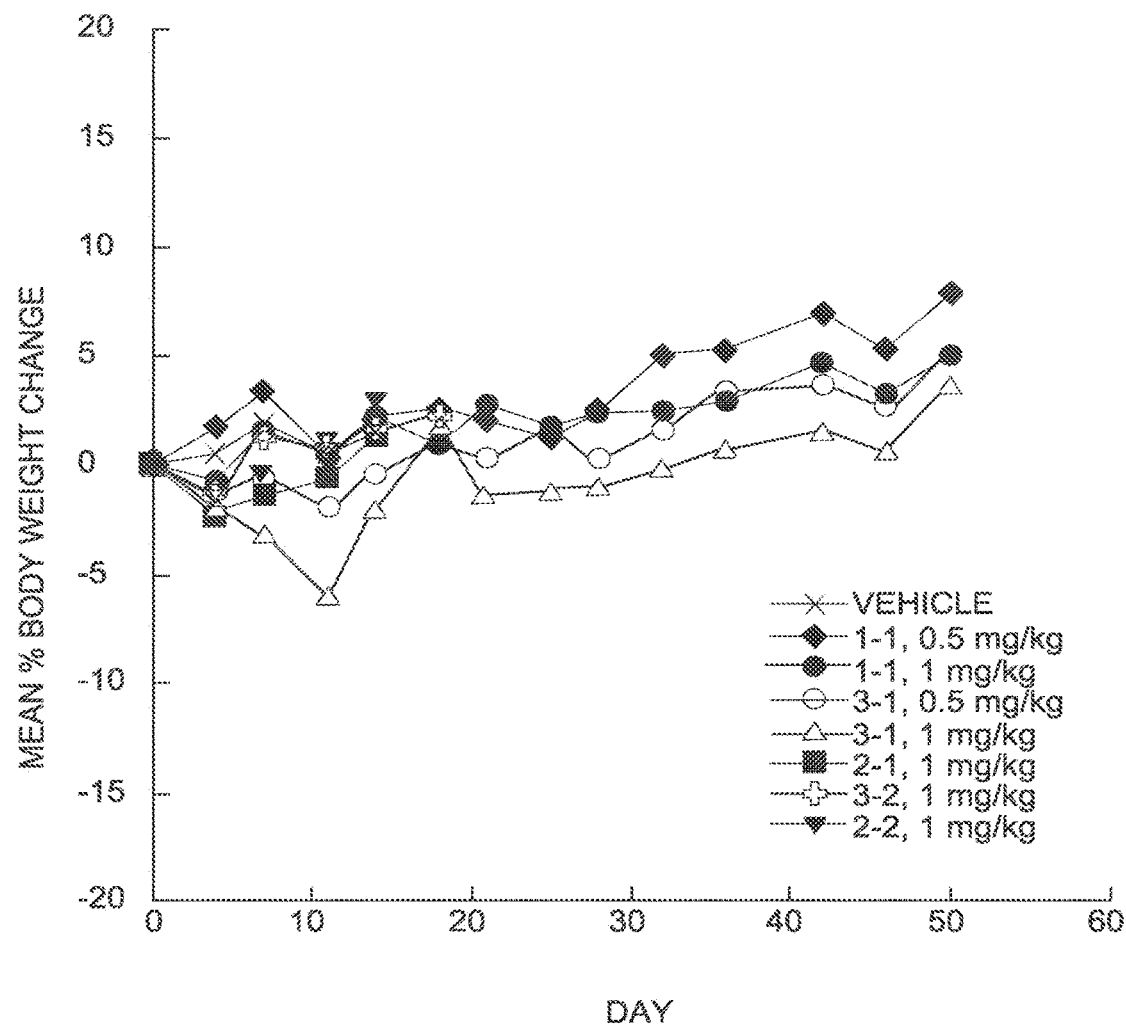

FIG. 17 depicts the tolerability of mice in mean % body weight change versus time (days) of compounds 1-1, 2-1, 3-1, 2-2 and 3-2 of FIG. 16.

Figure 18:
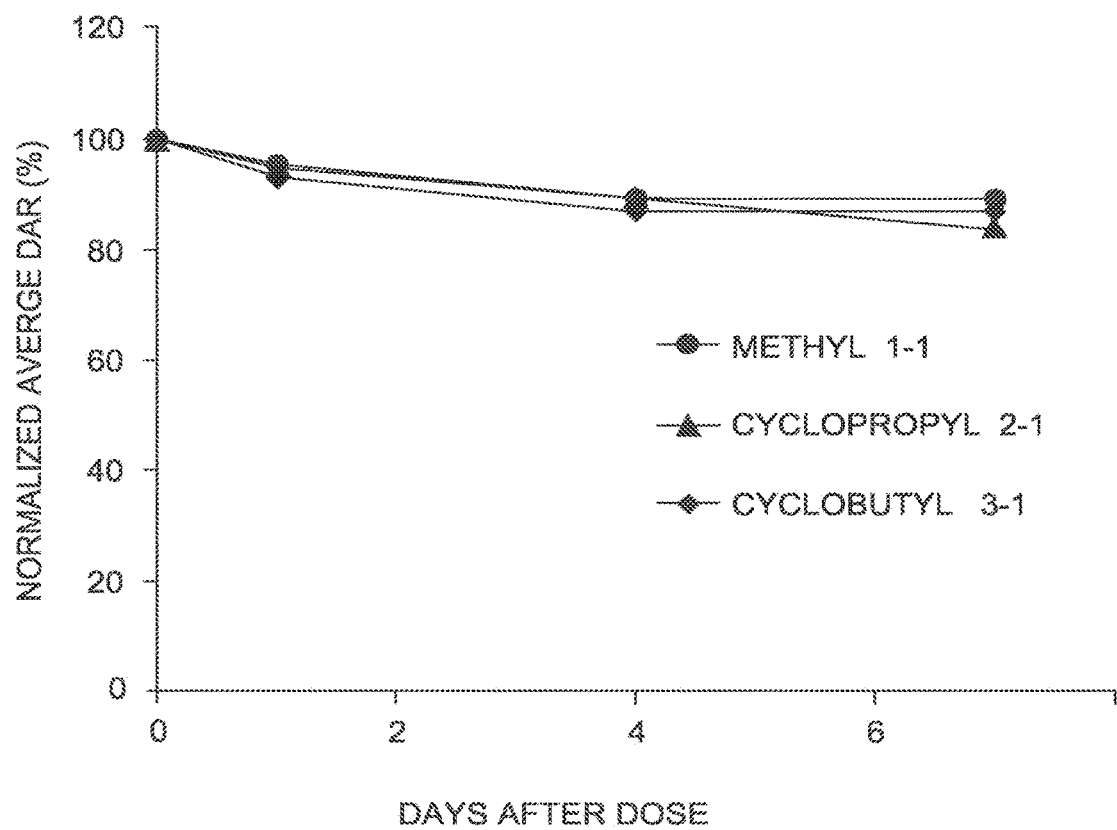

FIG. 18 depicts the in vivo stability of compounds 1-1, 2-1 and 3-1 of FIGS. 16 and 17 in terms of normalized average drug to antibody ratio (DAR) % versus time (days) post-dose.

Figure 19A:
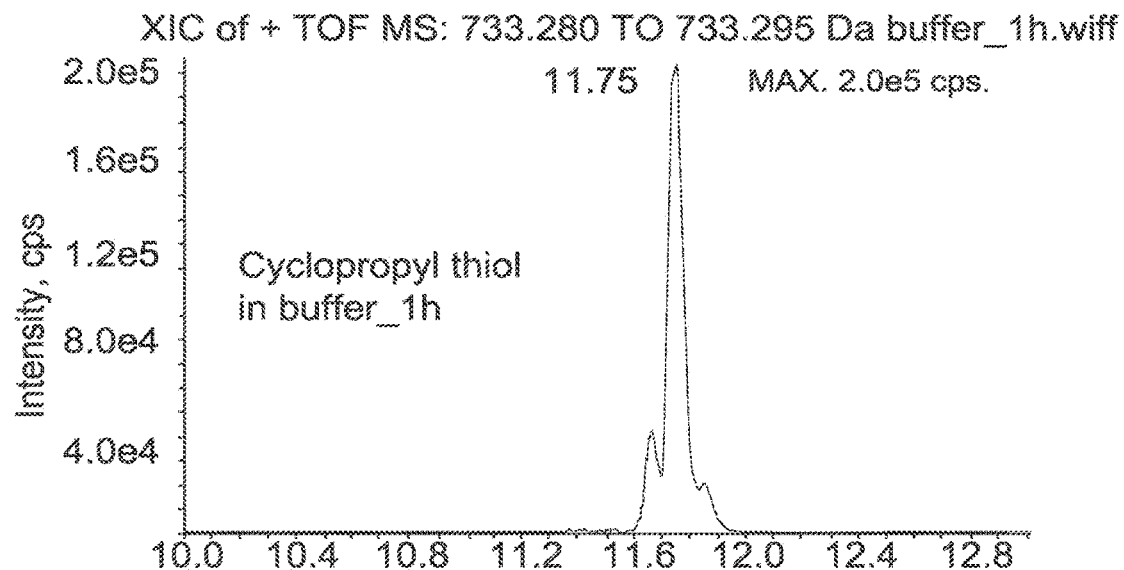
Figure 19B:
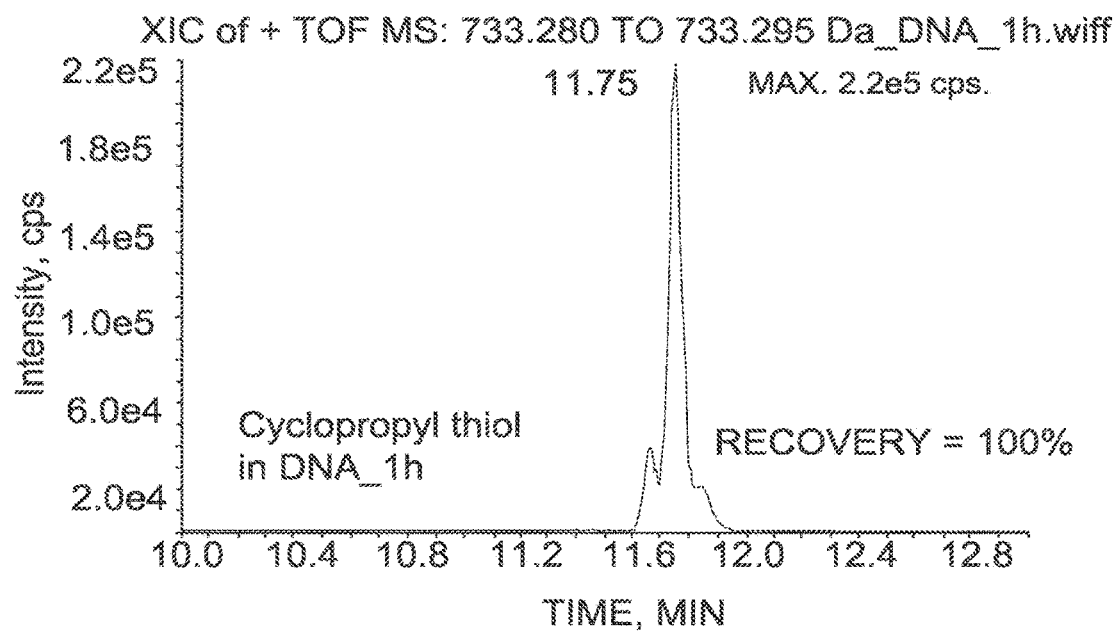
Figure 19C:
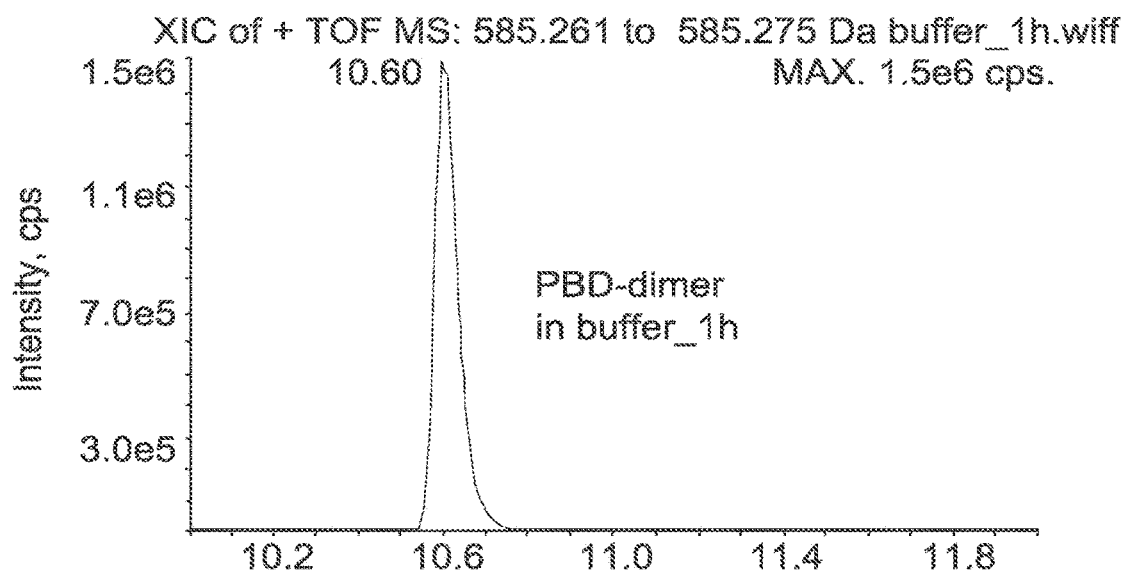
Figure 19D:
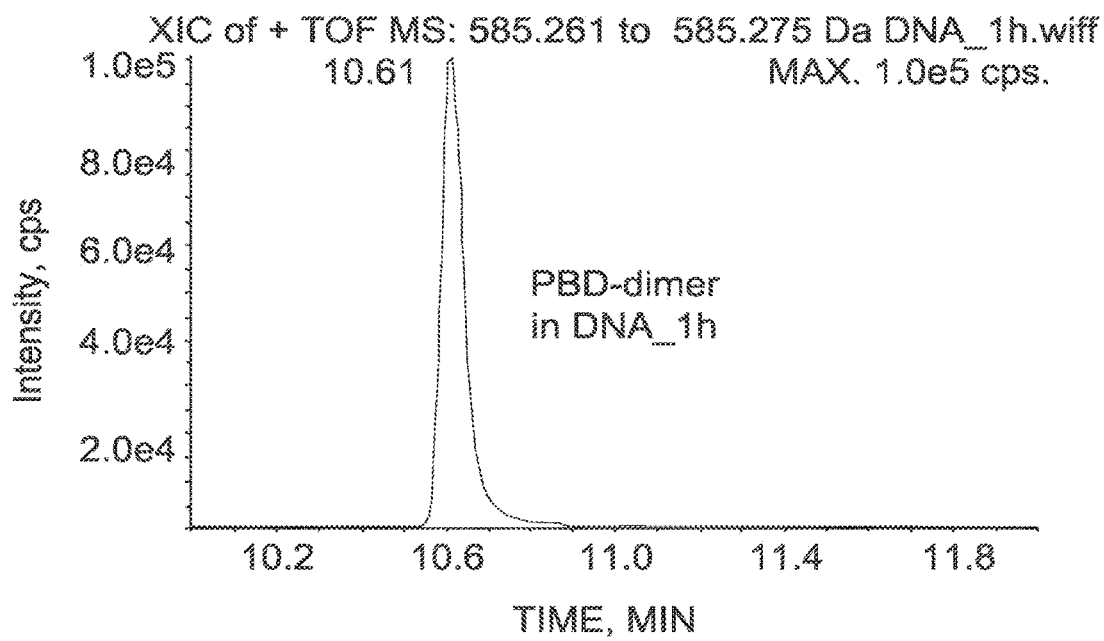

FIGS. 19A and 19B depict the DNA binding potential of cyclopropyl thiol compound 7 (a PBD having a cyclopropyl thiol moiety of the structure —C(O)—O—CH$_2$—C(cyclopropyl)-SH at one N10 position) incubated in buffer (FIG. 19A) or 1 mg/mL calf DNA at 37° C. for 1 h (FIG. 19B). FIGS. 19C and 19D depict the DNA binding potential of PBD dimer 8 incubated in buffer (FIG. 19C) or 1 mg/mL calf DNA at 37° C. for 1 h (FIG. 19D).

Figure 20:
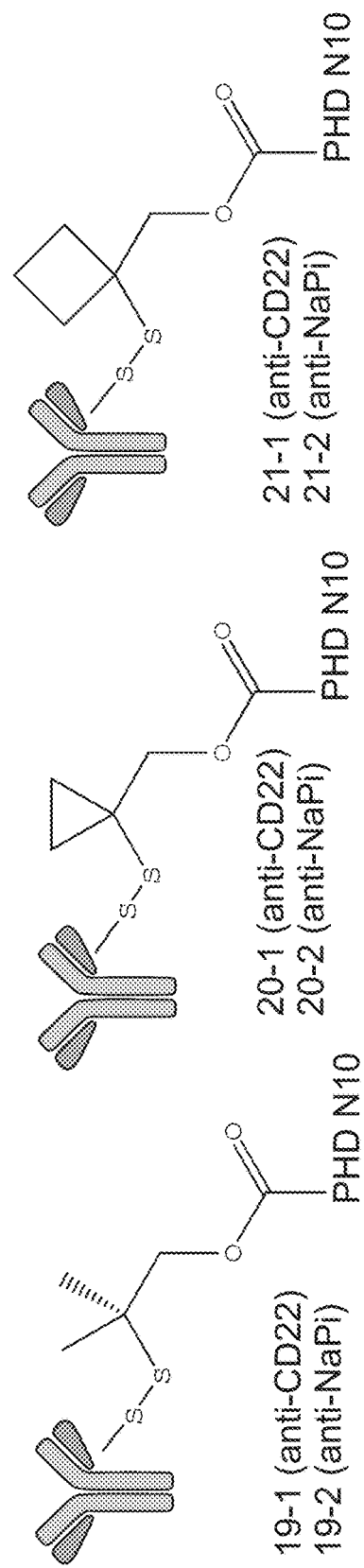

FIG. 20 shows LC-K149C-anti-CD22-PBD and LC-K149C-anti-NaPi2b-PBD ADCs were prepared where PBD-N10 corresponds to PBD compound designated as "R" above.

Figure 21:
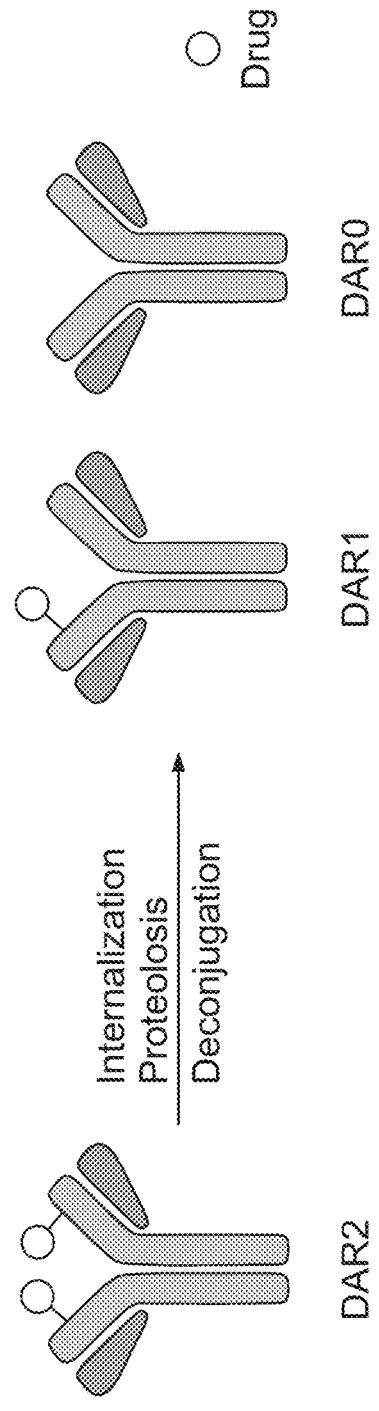

FIG. 21 depicts the distribution profile of DAR0, DAR1 and DAR2 species after internalization, proteolosis and deconjugation.

DETAILED DESCRIPTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

In some embodiments, the present disclosure is generally directed to a method of preparing a disulfide conjugate, as well as the disulfide conjugate itself, that enables the preparation of a conjugate having improved bloodstream stability and intracellular drug release. More particularly, the present disclosure is directed to such a disulfide conjugate comprising a selective carrier-S—S-hindered linker-drug conjugate, the method of preparation comprising forming a reaction mixture comprising a solvent comprising water or predominantly comprising water, a selective carrier having at least one cysteine sulfhydryl moiety and a leaving group-S—S-hindered linker-drug compound. The reaction mixture is reacted to form a reaction product mixture comprising the selective carrier-S—S-hindered linker-drug conjugate of structure (II).

In some embodiments, the present disclosure is further generally directed to linker-drug conjugate of the general structure (I); that is, a conjugate having the structure: leaving group-S—S-hindered linker-drug. The leaving groups of the present disclosure provide for sufficient reactivity to enable bio-conjugation of the hindered linker-drug to a cysteine thiol of a selective carrier in a solvent system comprising water or predominantly comprising water.

In some embodiments, the present disclosure is further generally directed to a disulfide conjugate having the general structure: selective carrier-S—S-hindered linker-drug (i.e., the structure (II)). The conjugates provide for stability in the bloodstream and also provide for effective intracellular drug release.

Other embodiments are directed to pharmaceutical compositions comprising disulfide conjugates of the present disclosure; methods of treating cancer by administering pharmaceutical compositions comprising the disulfide conjugates; use of the disulfide conjugates in the manufacture of a medicament for the treatment of cancer; a disulfide conjugate compound of the present disclosure for use in a method for treating cancer; a method of making a disulfide conjugate compound of the present disclosure, the method comprising reacting a carrier with a linker-drug compound of the present disclosure; and packaged disulfide conjugate pharmaceutical compositions of the present disclosure for use in the treatment of cancer.

Definitions

Unless defined otherwise, technical and scientific terms used herein have the same meaning as commonly understood by one of ordinary skill in the art to which this disclosure belongs, and are consistent with: Singleton et al. (1994) Dictionary of Microbiology and Molecular Biology, 2nd Ed., J. Wiley & Sons, New York, N.Y.; and Janeway, C., Travers, P., Walport, M., Shlomchik (2001) Immunobiology, 5th Ed., Garland Publishing, New York.

A "Linker" (L) is a bifunctional or multifunctional moiety that can be used to link one or more drug moieties (D) to a carrier such as an antibody (Ab) to form an carrier-linker-drug conjugate of the general formula

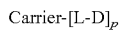

Carrier-[L-D]$_p$ wherein p may be 1, 2, 3, 4, 5, 6, 7 or 8. In some embodiments, carrier-D conjugates can be prepared using a linker having reactive functionalities for covalently attaching to the drug and to the carrier. For example, in some embodiments, the cysteine thiol of a cysteine-engineered antibody (Ab) can form a bond with a reactive functional group of a linker or a drug-linker intermediate to make an ADC. In one aspect, a linker has a functionality that is capable of reacting with a free cysteine present on an antibody to form a covalent disulfide bond (See, e.g., the conjugation method at page 766 of Klussman, et al (2004), Bioconjugate Chemistry 15(4):765-773, and the Examples herein, incorporated herein by reference in its entirety). A linker may comprise one or more "spacer" units between the disulfide group and the drug moiety. Exemplary spacer components include valine-citrulline ("val-cit" or "vc"), alanine-phenylalanine ("ala-phe"), and p-aminobenzyloxycarbonyl (a "PABC"). Various linker components are known in the art. In some aspects the spacer may be immolating.

"Immolating" refers to a moiety, such as a linker or spacer, that is cleavable in vitro and/or in vivo such as by an enzyme (e.g. a protease), glutathione and/or pH change.

"Hindered linker" refers to a linker having a carbon atom bearing a sulfur capable of forming a disulfide bond wherein the carbon atom is substituted with at least one substituent other than H, and more particularly is substituted with a hydrocarbyl or a substituted hydrocarbyl moiety as further detailed herein below.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are known in the art, any of which can be used for purposes of the present invention.

One illustrative method for measuring reactivity is where a "Kd" or "Kd value" may be measured by a radiolabeled antigen binding assay (RIA) performed with the Fab version of an antibody of interest and its antigen as described by the following assay that measures solution binding affinity of Fabs for antigen by equilibrating Fab with a minimal concentration of (125I)-labeled antigen in the presence of a titration series of unlabeled antigen, then capturing bound antigen with an anti-Fab antibody-coated plate (Chen, et al., (1999) J. Mol Biol 293:865-881). To establish conditions for the assay, microtiter plates (Dynex) may be coated overnight with 5 ug/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbant plate (Nunc #269620), 100 pM or 26 pM [125I]-antigen may be mixed with serial dilutions of a Fab of interest (e.g., consistent with assessment of an anti-VEGF antibody, Fab-12, in Presta et al., (1997) Cancer Res. 57:4593-4599). The Fab of interest may be then incubated overnight; however, the incubation may continue for a longer period (e.g., 65 hours) to insure that equilibrium is reached. Thereafter, the mixtures may be transferred to the capture plate for incubation at room temperature (e.g., for one hour). The solution may be then removed and the plate washed eight times with 0.1% Tween-20 in PBS. When the plates have dried, 150 ul/well of scintillant (MicroScint-20; Packard) may be added, and the plates may be counted on a Topcount gamma counter (Packard) for ten minutes. Concentrations of each Fab that give less than or equal to 20% of maximal binding may be chosen for use in competitive binding assays. According to another embodiment the Kd or Kd value may be measured by using surface plasmon resonance assays using a BIAcore™-2000 or a BIAcore™-3000 (BIAcore, Inc., Piscataway, N.J.) at 25° C. with immobilized antigen CM5 chips at about 10 response units (RU). Briefly, carboxymethylated dextran biosensor chips (CM5, BIAcore Inc.) may be activated with N-ethyl-N'-(3-dimethylaminopropyl)-carbodiimide hydrochloride (EDC) and N-hydroxysuccinimide (NHS) according to the supplier's instructions. Antigen may be diluted with 10 mM sodium acetate, pH 4.8, into 5 ug/ml (about 0.2 uM) before injection at a flow rate of 5 ul/minute to achieve approximately 10 response units (RU) of coupled protein. Following the injection of antigen, 1M ethanolamine may be injected to block unreacted groups. For kinetics measurements, two-fold serial dilutions of Fab (0.78 nM to 500 nM) may be injected in PBS with 0.05% Tween 20 (PBST) at 25° C. at a flow rate of approximately 25 ul/min. Association rates (kon) and dissociation rates (koff) may be calculated using a simple one-to-one Langmuir binding model (BIAcore Evaluation Software version 3.2) by simultaneous fitting the association and dissociation sensorgram. The equilibrium dissociation constant (Kd) may be calculated as the ratio koff/kon. See, e.g., Chen, Y., et al., (1999) J. Mol Biol 293:865-881. If the on-rate exceeds 106 M-1 S-1 by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-Aminco spectrophotometer (ThermoSpectronic) with a stir red cuvette.

An "on-rate" or "rate of association" or "association rate" or "kon" can also be determined with the same surface plasmon resonance technique described above using a BIAcore™-2000 or a BIAcore™-3000 (BIAcore, Inc., Piscataway, N.J.) at 25° C. with immobilized antigen CM5 chips at about 10 response units (RU). Briefly, carboxymethylated dextran biosensor chips (CM5, BIAcore Inc.) may be activated with N-ethyl-N'-(3-dimethylaminopropyl)-carbodiimide hydrochloride (EDC) and N-hydroxysuccinimide (NHS) according to the supplier's instructions. Antigen may be diluted with 10 mM sodium acetate, pH 4.8, into 5 ug/ml (about 0.2 uM) before injection at a flow rate of 5 ul/minute to achieve approximately 10 response units (RU) of coupled protein. Following the injection of 1M ethanolamine to block unreacted groups. For kinetics measurements, two-fold serial dilutions of Fab (0.78 nM to 500 nM) may be injected in PBS with 0.05% Tween 20 (PBST) at 25° C. at a flow rate of approximately 25 ul/min. Association rates (kon) and dissociation rates (koff) may be calculated using a simple one-to-one Langmuir binding model (BIAcore Evaluation Software version 3.2) by simultaneous fitting the association and dissociation sensorgram. The equilibrium dissociation constant (Kd) may be calculated as the ratio koff/kon. See, e.g., Chen, Y., et al., (1999) J. Mol Biol 293:865-881. However, if the on-rate exceeds 106 M-1 S-1 by the surface plasmon resonance assay above, then the on-rate may be preferably determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-Aminco spectrophotometer (ThermoSpectronic) with a stirred cuvette. In some aspects, the "Kd" or "Kd value" may be measured by a radiolabeled antigen binding assay (RIA) performed with the Fab version of the antibody and antigen molecule as described by the following assay that measures solution binding affinity of Fabs for antigen by equilibrating Fab with a minimal concentration of (125I)-labeled antigen in the presence of a titration series of unlabeled antigen, then capturing bound antigen with an anti-Fab antibody-coated plate (Chen, et al., (1999) J. Mol Biol 293:865-881). To establish conditions for the assay, microtiter plates (Dynex) may be coated overnight with 5 ug/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbant plate (Nunc #269620), 100 pM or 26 pM [125I]-antigen may be mixed with serial dilutions of a Fab of interest (consistent with assessment of an anti-VEGF antibody, Fab-12, in Presta et al., (1997) Cancer Res. 57:4593-4599). The Fab of interest may be then incubated overnight; however, the incubation may continue for a longer period (e.g., 65 hours) to insure that equilibrium is reached. Thereafter, the mixtures may be transferred to the capture plate for incubation at room temperature for one hour. The solution may be then removed and the plate washed eight times with 0.1% Tween-20 in PBS. When the plates have dried, 150 ul/well of scintillant (MicroScint-20; Packard) may be added, and the plates may be counted on a Topcount gamma counter (Packard) for ten minutes. Concentrations of each Fab that give less than or equal to 20% of maximal binding may be chosen for use in competitive binding assays. According to another embodiment, the Kd or Kd value may be measured by using surface plasmon resonance assays using a BIAcore™-2000 or a BIAcore™-3000 (BIAcore, Inc., Piscataway, N.J.) at 25° C. with immobilized antigen CM5 chips at about 10 response units (RU). Briefly, carboxymethylated dextran biosensor chips (CM5, BIAcore Inc.) may be activated with N-ethyl-N'-(3-dimethylaminopropyl)-carbodiimide hydrochloride (EDC) and N-hydroxysuccinimide (NHS) according to the supplier's instructions. Antigen may be diluted with 10 mM sodium acetate, pH 4.8, into 5 ug/ml (about 0.2 uM) before injection at a flow rate of 5 ul/minute to achieve approximately 10 response units (RU) of coupled protein. Following the injection of antigen, 1M ethanolamine may be injected to block unreacted groups. For kinetics measurements, two-fold serial dilutions of Fab (0.78 nM to 500 nM) may be injected in PBS with 0.05% Tween 20 (PBST) at 25° C. at a flow rate of approximately 25 ul/min. Association rates (kon) and dissociation rates (koff) may be calculated using a simple one-to-one Langmuir binding model (BIAcore Evaluation Software version 3.2) by simultaneous fitting the association and dissociation sensorgram. The equilibrium dissociation constant (Kd) may be calculated as the ratio koff/kon. See, e.g., Chen, Y., et al., (1999) J. Mol Biol 293:865-881. If the on-rate exceeds 106 M-1 S-1 by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stir red cuvette.

An "on-rate" or "rate of association" or "association rate" or "kon" may be determined with the same surface plasmon resonance technique described above using a BIAcore™-2000 or a BIAcore™-3000 (BIAcore, Inc., Piscataway, N.J.) at 25° C. with immobilized antigen CM5 chips at about 10 response units (RU). Briefly, carboxymethylated dextran biosensor chips (CM5, BIAcore Inc.) may be activated with N-ethyl-N'-(3-dimethylaminopropyl)-carbodiimide hydrochloride (EDC) and N-hydroxysuccinimide (NHS) according to the supplier's instructions. Antigen may be diluted with 10 mM sodium acetate, pH 4.8, into 5 ug/ml (about 0.2 uM) before injection at a flow rate of 5 ul/minute to achieve approximately 10 response units (RU) of coupled protein. Following the injection of 1M ethanolamine to block unreacted groups. For kinetics measurements, two-fold serial dilutions of Fab (0.78 nM to 500 nM) may be injected in PBS with 0.05% Tween 20 (PBST) at 25° C. at a flow rate of approximately 25 ul/min. Association rates (kon) and dissociation rates (koff) may be calculated using a simple one-to-one Langmuir binding model (BIAcore Evaluation Software version 3.2) by simultaneous fitting the association and dissociation sensorgram. The equilibrium dissociation constant (Kd) may be calculated as the ratio koff/kon. See, e.g., Chen, Y., et al., (1999) J. Mol Biol 293:865-881. However, if the on-rate exceeds 106 M-1 S-1 by the surface plasmon resonance assay above, then the on-rate may be preferably determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stirred cuvette.

"Carrier", "Selective Carrier" and "Cell Targeting Moiety" refer to a biological carrier such as an antibody, a peptide, a polypeptide, a hormone, a growth factor, a small molecule, and a protein. In some embodiments, the carrier has binding affinity for a target expressing an antigen.

"Predominantly Comprises" refers to at least 50%, at least 75%, at least 90%, at least 95% or at least 99% of a referenced component on a recited basis, such as for instance and without limitation, w/w %, v/v %, w/v %, mole % or equivalent % basis. "Consisting essentially of" generally limits a feature, composition or method to the recited elements and/or steps, but does not exclude the possibility of additional elements and/or steps that do not materially affect the function, composition and/or characteristics of the recited feature, composition or method.

The term "antibody" herein is used in the broadest sense and specifically covers monoclonal antibodies, polyclonal antibodies, dimers, multimers, multispecific antibodies (e.g., bispecific antibodies), and antibody fragments, so long as they exhibit the desired biological activity (Miller et al. (2003) Jour. of Immunology 170:4854-4861). Antibodies may be murine, human, humanized, chimeric, or derived from other species. An antibody is a protein generated by the immune system that is capable of recognizing and binding to a specific antigen. (Janeway, C., Travers, P., Walport, M., Shlomchik (2001) Immuno Biology, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one aspect, however, the immunoglobulin is of human, murine, or rabbit origin.

"Antibody fragments" comprise a portion of a full length antibody, generally the antigen binding or variable region thereof. Examples of antibody fragments include Fab, Fab', F(ab')2, and Fv fragments; diabodies; linear antibodies; minibodies (Olafsen et al. (2004) Protein Eng. Design & Sel. 17(4):315-323), fragments produced by a Fab expression library, anti-idiotypic (anti-Id) antibodies, CDR (complementary determining region), and epitope-binding fragments of any described herein which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler et al. (1975) Nature 256:495, or may be made by recombinant DNA methods (see for example: U.S. Pat. Nos. 4,816,567; 5,807,715). The monoclonal antibodies may also be isolated from phage antibody libraries using the techniques described in Clackson et al. (1991) Nature, 352:624-628; Marks et al. (1991) J. Mol. Biol., 222:581-597; for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al. (1984) Proc. Natl. Acad. Sci. USA, 81:6851-6855). Chimeric antibodies of interest herein include "primatized" antibodies comprising variable domain antigen-binding sequences derived from a non-human primate (e.g., Old World Monkey, Ape, etc.) and human constant region sequences.

An "intact antibody" herein is one comprising a VL and VH domains, as well as a light chain constant domain (CL) and heavy chain constant domains, CH1, CH2 and CH3. The constant domains may be native sequence constant domains (e.g., human native sequence constant domains) or amino acid sequence variant thereof. The intact antibody may have one or more "effector functions" which refer to those biological activities attributable to the Fc constant region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors such as B cell receptor and BCR.

Depending on the amino acid sequence of the constant domain of their heavy chains, intact antibodies can be assigned to different "classes." There are five major classes of intact immunoglobulin antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known. Ig forms include hinge-modifications or hingeless forms (Roux et al. (1998) J. Immunol. 161:4083-4090; Lund et al. (2000) Eur. J. Biochem. 267: 7246-7256; US 2005/0048572; US 2004/0229310).

A "cysteine engineered antibody" or "cysteine engineered antibody variant" is an antibody in which one or more residues of an antibody are substituted with a cysteine residue. In accordance with the present disclosure, the thiol group(s) of the cysteine engineered antibodies can be conjugated to a small molecule to form a THIOMAB™ antibody drug conjugate. In particular embodiments, the substituted residues occur at accessible sites of the antibody. By substituting those residues with cysteine, reactive thiol groups are thereby positioned at accessible sites of the antibody and may be used to conjugate the antibody to the drug moiety to create an immunoconjugate, as described further herein. For example, a THIOMAB™ antibody may be an antibody with a single mutation of a non-cysteine native residue to a cysteine in the light chain (e.g., G64C, K149C, S121C or R142C according to Kabat numbering) or in the heavy chain (e.g., D101C or V184C or T205C according to Kabat numbering). In specific examples, a THIOMAB™ antibody has a single cysteine mutation in the heavy or light chain such that each full-length antibody (i.e., an antibody with two heavy chains and two light chains) has two engineered cysteine residues. Cysteine engineered antibodies and preparatory methods are disclosed by US 2012/0121615 A1 (incorporated by reference herein in its entirety).

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include acute myeloid leukemia (AML), myelodysplastic syndrome (MDS), chronic myelogenous leukemia (CML), chronic myelomonocytic leukemia, acute promyelocytic leukemia (APL), chronic myeloproliferative disorder, thrombocytic leukemia, precursor B-cell acute lymphoblastic leukemia (pre-B-ALL), precursor T-cell acute lymphoblastic leukemia (preT-ALL), multiple myeloma (MM), mast cell disease, mast cell leukemia, mast cell sarcoma, myeloid sarcomas, lymphoid leukemia, and undifferentiated leukemia. In some embodiments, the cancer is myeloid leukemia. In some embodiments, the cancer is acute myeloid leukemia (AML).

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "epitope" refers to the particular site on an antigen molecule to which an antibody binds. In some embodiments, the particular site on an antigen molecule to which an antibody binds is determined by hydroxyl radical footprinting.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. Kuby Immunology, 6th ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest*, 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated antibody" is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., J. Chromatogr. B 848:79-87 (2007).

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this disclosure, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can, for example, be measured by assessing the time to disease progression (TTP) and/or determining the response rate (RR).

The term "leaving group," as used herein, refers to a moiety that is displaced by the sulfur atom on the antibody Cys residue (or "leaves") in the course of a chemical reaction involving the groups as described herein.

The term "hydrocarbyl" as used herein describes organic compounds or radicals consisting exclusively of the elements carbon and hydrogen. These moieties include, without limitation, alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms, 1 to 10 carbon atoms or 1 to 6 carbon atoms.

Unless otherwise indicated, the alkyl groups described herein are preferably lower alkyl containing from one to eight carbon atoms in the principal chain. They may be straight or branched chain or cyclic including, but not limited to, methyl, ethyl, propyl, isopropyl, allyl, benzyl, hexyl and the like.

Unless otherwise indicated, the alkynyl groups described herein are preferably lower alkynyl containing from two to eight carbon atoms in the principal chain and up to 20 carbon atoms. They may be straight or branched chain including, but not limited to, ethynyl, propynyl, butynyl, isobutynyl, hexynyl, and the like.

The term "aryl" as used herein alone or as part of another group denotes optionally substituted homocyclic aromatic groups, preferably monocyclic or bicyclic groups containing from 5 to 20 carbons, from 5 to 10 carbons, or from 5 to 6 carbons in the ring portion, including, but not limited to, phenyl, biphenyl, naphthyl, substituted phenyl, substituted biphenyl or substituted naphthyl. The aryl moieties may optionally comprise one or more hetero atoms selected from O, S and N. Such heteroaromatics may comprise 1 or 2 nitrogen atoms, 1 or 2 sulfur atoms, 1 or 2 oxygen atoms, and combinations thereof, in the ring, wherein the each hetero atom is bonded to the remainder of the molecule through a carbon. Non limiting exemplary groups include pyridine, pyrazine, pyrimidine, pyrazole, pyrrole, imidazole, thiopene, thiopyrrilium, parathiazine, indole, purine, benzimidazole, quinolone, phenothiazine. Non-limiting exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The "substituted" moieties described herein are moieties such as hydrocarbyl, alkyl and aryl which are substituted with at least one atom other than carbon, including moieties in which a carbon chain atom is substituted with a hetero atom such as nitrogen, oxygen, silicon, phosphorous, boron, sulfur, or a halogen atom. These substituents include, but are not limited to, halogen, heterocyclo, alkoxy, alkenoxy, alkynoxy, aryloxy, hydroxy, keto, acyl, acyloxy, nitro, tertiary amino, amido, nitro, cyano, thio, sulfinate, sulfonamide, ketals, acetals, esters and ethers.

The terms "carbocycle", "carbocyclic ring" and "cycloalkyl" refer to a monovalent non-aromatic, saturated or partially unsaturated ring having 3 to 12 carbon atoms ($C_{3-12}$) as a monocyclic ring or 7 to 12 carbon atoms as a bicyclic ring. Bicyclic carbocycles having 7 to 12 atoms can be arranged, e.g., as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

The terms "halogen" as used herein alone or as part of another group refer to chlorine, bromine, fluorine, and iodine.

Hindered Linker

The hindered linkers of the present disclosure generally conform to the following structure wherein the carbon atom bearing the S atom is substituted, such that at least one of $R^1$ and $R^2$ is not hydrogen:

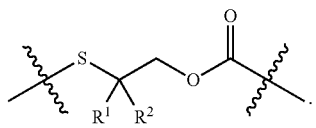

In some aspects, the wavy bond at the sulfur atom indicates the point of attachment to a thiol leaving group. In some other aspects, the wavy bond at the sulfur atom indicates the point of attachment to a carrier cysteine sulfur atom. In any such aspect, the point of attachment at the carbon atom bearing the carbonyl moiety indicates a direct or indirect point of attachment to a drug or to a spacer-drug. In some aspects, $R^1$ and $R^2$ are independently selected from H and $C_{1-3}$ alkyl, wherein only one of $R^1$ and $R^2$ may be H. In some particular such aspects, $R^1$ and $R^2$ are independently selected from H, $-CH_3$ and $-CH_2CH_3$, wherein only one of $R^1$ and $R^2$ is H. In some other aspects, $R^1$ and $R^2$ together with the carbon atom to which they are bound form a three- to six-membered ring optionally comprising an oxygen heteroatom. In some particular such aspects, $R^1$ and $R^2$ together with the carbon atom to which they are bound form a ring selected from cyclopropyl, cyclobutyl, cyclopentyl, tetrahydrofuran, cyclohexyl and tetrahydropyran.

Examples of hindered linkers are as follows where the wavy line at the sulfur atom refers to the point of attachment to a leaving group as defined elsewhere herein and wherein the wavy line at the carbonyl moiety refers to the point of attachment to a moiety comprising a drug:

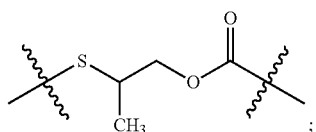

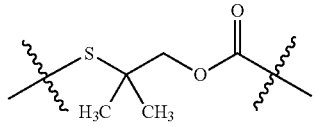

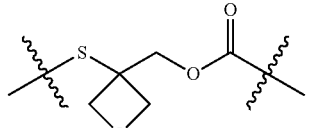

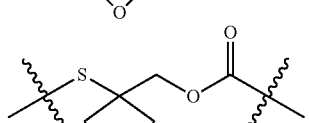

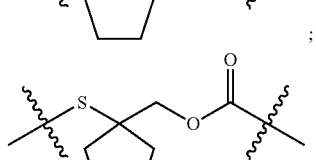

-continued

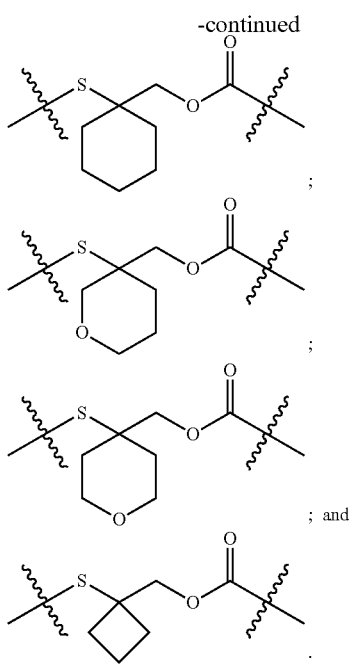
;

;

; and

.

In accordance with the present disclosure and based on experimental evidence to date, it has been discovered that the hindered linking group component of the conjugates of the present disclosure are intracellularly immolative. Without being bound to any particular theory, the intracellular release mechanism is believed to proceed according to the following mechanism wherein linker immolation and drug release is mediated by glutathione:

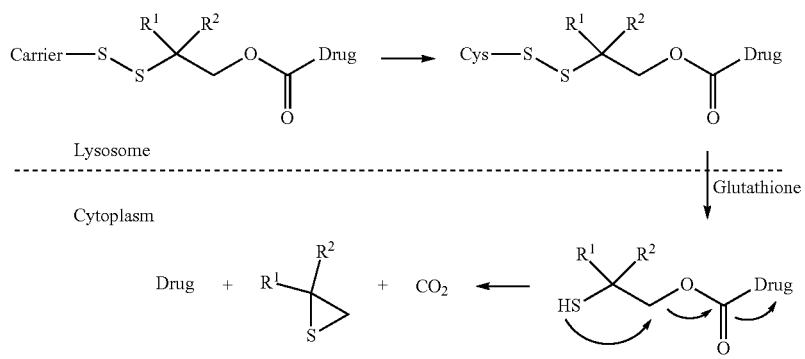

Based on experimental evidence to date, it is believed that certain of the hindered linker component of the conjugates of the present disclosure improves drug stability and release and provides for improved bloodstream stability and intracellular drug release (immolation) as compared to conjugates not comprising a hindered linking group. Further based on experimental evidence to date, and without being bound to any particular theory, it is believed that the leaving groups of the present disclosure, described elsewhere herein, function to direct reaction of the sulfur atom bound to the hindered carbon with a cysteine thiol and thereby provide for improved specificity and reactivity, such that the carrier-linker conjugation may be carried out in solvent systems comprising water, predominantly comprising water, or consisting essentially of water, as further described herein. Further, based on experimental evidence to date, and without being bound to any particular theory, it is believed that the leaving groups of the present disclosure, described elsewhere herein, can be preferentially displaced by Cys residues placed at certain sites on an antibody versus other sites, enabling site-specific multi-drug conjugation to an antibody.

Leaving Group

In some aspects of the disclosure, the leaving group may suitably be selected from the following:

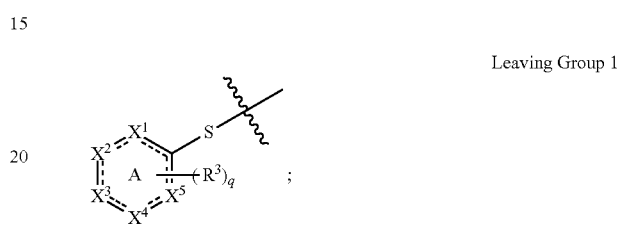

Leaving Group 1

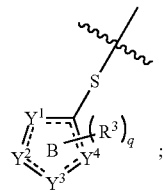

Leaving Group 2

;

-continued

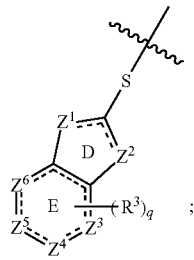

Leaving Group 3

;

-continued

Leaving Group 4

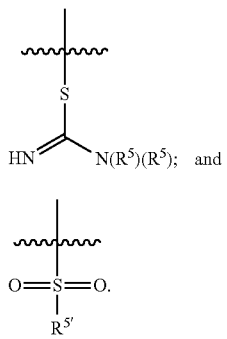

HN N(R⁵)(R⁵); and

Leaving Group 5

$$\underset{R^{5'}}{O=S=O.}$$

In such aspects, the wavy lines indicate the point of attachment of the leaving group to the hindered linker S atom thereby forming a disulfide bond. $X^1$, $X^2$, $X^3$, $X^4$ and $X^5$ are independently C, N, S or O, provided at least one of $X^1$ to $X^5$ is N, the dashed lines represent optional double bonds, and A denotes a six-membered ring. $Y^1$, $Y^2$, $Y^3$ and $Y^4$ are independently C, N, S or O, provided at least one of $Y^1$ to $Y^4$ is N, the dashed lines represent optional double bonds, and B denotes a five-membered ring. $Z^1$, $Z^2$, $Z^3$, $Z^4$, $Z^5$ and $Z^6$ are independently C, N, S or O, provided at least one of $Z^1$ and $Z^2$ is N, the dashed lines represent optional double bonds, E denotes a six-membered ring, and D denotes a fused five-membered ring. Each $R^3$ is independently selected from —$NO_2$, —$NH_2$, —C(O)OH, —S(O)(O)$R^5$, —$OR^{5'}$, —C(O)N($R^5$)($R^5$), —Cl, —F, —CN and —Br. Each $R^5$ is independently selected from H, optionally substituted $C_{1-6}$ hydrocarbyl, optionally substituted $C_{5-6}$ carbocycle, and optionally substituted $C_{5-6}$ heterocycle. $R^{5'}$ is $C_{1-4}$ alkyl. q is 0, 1, 2 or 3. Each carbon atom in the ring structure of leaving group 1, leaving group 2, leaving group 3 and/or leaving group 4 is optionally substituted with $R^5$. Each nitrogen atom in the ring structure of leaving group 1, leaving group 2, leaving group 3 and/or leaving group 4 is optionally substituted with $R^5$ to form a tertiary amine or a quaternary amine.

In some particular such aspects, $X^1$, $X^2$, $X^3$, $X^4$ and $X^5$ are independently C or N, no more than two of $X^1$ to $X^5$ are N, and ring A is unsaturated. In other particular aspects, $Y^1$, $Y^2$ $Y^3$ and $Y^4$ are independently C or N, and B ring is unsaturated. In yet other particular aspects, $Z^1$ is N, $Z^2$ is selected from N, S and O, $Z^3$ to $Z^6$ are selected from C and N, no more than two of $Z^3$ to $Z^6$ are N, and ring E is unsaturated. In still other particular aspects, Each $R^3$ is independently selected from —$NO_2$, —$NH_2$, —C(O)OH, $H_3$CS(O)(O)— and —C(O)N($CH_3$)$_2$.

Some examples of leaving groups of the present disclosure are illustrated below:

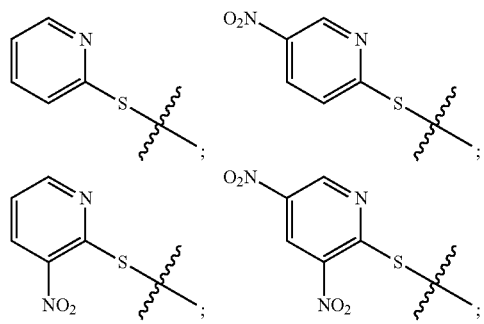

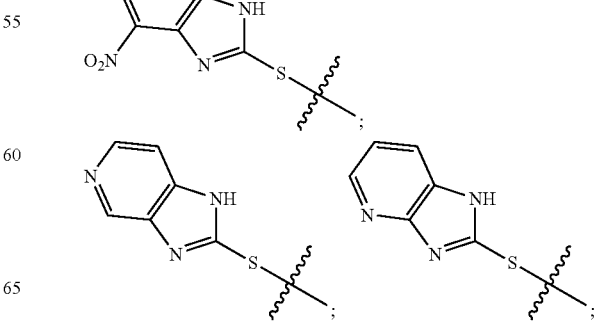

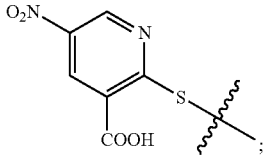

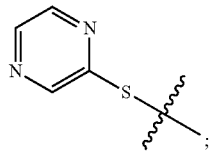

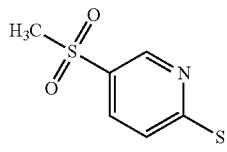

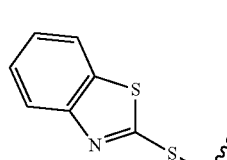




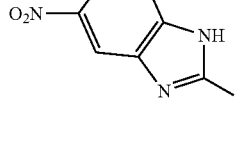

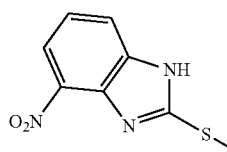

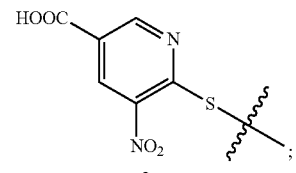

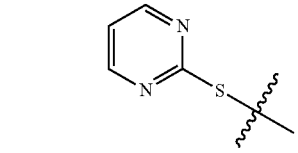

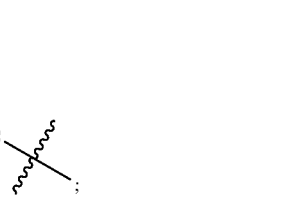

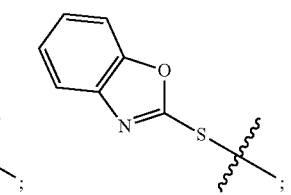

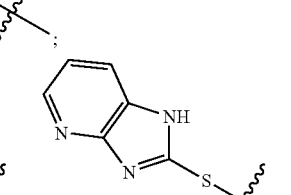

-continued

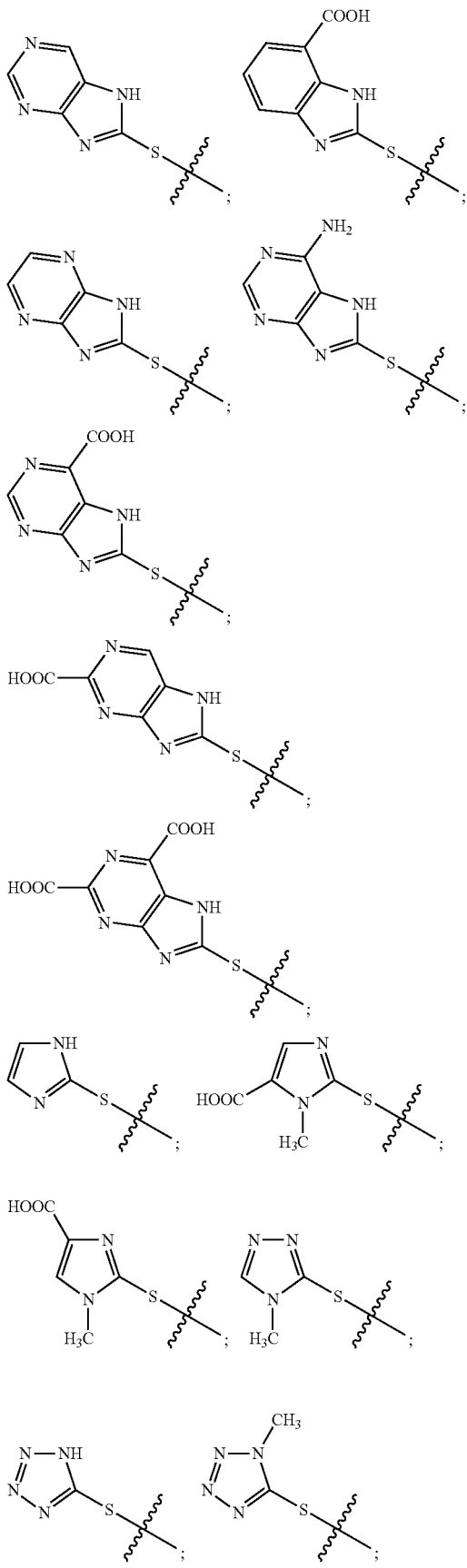

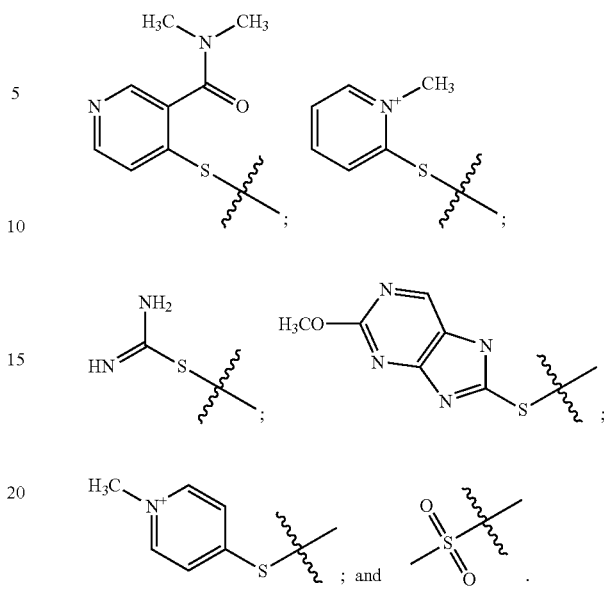

Based on experimental evidence to date, and without being bound to any particular theory, it is believed that the leaving groups of the present disclosure, when present as a component in the leaving group-linker-drug conjugates and the carrier-leaving group conjugates of the present disclosure, provide for improved leaving group displacement. Without being bound to any particular theory, it is believed that electron-deficient leaving groups improve conjugation regioselectivity and that leaving groups with lower pKa values are more effectively displaced. In some aspects, the pKa is from about −4 to about 12 or from about 2 to about 12. Improved leaving group displacement, in turn, allows for direct conjugation of a carrier cysteine thiol to a linker of the present disclosure by a disulfide bond in aqueous reaction systems and at mild reaction conditions of temperature and pH with high selectivity and yield. Such mild reaction conditions are typically required to maintain the selectivity and targeting characteristics of labile biologic carriers.

Activated Hindered Linkers

Some embodiments of the disclosure are directed to activated hindered linkers of structure (I):

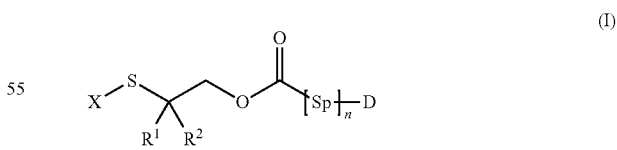

(I)

wherein X, $R^1$, and $R^2$ are as defined elsewhere herein, n is 0 or 1, and Sp is a spacer. In some aspects, when n is 1, the spacer may comprise p-aminobenzyloxycarbonyl of the following structure wherein the wavy line indicates the point of attachment to the hindered linker carbonyl carbon atom and wherein $R^{30}$ is selected from H, optionally substituted $C_{1-6}$ hydrocarbyl, optionally substituted $C_{5-6}$ carbocycle, and optionally substituted $C_{5-6}$ heterocycle:

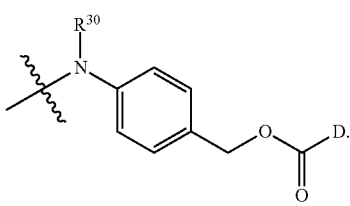

In some particular aspects, $R^{30}$ is H.

When n is 0, as described elsewhere herein, the bond between the hindered linker carbonyl carbon atom and the drug moiety may suitably be an ether or may be a tertiary amine formed from an acyclic or cyclic amine drug atom. When n is 1, the linkage of the spacer carbonyl carbon atom to the drug moiety, as described elsewhere herein, may suitably be a secondary amine formed from an aliphatic (acyclic) primary amine drug atom, may suitably be a tertiary amine formed from an aliphatic secondary amine drug atom, or may suitably be a tertiary amine formed from a cyclic amine drug atom.

In some aspects, activated hindered linking groups suitable for conjugation to a drug may be suitably prepared according to the following reaction scheme (1)

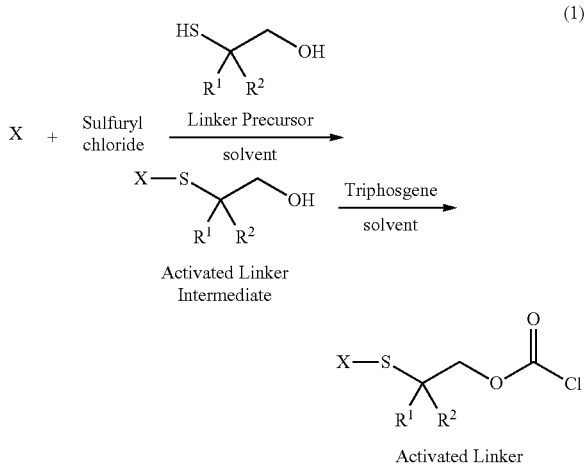

wherein X, $R^1$ and $R^2$ are as described elsewhere herein and X is bound to the linker by a disulfide bond.

In the first step, a stoichiometric excess of sulfuryl chloride is added to a stirred suspension or solution of a leaving group, X, in a dry solvent. The reaction product may optionally be isolated, such as for instance by solvent evaporation. The leaving group reaction product is combined with a linker precursor solution in a dry solvent and reacted with stirring to form a reaction product mixture comprising the activated linker intermediate. Suitable solvents and reaction conditions are derivable by those skilled in the art. An example of a solvent is dichloromethane ("DCM"), the leaving group concentration may be from about 0.1 to about 1 mol/L, the linker group concentration may be from about 0.1 to about 1 mol/L, the temperature for each reaction may be from about −10° C. to about 30° C., and each reaction may be done under an inert atmosphere. In some aspects, each reaction is initiated at from about −10° C. to about 5° C. and then warmed to room temperature and held for a period of time sufficient to complete the reaction. Reaction completion may be determined by analytical methods known to those skilled in the art, such as LC/MS. The activated linker intermediate may be isolated from the reaction product mixture by methods known in the art. For instance, precipitate in the reaction product mixture may be removed by solid-liquid methods known to those skilled in the art, such as filtration or centrifugation. The activated linker intermediate may then be isolated from the filtrate by solvent evaporation. The isolated activated linker intermediate may optionally be purified. For instance, the isolated activated linker intermediate may be: (1) treated with basified water; (2) extracted into a solvent (e.g., DCM); (3) washed with water and/or brine; (4) dried (e.g., with $MgSO_4$); (5) filtered and isolated as a solid by solvent removal (e.g., evaporation); and, optionally, (6) purified by a chromatographic method known the art, such as reverse phase high pressure liquid chromatography, ion exchange chromatography or flash chromatography.

In the second step, an equivalent excess of triphosgene (or diphosgene or phosgene) is added to a stirred solution of the activated linker intermediate in dry solvent (e.g., DCM) and reacted under an inert atmosphere until completion to form the activated linker. The activated linker intermediate concentration may be from about 0.05 to about 0.5 mol/L. The activated linker may be isolated as a solid by solvent removal or may be directly conjugated with a drug as described elsewhere herein.

Carriers

The carriers of the present disclosure are any cell-targeting biologic compound comprising at least one cysteine sulfhydryl moiety. Cell-targeting compounds include antibodies, peptides and polypeptides, hormones, growth factors and proteins.

Certain types of cells, such as cancer cells, express surface molecules (antigens) that are unique as compared to surrounding tissue. Cell targeting moieties that bind to these surface molecules enable the targeted delivery of a drug described elsewhere herein specifically to the target cells. For instance and without limitation, a cell targeting moiety may bind to and be internalized by a lung, breast, brain, prostate, spleen, pancreatic, cervical, ovarian, head and neck, esophageal, liver, skin, kidney, leukemia, bone, testicular, colon or bladder cell.

Tumor Associated Antigens

In some particular aspects of the disclosure, the target cells are cancer cells that express tumor-associated antigens (TAA). Tumor-associated antigens are known in the art, and can be prepared for use in generating antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

Examples of tumor-associated antigens TAA include, but are not limited to, TAA (1)-(53) listed herein. For convenience, information relating to these antigens, all of which are known in the art, is listed herein and includes names, alternative names, Genbank accession numbers and primary reference(s), following nucleic acid and protein sequence identification conventions of the National Center for Biotechnology Information (NCBI). Nucleic acid and protein sequences corresponding to TAA (1)-(53) are available in public databases such as GenBank. Tumor-associated antigens targeted by antibodies include all amino acid sequence variants and isoforms possessing at least about 70%, 80%, 85%, 90%, or 95% sequence identity relative to the sequences identified in the cited references, or which exhibit substantially the same biological properties or characteristics as a TAA having a sequence found in the cited references. For example, a TAA having a variant sequence generally is able to bind specifically to an antibody that binds specifically to the TAA with the corresponding sequence listed. The sequences and disclosure in the reference specifically recited herein are expressly incorporated by reference.

Figure 4A:
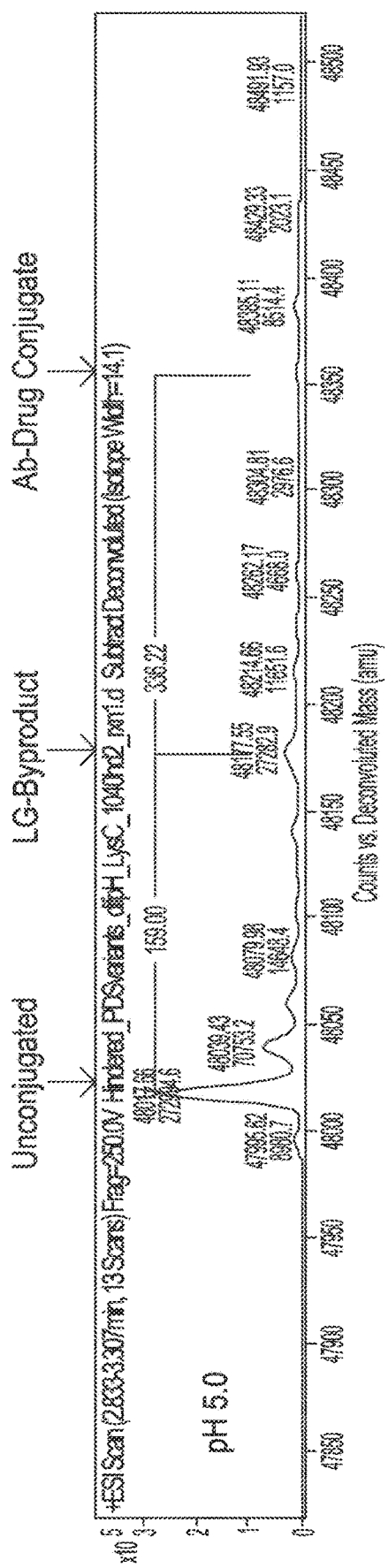

(1) BMPR1B (bone morphogenetic protein receptor-type IB, Genbank accession no. NM_001203) ten Dijke, P., et al. Science 264 (5155):101-104 (1994), Oncogene 14 (11): 1377-1382 (1997)); WO2004063362 (Claim 2); WO2003042661 (Claim 12); US2003134790-A1 (Page 38-39); WO2002102235 (Claim 13; Page 296); WO2003055443 (Page 91-92); WO200299122 (Example 2; Page 528-530); WO2003029421 (Claim 6); WO2003024392 (Claim 2; FIG. 112); WO200298358 (Claim 1; Page 183); WO200254940 (Page 100-101); WO200259377(Page 349-350); WO200230268 (Claim 27; Page 376); WO200148204 (Example; FIG. 4) NP_001194 bone morphogenetic protein receptor, type IB/pid=NP_001194.1—Cross-references: MIM:603248; NP_001194.1; AY065994.

(2) E16 (LAT1, SLC7A5, Genbank accession no. NM_003486) Biochem. Biophys. Res. Commun. 255 (2), 283-288 (1999), Nature 395 (6699):288-291 (1998), Gaugitsch, H. W., et al. (1992) J. Biol. Chem. 267 (16):11267-11273); WO2004048938 (Example 2); WO2004032842 (Example IV); WO2003042661 (Claim 12); WO2003016475 (Claim 1); WO200278524 (Example 2); WO200299074 (Claim 19; Page 127-129); WO200286443 (Claim 27; Pages 222, 393); WO2003003906 (Claim 10; Page 293); WO200264798 (Claim 33; Page 93-95); WO200014228 (Claim 5; Page 133-136); US2003224454 (FIG. 3); WO2003025138 (Claim 12; Page 150); NP_003477 solute carrier family 7 (cationic amino acid transporter, y+ system), member 5/pid=NP_003477.3—*Homo sapiens* Cross-references: MIM:600182; NP_003477.3; NM_015923; NM_003486_1.

Figure 1:
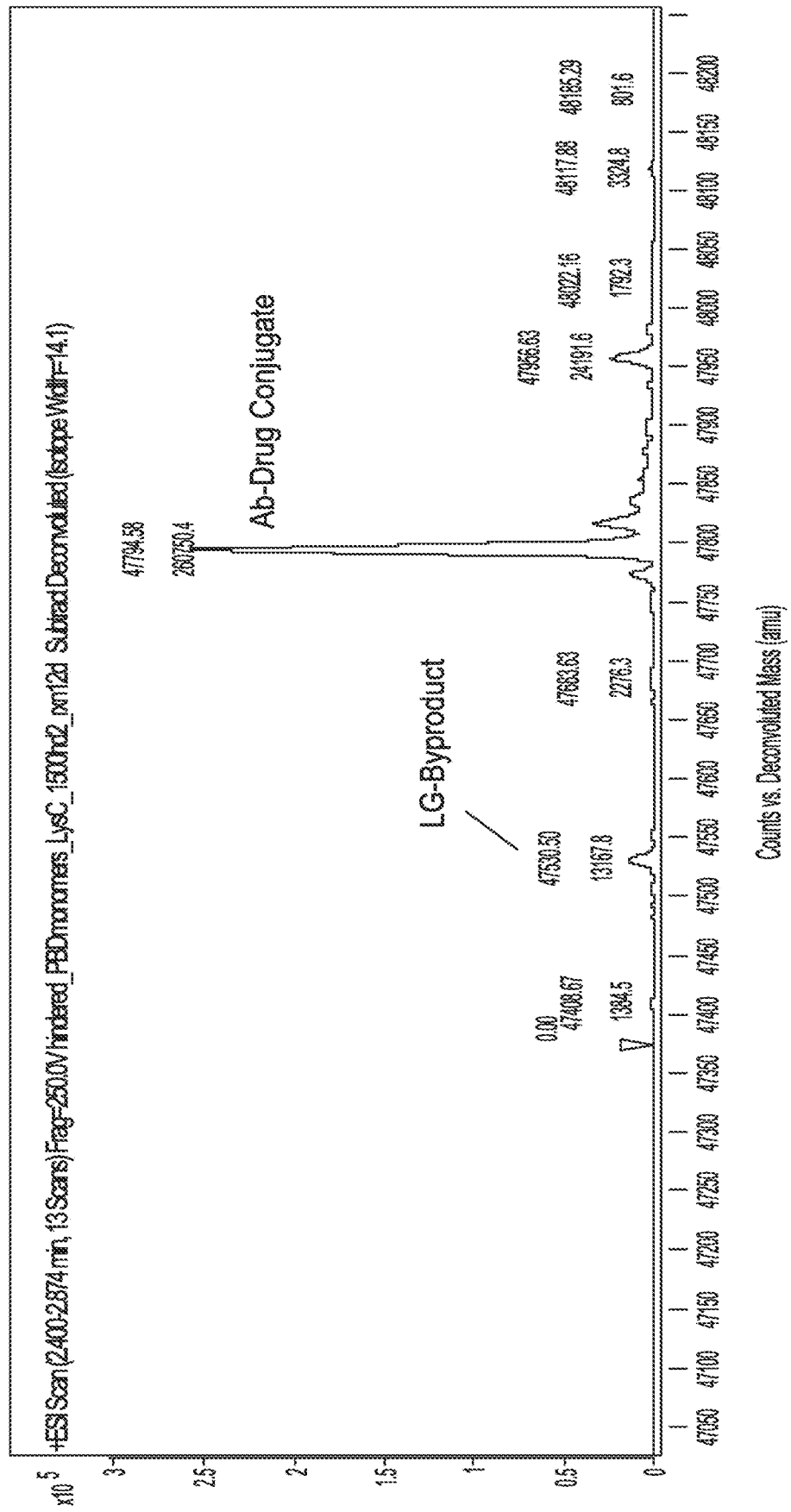
FIG. 1 is a LC/MS ESI scan depicting the purity by area percent for a reaction product mixture comprising an antibody-linker-drug conjugate having the antibody bound to a linker by a disulfide bond and formed by reacting one or more Herceptin 4D5 HC A118C antibody cysteine thiol groups with a leaving group-S-linker-drug component wherein the leaving group was 5-nitropyridine, the linker carbon atom bearing the sulfur atom was hindered with cyclopropyl, and the drug was a pyrrolobenzodiazepine (as further discussed in example 4, below).
Figure 2:
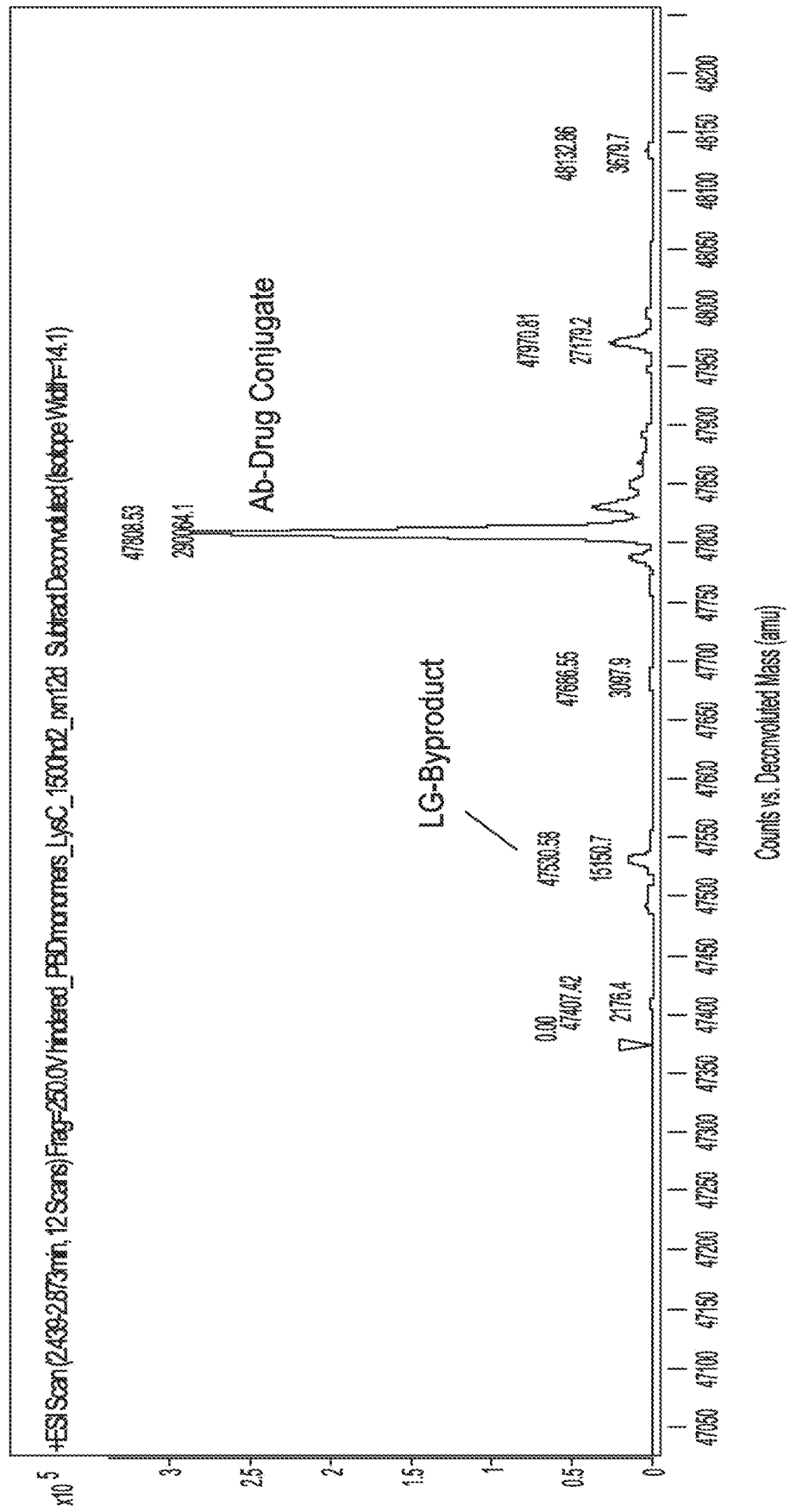
FIG. 2 is a LC/MS ESI scan depicting the purity by area percent for a reaction product mixture comprising an antibody-linker-drug conjugate having the antibody bound to a linker by a disulfide bond and formed by reacting one or more Herceptin 4D5 HC A118C antibody cysteine thiol groups with a leaving group-S-linker-drug component wherein the leaving group was 5-nitropyridine and the linker carbon atom bearing the sulfur atom was hindered with cyclobutyl, and the drug was a pyrrolobenzodiazepine (as further discussed in example 4, below).

(3) STEAP1 (six transmembrane epithelial antigen of prostate, Genbank accession no. NM_012449) Cancer Res. 61 (15), 5857-5860 (2001), Hubert, R. S., et al. (1999) Proc. Natl. Acad. Sci. U.S.A. 96 (25):14523-14528); WO2004065577 (Claim 6); WO2004027049 (FIG. 1L); EP1394274 (Example 11); WO2004016225 (Claim 2); WO2003042661 (Claim 12); US2003157089 (Example 5); US2003185830 (Example 5); US2003064397 (FIG. 2); WO200289747 (Example 5; Page 618-619); WO2003022995 (Example 9; FIG. 13A, Example 53; Page 173, Example 2; FIG. 2A); NP_036581 six transmembrane epithelial antigen of the prostate Cross-references: MIM: 604415; NP_036581.1; NM_012449_1.

(4) 0772P (CA125, MUC16, Genbank accession no. AF361486) J. Biol. Chem. 276 (29):27371-27375 (2001)); WO2004045553 (Claim 14); WO200292836 (Claim 6; FIG. 12); WO200283866 (Claim 15; Page 116-121); US2003124140 (Example 16); U.S. Pat. No. 798,959. Cross-references: GI:34501467; AAK74120.3; AF361486_1.

(5) MPF (MPF, MSLN, SMR, megakaryocyte potentiating factor, mesothelin, Genbank accession no. NM_005823) Yamaguchi, N., et al. Biol. Chem. 269 (2), 805-808 (1994), Proc. Natl. Acad. Sci. U.S.A. 96 (20):11531-11536 (1999), Proc. Natl. Acad. Sci. U.S.A. 93 (1):136-140 (1996), J. Biol. Chem. 270 (37):21984-21990 (1995)); WO2003101283 (Claim 14); (WO2002102235 (Claim 13; Page 287-288); WO2002101075 (Claim 4; Page 308-309); WO200271928 (Page 320-321); WO9410312 (Page 52-57); Cross-references: MIM:601051; NP_005814.2; NM_005823_1.

(6) Napi3b (NAPI-3B, NPTIIb, SLC34A2, solute carrier family 34 (sodium phosphate), member 2, type II sodium-dependent phosphate transporter 3b, Genbank accession no. NM_006424) J. Biol. Chem. 277 (22):19665-19672 (2002), Genomics 62 (2):281-284 (1999), Feild, J. A., et al. (1999) Biochem. Biophys. Res. Commun. 258 (3):578-582); WO2004022778 (Claim 2); EP1394274 (Example 11); WO2002102235 (Claim 13; Page 326); EP875569 (Claim 1; Page 17-19); WO200157188 (Claim 20; Page 329); WO2004032842 (Example IV); WO200175177 (Claim 24; Page 139-140); Cross-references: MIM:604217; NP_006415.1; NM_006424_1.

(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB040878) Nagase T., et al. (2000) DNA Res. 7 (2):143-150); WO2004000997 (Claim 1); WO2003003984 (Claim 1); WO200206339 (Claim 1; Page 50); WO200188133 (Claim 1; Page 41-43, 48-58); WO2003054152 (Claim 20); WO2003101400 (Claim 11); Accession: Q9P283; EMBL; AB040878; BAA95969.1. Genew; HGNC:10737.

(8) PSCA hlg (2700050C12Rik, C530008016Rik, RIKEN cDNA 2700050C12, RIKEN cDNA 2700050C12 gene, Genbank accession no. AY358628); Ross et al. (2002) Cancer Res. 62:2546-2553; US2003129192 (Claim 2); US2004044180 (Claim 12); US2004044179 (Claim 11); US2003096961 (Claim 11); US2003232056 (Example 5); WO2003105758 (Claim 12); US2003206918 (Example 5); EP1347046 (Claim 1); WO2003025148 (Claim 20); Cross-references: GI:37182378; AAQ88991.1; AY358628_1.

(9) ETBR (Endothelin type B receptor, Genbank accession no. AY275463); Nakamuta M., et al. Biochem. Biophys. Res. Commun. 177, 34-39, 1991; Ogawa Y., et al. Biochem. Biophys. Res. Commun. 178, 248-255, 1991; Arai H., et al. Jpn. Circ. J. 56, 1303-1307, 1992; Arai H., et al. J. Biol. Chem. 268, 3463-3470, 1993; Sakamoto A., Yanagisawa M., et al. Biochem. Biophys. Res. Commun. 178, 656-663, 1991; Elshourbagy N. A., et al. J. Biol. Chem. 268, 3873-3879, 1993; Haendler B., et al. J. Cardiovasc. Pharmacol. 20, s1-S4, 1992; Tsutsumi M., et al. Gene 228, 43-49, 1999; Strausberg R. L., et al. Proc. Natl. Acad. Sci. U.S.A. 99, 16899-16903, 2002; Bourgeois C., et al. J. Clin. Endocrinol. Metab. 82, 3116-3123, 1997; Okamoto Y., et al. Biol. Chem. 272, 21589-21596, 1997; Verheij J. B., et al. Am. J. Med. Genet. 108, 223-225, 2002; Hofstra R. M. W., et al. Eur. J. Hum. Genet. 5, 180-185, 1997; Puffenberger E. G., et al. Cell 79, 1257-1266, 1994; Attie T., et al., Hum. Mol. Genet. 4, 2407-2409, 1995; Auricchio A., et al. Hum. Mol. Genet. 5:351-354, 1996; Amiel J., et al. Hum. Mol. Genet. 5, 355-357, 1996; Hofstra R. M. W., et al. Nat. Genet. 12, 445-447, 1996; Svensson P. J., et al. Hum. Genet. 103, 145-148, 1998; Fuchs S., et al. Mol. Med. 7, 115-124, 2001; Pingault V., et al. (2002) Hum. Genet. 111, 198-206; WO2004045516 (Claim 1); WO2004048938 (Example 2); WO2004040000 (Claim 151); WO2003087768 (Claim 1);

WO2003016475 (Claim 1); WO2003016475 (Claim 1); WO200261087 (FIG. 1); WO2003016494 (FIG. 6); WO2003025138 (Claim 12; Page 144); WO200198351 (Claim 1; Page 124-125); EP522868 (Claim 8; FIG. 2); WO200177172 (Claim 1; Page 297-299); US2003109676; U.S. Pat. No. 6,518,404 (FIG. 3); U.S. Pat. No. 5,773,223 (Claim 1a; Col 31-34); WO2004001004.

(10) MSG783 (RNF124, hypothetical protein FLJ20315, Genbank accession no. NM_017763); WO2003104275 (Claim 1); WO2004046342 (Example 2); WO2003042661 (Claim 12); WO2003083074 (Claim 14; Page 61); WO2003018621 (Claim 1); WO2003024392 (Claim 2; FIG. 93); WO200166689 (Example 6); Cross-references: LocusID:54894; NP_060233.2; NM_017763_1.

Figure 4B:
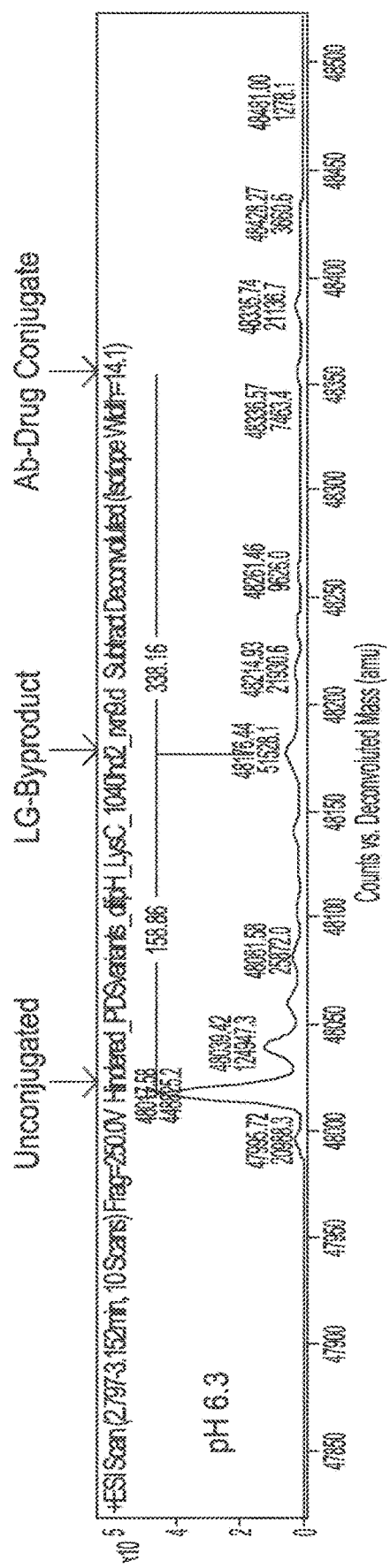

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138) Lab. Invest. 82 (11):1573-1582 (2002)); WO2003087306; US2003064397 (Claim 1; FIG. 1); WO200272596 (Claim 13; Page 54-55); WO200172962 (Claim 1; FIG. 4B); WO2003104270 (Claim 11); WO2003104270 (Claim 16); US2004005598 (Claim 22); WO2003042661 (Claim 12); US2003060612 (Claim 12; FIG. 10); WO200226822 (Claim 23; FIG. 2); WO200216429 (Claim 12; FIG. 10); Cross-references: GI:22655488; AAN04080.1; AF455138_1.

(12) TrpM4 (BR22450, FLJ20041, TRPM4, TRPM4B, transient receptor potential cation channel, subfamily M, member 4, Genbank accession no. NM_017636) Xu, X. Z., et al. Proc. Natl. Acad. Sci. U.S.A. 98 (19):10692-10697 (2001), Cell 109 (3):397-407 (2002), J. Biol. Chem. 278 (33):30813-30820 (2003)); US2003143557 (Claim 4); WO200040614 (Claim 14; Page 100-103); WO200210382 (Claim 1; FIG. 9A); WO2003042661 (Claim 12); WO200230268 (Claim 27; Page 391); US2003219806 (Claim 4); WO200162794 (Claim 14; FIG. 1A-D); Cross-references: MIM:606936; NP_060106.2; NM_017636_1.

(13) CRIPTO (CR, CR1, CRGF, CRIPTO, TDGF1, teratocarcinoma-derived growth factor, Genbank accession no. NP_003203 or NM_003212) Ciccodicola, A., et al. EMBO J. 8 (7):1987-1991 (1989), Am. J. Hum. Genet. 49 (3):555-565 (1991)); US2003224411 (Claim 1); WO2003083041 (Example 1); WO2003034984 (Claim 12); WO200288170 (Claim 2; Page 52-53); WO2003024392 (Claim 2; FIG. 58); WO200216413 (Claim 1; Page 94-95, 105); WO200222808 (Claim 2; FIG. 1); U.S. Pat. No. 5,854,399 (Example 2; Col 17-18); U.S. Pat. No. 5,792,616 (FIG. 2); Cross-references: MIM:187395; NP_003203.1; NM_003212_1.

(14) CD21 (CR2 (Complement receptor 2) or C3DR (C3d/Epstein Barr virus receptor) or Hs.73792 Genbank accession no. M26004) Fujisaku et al. (1989) J. Biol. Chem. 264 (4):2118-2125); Weis J. J., et al. J. Exp. Med. 167, 1047-1066, 1988; Moore M., et al. Proc. Natl. Acad. Sci. U.S.A. 84, 9194-9198, 1987; Barel M., et al. Mol. Immunol. 35, 1025-1031, 1998; Weis J. J., et al. Proc. Natl. Acad. Sci. U.S.A. 83, 5639-5643, 1986; Sinha S. K., et al. (1993) J. Immunol. 150, 5311-5320; WO2004045520 (Example 4); US2004005538 (Example 1); WO2003062401 (Claim 9); WO2004045520 (Example 4); WO9102536 (FIGS. 9.1-9.9); WO2004020595 (Claim 1); Accession: P20023; Q13866; Q14212; EMBL; M26004; AAA35786.1.

(15) CD79b (CD79B, CD790, IGb (immunoglobulin-associated beta), B29, Genbank accession no. NM_000626 or 11038674) Proc. Natl. Acad. Sci. U.S.A. (2003) 100 (7):4126-4131, Blood (2002) 100 (9):3068-3076, Muller et al. (1992) Eur. J. Immunol. 22 (6):1621-1625); WO2004016225 (claim 2, FIG. 140); WO2003087768, US2004101874 (claim 1, page 102); WO2003062401 (claim 9); WO200278524 (Example 2); US2002150573 (claim 5, page 15); U.S. Pat. No. 5,644,033; WO2003048202 (claim 1, pages 306 and 309); WO 99/558658, U.S. Pat. No. 6,534,482 (claim 13, FIG. 17A/B); WO200055351 (claim 11, pages 1145-1146); Cross-references: MIM:147245; NP_000617.1; NM_000626_1.

(16) FcRH2 (IFGP4, IRTA4, SPAP1A (SH2 domain containing phosphatase anchor protein 1a), SPAP1B, SPAP1C, Genbank accession no. NM_030764, AY358130) Genome Res. 13 (10):2265-2270 (2003), Immunogenetics 54 (2):87-95 (2002), Blood 99 (8):2662-2669 (2002), Proc. Natl. Acad. Sci. U.S.A. 98 (17):9772-9777 (2001), Xu, M. J., et al. (2001) Biochem. Biophys. Res. Commun. 280 (3):768-775; WO2004016225 (Claim 2); WO2003077836; WO200138490 (Claim 5; FIG. 18D-1-18D-2); WO2003097803 (Claim 12); WO2003089624 (Claim 25); Cross-references: MIM:606509; NP_110391.2; NM_030764_1.

Figure 5A:
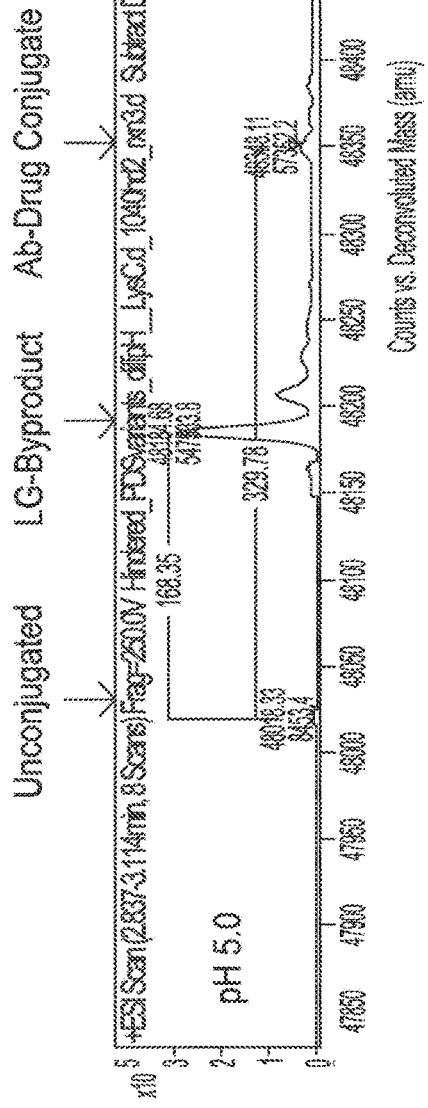
FIGS. 5A to 5D are LC/MS ESI scans depicting the purity by area percent for a reaction product mixture formed at varying pH and comprising an antibody-linker-probe conjugate having the antibody bound to a linker by a disulfide bond and formed by reacting one or more CD22 LC K149C antibody cysteine thiol groups with a leaving group-S-linker-probe component wherein the leaving group was 3,5-dinitropyridine and the linker carbon atom bearing the sulfur atom was hindered with two methyl groups.
Figure 5B:
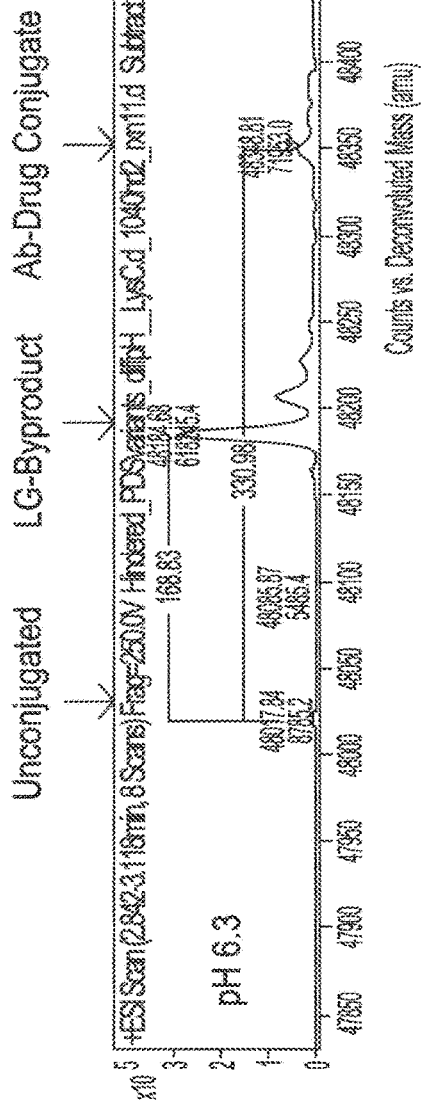
Figure 5C:
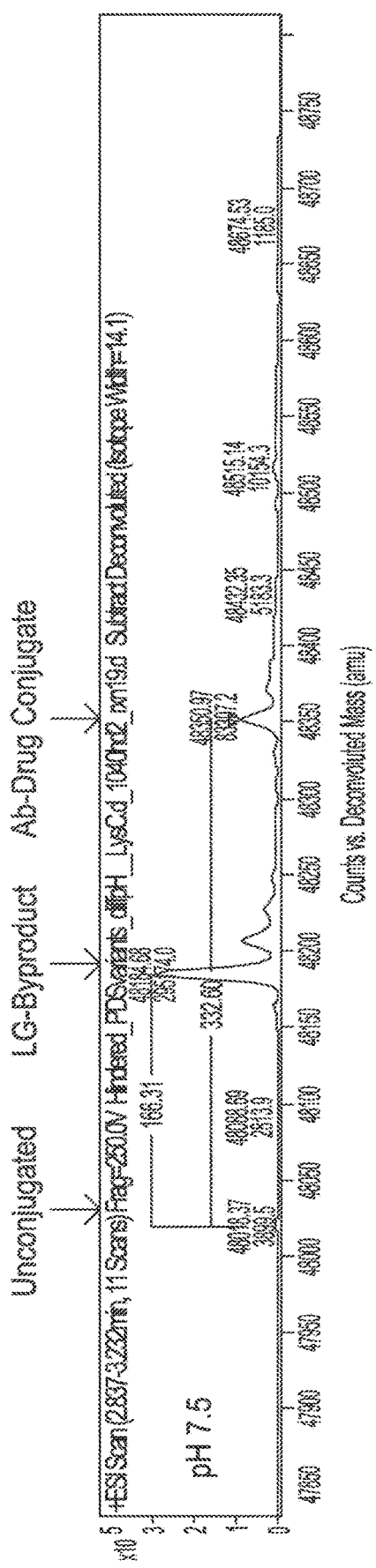
Figure 5D:

(17) HER2 (ErbB2, Genbank accession no. M11730) Coussens L., et al. Science (1985) 230(4730):1132-1139); Yamamoto T., et al. Nature 319, 230-234, 1986; Semba K., et al. Proc. Natl. Acad. Sci. U.S.A. 82, 6497-6501, 1985; Swiercz J. M., et al. J. Cell Biol. 165, 869-880, 2004; Kuhns J. J., et al. J. Biol. Chem. 274, 36422-36427, 1999; Cho H.-S., et al. Nature 421, 756-760, 2003; Ehsani A., et al. (1993) Genomics 15, 426-429; WO2004048938 (Example 2); WO2004027049 (FIG. 1I); WO2004009622; WO2003081210; WO2003089904 (Claim 9); WO2003016475 (Claim 1); US2003118592; WO2003008537 (Claim 1); WO2003055439 (Claim 29; FIG. 1A-B); WO2003025228 (Claim 37; FIG. 5C); WO200222636 (Example 13; Page 95-107); WO200212341 (Claim 68; FIG. 7); WO200213847 (Page 71-74); WO200214503 (Page 114-117); WO200153463 (Claim 2; Page 41-46); WO200141787 (Page 15); WO200044899 (Claim 52; FIG. 7); WO200020579 (Claim 3; FIG. 2); U.S. Pat. No. 5,869,445 (Claim 3; Col 31-38); WO9630514 (Claim 2; Page 56-61); EP1439393 (Claim 7); WO2004043361 (Claim 7); WO2004022709; WO200100244 (Example 3; FIG. 4); Accession: P04626; EMBL; M11767; AAA35808.1. EMBL; M11761; AAA35808.1.

(18) NCA (CEACAM6, Genbank accession no. M18728); Barnett T., et al. Genomics 3, 59-66, 1988; Tawaragi Y., et al. Biochem. Biophys. Res. Commun. 150, 89-96, 1988; Strausberg R. L., et al. Proc. Natl. Acad. Sci. U.S.A. 99:16899-16903, 2002; WO2004063709; EP1439393 (Claim 7); WO2004044178 (Example 4); WO2004031238; WO2003042661 (Claim 12); WO200278524 (Example 2); WO200286443 (Claim 27; Page 427); WO200260317 (Claim 2); Accession: P40199; Q14920; EMBL; M29541; AAA59915.1. EMBL; M18728.

(19) MDP (DPEP1, Genbank accession no. BC017023) Proc. Natl. Acad. Sci. U.S.A. 99 (26):16899-16903 (2002)); WO2003016475 (Claim 1); WO200264798 (Claim 33; Page 85-87); JP05003790 (FIG. 6-8); WO9946284 (FIG. 9); Cross-references: MIM:179780; AAH17023.1; BC017023_1.

(20) IL20Rα (IL20Ra, ZCYTOR7, Genbank accession no. AF184971); Clark H. F., et al. Genome Res. 13, 2265-2270, 2003; Mungall A. J., et al. Nature 425, 805-811, 2003; Blumberg H., et al. Cell 104, 9-19, 2001; Dumoutier L., et al. J. Immunol. 167, 3545-3549, 2001; Parrish-Novak J., et al. J. Biol. Chem. 277, 47517-47523, 2002; Pletnev S., et al.

(2003) Biochemistry 42:12617-12624; Sheikh F., et al. (2004) J. Immunol. 172, 2006-2010; EP1394274 (Example 11); US2004005320 (Example 5); WO2003029262 (Page 74-75); WO2003002717 (Claim 2; Page 63); WO2003222153 (Page 45-47); US2002042366 (Page 20-21); WO200146261 (Page 57-59); WO200146232 (Page 63-65); WO9837193 (Claim 1; Page 55-59); Accession: Q9UHF4; Q6UWA9; Q96SH8; EMBL; AF184971; AAF01320.1.

(21) Brevican (BCAN, BEHAB, Genbank accession no. AF229053) Gary S. C., et al. Gene 256, 139-147, 2000; Clark H. F., et al. Genome Res. 13, 2265-2270, 2003; Strausberg R. L., et al. Proc. Natl. Acad. Sci. U.S.A. 99, 16899-16903, 2002; US2003186372 (Claim 11); US2003186373 (Claim 11); US2003119131 (Claim 1; FIG. 52); US2003119122 (Claim 1; FIG. 52); US2003119126 (Claim 1); US2003119121 (Claim 1; FIG. 52); US2003119129 (Claim 1); US2003119130 (Claim 1); US2003119128 (Claim 1; FIG. 52); US2003119125 (Claim 1); WO2003016475 (Claim 1); WO200202634 (Claim 1).

(22) EphB2R (DRT, ERK, Hek5, EPHT3, Tyro5, Genbank accession no. NM_004442) Chan, J. and Watt, V. M., Oncogene 6 (6), 1057-1061 (1991) Oncogene 10 (5):897-905 (1995), Annu. Rev. Neurosci. 21:309-345 (1998), Int. Rev. Cytol. 196:177-244 (2000)); WO2003042661 (Claim 12); WO200053216 (Claim 1; Page 41); WO2004065576 (Claim 1); WO2004020583 (Claim 9); WO2003004529 (Page 128-132); WO200053216 (Claim 1; Page 42); Cross-references: MIM:600997; NP_004433.2; NM_004442_1.

(23) ASLG659 (B7 h, Genbank accession no. AX092328) US20040101899 (Claim 2); WO2003104399 (Claim 11); WO2004000221 (FIG. 3); US2003165504 (Claim 1); US2003124140 (Example 2); US2003065143 (FIG. 60); WO2002102235 (Claim 13; Page 299); US2003091580 (Example 2); WO200210187 (Claim 6; FIG. 10); WO200194641 (Claim 12; FIG. 7b); WO200202624 (Claim 13; FIG. 1A-1B); US2002034749 (Claim 54; Page 45-46); WO200206317 (Example 2; Page 320-321, Claim 34; Page 321-322); WO200271928 (Page 468-469); WO200202587 (Example 1; FIG. 1); WO200140269 (Example 3; Pages 190-192); WO200036107 (Example 2; Page 205-207); WO2004053079 (Claim 12); WO2003004989 (Claim 1); WO200271928 (Page 233-234, 452-453); WO 0116318.

(24) PSCA (Prostate stem cell antigen precursor, Genbank accession no. AJ297436) Reiter R. E., et al. Proc. Natl. Acad. Sci. U.S.A. 95, 1735-1740, 1998; Gu Z., et al. Oncogene 19, 1288-1296, 2000; Biochem. Biophys. Res. Commun. (2000) 275(3):783-788; WO2004022709; EP1394274 (Example 11); US2004018553 (Claim 17); WO2003008537 (Claim 1); WO200281646 (Claim 1; Page 164); WO2003003906 (Claim 10; Page 288); WO200140309 (Example 1; FIG. 17); US2001055751 (Example 1; FIG. 1b); WO200032752 (Claim 18; FIG. 1); WO9851805 (Claim 17; Page 97); WO9851824 (Claim 10; Page 94); WO9840403 (Claim 2; FIG. 1B); Accession: O43653; EMBL; AF043498; AAC39607.1.

(25) GEDA (Genbank accession No. AY260763); AAP14954 lipoma HMGIC fusion-partner-like protein/pid=AAP14954.1—*Homo sapiens* Species: *Homo sapiens* (human) WO2003054152 (Claim 20); WO2003000842 (Claim 1); WO2003023013 (Example 3, Claim 20); US2003194704 (Claim 45); Cross-references: GI:30102449; AAP14954.1; AY260763_1.

Figure 6A:
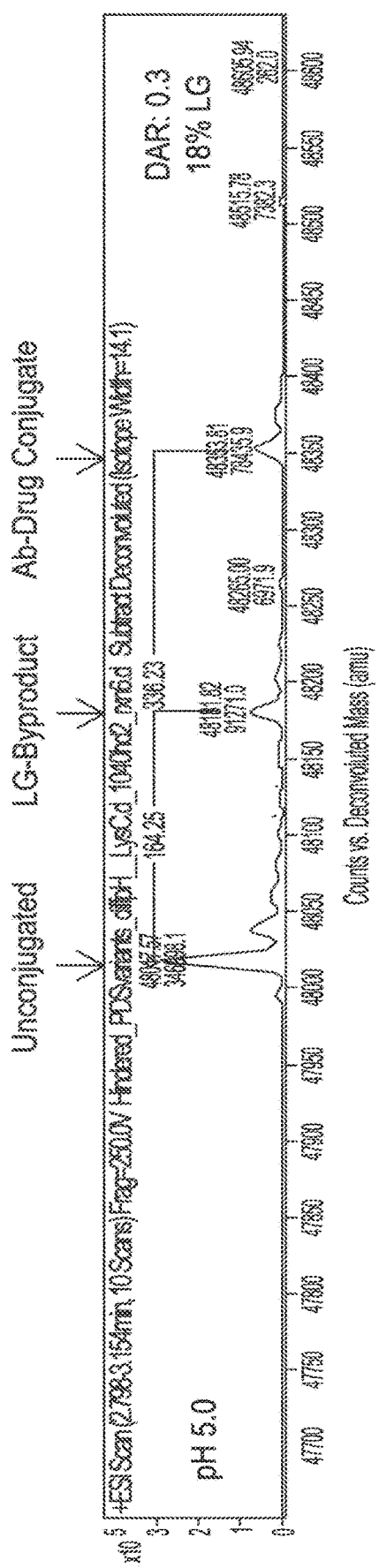
Figure 6B:
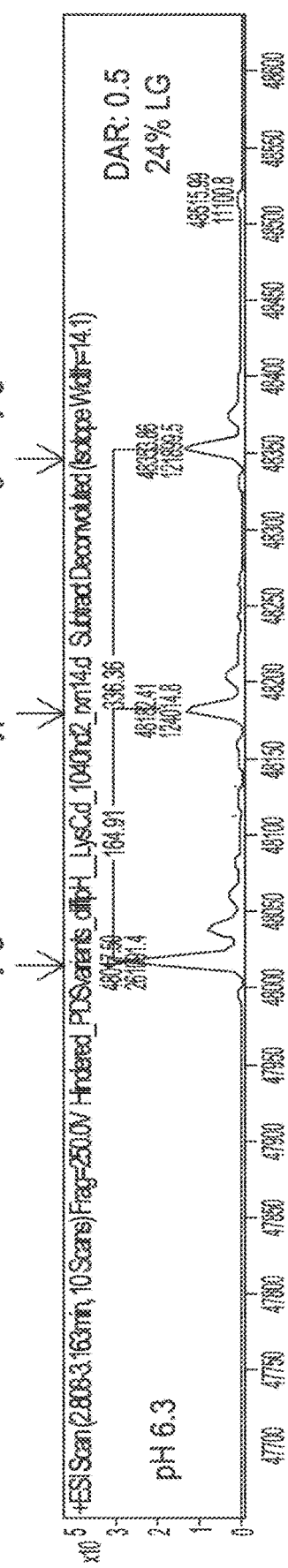

(26) BAFF-R (B cell-activating factor receptor, BLyS receptor 3, BR3, Genbank accession No. AF116456); BAFF receptor/pid=NP_443177.1—*Homo sapiens* Thompson, J. S., et al. Science 293 (5537), 2108-2111 (2001); WO2004058309; WO2004011611; WO2003045422 (Example; Page 32-33); WO2003014294 (Claim 35; FIG. 6B); WO2003035846 (Claim 70; Page 615-616); WO200294852 (Col 136-137); WO200238766 (Claim 3; Page 133); WO200224909 (Example 3; FIG. 3); Cross-references: MIM:606269; NP_443177.1; NM_052945_1; AF132600.

(27) CD22 (B-cell receptor CD22-B isoform, BL-CAM, Lyb-8, Lyb8, SIGLEC-2, FLJ22814, Genbank accession No. AK026467); Wilson et al. (1991) J. Exp. Med. 173:137-146; WO2003072036 (Claim 1; FIG. 1); Cross-references: MIM: 107266; NP_001762.1; NM_001771_1.

(28) CD79a (CD79A, CD79c, immunoglobulin-associated alpha, a B cell-specific protein that covalently interacts with Ig beta (CD79B) and forms a complex on the surface with Ig M molecules, transduces a signal involved in B-cell differentiation), pI: 4.84, MW: 25028 TM: 2 [P] Gene Chromosome: 19q13.2, Genbank accession No. NP_001774.10) WO2003088808, US20030228319; WO2003062401 (claim 9); US2002150573 (claim 4, pages 13-14); WO9958658 (claim 13, FIG. 16); WO9207574 (FIG. 1); U.S. Pat. No. 5,644,033; Ha et al. (1992) J. Immunol. 148(5):1526-1531; Mueller et al. (1992) Eur. J. Biochem. 22:1621-1625; Hashimoto et al. (1994) Immunogenetics 40(4):287-295; Preud'homme et al. (1992) Clin. Exp. Immunol. 90(1):141-146; Yu et al. (1992) J. Immunol. 148(2) 633-637; Sakaguchi et al. (1988) EMBO J. 7(11): 3457-3464.

(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia); 372 aa, pI: 8.54 MW: 41959 TM: 7 [P] Gene Chromosome: 11q23.3, Genbank accession No. NP_001707.1) WO2004040000; WO2004015426; US2003105292 (Example 2); U.S. Pat. No. 6,555,339 (Example 2); WO200261087 (FIG. 1); WO200157188 (Claim 20, page 269); WO200172830 (pages 12-13); WO200022129 (Example 1, pages 152-153, Example 2, pages 254-256); WO9928468 (claim 1, page 38); U.S. Pat. No. 5,440,021 (Example 2, col 49-52); WO9428931 (pages 56-58); WO9217497 (claim 7, FIG. 5); Dobner et al. (1992) Eur. J. Immunol. 22:2795-2799; Barella et al. (1995) Biochem. J. 309:773-779.

(30) HLA-DOB (Beta subunit of MHC class II molecule (Ia antigen) that binds peptides and presents them to CD4+T lymphocytes); 273 aa, pI: 6.56 MW: 30820 TM: 1 [P] Gene Chromosome: 6p21.3, Genbank accession No. NP_002111.1) Tonnelle et al. (1985) EMBO J. 4(11):2839-2847; Jonsson et al. (1989) Immunogenetics 29(6):411-413; Beck et al. (1992) J. Mol. Biol. 228:433-441; Strausberg et al. (2002) Proc. Natl. Acad. Sci USA 99:16899-16903; Servenius et al. (1987) J. Biol. Chem. 262:8759-8766; Beck et al. (1996) J. Mol. Biol. 255:1-13; Naruse et al. (2002) Tissue Antigens 59:512-519; WO9958658 (claim 13, FIG. 15); U.S. Pat. No. 6,153,408 (Col 35-38); U.S. Pat. No. 5,976,551 (col 168-170); U.S. Pat. No. 6,011,146 (col 145-146); Kasahara et al. (1989) Immunogenetics 30(1):66-68; Larhammar et al. (1985) J. Biol. Chem. 260(26): 14111-14119.

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability); 422 aa), pI: 7.63, MW: 47206 TM: 1 [P] Gene Chromosome: 17p13.3, Genbank accession No. NP_002552.2) Le et al. (1997) FEBS Lett. 418(1-2):195-199; WO2004047749; WO2003072035 (claim 10); Touchman et al. (2000) Genome Res. 10:165-173; WO200222660 (claim 20); WO2003093444 (claim 1); WO2003087768 (claim 1); WO2003029277 (page 82).

(32) CD72 (B-cell differentiation antigen CD72, Lyb-2) PROTEIN SEQUENCE Full maeaity . . . tafrfpd (1 . . . 359; 359 aa), pI: 8.66, MW: 40225 TM: 1 [P] Gene Chromosome: 9p13.3, Genbank accession No. NP_001773.1) WO2004042346 (claim 65); WO2003026493 (pages 51-52, 57-58); WO200075655 (pages 105-106); Von Hoegen et al. (1990) J. Immunol. 144(12):4870-4877; Strausberg et al. (2002) Proc. Natl. Acad. Sci USA 99:16899-16903.

(33) LY64 (Lymphocyte antigen 64 (RP 105), type I membrane protein of the leucine rich repeat (LRR) family, regulates B-cell activation and apoptosis, loss of function is associated with increased disease activity in patients with systemic lupus erythematosis); 661 aa, pI: 6.20, MW: 74147 TM: 1 [P] Gene Chromosome: 5q12, Genbank accession No. NP_005573.1) US2002193567; WO9707198 (claim 11, pages 39-42); Miura et al. (1996) Genomics 38(3):299-304; Miura et al. (1998) Blood 92:2815-2822; WO2003083047; WO9744452 (claim 8, pages 57-61); WO200012130 (pages 24-26).

(34) FcRH1 (Fc receptor-like protein 1, a putative receptor for the immunoglobulin Fc domain that contains C2 type Ig-like and ITAM domains, may have a role in B-lymphocyte differentiation); 429 aa, pI: 5.28, MW: 46925 TM: 1 [P] Gene Chromosome: 1q21-1q22, Genbank accession No. NP_443170.1) WO2003077836; WO200138490 (claim 6, FIG. 18E-1-18-E-2); Davis et al. (2001) Proc. Natl. Acad. Sci USA 98(17):9772-9777; WO2003089624 (claim 8); EP1347046 (claim 1); WO2003089624 (claim 7).

(35) IRTA2 (Immunoglobulin superfamily receptor translocation associated 2, a putative immunoreceptor with possible roles in B cell development and lymphomagenesis; deregulation of the gene by translocation occurs in some B cell malignancies); 977 aa, pI: 6.88 MW: 106468 TM: 1 [P] Gene Chromosome: 1q21, Genbank accession No. Human: AF343662, AF343663, AF343664, AF343665, AF369794, AF397453, AK090423, AK090475, AL834187, AY358085; Mouse: AK089756, AY158090, AY506558; NP_112571.1. WO2003024392 (claim 2, FIG. 97); Nakayama et al. (2000) Biochem. Biophys. Res. Commun. 277(1):124-127; WO2003077836; WO200138490 (claim 3, FIG. 18B-1-18B-2).

(36) TENB2 (TMEFF2, tomoregulin, TPEF, HPP1, TR, putative transmembrane proteoglycan, related to the EGF/heregulin family of growth factors and follistatin); 374 aa, NCBI Accession: AAD55776, AAF91397, AAG49451, NCBI RefSeq: NP_057276; NCBI Gene: 23671; OMIM: 605734; SwissProt Q9UIK5; Genbank accession No. AF179274; AY358907, CAF85723, CQ782436 WO2004074320 (SEQ ID NO 810); JP2004113151 (SEQ ID NOS 2, 4, 8); WO2003042661 (SEQ ID NO 580); WO2003009814 (SEQ ID NO 411); EP1295944 (pages 69-70); WO200230268 (page 329); WO200190304 (SEQ ID NO 2706); US2004249130; US2004022727; WO2004063355; US2004197325; US2003232350; US2004005563; US2003124579; Horie et al. (2000) Genomics 67:146-152; Uchida et al. (1999) Biochem. Biophys. Res. Commun. 266:593-602; Liang et al. (2000) Cancer Res. 60:4907-12; Glynne-Jones et al. (2001) Int J Cancer. October 15; 94(2):178-84.

(37) PMEL17 (silver homolog; SILV; D12S53E; PMEL17; SI; SIL); ME20; gp100) BC001414; BT007202; M32295; M77348; NM_006928; McGlinchey, R. P. et al. (2009) Proc. Natl. Acad. Sci. U.S.A. 106 (33), 13731-13736; Kummer, M. P. et al. (2009) J. Biol. Chem. 284 (4), 2296-2306.

(38) TMEFF1 (transmembrane protein with EGF-like and two follistatin-like domains 1; Tomoregulin-1); H7365; C9orf2; C9ORF2; U19878; X83961; NM_080655; NM_003692; Harms, P. W. (2003) Genes Dev. 17 (21), 2624-2629; Gery, S. et al. (2003) Oncogene 22 (18):2723-2727.

(39) GDNF-Ra1 (GDNF family receptor alpha 1; GFRA1; GDNFR; GDNFRA; RETL1; TRNR1; RET1L; GDNFR-alpha1; GFR-ALPHA-1); U95847; BC014962; NM_145793 NM_005264; Kim, M. H. et al. (2009) Mol. Cell. Biol. 29 (8), 2264-2277; Treanor, J. J. et al. (1996) Nature 382 (6586):80-83.

(40) Ly6E (lymphocyte antigen 6 complex, locus E; Ly67,RIG-E,SCA-2,TSA-1); NP_002337.1; NM_002346.2; de Nooij-van Dalen, A. G. et al. (2003) Int. J. Cancer 103 (6), 768-774; Zammit, D. J. et al. (2002) Mol. Cell. Biol. 22 (3):946-952.

(41) TMEM46 (shisa homolog 2 (*Xenopus laevis*); SHISA2); NP_001007539.1; NM_001007538.1; Furushima, K. et al. (2007) Dev. Biol. 306 (2), 480-492; Clark, H. F. et al. (2003) Genome Res. 13 (10):2265-2270.

(42) Ly6G6D (lymphocyte antigen 6 complex, locus G6D; Ly6-D, MEGT1); NP_067079.2; NM_021246.2; Mallya, M. et al. (2002) Genomics 80 (1):113-123; Ribas, G. et al. (1999) J. Immunol. 163 (1):278-287.

(43) LGR5 (leucine-rich repeat-containing G protein-coupled receptor 5; GPR49, GPR67); NP_003658.1; NM_003667.2; Salanti, G. et al. (2009) Am. J. Epidemiol. 170 (5):537-545; Yamamoto, Y. et al. (2003) Hepatology 37 (3):528-533.

(44) RET (ret proto-oncogene; MEN2A; HSCR1; MEN2B; MTC1; PTC; CDHF12; Hs.168114; RET51; RET-ELE1); NP_066124.1; NM_020975.4; Tsukamoto, H. et al. (2009) Cancer Sci. 100 (10):1895-1901; Narita, N. et al. (2009) Oncogene 28 (34):3058-3068.

(45) LY6K (lymphocyte antigen 6 complex, locus K; LY6K; HSJ001348; FLJ35226); NP_059997.3; NM_017527.3; Ishikawa, N. et al. (2007) Cancer Res. 67 (24):11601-11611; de Nooij-van Dalen, A. G. et al. (2003) Int. J. Cancer 103 (6):768-774.

(46) GPR19 (G protein-coupled receptor 19; Mm.4787); NP_006134.1; NM_006143.2; Montpetit, A. and Sinnett, D. (1999) Hum. Genet. 105 (1-2):162-164; O'Dowd, B. F. et al. (1996) FEBS Lett. 394 (3):325-329.

(47) GPR54 (KISS1 receptor; KISS1R; GPR54; HOT7T175; AXOR12); NP_115940.2; NM_032551.4; Navenot, J. M. et al. (2009) Mol. Pharmacol. 75 (6):1300-1306; Hata, K. et al. (2009) Anticancer Res. 29 (2):617-623.

(48) ASPHD1 (aspartate beta-hydroxylase domain containing 1; LOC253982); NP_859069.2; NM_181718.3; Gerhard, D. S. et al. (2004) Genome Res. 14 (10B):2121-2127.

(49) Tyrosinase (TYR; OCAIA; OCA1A; tyrosinase; SHEP3); NP_000363.1; NM_000372.4; Bishop, D. T. et al. (2009) Nat. Genet. 41 (8):920-925; Nan, H. et al. (2009) Int. J. Cancer 125 (4):909-917.

(50) TMEM118 (ring finger protein, transmembrane 2; RNFT2; FLJ14627); NP_001103373.1; NM_001109903.1; Clark, H. F. et al. (2003) Genome Res. 13 (10):2265-2270; Scherer, S. E. et al. (2006) Nature 440 (7082):346-351.

(51) GPR172A (G protein-coupled receptor 172A; GPCR41; FLJ11856; D15Ertd747e); NP_078807.1; NM_024531.3; Ericsson, T. A. et al. (2003) Proc. Natl. Acad. Sci. U.S.A. 100 (11):6759-6764; Takeda, S. et al. (2002) FEBS Lett. 520 (1-3):97-101.

(52) CD33, a member of the sialic acid binding, immunoglobulin-like lectin family, is a 67-kDa glycosylated transmembrane protein. CD33 is expressed on most myeloid and monocytic leukemia cells in addition to committed myelomonocytic and erythroid progenitor cells. It is not seen on the earliest pluripotent stem cells, mature granulocytes, lymphoid cells, or nonhematopoietic cells (Sabbath et al., (1985) *J. Clin. Invest.* 75:756-56; Andrews et al., (1986) *Blood* 68:1030-5). CD33 contains two tyrosine residues on its cytoplasmic tail, each of which is followed by hydrophobic residues similar to the immunoreceptor tyrosine-based inhibitory motif (ITIM) seen in many inhibitory receptors.

(53) CLL-1 (CLEC12A, MICL, and DCAL2), encodes a member of the C-type lectin/C-type lectin-like domain (CTL/CTLD) superfamily. Members of this family share a common protein fold and have diverse functions, such as cell adhesion, cell-cell signaling, glycoprotein turnover, and roles in inflammation and immune response. The protein encoded by this gene is a negative regulator of granulocyte and monocyte function. Several alternatively spliced transcript variants of this gene have been described, but the full-length nature of some of these variants has not been determined. This gene is closely linked to other CTL/CTLD superfamily members in the natural killer gene complex region on chromosome 12p13 (Drickamer K (1999) Curr. Opin. Struct. Biol. 9 (5):585-90; van Rhenen A, et al., (2007) Blood 110 (7):2659-66; Chen C H, et al. (2006) Blood 107 (4):1459-67; Marshall A S, et al. (2006) Eur. J. Immunol. 36 (8):2159-69; Bakker A B, et al. (2005) Cancer Res. 64 (22):8443-50; Marshall A S, et al. (2004) J. Biol. Chem. 279 (15):14792-802). CLL-1 has been shown to be a type II transmembrane receptor comprising a single C-type lectin-like domain (which is not predicted to bind either calcium or sugar), a stalk region, a transmembrane domain and a short cytoplasmic tail containing an ITIM motif.

Antibodies

In any of the antibody embodiments of the disclosure, an antibody is humanized. In one embodiment, an antibody comprises HVRs as in any of the embodiments of the disclosure, and further comprises a human acceptor framework, e.g. a human immunoglobulin framework or a human consensus framework. In certain embodiments, the human acceptor framework is the human VL kappa I consensus (VLKI) framework and/or the VH framework VH1. In certain embodiments, the human acceptor framework is the human VL kappa I consensus (VLKI) framework and/or the VH framework VH1 comprising any one of the following mutations.

In another aspect, the antibody comprises a VH as in any of the embodiments provided herein, and a VL as in any of the embodiments provided herein.

In a further aspect of the disclosure, an antibody according to any of the embodiments herein is a monoclonal antibody, including a human antibody. In one embodiment, an antibody is an antibody fragment, e.g., a Fv, Fab, Fab', scFv, diabody, or F(ab')2 fragment. In another embodiment, the antibody is a substantially full length antibody, e.g., an IgG1 antibody, IgG2a antibody or other antibody class or isotype as defined herein.

In a further aspect, an antibody according to any of the embodiments herein may incorporate any of the features, singly or in combination, as described herein.

1. Antibody Affinity

In certain embodiments, an antibody provided herein has a dissociation constant (Kd) of ≤1M, ≤100 nM, ≤50 nM, ≤10 nM, ≤5 nM, ≤1 nM, ≤0.1 nM, ≤0.01 nM, or ≤0.001 nM, and optionally is ≥$10^{-13}$ M. (e.g. $10^{-8}$ M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., Cancer Res. 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20) in PBS. When the plates have dried, 150 l/well of scintillant (MICROSCINT-20™ Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000, BIACORE®-T200 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) and/or HBS-P (0.01 M Hepes pH7.4, 0.15M NaCl, 0.005% Surfactant P20) before injection at a flow rate of 5 l/minute and/or 30 l/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate (TWEEN-20™) surfactant (PBST) at 25° C. at a flow rate of approximately 25 μl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds 106 $M^{-1}$ $s^{-1}$ by the surface plasmon resonance assay describe herein, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')2, Fv, and scFv fragments, and other fragments described herein. For a review of certain antibody fragments, see Hudson et al. Nat. Med. 9:129-134 (2003). For a review of scFv fragments, see, e.g., Pluckthün, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. E. coli or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., Proc. Natl. Acad. Sci. USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing SDR (a-CDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J Biol. Chem. 272:10678-10684 (1997) and Rosok et al., J. Biol. Chem. 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, Curr. Opin. Pharmacol. 5: 368-74 (2001) and Lonberg, Curr. Opin. Immunol. 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENO-MOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).) Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, Histology and Histopathology, 20(3):927-937

(2005) and Vollmers and Brandlein, *Methods and Findings in Experimental and Clinical Pharmacology,* 27(3): 185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described herein.

5. Library-Derived Antibodies

Antibodies of the disclosure may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., Nature 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. The term "multispecific antibody" is used in the broadest sense and specifically covers an antibody comprising an antigen-binding domain that has polyepitopic specificity (i.e., is capable of specifically binding to two, or more, different epitopes on one biological molecule or is capable of specifically binding to epitopes on two, or more, different biological molecules). In some embodiments, multispecific antibodies are monoclonal antibodies that have binding specificities for at least two different sites. In some embodiments, an antigen-binding domain of a multispecific antibody (such as a bispecific antibody) comprises two VH/VL units, wherein a first VH/VL unit specifically binds to a first epitope and a second VH/VL unit specifically binds to a second epitope, wherein each VH/VL unit comprises a heavy chain variable domain (VH) and a light chain variable domain (VL). Such multispecific antibodies include, but are not limited to, full length antibodies, antibodies having two or more VL and VH domains, antibody fragments such as Fab, Fv, dsFv, scFv, diabodies, bispecific diabodies and triabodies, antibody fragments that have been linked covalently or non-covalently. A VH/VL unit that further comprises at least a portion of a heavy chain variable region and/or at least a portion of a light chain variable region may also be referred to as an "arm" or "hemimer" or "half antibody." In some embodiments, a hemimer comprises a sufficient portion of a heavy chain variable region to allow intramolecular disulfide bonds to be formed with a second hemimer. In some embodiments, a hemimer comprises a knob mutation or a hole mutation, for example, to allow heterodimerization with a second hemimer or half antibody that comprises a complementary hole mutation or knob mutation. Knob mutations and hole mutations are discussed further herein.

In certain embodiments, a multispecific antibody provided herein may be a bispecific antibody. The term "bispecific antibody" is used in the broadest sense and covers a multispecific antibody comprising an antigen-binding domain that is capable of specifically binding to two different epitopes on one biological molecule or is capable of specifically binding to epitopes on two different biological molecules. A bispecific antibody may also be referred to herein as having "dual specificity" or as being "dual specific." Bispecific antibodies can be prepared as full length antibodies or antibody fragments. The term "biparatopic antibody" as used herein, refers to a bispecific antibody where a first antigen-binding domain and a second antigen-binding domain bind to two different epitopes on the same antigen molecule or it may bind to epitopes on two different antigen molecules.

In some embodiments, the first antigen-binding domain and the second antigen-binding domain of the biparatopic antibody may bind the two epitopes within one and the same antigen molecule (intramolecular binding). For example, the first antigen-binding domain and the second antigen-binding domain of the biparatopic antibody may bind to two different epitopes on the same antibody molecule. In certain embodiments, the two different epitopes that a biparatopic antibody binds are epitopes that are not normally bound at the same time by one monospecific antibody, such as e.g. a conventional antibody or one immunoglobulin single variable domain.

In some embodiments, the first antigen-binding domain and the second antigen-binding domain of the biparatopic antibody may bind epitopes located within two distinct antigen molecules.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168), WO2009/089004, US2009/0182127, US2011/0287009, Marvin and Zhu, Acta Pharmacol. Sin. (2005) 26(6):649-658, and Kontermann (2005) Acta Pharmacol. Sin., 26:1-9). The term "knob-into-hole" or "KnH" technology as used herein refers to the technology directing the pairing of two polypeptides together in vitro or in vivo by introducing a protuberance (knob) into one polypeptide and a cavity (hole) into the other polypeptide at an interface in which they interact. For example, KnHs have been introduced in the Fc:Fc binding interfaces, CL:CH1 interfaces or VH/VL interfaces of antibodies (see, e.g., US 2011/0287009, US2007/0178552, WO 96/027011, WO 98/050431, and Zhu et al., 1997, Protein Science 6:781-788). In some embodiments, KnHs drive the pairing of two different heavy chains together during the manufacture of multispecific antibodies. For example, multispecific antibodies having KnH in their Fc regions can further comprise single variable domains linked to each Fc region, or further comprise different heavy chain variable domains that pair with similar or different light chain variable domains. KnH technology can be also be used to pair two different receptor extracellular domains together or any other polypeptide sequences that comprises different target recognition sequences (e.g., including affibodies, peptibodies and other Fc fusions).

The term "knob mutation" as used herein refers to a mutation that introduces a protuberance (knob) into a polypeptide at an interface in which the polypeptide interacts with another polypeptide. In some embodiments, the other polypeptide has a hole mutation.

A "protuberance" refers to at least one amino acid side chain which projects from the interface of a first polypeptide and is therefore positionable in a compensatory cavity in the adjacent interface (i.e. the interface of a second polypeptide) so as to stabilize the heteromultimer, and thereby favor heteromultimer formation over homomultimer formation, for example. The protuberance may exist in the original interface or may be introduced synthetically (e.g. by altering nucleic acid encoding the interface). In some embodiments, nucleic acid encoding the interface of the first polypeptide is altered to encode the protuberance. To achieve this, the nucleic acid encoding at least one "original" amino acid residue in the interface of the first polypeptide is replaced with nucleic acid encoding at least one "import" amino acid residue which has a larger side chain volume than the original amino acid residue. It will be appreciated that there can be more than one original and corresponding import residue. The side chain volumes of the various amino residues are shown, for example, in Table 1 of US2011/0287009. A mutation to introduce a "protuberance" may be referred to as a "knob mutation."

In some embodiments, import residues for the formation of a protuberance are naturally occurring amino acid residues selected from arginine (R), phenylalanine (F), tyrosine (Y) and tryptophan (W). In some embodiments, an import residue is tryptophan or tyrosine. In some embodiment, the original residue for the formation of the protuberance has a small side chain volume, such as alanine, asparagine, aspartic acid, glycine, serine, threonine or valine.

A "cavity" refers to at least one amino acid side chain which is recessed from the interface of a second polypeptide and therefore accommodates a corresponding protuberance on the adjacent interface of a first polypeptide. The cavity may exist in the original interface or may be introduced synthetically (e.g. by altering nucleic acid encoding the interface). In some embodiments, nucleic acid encoding the interface of the second polypeptide is altered to encode the cavity. To achieve this, the nucleic acid encoding at least one "original" amino acid residue in the interface of the second polypeptide is replaced with DNA encoding at least one "import" amino acid residue which has a smaller side chain volume than the original amino acid residue. It will be appreciated that there can be more than one original and corresponding import residue. In some embodiments, import residues for the formation of a cavity are naturally occurring amino acid residues selected from alanine (A), serine (S), threonine (T) and valine (V). In some embodiments, an import residue is serine, alanine or threonine. In some embodiments, the original residue for the formation of the cavity has a large side chain volume, such as tyrosine, arginine, phenylalanine or tryptophan. A mutation to introduce a "cavity" may be referred to as a "hole mutation."

The protuberance is "positionable" in the cavity which means that the spatial location of the protuberance and cavity on the interface of a first polypeptide and second polypeptide respectively and the sizes of the protuberance and cavity are such that the protuberance can be located in the cavity without significantly perturbing the normal association of the first and second polypeptides at the interface. Since protuberances such as Tyr, Phe and Trp do not typically extend perpendicularly from the axis of the interface and have preferred conformations, the alignment of a protuberance with a corresponding cavity may, in some instances, rely on modeling the protuberance/cavity pair based upon a three-dimensional structure such as that obtained by X-ray crystallography or nuclear magnetic resonance (NMR). This can be achieved using widely accepted techniques in the art.

In some embodiments, a knob mutation in an IgG1 constant region is T366W. In some embodiments, a hole mutation in an IgG1 constant region comprises one or more mutations selected from T366S, L368A and Y407V. In some embodiments, a hole mutation in an IgG1 constant region comprises T366S, L368A and Y407V.

In some embodiments, a knob mutation in an IgG4 constant region is T366W. In some embodiments, a hole mutation in an IgG4 constant region comprises one or more mutations selected from T366S, L368A, and Y407V. In some embodiments, a hole mutation in an IgG4 constant region comprises T366S, L368A, and Y407V.

Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J. Immunol., 148(5):1547-1553 (1992)); using "diabody" technology for making bispecific antibody fragments (Hollinger et al., Proc. Natl. Acad. Sci. USA, 90:6444-6448 (1993)); and using single-chain Fv (sFv) dimers (Gruber et al., J. Immunol., 152:5368 (1994)); and preparing trispecific antibodies as described, e.g., in Tutt et al. J. Immunol. 147: 60 (1991).

Engineered antibodies with three or more functional antigen binding sites, including "Octopus antibodies" or "dual-variable domain immunoglobulins" (DVDs) are also included herein (US 2006/0025576A1, and Wu et al. (2007) *Nature Biotechnology*).

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the disclosure contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACT™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

In certain embodiments Pro329 of a wild-type human Fc region is substituted with glycine or arginine or an amino acid residue large enough to destroy the proline sandwich within the Fc/Fcγ receptor interface, that is formed between the proline329 of the Fc and tryptophan residues Trp 87 and Trp 110 of FcgRIII (Sondermann et al.: Nature 406, 267-273 (20 Jul. 2000)). In a further embodiment, at least one further amino acid substitution in the Fc variant is S228P, E233P, L234A, L235A, L235E, N297A, N297D, or P331S and still in another embodiment said at least one further amino acid substitution is L234A and L235A of the human IgG1 Fc region or S228P and L235E of the human IgG4 Fc region (U.S. Pat. No. 8,969,526 which is incorporated by reference in its entirety).

In certain embodiments, a polypeptide comprises the Fc variant of a wild-type human IgG Fc region wherein the polypeptide has Pro329 of the human IgG Fc region substituted with glycine and wherein the Fc variant comprises at least two further amino acid substitutions at L234A and L235A of the human IgG1 Fc region or S228P and L235E of the human IgG4 Fc region, and wherein the residues are numbered according to the EU index of Kabat (U.S. Pat. No. 8,969,526 which is incorporated by reference in its entirety). In certain embodiments, the polypeptide comprising the P329G, L234A and L235A substitutions exhibit a reduced affinity to the human FcγRIIIA and FcγRIIA, for down-modulation of ADCC to at least 20% of the ADCC induced by the polypeptide comprising the wild type human IgG Fc region, and/or for down-modulation of ADCP (U.S. Pat. No. 8,969,526 which is incorporated by reference in its entirety).

In a specific embodiment the polypeptide comprising an Fc variant of a wild type human Fc polypeptide comprises a triple mutation: an amino acid substitution at position Pro329, a L234A and a L235A mutation (P329/LALA) (U.S. Pat. No. 8,969,526 which is incorporated by reference in its entirety). In specific embodiments, the polypeptide comprises the following amino acid substitutions: P329G, L234A, and L235A.

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001)).

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al., *J. Immunol.* 164: 4178-4184 (2000).

Antibodies with increased half-lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, Nature 322:738-40 (1988); U.S. Pat. Nos. 5,648,260; 5,624,821; and WO 94/29351 concerning other examples of Fc region variants.

7. Cysteine Engineered Antibody Variants

In certain embodiments, it may be desirable to create cysteine engineered antibodies, e.g., "THIOMAB™ antibody," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to the drug moiety to create an immunoconjugate, as described further herein. In certain embodiments, any one or more of the following residues may be substituted with cysteine: V205 (Kabat numbering) of the light chain; K149 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

In some aspects, a THIOMAB™ antibody comprises one of the heavy or light chain cysteine substitutions listed in Table A below.

TABLE A

| Chain (HC/LC) | Residue | Screening Mutation Site # | GNE Mutation Site # | Kabat Mutation Site # |
|---|---|---|---|---|
| LC | T | 22 | 22 | 22 |
| LC | K | 39 | 39 | 39 |
| LC | Y | 49 | 49 | 49 |
| LC | Y | 55 | 55 | 55 |
| LC | T | 85 | 85 | 85 |
| LC | T | 97 | 97 | 97 |
| LC | I | 106 | 106 | 106 |
| LC | R | 108 | 108 | 108 |
| LC | S | 121 | 121 | 121 |
| LC | R | 142 | 142 | 142 |
| LC | K | 149 | 149 | 149 |
| LC | V | 205 | 205 | 205 |
| HC | T | 117 | 114 | 110 |
| HC | A | 143 | 140 | 136 |
| HC | L | 177 | 174 | 170 |
| HC | L | 182 | 179 | 175 |
| HC | T | 190 | 187 | 183 |
| HC | T | 212 | 209 | 205 |
| HC | V | 265 | 262 | 258 |
| HC | G | 374 | 371 | 367 |
| HC | Y | 376 | 373 | 369 |
| HC | E | 385 | 382 | 378 |
| HC | S | 427 | 424 | 420 |
| HC | N | 437 | 434 | 430 |
| HC | Q | 441 | 438 | 434 |

In other aspects, a THIOMAB™ antibody comprises one of the heavy chain cysteine substitutions listed in Table B.

TABLE B

| Chain (HC/LC) | Residue | Screening Mutation Site # | GNE Mutation Site # | Kabat Mutation Site # |
|---|---|---|---|---|
| HC | T | 117 | 114 | 110 |
| HC | A | 121 | 118 | 114 |
| HC | A | 143 | 140 | 136 |
| HC | L | 177 | 174 | 170 |
| HC | L | 182 | 179 | 175 |
| HC | T | 190 | 187 | 183 |
| HC | T | 212 | 209 | 205 |
| HC | V | 265 | 262 | 258 |
| HC | G | 374 | 371 | 367 |
| HC | Y | 376 | 373 | 369 |
| HC | E | 385 | 382 | 378 |
| HC | S | 427 | 424 | 420 |
| HC | N | 437 | 434 | 430 |
| HC | Q | 441 | 438 | 434 |

In some other aspects, a THIOMAB™ antibody comprises one of the light chain cysteine substitutions listed in Table C.

TABLE C

| Chain (HC/LC) | Residue | Screening Mutation Site # | GNE Mutation Site # | Kabat Mutation Site # |
|---|---|---|---|---|
| LC | I | 106 | 106 | 106 |
| LC | R | 108 | 108 | 108 |
| LC | K | 121 | 121 | 121 |
| LC | R | 142 | 142 | 142 |
| LC | K | 149 | 149 | 149 |

In some other aspects, a THIOMAB™ antibody comprises one of the heavy or light chain cysteine substitutions listed in Table D.

TABLE D

| Chain (HC/LC) | Residue | Screening Mutation Site # | GNE Mutation Site # | Kabat Mutation Site # |
|---|---|---|---|---|
| HC | A | 118 | 118 | 118 |
| LC | S | 121 | 121 | 121 |
| LC | K | 149 | 149 | 149 |
| HC | A | 143 | 140 | 136 |
| HC | A | 121 | 118 | 114 |
| LC | V | 205 | 205 | 205 |

In some other aspects, a THIOMAB™ antibody comprises a pair of heavy or light chain cysteine substitutions listed in any of Table A to D. Non-limiting examples of such pairs include: (i) LC K149C and LC S121C; (ii) HC A118C and LC S121C, and (iii) LC K149C and LC V205C.

Cysteine engineered antibodies which may be useful in the antibody-drug conjugates of the disclosure in the treatment of cancer include, but are not limited to, antibodies against cell surface receptors and tumor-associated antigens (TAA). Tumor-associated antigens are known in the art, and can be prepared for use in generating antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

Examples of tumor-associated antigens TAA include, but are not limited to, TAA (1)-(53) listed herein. For convenience, information relating to these antigens, all of which are known in the art, is listed herein and includes names, alternative names, Genbank accession numbers and primary reference(s), following nucleic acid and protein sequence identification conventions of the National Center for Biotechnology Information (NCBI). Nucleic acid and protein sequences corresponding to TAA (1)-(53) are available in public databases such as GenBank. Tumor-associated antigens targeted by antibodies include all amino acid sequence variants and isoforms possessing at least about 70%, 80%, 85%, 90%, or 95% sequence identity relative to the sequences identified in the cited references, or which exhibit substantially the same biological properties or characteristics as a TAA having a sequence found in the cited references. For example, a TAA having a variant sequence generally is able to bind specifically to an antibody that binds specifically to the TAA with the corresponding sequence listed. The sequences and disclosure in the reference specifically recited herein are expressly incorporated by reference.

Peptides and Polypeptides

In some embodiments of the present disclosure, the carrier may be a cell-penetrating peptide ("CPP"). CPPs are small peptides, typically consisting of less than 30 amino acids, that exhibit tumor-penetration and internalization ability. CPP drug conjugates are capable of translocation and internalization and therefore provide delivery of the drug payload. CPPs are known in the art and examples include the Tat protein from the HIV-1 virus and the *Drosophila mela-*

*nogaster* Antennapedia homeodomain. CPPs further include engineered cationic peptides such as See. e.g., US 2015/0239947; Regberg, Jakob, et al., "Applications of Cell-Penetrating Peptides for Tumor Targeting and Future Cancer Therapies", Pharmaceuticals 2012, 5, 991-1007; Munyendo, L L, et al., "Cell Penetrating Peptides in the Delivery of Biopharmaceuticals", Biomolecules 2012, 2, 187-202; and US 2005/0260715, each of which is incorporated by reference herein in its entirety. The linker may be conjugated to a CPP cysteine sulfhydryl moiety by way of a disulfide bond. In some such aspects, the CPP comprises at least one cysteine residue per equivalent. In some other such aspects, a cysteine residue may be inserted at one or both ends of a linear CPP.

In some embodiments of the present disclosure, the carrier may be a cell targeting peptide or polypeptide ("CTP") having a least one cysteine thiol moiety per equivalent.

CTPs having specificity and affinity for targeted cell lines are known in the art. For instance, MimoDB is a publically available mimotope database of over 20,000 peptide sequences and over 1400 targets wherein CTP-target affinity values are specifically provided. Further, TumorHoPe is a database of over 700 peptide sequences that references the target tumor and affinity.

In some embodiments of the disclosure, CTPs may be identified using in vivo phase display technology (biopanning) methods known in the art wherein peptide libraries may be screened against one or more cancer cell lines to identify peptides that may be suitable for use as a carrier having sufficient specificity for the cancer cell. In general, in phage display, a random peptide is expressed on the phage surface by fusion of the corresponding coding sequence to a gene encoding one of the phage surface proteins. The desired phages are selected on the basis of their binding to the target such as isolated organ fragments (ex vivo procedure) or cultured cells (in vitro procedure). Identification of targeting peptides can also be done by an in vivo procedure that is achieved by injecting phage libraries into mice and subsequently rescuing the bound phages from the targeted organs. Selected peptides are identified by sequencing the genome phage region encoding the displayed peptide. In vivo organ screening can be successfully applied to isolate peptide sequences that conferred selective phage homing to the brain and kidney (Pasqualini et al., Nature 380 (1996) 364-366, incorporated by reference herein in its entirety), to the vasculature of lung, skin and pancreas (Rajotte et al., J. Clin. Invest. 102 (1998) 430-437, incorporated by reference herein in its entirety) and to several tumor types (Pasqualini et al., Nature Biotechnology 15 (1997) 542-546, incorporated by reference herein in its entirety). See further: Smith G P, "Filamentous fusion phage: novel expression vectors that display cloned antigens on the virion surface", Science 228 (1985), 1315-7; Scott J K and Smith G P, "Searching for peptide ligands with an epitope library", Science 249 (1990) 386-390; McGuire M J, et al., "Identification and Characterization of a Suite of Tumor Targeting Peptides for Non-Small Cell Lung Cancer, Scientific Reports 4:4480 (2014); Thundimadathil, Jyothi "Cancer Treatment Using Peptides: Current Therapies and Future Prospects" Journal of Amino Acids, Vol. 2012, Article ID 967347 (2012); and Zhi, J L and Chi, H C, "Peptides as targeting probes against tumor vasculature for diagnosis and drug delivery" Journal of Translational Medicine 2012, 10 (Suppl 1):S1). Each of Smith, Scott, McGuire, Thundimadathil and Zhi are incorporated herein in its entirety. The displaying phage may then be screened against one or more cell types of interest, and phages that interact with an antigen expressed by the cell may be amplified and isolated. The targeting peptide may then be sequenced and identified.

In some aspects of the disclosure, CTPs may be isolated from natural sources using standard techniques (see, for instance, U.S. published app. no. 2003/0232013, incorporated by reference herein in its entirety). In some other aspects, CTPs may be synthesized using standard techniques. For instance, CTPs may be synthesized using the solid-phase synthetic techniques (see, for instance, Merrifield, R B, "Solid Phase Peptide Synthesis. I. Synthesis of a Tetrapeptide", J. Am. Chem. Soc. 1963, 85(14), 2149-2154, incorporated by reference herein in its entirety). Other peptide synthesis techniques are well known to those of skill in the art (see, for instance, Bodanszky et al.: "Peptide Synthesis", Wiley-Interscience, 1976 ($2^{nd}$ ed.); and "Principles of Peptide Synthesis", Springer-Verlag 1985. Each is incorporated by reference herein in its entirety). Appropriate protective groups for use in such syntheses will be found in the above texts, as well as in Protective Groups in Organic Chemistry, 1973 (incorporated by reference herein in its entirety). These synthetic methods involve the sequential addition of one or more amino acid residues or suitable protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group, such as lysine and cysteine.

Optionally, to increase affinity of the targeting peptide to an antigen, the peptide may be tetramerized on a trilysine core (see McGuire M J, et al.). As disclosed by McGuire, tetramerization enhances affinity by providing for multivalent bonding to a cell, and by maintaining the peptide valency and orientation displayed on the phage. In some aspects of the disclosure, targeting peptide monomers may be oligomerized on a tetracysteine core.

The linker may be conjugated to a CTP cysteine sulfhydryl moiety by way of a disulfide bond. In some such aspects, the CTP comprises at least one cysteine residue per equivalent. In some other such aspects, a cysteine residue may be inserted at one or both ends of a linear CTP. In yet other aspects, a core bearing one or more CTPs may comprise at least one cysteine residue, or at least one cysteine residue may be derivatized to such a core.

Other Carriers

In some embodiments of the present disclosure, the carrier may be a growth factor, a hormone, a cytokine or a protein having at least one cysteine thiol moiety per equivalent.

In some such aspects, the cell targeting moiety may be a growth factor (see, for instance, U.S. published app. no. 2014/0349944, incorporated by reference herein in its entirety). For example, transforming growth factors, epidermal growth factors, insulin-like growth factor, fibroblast growth factors (1-23), B lymphocyte stimulator (BLyS), heregulin, platelet-derived growth factors, vascular endothelial growth factor (VEGF), or hypoxia inducible factor may be used as a cell targeting moiety according to the disclosure. These growth factors enable the targeting of constructs to cells that express the cognate growth factor receptors. For example, VEGF can be used to target cells that express FLK-1 and/or Flt-1.

In further aspects of the disclosure, the cell targeting moiety may be a hormone (see, for instance, U.S. 2014/0349944). Some examples of hormones for use in the disclosure include, but are not limited to, human chorionic gonadotropin, gonadotropin releasing hormone, an androgen, an estrogen, thyroid-stimulating hormone, follicle-stimulating hormone, luteinizing hormone, prolactin, growth hormone, adrenocorticotropic hormone, antidiuretic hormone, oxytocin, thyrotropin-releasing hormone, growth hormone releasing hormone, corticotropin-releasing hormone, somatostatin, dopamine, melatonin, thyroxine, calcitonin, parathyroid hormone, glucocorticoids, mineralocorticoids, adrenaline, noradrenaline, progesterone, insulin, glucagon, amylin, erythropoitin, calcitriol, calciferol, atrial-natriuretic peptide, gastrin, secretin, cholecystokinin, neuropeptide Y, ghrelin, PYY3-36, insulin-like growth factor-1, leptin, thrombopoietin, angiotensinogen, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, or IL-36. In such aspects, targeting constructs that comprise a hormone enable method of targeting cell populations that comprise extracellular receptors for the indicated hormone.

In yet further such aspects, cell targeting moieties may be cytokines, such as, granulocyte-colony stimulating factor, macrophage-colony stimulating factor, granulocyte-macrophage colony stimulating factor, leukemia inhibitory factor, erythropoietin, granulocyte macrophage colony stimulating factor, oncostatin M, leukemia inhibitory factor, IFN-γ, IFN-α, IFN-β, LT-β, CD40 ligand, Fas ligand, CD27 ligand, CD30 ligand, 4-1BBL, TGF-β, IL 1α, IL-1β, IL-1 RA, MIF and IGIF (see, for instance, U.S. 2014/0349944).

In still other aspects of the disclosure, the carrier may be a protein. Examples of such proteins include cell adhesion proteins such as selectins, integrins and cadherins, including but not limited to, albumin, fibronectin, collagen, alpha-1-antitrypsin, alpha-2-macroglobulin, ceruloplasmin, transferrin, laminin, thrombospondin, integrins, N-CAM, PECAM, CD44. (See, e.g., U.S. published app. no. 2010/0168019. See also, Gumbiner, B M (1996). "Cell Adhesion: The Molecular Basis of Tissue Architecture and Morphogenesis", Cell 84 (3): 345-357. Each reference is incorporated herein in its entirety). Other examples include lipid binding proteins that form complexes with fatty acids or other hydrophobic ligands, and include, but are not limited to, myelin basic protein, spectrin, lipoprotein lipase, apolipoprotein B and E, LDL (see, e.g., US 2010/0168019. See also, Bernlohr, D A, et al., "Intracellular Lipid-Binding Proteins and their Genes", Annual Review of Nutrition, Vol. 17:277-303 (1997), incorporated by reference herein).

The linker may be conjugated to a growth factor, a hormone, a cytokine or a protein cysteine sulfhydryl moiety by way of a disulfide bond. In some such aspects, the growth factor, hormone, cytokine or protein comprises at least one cysteine residue. In some other such aspects, a cysteine residue may be inserted into or at one or both ends of the growth factor, hormone, cytokine or protein.

Drug

In any of the various aspects of the disclosure, the drug is generally any drug comprising a functional group suitable for forming a conjugate with a linker. Examples of such linking conjugates include an aliphatic (acyclic) amine, a cyclic amine, an aliphatic alcohol, and a cyclic alcohol. As used herein "drug moiety" refers to the drug constituent of the conjugates of the present disclosure. The drug moiety is covalently bound to the linker or, optionally, to a spacer. The aliphatic amine may suitably be a primary amine or a secondary amine. An example of a drug having a secondary amine conjugation moiety is monomethyl auristatin E ("MMAE"). The cyclic amine comprises a nitrogen heteroatom in an unsaturated ring (e.g., aryl), partially saturated ring, or completely saturated ring. An example of a drug having a cyclic nitrogen conjugation moiety in an unsaturated ring is a pyrrolobenzodiazepine. An example of a drug having a cyclic alcohol conjugation moiety on an unsaturated ring is a maytansinoid.

In some embodiments, the drug is a maytansinoid. Maytansinoids are derivatives of maytansine, and are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinoids are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533. Each patent cited in this paragraph is incorporated by reference herein in its entirety.

Maytansinoid drug moieties are attractive drug moieties in antibody-drug conjugates because they are: (i) relatively accessible to prepare by fermentation or chemical modification or derivatization of fermentation products, (ii) amenable to derivatization with functional groups suitable for conjugation through non-disulfide linkers to antibodies, (iii) stable in plasma, and (iv) effective against a variety of tumor cell lines.

Certain maytansinoids suitable for use as maytansinoid drug moieties are known in the art and can be isolated from natural sources according to known methods or produced using genetic engineering techniques (see, e.g., Yu et al (2002) PNAS 99:7968-7973, incorporated by reference herein in its entirety). Maytansinoids may also be prepared synthetically according to known methods.

Exemplary maytansinoid drug moieties include, but are not limited to, those having a modified aromatic ring, such as: C-19-dechloro (U.S. Pat. No. 4,256,746) (prepared, for example, by lithium aluminum hydride reduction of ansamytocin P2); C-20-hydroxy (or C-20-demethyl) +/−C-19-dechloro (U.S. Pat. Nos. 4,361,650 and 4,307,016) (prepared, for example, by demethylation using *Streptomyces* or *Actinomyces* or dechlorination using LAH); and C-20-demethoxy, C-20-acyloxy (—OCOR), +/−dechloro (U.S. Pat. No. 4,294,757) (prepared, for example, by acylation using acyl chlorides), and those having modifications at other positions of the aromatic ring. Each patent cited in this paragraph is incorporated by reference herein in its entirety.

Exemplary maytansinoid drug moieties also include those having modifications such as: C-9-SH (U.S. Pat. No. 4,424,219) (prepared, for example, by the reaction of maytansinol with $H_2S$ or $P_2S_5$); C-14-alkoxymethyl(demethoxy/$CH_2OR$) (U.S. Pat. No. 4,331,598); C-14-hydroxymethyl or acyloxymethyl ($CH_2OH$ or $CH_2OAc$) (U.S. Pat. No. 4,450,254) (prepared, for example, from *Nocardia*); C-15-hydroxy/acyloxy (U.S. Pat. No. 4,364,866) (prepared, for example, by the conversion of maytansinol by *Streptomyces*); C-15-methoxy (U.S. Pat. Nos. 4,313,946 and 4,315,929) (for example, isolated from *Trewia nudlflora*); C-18-N-demethyl (U.S. Pat. Nos. 4,362,663 and 4,322,348) (prepared, for example, by the demethylation of maytansinol by *Streptomyces*); and 4,5-deoxy (U.S. Pat. No. 4,371,533) (prepared, for example, by the titanium trichloride/LAH reduction of maytansinol). Each patent cited in this paragraph is incorporated by reference herein in its entirety.

Many positions on maytansinoid compounds are useful as the linkage position. For example, an ester linkage may be formed by reaction with a hydroxyl group using conventional coupling techniques. In some embodiments, the reaction may occur at the C-3 position having a hydroxyl group, the C-14 position modified with hydroxymethyl, the C-15 position modified with a hydroxyl group, and the C-20 position having a hydroxyl group. In some embodiments, the linkage is formed at the C-3 position of maytansinol or a maytansinol analogue.

Maytansinoid drug moieties within the scope of the present disclosure include those having the structure:

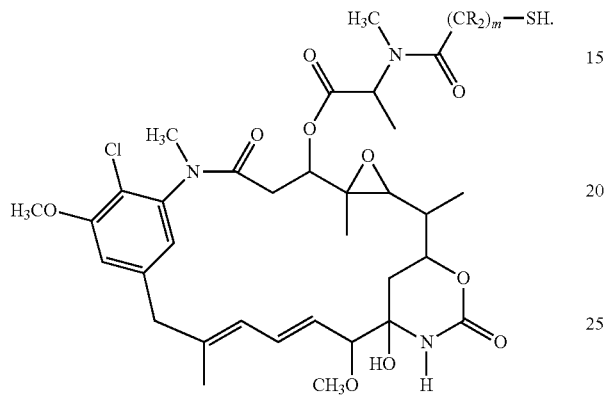

wherein each R may independently be H or a $C_1$-$C_6$ alkyl. The alkylene chain attaching the amide group to the sulfur atom may be methanyl, ethanyl, or propyl, i.e., m is 1, 2, or 3 (U.S. Pat. No. 633,410; U.S. Pat. No. 5,208,020; Chari et al (1992) *Cancer Res.* 52:127-131; and Liu et al (1996) *Proc. Natl. Acad. Sci USA* 93:8618-8623, each of which is incorporated by reference herein in its entirety).

All stereoisomers of the maytansinoid drug moiety are contemplated for the conjugates of the disclosure, i.e. any combination of R and S configurations at the chiral carbons (U.S. Pat. Nos. 7,276,497; 6,913,748; 6,441,163; U.S. Pat. No. 633,410 (RE39151); U.S. Pat. No. 5,208,020; Widdison et al (2006) *J. Med. Chem.* 49:4392-4408, each of which are incorporated by reference herein in its entirety). In some embodiments, the maytansinoid drug moiety has the following stereochemistry:

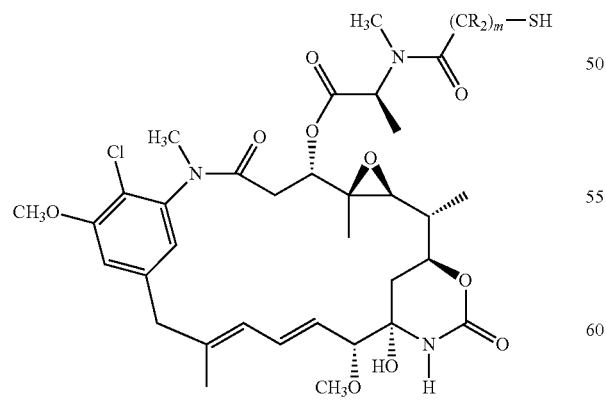

Exemplary embodiments of maytansinoid drug moieties include, but are not limited to, DM1; DM3; and DM4, having the structures:

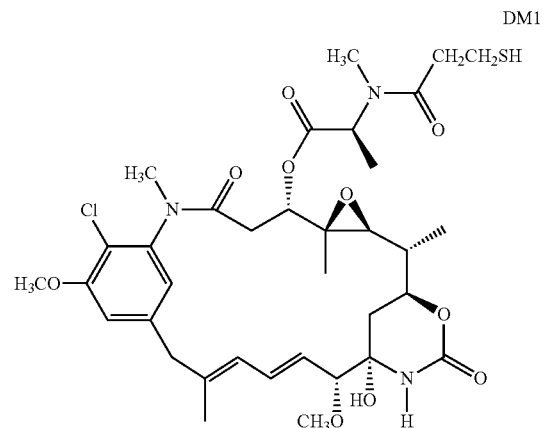

DM1

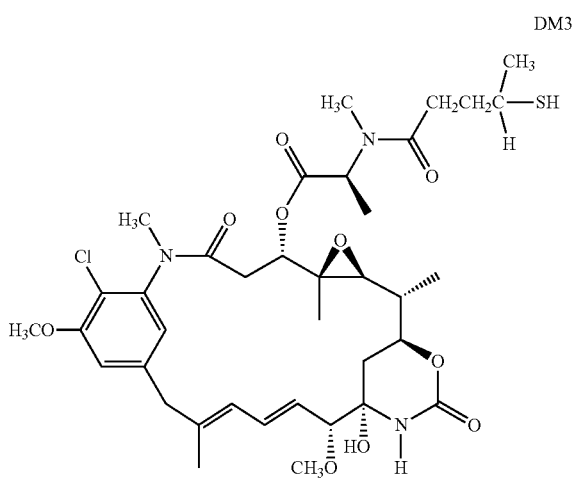

DM3

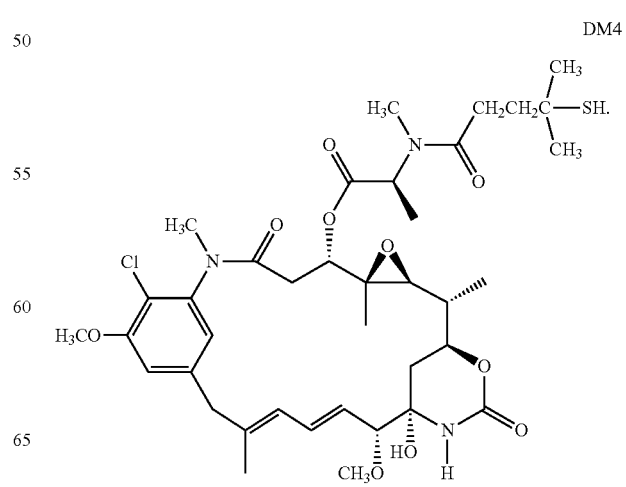

DM4

Immunoconjugates containing maytansinoids, methods of making the same, and their therapeutic use are disclosed, for example, in U.S. Pat. Nos. 5,208,020 and 5,416,064; US 2005/0276812 A1; and European Patent EP 0 425 235 B1, the disclosures of which are hereby expressly incorporated by reference. See also Liu et al. *Proc. Natl. Acad. Sci. USA* 93:8618-8623 (1996); and Chari et al. *Cancer Research* 52:127-131 (1992).

In some embodiments, antibody-maytansinoid conjugates may be prepared by chemically linking a carrier (e.g., an antibody) to a maytansinoid molecule without significantly diminishing the biological activity of either the antibody or the maytansinoid molecule. See, e.g., U.S. Pat. No. 5,208,020 (the disclosure of which is hereby expressly incorporated by reference). In some embodiments, ADC with an average of 3-4 maytansinoid molecules conjugated per antibody molecule has shown efficacy in enhancing cytotoxicity of target cells without negatively affecting the function or solubility of the antibody. In some instances, even one molecule of toxin/antibody is expected to enhance cytotoxicity over the use of naked antibody.

In some embodiments, the drugs are dolastatins, auristatins, and analogs and derivatives thereof (U.S. Pat. Nos. 5,635,483; 5,780,588; 5,767,237; 6,124,431). Auristatins are derivatives of the marine mollusk compound dolastatin-10. While not intending to be bound by any particular theory, dolastatins and auristatins have been shown to interfere with microtubule dynamics, GTP hydrolysis, and nuclear and cellular division (Woyke et al (2001) *Antimicrob. Agents and Chemother.* 45(12):3580-3584) and have anticancer (U.S. Pat. No. 5,663,149) and antifungal activity (Pettit et al (1998) *Antimicrob. Agents Chemother.* 42:2961-2965). The dolastatin/auristatin drug moiety may be attached to the antibody through the N (amino) terminus or the C (carboxyl) terminus of the peptidic drug moiety (WO 02/088172; Doronina et al (2003) *Nature Biotechnology* 21(7):778-784; Francisco et al (2003) *Blood* 102(4):1458-1465). Each reference cited in this paragraph is incorporated by reference herein in its entirety.

Exemplary auristatin embodiments include the N-terminus linked monomethylauristatin drug moieties $D_E$ and $D_F$, disclosed in U.S. Pat. Nos. 7,498,298 and 7,659,241, the disclosures of which are expressly incorporated by reference in its entirety:

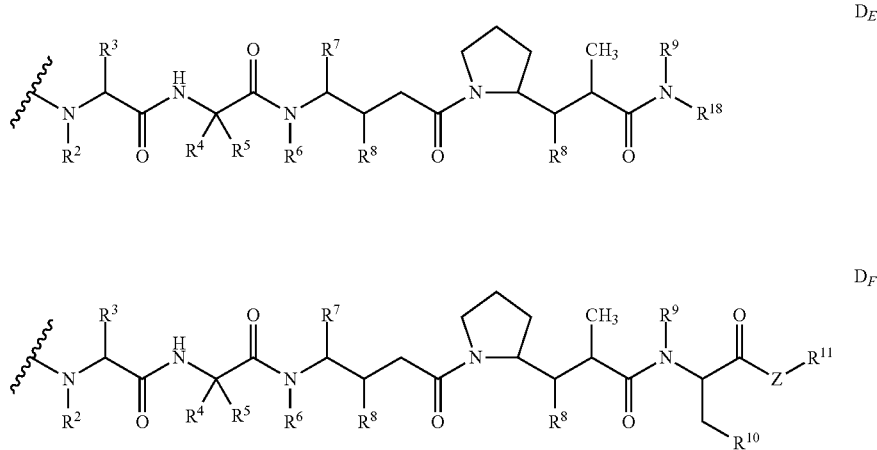

wherein the wavy line of $D_E$ and $D_F$ indicates the covalent attachment site to a hindered linker. Independently at each location: $R^2$ is selected from H and $C_1$-$C_8$ alkyl; $R^3$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle); $R^4$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle); $R^5$ is selected from H and methyl; $R^6$ is selected from H and $C_1$-$C_8$ alkyl; $R^7$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle); each $R^8$ is independently selected from H, OH, $C_1$-$C_8$ alkyl, $C_3$-$C_8$ carbocycle and O—($C_1$-$C_8$ alkyl); $R^9$ is selected from H and $C_1$-$C_8$ alkyl; $R^{10}$ is selected from aryl or $C_3$-$C_8$ heterocycle; Z is O, S, NH, or $NR^{12}$, wherein $R^{12}$ is $C_1$-$C_8$ alkyl; $R^{11}$ is selected from H, $C_1$-$C_{20}$ alkyl, aryl, $C_3$-$C_8$ heterocycle, —$(R^{13}O)_m$—$R^{14}$, or —$(R^{13}O)_m$—$CH(R^{15})_2$; m is an integer ranging from 1-1000; $R^{13}$ is $C_2$-$C_8$ alkyl; $R^{14}$ is H or $C_1$-$C_8$ alkyl; each occurrence of $R^{15}$ is independently H, COOH, —$(CH_2)_n$—$N(R^{16})_2$, —$(CH_2)_n$—$SO_3H$, or —$(CH_2)_n$—$SO_3$—$C_1$-$C_8$ alkyl; each occurrence of $R^{16}$ is independently H, $C_1$-$C_8$ alkyl, or —$(CH_2)_n$—COOH; $R^{18}$ is selected from —$C(R^8)_2$—$C(R^8)_2$-aryl, —$C(R^8)_2$—$C(R^8)_2$—($C_3$-$C_8$ heterocycle), and —$C(R^8)_2$—$C(R^8)_2$—($C_3$-$C_8$ carbocycle); and n is an integer ranging from 0 to 6. Optionally, $R^4$ and $R^5$ jointly form a carbocyclic ring and have the formula —$(CR^aR^b)_n$— wherein $R^a$ and $R^b$ are independently selected from H, $C_1$-$C_8$ alkyl and $C_3$-$C_8$ carbocycle and n is selected from 2, 3, 4, 5 and 6.

In some aspects, $R^3$, $R^4$ and $R^7$ are independently isopropyl or sec-butyl and $R^5$ is —H or methyl. In an exemplary embodiment, $R^3$ and $R^4$ are each isopropyl, $R^5$ is —H, and $R^7$ is sec-butyl. In other aspects, $R^2$ and $R^6$ are each methyl, and $R^9$ is —H. In other aspects, each occurrence of $R^8$ is —$OCH_3$. In other aspects, $R^3$ and $R^4$ are each isopropyl, $R^2$ and $R^6$ are each methyl, $R^5$ is —H, $R^7$ is sec-butyl, each occurrence of $R^8$ is —$OCH_3$, and $R^9$ is —H. In other aspects, Z is —O— or —NH—. In other aspects, $R^{10}$ is aryl. In other aspects, $R^{10}$ is -phenyl. In other aspects, when Z is —O—, $R^{11}$ is —H, methyl or t-butyl. In other aspects, when Z is —NH, $R^{11}$ is —$CH(R^{15})_2$, wherein $R^{15}$ is —$(CH_2)_n$—N$(R^{16})_2$, and $R^{16}$ is —$C_1$-$C_8$ alkyl or —$(CH_2)_n$—COOH. In other aspects, when Z is —NH, $R^{11}$ is —$CH(R^{15})_2$, wherein $R^{15}$ is —$(CH_2)_n$—$SO_3H$.

An exemplary auristatin embodiment of formula $D_E$ is MMAE, wherein the wavy line indicates the covalent attachment to a linker (L) of an antibody-drug conjugate:

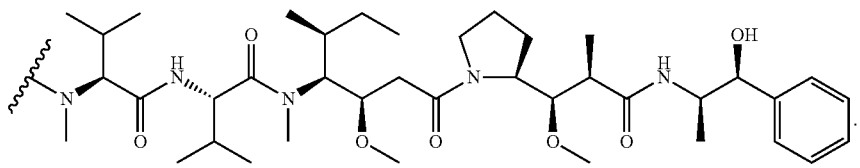

MMAE

An exemplary auristatin embodiment of formula $D_F$ is MMAF, wherein the wavy line indicates the covalent attachment to a linker (L) of an antibody-drug conjugate:

MMAF

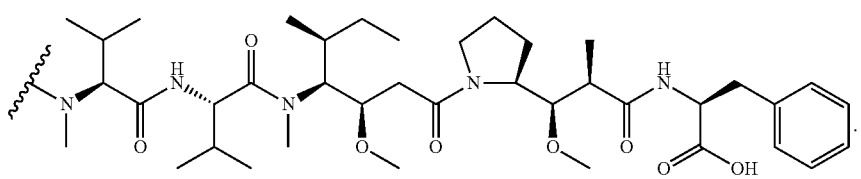

Other exemplary embodiments include monomethylvaline compounds having phenylalanine carboxy modifications at the C-terminus of the pentapeptide auristatin drug moiety (WO 2007/008848) and monomethylvaline compounds having phenylalanine sidechain modifications at the C-terminus of the pentapeptide auristatin drug moiety (WO 2007/008603). Each publication cited in this paragraph is incorporated by reference herein in its entirety.

Typically, peptide-based drug moieties can be prepared by forming a peptide bond between two or more amino acids and/or peptide fragments. Such peptide bonds can be prepared, for example, according to a liquid phase synthesis method (see, e.g., E. Schroder and K. Lübke, "The Peptides", volume 1, pp 76-136, 1965, Academic Press). Auristatin/dolastatin drug moieties may, in some embodiments, be prepared according to the methods of: U.S. Pat. Nos. 7,498,298; 5,635,483; 5,780,588; Pettit et al (1989) *J. Am. Chem. Soc.* 111:5463-5465; Pettit et al (1998) *Anti-Cancer Drug Design* 13:243-277; Pettit, G. R., et al. *Synthesis*, 1996, 719-725; Pettit et al (1996) *J. Chem. Soc. Perkin Trans.* 1 5:859-863; and Doronina (2003) *Nat. Biotechnol.* 21(7):778-784. Each reference cited in this paragraph is incorporated by reference herein in its entirety.

In some embodiments, auristatin/dolastatin drug moieties of formulas $D_E$ such as MMAE, and $D_F$, such as MMAF, and drug-linker intermediates and derivatives thereof, such as MC-MMAF, MC-MMAE, MC-vc-PAB-MMAF, and MC-vc-PAB-MMAE, may be prepared using methods described in U.S. Pat. No. 7,498,298; Doronina et al. (2006) *Bioconjugate Chem.* 17:114-124; and Doronina et al. (2003) *Nat. Biotech.* 21:778-784 and then conjugated to an antibody of interest. Each reference cited in this paragraph is incorporated by reference herein in its entirety.

In some embodiments, the drug is calicheamicin. The calicheamicin family of antibiotics, and analogues thereof, are capable of producing double-stranded DNA breaks at sub-picomolar concentrations (Hinman et al., (1993) *Cancer Research* 53:3336-3342; Lode et al., (1998) *Cancer Research* 58:2925-2928). Calicheamicin has intracellular sites of action but, in certain instances, does not readily cross the plasma membrane. Therefore, cellular uptake of these agents through antibody-mediated internalization may, in some embodiments, greatly enhances their cytotoxic effects. Nonlimiting exemplary methods of preparing antibody-drug conjugates with a calicheamicin drug moiety are described, for example, in U.S. Pat. Nos. 5,712,374; 5,714,586; 5,739,116; and 5,767,285, each of which is incorporated by reference herein in its entirety.

In some aspects, the drug moiety is a calicheamicin compound having the formula:

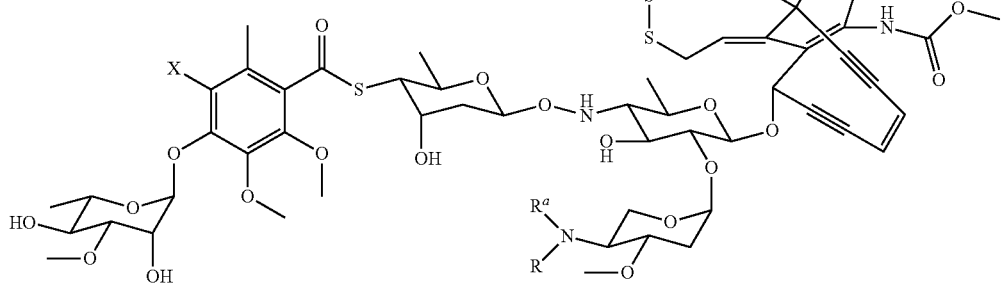

wherein X is Br or I; L is a linker; R is hydrogen, $C_{1-6}$ alkyl, or —C(=O) $C_{1-6}$ alkyl; and $R^a$ is hydrogen or $C_{1-6}$ alkyl. Many positions on calicheamicin compounds are useful as the linkage position. For example, an ester linkage may be formed by reaction with a hydroxyl group using conventional coupling techniques.

In some embodiments, the drug is a pyrrolobenzodiazepine (PBD). In some embodiments, PDB dimers recognize and bind to specific DNA sequences. The natural product anthramycin, a PBD, was first reported in 1965 (Leimgruber, et al., (1965) *J Am. Chem. Soc.*, 87:5793-5795; Leimgruber, et al., (1965) *J. Am. Chem. Soc.*, 87:5791-5793). Since then, a number of PBDs, both naturally-occurring and analogues, have been reported (Thurston, et al., (1994) Chem. Rev. 1994, 433-465 including dimers of the tricyclic PBD scaffold (U.S. Pat. Nos. 6,884,799; 7,049,311; 7,067,511; 7,265,105; 7,511,032; 7,528,126; 7,557,099). Without intending to be bound by any particular theory, it is believed that the dimer structure imparts the appropriate three-dimensional shape for isohelicity with the minor groove of B-form DNA, leading to a snug fit at the binding site (Kohn, In Antibiotics III. Springer-Verlag, New York, pp. 3-11 (1975); Hurley and Needham-VanDevanter, (1986) *Acc. Chem. Res.,* 19:230-

237). Dimeric PBD compounds bearing C2 aryl substituents have been shown to be useful as cytotoxic agents (Hartley et al (2010) *Cancer Res.* 70(17):6849-6858; Antonow (2010) *J. Med. Chem.* 53(7):2927-2941; Howard et al (2009) *Bioorganic and Med. Chem. Letters* 19(22):6463-6466). Each reference cited in this paragraph is incorporated by reference herein in its entirety.

In some embodiments, PBD compounds can be employed as prodrugs by protecting them at the N10 position with a nitrogen protecting group which is removable in vivo (see WO 00/12507 and WO 2005/023814, each of which are incorporated by reference herein in its entirety).

PBD dimers have been conjugated to antibodies and the resulting ADC shown to have anti-cancer properties (US 2010/0203007). Nonlimiting exemplary linkage sites on the PBD dimer include the five-membered pyrrolo ring, the tether between the PBD units, and the N10-C11 imine group (WO 2009/016516; US 2009/304710; US 2010/047257; US 2009/036431; US 2011/0256157; WO 2011/130598). Each reference cited in this paragraph is incorporated by reference herein in its entirety.

In some embodiments, a linker may be attached at one of various sites of the PBD dimer drug moiety, including the N10 imine of the B ring, the C-2 endo/exo position of the C ring, or the tether unit linking the A rings (see structures C(I) and C(II) below).

Nonlimiting exemplary N-10 linked PBD dimer components of ADC are of Formula A:

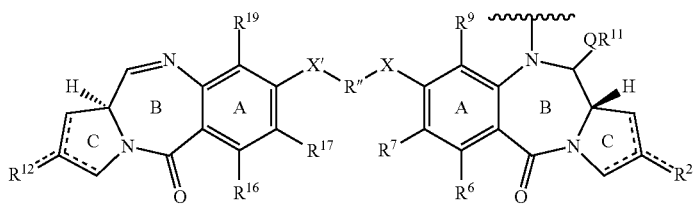

A and salts and solvates thereof, wherein: the wavy line indicates the covalent attachment site to the linker; the dotted lines indicate an optional double bond between C1 and C2 or C2 and C3; $R^2$ is independently selected from H, OH, =O, =CH$_2$, CN, R, OR, =CH—$R^D$, =C($R^D$)$_2$, O—SO$_2$—R, CO$_2$R and COR, and optionally further selected from halo or dihalo, wherein $R^D$ is independently selected from R, CO$_2$R, COR, CHO, CO$_2$H, and halo; $R^6$ and $R^9$ are independently selected from H, R, OH, OR, SH, SR, NH$_2$, NHR, NRR', NO$_2$, Me$_3$Sn and halo; $R^7$ is independently selected from H, R, OH, OR, SH, SR, NH$_2$, NHR, NRR', NO$_2$, Me$_3$Sn and halo; Q is independently selected from O, S and NH; $R^{11}$ is either H, or R or, where Q is O, SO$_3$M, where M is a metal cation; R and R' are each independently selected from optionally substituted C$_{1-8}$ alkyl, C$_{1-12}$ alkyl, C$_{3-8}$ heterocyclyl, C$_{3-20}$ heterocycle, and C$_{5-20}$ aryl groups, and optionally in relation to the group NRR', R and R' together with the nitrogen atom to which they are attached form an optionally substituted 4-, 5-, 6- or 7-membered heterocyclic ring; $R^{12}$, $R^{16}$, $R^{19}$ and $R^{17}$ are as defined for $R^2$, $R^6$, $R^9$ and $R^7$ respectively; $R''$ is a C$_{3-12}$ alkylene group, which chain may be interrupted by one or more heteroatoms, e.g. O, S, N(H), NMe and/or aromatic rings, e.g. benzene or pyridine, which rings are optionally substituted; and X and X' are independently selected from O, S and N(H).

In some aspects, R and R' are each independently selected from optionally substituted C$_{1-12}$ alkyl, C$_{3-20}$ heterocycle, and C$_{5-20}$ aryl groups, and optionally in relation to the group NRR', R and R' together with the nitrogen atom to which they are attached form an optionally substituted 4-, 5-, 6- or 7-membered heterocyclic ring. In some aspects, $R^9$ and $R^{19}$ are H. In some aspects, $R^6$ and $R^{16}$ are H. In some aspects, $R^7$ are $R^{17}$ are both OR$^{7A}$, where $R^{7A}$ is optionally substituted C$_{1-4}$ alkyl. In some embodiments, $R^{7A}$ is Me. In some such aspects $R^{7A}$ is Ch$_2$Ph, where Ph is a phenyl group. In some aspects, X is O. In some aspects, $R^{11}$ is H. In some aspects, there is a double bond between C2 and C3 in each monomer unit.

In some aspects, $R^2$ and $R^{12}$ are independently selected from H and R. In some aspects, $R^2$ and $R^{12}$ are independently R. In some aspects, $R^2$ and $R^{12}$ are independently optionally substituted C$_{5-20}$ aryl or C$_{5-7}$ aryl or C$_{8-10}$ aryl. In some aspects, $R^2$ and $R^{12}$ are independently optionally substituted phenyl, thienyl, napthyl, pyridyl, quinolinyl, or isoquinolinyl. In some aspects, $R^2$ and $R^{12}$ are independently selected from =O, =CH$_2$, =CH—$R^D$, and =C($R^D$)$_2$. In some aspects, $R^2$ and $R^{12}$ are each =CH$_2$. In some aspects, $R^2$ and $R^{12}$ are each H. In some aspects, $R^2$ and $R^{12}$ are each =O. In some aspects, $R^2$ and $R^{12}$ are each =CF$_2$. In some aspects, $R^2$ and/or $R^{12}$ are independently =C($R^D$)$_2$. In some aspects, $R^2$ and/or $R^{12}$ are independently =CH—$R^D$.

In some aspects, when $R^2$ and/or $R^{12}$ is =CH—$R^D$, each group may independently have either configuration shown below:

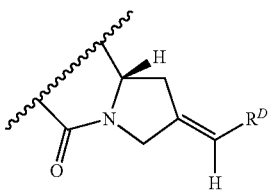

(I)

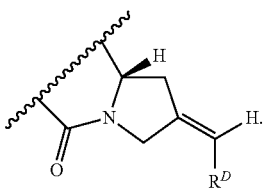

(II)

In some such aspects, a =CH—$R^D$ is in configuration (I). In some aspects, $R''$ is a C$_3$ alkylene group or a C$_5$ alkylene group.

In some aspects, an exemplary PBD dimer component of an ADC has the structure of Formula A-1:

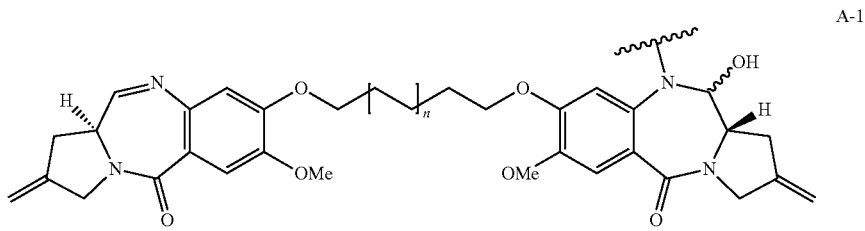

A-1 wherein n is 0 or 1.

In some aspects, an exemplary PBD dimer component of an ADC has the structure of Formula A-2:

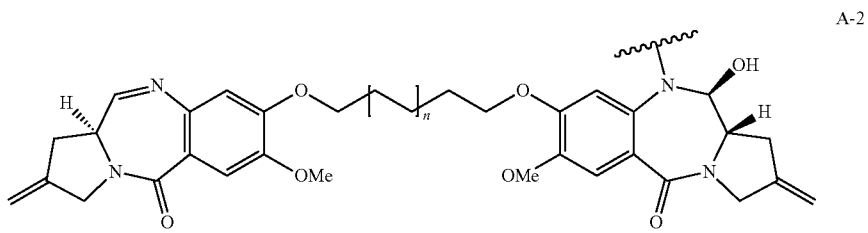

A-2 wherein n is 0 or 1.

In some aspects, an exemplary PBD dimer component of an ADC has the structure of Formula A-3:

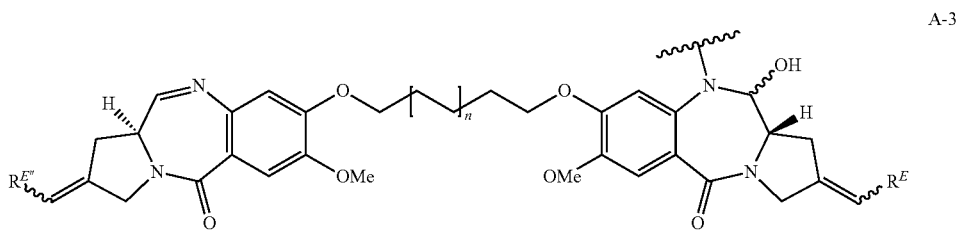

A-3 wherein $R^E$ and $R^{E''}$ are each independently selected from H or $R^D$, wherein $R^D$ is defined as above; and wherein n is 0 or 1. In some such aspects, n is 0. In some aspects, n is 1. In some aspects, $R^E$ and/or $R^{E''}$ is H. In some aspects, $R^E$ and $R^{E''}$ are H. In some aspects, $R^E$ and/or $R^{E''}$ is $R^D$, wherein $R^D$ is optionally substituted $C_{1-12}$ alkyl. In some aspects, $R^E$ and/or $R^{E''}$ is $R^D$, wherein $R^D$ is methyl.

In some aspects, an exemplary PBD dimer component of an ADC has the structure of Formula A-4:

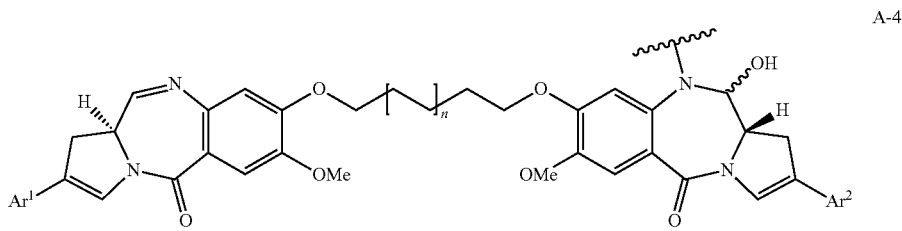

A-4 wherein Ar¹ and Ar² are each independently optionally substituted $C_{5-20}$ aryl; wherein Ar¹ and Ar² may be the same or different; and wherein n is 0 or 1.

In some aspects, an exemplary PBD dimer component of an ADC has the structure of Formula A-5:

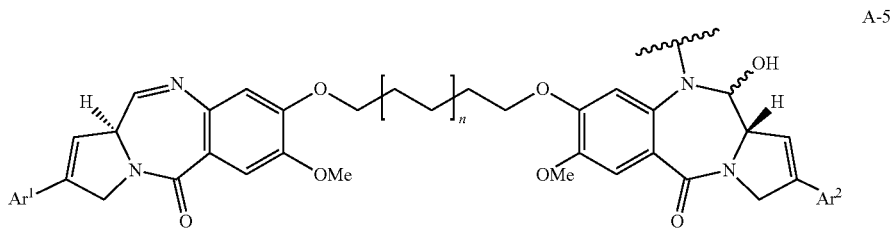

A-5 wherein Ar¹ and Ar² are each independently optionally substituted $C_{5-20}$ aryl; wherein Ar¹ and Ar² may be the same or different; and wherein n is 0 or 1.

In some aspects, Ar¹ and Ar² are each independently selected from optionally substituted phenyl, furanyl, thiophenyl and pyridyl. In some aspects, Ar¹ and Ar² are each independently optionally substituted phenyl. In some aspects, Ar¹ and Ar² are each independently optionally substituted thien-2-yl or thien-3-yl. In some embodiments, Ar¹ and Ar² are each independently optionally substituted quinolinyl or isoquinolinyl. The quinolinyl or isoquinolinyl group may be bound to the PBD core through any available ring position. For example, the quinolinyl may be quinolin-2-yl, quinolin-3-yl, quinolin-4yl, quinolin-5-yl, quinolin-6-yl, quinolin-7-yl and quinolin-8-yl. In some aspects, the quinolinyl is selected from quinolin-3-yl and quinolin-6-yl. The isoquinolinyl may be isoquinolin-1-yl, isoquinolin-3-yl, isoquinolin-4yl, isoquinolin-5-yl, isoquinolin-6-yl, isoquinolin-7-yl and isoquinolin-8-yl. In some embodiments, the isoquinolinyl is selected from isoquinolin-3-yl and isoquinolin-6-yl.

In some aspects, an exemplary PBD dimer component of an ADC has the structure of Formula A-6:

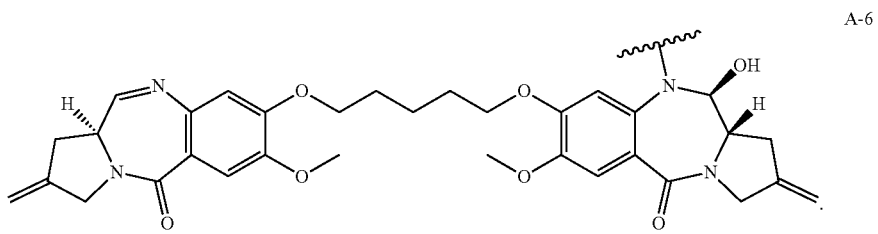

A-6

Further nonlimiting exemplary PBD dimer drug components are of Formula B:

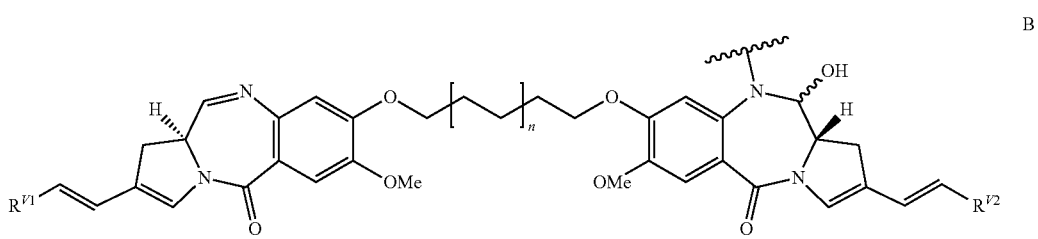

B and salts and solvates thereof wherein the wavy line indicates the covalent attachment site to the linker, and wherein the OH moiety illustrated with a wavy line indicates the S or R configuration. $R^{V1}$ and $R^{V2}$ are independently selected from H, methyl, ethyl and phenyl (which phenyl may be optionally substituted with fluoro, particularly in the 4 position) and $C_{5-6}$ heterocyclyl; wherein $R^{V1}$ and $R^{V2}$ may be the same or different. n is 0 or 1.

Other nonlimiting exemplary PBD dimer drugs include tether-linked Formulas C(I) and C(II):

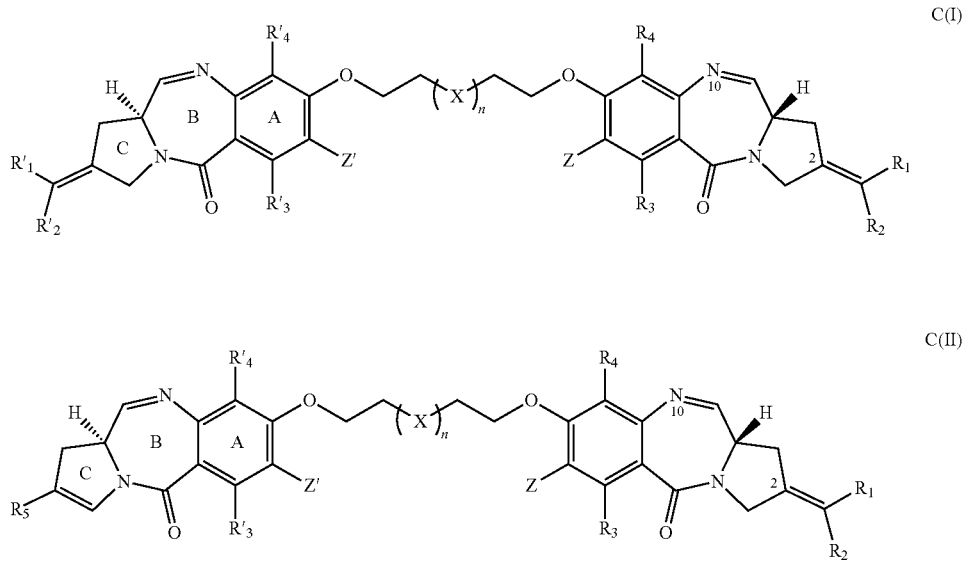

Formulae C(I) and C(II) are are shown in their N10-C11 imine form.

Exemplary PBD drug moieties also include the carbinolamine and protected carbinolamine forms as well, as shown in the table below wherein the indicated from in the table refers to one or both of the seven-membered rings in the structure C(II) PBD illustrated above:

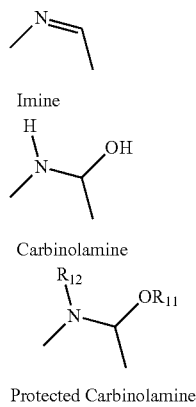

Imine

Carbinolamine

Protected Carbinolamine wherein: X is $CH_2$ (n=1 to 5), N, or O; Z and Z' are independently selected from OR and $NR_2$, where R is a primary, secondary or tertiary alkyl chain containing 1 to 5 carbon atoms; $R_1$, $R'_1$, $R_2$ and $R'_2$ are each independently selected from H, $C_1$-$C_8$ alkyl, $C_2$-$C_8$ alkenyl, $C_2$-$C_8$ alkynyl, $C_{5-20}$ aryl (including substituted aryls), $C_{5-20}$ heteroaryl groups, $-NH_2$, $-NHMe$, $-OH$, and $-SH$, where, in some embodiments, alkyl, alkenyl and alkynyl chains comprise up to 5 carbon atoms; $R_3$ and $R'_3$ are independently selected from H, OR, NHR, and $NR_2$, where R is a primary, secondary or tertiary alkyl chain containing 1 to 5 carbon atoms; $R_4$ and $R'_4$ are independently selected from H, Me, and OMe; $R_5$ is selected from $C_1$-$C_8$ alkyl, $C_2$-$C_8$ alkenyl, $C_2$-$C_8$ alkynyl, $C_{5-20}$ aryl (including aryls substituted by halo, nitro, cyano, alkoxy, alkyl, heterocyclyl) and $C_{5-20}$ heteroaryl groups, where, in some embodiments, alkyl, alkenyl and alkynyl chains comprise up to 5 carbon atoms; $R_{11}$ is H, $C_1$-$C_8$ alkyl, or a protecting group (such as acetyl, trifluoroacetyl, t-butoxycarbonyl (BOC), benzyloxycarbonyl (CBZ), 9-fluorenylmethylenoxycarbonyl (Fmoc), or a moiety comprising a self-immolating unit such as valine-citrulline-PAB); $R_{12}$ is H, $C_1$-$C_8$ alkyl, or a protecting group; and wherein a hydrogen of one of $R_1$, $R'_1$, $R_2$, $R'_2$, $R_5$, or $R_{12}$ or a hydrogen of the $-OCH_2CH_2(X)_nCH_2CH_2O-$ spacer between the A rings is replaced with a bond connected to the linker of the ADC.

In some embodiments, a conjugate comprising a PBD dimer described herein may be made by conjugating a linker-drug intermediate including a leaving group (as described elsewhere herein) via a sulfur atom with a cysteine thiol of a carrier (as described elsewhere herein) to form a disulfide linkage. Further, in some embodiments, a conjugate comprising a PBD dimer described herein may be made by conjugating a linker-drug intermediate including a leaving group (as described elsewhere herein). In some particular aspects, the leaving group comprises a pyridyl ring monosubstituted with $-NO_2$. In some such aspects, the $-NO_2$ monosubstitution is para relative to the disulfide. In some aspects, the PBD dimer is connected through the N10 position. For example, an exemplary ADC comprising a PBD dimer may be made by conjugating a monomethylethyl pyridyl disulfide, N10-linked PBD linker intermediate (shown below) to a carrier (e.g., an antibody):

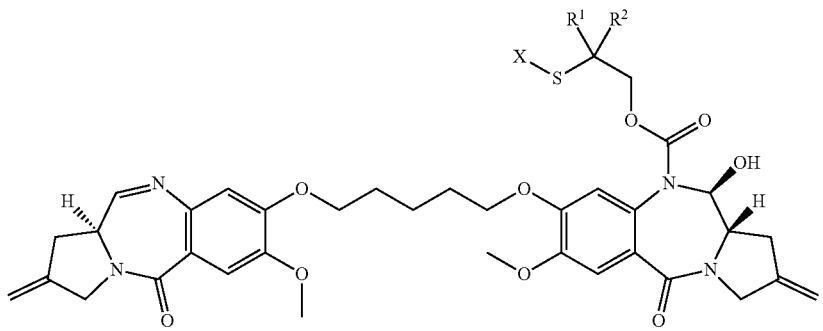

wherein X, R¹ and R² are as defined elsewhere herein. A non-limiting example of R¹ is CH₃, a non-limiting example of R² is H, and non-limiting examples of X are below as described elsewhere herein:

Leaving Group 1

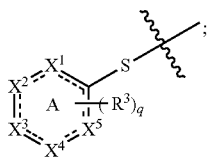

Leaving Group 2

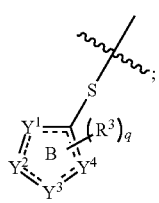

Leaving Group 3

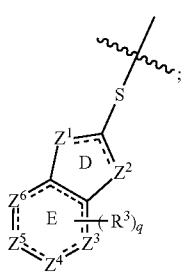

Leaving Group 4

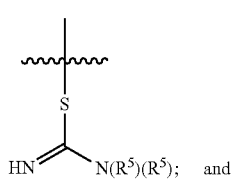

Leaving Group 5

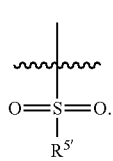

PBD dimers and ADCs comprising PBD dimers may be prepared according to methods known in the art. See, e.g., WO 2009/016516; US 2009/304710; US 2010/047257; US 2009/036431; US 2011/0256157; WO 2011/130598; WO 2013/055987, each of which is incorporated by reference herein in its entirety.

In some embodiments, the drug is an anthracycline. Anthracyclines are antibiotic compounds that exhibit cytotoxic activity. While not intending to be bound by any particular theory, studies have indicated that anthracyclines may operate to kill cells by a number of different mechanisms, including: 1) intercalation of the drug molecules into the DNA of the cell thereby inhibiting DNA-dependent nucleic acid synthesis; 2) production by the drug of free radicals which then react with cellular macromolecules to cause damage to the cells, and/or 3) interactions of the drug molecules with the cell membrane (see, e.g., C. Peterson et al., "Transport And Storage Of Anthracycline In Experimental Systems And Human Leukemia" in Anthracycline Antibiotics In Cancer Therapy; N. R. Bachur, "Free Radical Damage" id. at pp. 97-102). Because of their cytotoxic potential anthracyclines have been used in the treatment of numerous cancers such as leukemia, breast carcinoma, lung carcinoma, ovarian adenocarcinoma and sarcomas (see e.g., P. H-Wiernik, in Anthracycline: Current Status And New Developments p 11).

Nonlimiting exemplary anthracyclines include doxorubicin, epirubicin, idarubicin, daunomycin, nemorubicin, and derivatives thereof. Immunoconjugates and prodrugs of daunorubicin and doxorubicin have been prepared and studied (Kratz et al (2006) Current Med. Chem. 13:477-523; Jeffrey et al (2006) Bioorganic & Med. Chem. Letters 16:358-362; Torgov et al (2005) Bioconj. Chem. 16:717-721; Nagy et al (2000) Proc. Natl. Acad. Sci. USA 97:829-834; Dubowchik et al (2002) Bioorg. & Med. Chem. Letters 12:1529-1532; King et al (2002) J Med. Chem. 45:4336-4343; EP 0328147; U.S. Pat. No. 6,630,579). The antibody-drug conjugate BR96-doxorubicin reacts specifically with the tumor-associated antigen Lewis-Y and has been evaluated in phase I and II studies (Saleh et al (2000) J. Clin. Oncology 18:2282-2292; Ajani et al (2000) Cancer Jour. 6:78-81; Tolcher et al (1999) J. Clin. Oncology 17:478-484). Each reference cited in this paragraph is incorporated by reference herein in its entirety.

PNU-159682 is a potent metabolite (or derivative) of nemorubicin (Quintieri, et al. (2005) Clinical Cancer Research 11(4):1608-1617). Nemorubicin is a semisynthetic analog of doxorubicin with a 2-methoxymorpholino group on the glycoside amino of doxorubicin and has been under clinical evaluation (Grandi et al (1990) Cancer Treat. Rev. 17:133; Ripamonti et al (1992) Brit. J. Cancer 65:703), including phase II/III trials for hepatocellular carcinoma (Sun et al (2003) Proceedings of the American Society for Clinical Oncology 22, Abs1448; Quintieri (2003) Proceedings of the American Association of Cancer Research, 44:1st Ed, Abs 4649; Pacciarini et al (2006) Jour. Clin. Oncology 24:14116). Each reference cited in this paragraph is incorporated by reference herein in its entirety.

Anthracyclines, including PNU-159682, may be conjugated to antibodies through several linkage sites and a variety of linkers (see US 2011/0076287, WO2009/099741, US 2010/0034837 and WO 2010/009124, each of which is incorporated by reference herein in its entirety), including the linkers described herein. For example, an ester linkage may be formed by reaction with a hydroxyl group using conventional coupling techniques.

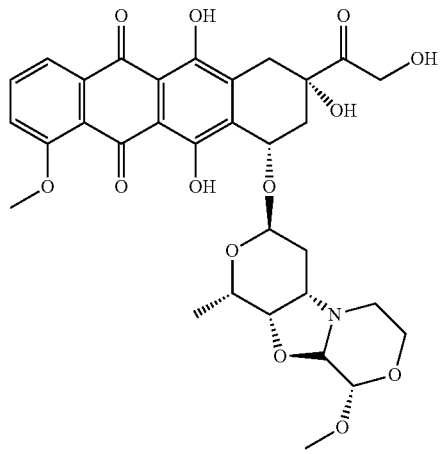

In some embodiments, the drug is 1-(chloromethyl)-2,3-dihydro-1H-benzo[e]indole (CBI). The 5-amino-1-(chloromethyl)-1,2-dihydro-3H-benz[e]indole (amino CBI) class of DNA minor groove alkylators are potent cytotoxins (Atwell, et al (1999) J. Med. Chem., 42:3400), and have been utilized as effector units in a number of classes of prodrugs designed for cancer therapy. These have included antibody conjugates, (Jeffrey, et al. (2005) J. Med. Chem., 48:1344), prodrugs for gene therapy based on nitrobenzyl carbamates (Hay, et al (2003) J. Med. Chem. 46:2456) and the corresponding nitro-CBI derivatives as hypoxia-activated prodrugs (Tercel, et al (2011) Angew. Chem., Int. Ed., 50:2606-2609). The CBI and pyrrolo[2,1-c][1,4]benzodiazepine (PBD) pharmacophores have been linked together by an alkyl chain (Tercel et al (2003) J. Med. Chem 46:2132-2151). Each reference cited in this paragraph is incorporated by reference herein in its entirety.

In some aspects the drug is a 1-(chloromethyl)-2,3-dihydro-1H-benzo[e]indole (CBI) dimer (WO 2015/023355, incorporated by reference herein in its entirety). In some such embodiments, the dimer is a heterodimer wherein one half of the dimer is a CBI moiety and the other half of the dimer is a PBD moiety.

In some aspects, a CBI dimer comprises the formula:

wherein: $R^{41}$ is selected from H, $P(O)_3H_2$, $C(O)NR^aR^b$, or a bond to a linker (L); $R^{42}$ is selected from H, $P(O)_3H_2$, $C(O)NR^aR^b$, or a bond to a linker (L); $R^a$ and $R^b$ are independently selected from H and $C_1$-$C_6$ alkyl optionally substituted with one or more F, or $R^a$ and $R^b$ form a five or six membered heterocyclyl group; T is a tether group selected from $C_3$-$C_{12}$ alkylene, Y, ($C_1$-$C_6$ alkylene)-Y—($C_1$-$C_6$ alkylene), ($C_1$-$C_6$ alkylene)-Y—($C_1$-$C_6$ alkylene)-Y—($C_1$-$C_6$ alkylene), ($C_2$-$C_6$ alkenylene)-Y—($C_2$-$C_6$ alkenylene), and ($C_2$-$C_6$ alkynylene)-Y—($C_2$-$C_6$ alkynylene); Y is independently selected from O, S, $NR^{41}$, aryl, and heteroaryl; alkylene, alkenylene, aryl, and heteroaryl are independently and optionally substituted with F, OH, O($C_1$-$C_6$ alkyl), $NH_2$, $NHCH_3$, $N(CH_3)_2$, $OP(O)_3H_2$, and $C_1$-$C_6$ alkyl, where alkyl is optionally substituted with one or more F; or alkylene, alkenylene, aryl, and heteroaryl are independently and optionally substituted with a bond to L. D' is a drug moiety selected from:

wherein: the wavy line indicates the site of attachment to T; $X^1$ and $X^2$ are independently selected from O and $NR^{43}$, where $R^{43}$ is selected from H and $C_1$-$C_6$ alkyl optionally substituted with one or more F; $R^{44}$ is H, $CO_2R$, or a bond to a linker (L), where R is $C_1$-$C_6$ alkyl or benzyl; and $R^{45}$ is H or $C_1$-$C_6$ alkyl. Conjugation to the linker is as described elsewhere herein in connection with PBD.

In some embodiments, the drug is an amatoxin. Amatoxins are cyclic peptides composed of 8 amino acids and can be isolated from *Amanita phalloides* mushrooms or prepared synthetically. Amatoxins specifically inhibit the DNA-dependent RNA polymerase II of mammalian cells, and thereby also the transcription and protein biosynthesis of the affected cells. Inhibition of transcription in a cell causes stop of growth and proliferation. See e.g., Moldenhauer et al. JNCI 104:1-13 (2012), WO2010115629, WO2012041504, WO2012119787, WO2014043403, WO2014135282, and WO2012119787, each of which incorporated herein in its entirety. In some embodiments, the one or more amatoxin molecules are one or more α-amanitin molecules.

Other drug moieties within the scope of the present disclosure include geldanamycin (Mandler et al (2000) *J. Nat. Cancer Inst.* 92(19):1573-1581; Mandler et al (2000) *Bioorganic & Med. Chem. Letters* 10:1025-1028; Mandler et al (2002) *Bioconjugate Chem.* 13:786-791); and enzymatically active toxins and fragments thereof, including, but not limited to, diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. See, e.g., WO 93/21232. Each reference cited in this paragraph is incorporated by reference herein in its entirety.

Yet further drug moieties include cyclopropane dolines, analogs thereof, derivatives thereof and/or stereoisomers thereof (see, e.g., US 2012/0165292, incorporated herein by reference in its entirety).

Other drug moieties include cyclopropylbenzindoles (CBI), analogs thereof, derivatives thereof and/or stereoisomers thereof (see, e.g., U.S. Pat. Nos. 5,585,499 and 5,846,545, each of which is incorporated herein by reference in its entirety).

Other drug moieties include elinafides, analogs thereof, derivatives thereof and/or stereoisomers thereof (see, e.g., Bailly, C; Brana, M. F.; Waring, M. J. Eur. J. Biochem. 1996, 240, 195.; Brana, M. F.; Castellano, J. M.; Mora, M.; Vega, M. J. P; Romerdahl, C. R.; Qian, X. D.; Bousquet, P.; Emling, F.; Schlick, R; Keilhauer, G. Anticancer Drug Des. 1993, 8, 257.; Brana, M. F.; Castellano, I M.; Mora, M.; Vega, M. J. P; Perron, D.; Conlon, D.; Bousquet, P. F.; Romerdahl, C. A.; Robinson, S. P. Anticancer Drug Des. 1996, 11, 297; Thompson, J.; Pratt, C. B.; Stewart, C. F.; Bowman, L.; Zamboni, W. C; Pappo, A. InVest. New Drugs 1998, 16, 45, each of which is incorporated herein by reference in its entirety).

Drug moieties also include compounds with nucleolytic activity (e.g., a ribonuclease or a DNA endonuclease). It is to be understood that where more than one nucleophilic group reacts with a drug-linker intermediate or linker reagent, then the resulting product is a mixture of ADC compounds with a distribution of one or more drug moieties attached to an antibody. The average number of drugs per antibody (DAR) may be calculated from the mixture by a dual ELISA antibody assay, which is specific for antibody and specific for the drug. Individual ADC molecules may be identified in the mixture by mass spectroscopy and separated by HPLC, e.g. hydrophobic interaction chromatography (see, e.g., McDonagh et al (2006) *Prot. Engr. Design & Selection* 19(7):299-307; Hamblett et al (2004) *Clin. Cancer Res.* 10:7063-7070; Hamblett, K. J., et al. "Effect of drug loading on the pharmacology, pharmacokinetics, and toxicity of an anti-CD30 antibody-drug conjugate," Abstract No. 624, American Association for Cancer Research, 2004 Annual Meeting, Mar. 27-31, 2004, Proceedings of the AACR, Volume 45, March 2004; Alley, S. C., et al. "Controlling the location of drug attachment in antibody-drug conjugates," Abstract No. 627, American Association for Cancer Research, 2004 Annual Meeting, Mar. 27-31, 2004, Proceedings of the AACR, Volume 45, March 2004). In certain embodiments, a homogeneous ADC with a single loading value may be isolated from the conjugation mixture by electrophoresis or chromatography. Each reference cited in this paragraph is incorporated by reference herein in its entirety.

Linker-Drug Conjugation

Conjugation of the linker to a drug amine may suitably be done according to the methods of WO 2013/055987, WO 2015/023355, WO 2010/009124 and WO 2015/095227, each of which is incorporated by reference herein in its entirety. In some such aspects, the activated linker as described elsewhere herein is combined with a solution of a drug to form a linker-drug conjugate. Generally, any solvent capable of providing a solution comprising from about 0.05 to about 1 mole per liter drug is suitable. In some aspects, the solvent is DCM. In some other linker-drug conjugation aspects, a solution of the drug, a stoichiometric excess of triphosgene (or diphosgene or phosgene), a base (e.g., 4-dimethylaminopyridine) is formed in a solvent (e.g., dry DCM). The linker intermediate having an alcohol moiety (as described elsewhere herein) is combined with the drug solution to form a reaction mixture that is stirred until the reaction is complete to form a product mixture comprising the linker-drug conjugate. The reaction mixture may suitably comprise from about drug concentration is suitably from about 0.005 moles per liter to about 0.5 moles per liter of the drug, from about 2 to about 10 equivalents of linker intermediate per equivalent of drug, from about 0.02 to about 0.5 equivalents of base. After reaction completion, the linker-drug conjugate may be isolated, such as by solvent evaporation, and purified by methods known in the art such as one or more of extraction, reverse phase high pressure liquid chromatography, ion exchange chromatography or flash chromatography.

In aspects of the disclosure wherein the drug comprises an aliphatic alcohol, the drug-linker conjugates of the present disclosure are ethers of the following general structure:

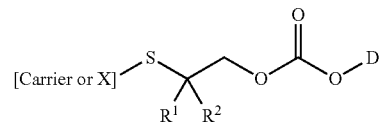

wherein the Carrier, X, $R^1$, $R^2$ and D are as defined elsewhere herein.

In some aspects of the disclosure, the hindered linking group-drug conjugate further may further comprise a spacer comprising para-amino benzyl alcohol as illustrated below thereby forming a linking group-spacer-drug conjugate:

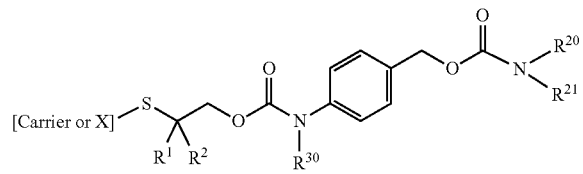

wherein the Carrier, X, $R^1$, $R^2$ and $R^{30}$ are as defined elsewhere herein, $R^{20}$ is a drug alkyl moiety and $R^{21}$ is optionally H or substituted alkyl.

Preparation of Disulfide Conjugate Compounds

In some embodiments, disulfide conjugate compounds of the disclosure of structure (II)

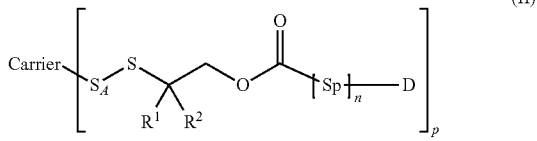

may be prepared by forming a reaction mixture comprising (1) a solvent system comprising water, (2) a source of a carrier comprising at least one cysteine having a sulfhydryl moiety, and (3) a stoichiometric excess of a source of a linker-drug conjugate of structure (I)

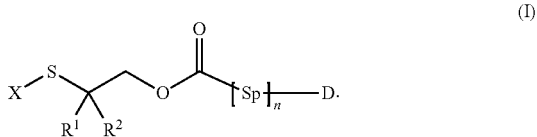

The carrier, X, $R^1$, $R^2$, $S_A$, Sp, n and D are as described elsewhere herein. The reaction mixture is reacted to form a reaction mixture comprising the disulfide conjugate compound of structure (II) wherein p is 1, 2, 3, 4, 5, 6, 7 or 8. Although the individual disulfide conjugate compounds in a mixture may have a p value of from 1 to 8, and some carrier molecules in such a mixture may be unconjugated (p=0), the drug to carrier ratio for a plurality of formed disulfide conjugate compounds in the product mixture, expressed as the ratio of drug equivalents to carrier equivalents, is from about 1 to about 5, from about 1.5 to about 3, from about 1.5 to about 2.5, from about 1.7 to about 2.3, from about 1.8 to about 2.2, or about 2.

In any of the various aspects of such embodiments, the source of the carrier may be provided in solution in an aqueous buffer. In some such aspects, the buffer may suitably be N-(2-Acetamido)-aminoethanesulfonic acid ("ACES"); acetate salt; N-(2-Acetamido)-iminodiacetic acid ("ADA"); 2-Aminoethanesulfonic acid, Taurine ("AES"); 2-Amino-2-methyl-1-propanol ("AMP"); 2-Amino-2-methyl-1,3-propanediol, Ammediol ("AMPD"); N-(1,1-Dimethyl-2-hydroxyethyl)-3-amino-2-hydroxypropanesulfonic acid ("AMPSO"); N,N-Bis-(2-hydroxyethyl)-2-aminoethanesulfonic acid ("BES"); N,N'-Bis(2-hydroxyethyl)-glycine ("Bicine"); [Bis-(2-hydroxyethyl)-imino]-tris-(hydroxymethylmethane) ("BIS-Tris"); 1,3-Bis[tris(hydroxymethyl)-methylamino]propane ("BIS-Tris-Propane"); Dimethylarsinic acid ("Cacodylate"); 3-(Cyclohexylamino)-2-hydroxy-1-propanesulfonic acid ("CAPSO"); Cyclohexylaminoethanesulfonic acid ("CHES"); citric acid salt; 3-[N-Bis(hydroxyethyl)amino]-2-hydroxypropanesulfonic acid ("DIPSO"); N-(2-Hydroxyethyl)-piperazine-N'-ethanesulfonic acid ("HEPES"); N-(2-Hydroxyethyl)-piperazine-N'-3-propanesulfonic acid ("HEPPS, EPPS"); N-(2-Hydroxyethyl)-piperazine-N'-2-hydroxypropanesulfonic acid ("HEPPSO"); 2-(N-Morpholino)-ethanesulfonic acid ("MES"); 3-(N-Morpholino)-propanesulfonic acid ("MOPS"); 3-(N-Morpholino)-2-hydroxypropanesulfonic acid ("MOPSO"); Piperazine-N,N'-bis(2-ethanesulfonic acid) ("PIPES"); Piperazine-N,N'-bis(2-hydroxypropanesulfonic acid) ("POPSO"); salt of succinic acid; 3-{[Tris(hydroxymethyl)-methyl]-amino}-propanesulfonic acid ("TAPS"); 3-[N-Tris(hydroxymethyl)-methylamino]-2-hydroxypropanesulfonic acid ("TAPSO"); 2-Aminoethanesulfonic acid, AES ("Taurine"); Triethanolamine ("TEA"); 2-[Tris(hydroxymethyl)-methylamino]-ethanesulfonic acid ("TES"); N-[Tris(hydroxymethyl)-methyl]-glycine ("Tricine"); Tris(hydroxymethyl)-aminomethane ("TRIS"). In some such aspects, the buffer may be succinate or tris. The buffer concentration is suitably about 5 mM, about 10 mM, about 15 mM, about 20 mM, about 50 mM, about 100 mM, or about 150 nM, such as from about 5 mM to about 150 mM, from about 5 mM to about 30 mM, from about 5 mM to about 20 mM, from about 5 mM to about 10 mM, or from about 50 mM to about 100 nM. The concentration of the carrier in the buffer may be about 1 mg/mL, about 5 mg/mL, about 10 mg/mL or more. The pH of the carrier solution is suitably from about 4 to about 8, from about 4 to about 6, or about 5.

In any of the various aspects of such embodiments, the source of a linker-drug conjugate compound ("activated linker-drug conjugate") may generally be formed by dissolving an activated hindered linker-drug conjugate in a solvent comprising at least one polar aprotic solvent selected from acetonitrile, tetrahydrofuran, ethyl acetate, acetone, N,N-dimethylformamide, dimethyl acetamide, dimethylsulfoxide, propylene glycol, ethylene glycol and dichloromethane. In some aspects, the solvent comprises, predominantly comprises, or consists essentially of N,N-dimethylformamide and/or dimethyl acetamide.

The source of the carrier and the source of the activated linker-drug conjugate may suitably be admixed to form a reaction mixture. The carrier concentration in the reaction mixture is suitably about 1 mg/mL, about 5 mg/mL, about 10 mg/mL, about 15 mg/mL, about 20 mg/mL, or about 25 mg/mL, and ranges thereof, such as from about 1 mg/mL to about 25 mg/mL, from about 1 mg/mL to about 20 mg/mL, from about 1 mg/mL to about 15 mg/mL, from about 1 mg/mL to about 10 mg/mL, from about 5 mg/mL to about 25 mg/mL, from about 5 mg/mL to about 20 mg/mL or from about 5 mg/mL to about 15 mg/mL. The equivalent ratio of activated linker-drug conjugate to the carrier is suitably about 2:1, about 3:1, about 5:1, about 10:1, about 15:1 or about 20:1, and ranges thereof, such as from about 2:1 to about 20:1, from about 3:1 to about 15:1, from about 3:1 to about 10:1, or from about 5:1 to about 10:1. In some aspects of the present disclosure, the reaction mixture solvent system predominantly comprises water. In some other aspects, the reaction mixture solvent system may generally comprise at least 75 v/v % of a buffer as described elsewhere herein and about 5 v/v %, about 10 v/v %, about 15 v/v %, about 20 v/v %, about 25 v/v % or about 30 v/v %, and ranges thereof, such as from about 5 v/v % to about 30 v/v %, from about 5 v/v % to about 20 v/v %, from about 5 v/v % to about 15 v/v %, or about 10 v/v % of a polar aprotic solvent as described elsewhere herein. In some other aspects, the reaction mixture solvent system may generally comprise at least 50 v/v % of a buffer as described elsewhere herein and between about 10 v/v % and about 50 v/v %, such as about 10 v/v %, about 20 v/v %, about 30 v/v % about 40 v/v % or above 50 v/v % propylene glycol or ethylene glycol. Alternatively stated, the reaction mixture solvent system may comprise, about 50 v/v %, about 60 v/v %, about 70 v/v %, 75 v/v %, about 80 v/v %, about 85 v/v %, about 90 v/v % or about 95 v/v % water to about 95 v/v %, and ranges thereof, such as from about 50 v/v % to about 95 v/v % water, from about 75 v/v % to about 95 v/v % water, from about 80 v/v % to about 95 v/v % water or from about 85 v/v % to about 95 v/v % water. The pH of the reaction mixture is suitably about 5.0, about 5.5, about 6.0, about 6.5, about 7.0, about 7.5, about 8.0, about 8.5 or about 9.0, and ranges thereof, such as from about 5.0 to about 9.0, from about 5.0 to about 9.0, from about 6.0 to about 9.0, from about 6.5 to about 9.0, or from about 7.0 to about 9.0, or from about 7.5 to about 8.5.

The reaction mixture is incubated at about 10° C., about 15° C., about 20° C., about 25° C., about 30° C., about 35° C., about 40° C., about 45° C. or about 50° C., and ranges thereof such as from about 10° C. to about 50° C., from about 15° C. to about 45° C., from about 15° C. to about 40° C., from about 20° C. to about 40° C., from about 20° C. to about 35° C., or from about 20° C. to about 30° C. for about 0.5 hours, about 1 hour, about 4 hours, about 8 hours, about 12 hours, about 18 hours about 24 hours, about 36 hours or about 48 hours, and ranges thereof, such as from about 0.5 hours to about 48 hours, or from about 1 hour to about 24 hours to form a product mixture comprising the disulfide conjugate compound of structure (II).

The product mixture may comprise at least 60 A % carrier-linker-drug conjugate as determined by MS/LC, at least 65 area %, at least 70 area %, at least 75 area %, at least 80 area %, at least 85 area %, or at least 90 area %. The product mixture may further comprise at least one leaving group byproduct species. In some aspects, the area percentage of total leaving group byproduct species as compared to the area percentage of formed disulfide conjugate compound as measured by MS/LC is less than 10 area %, less than 5 area %, less than 4 area %, less than 3 area %, less than 2 area %, less than 1 area %, less than 0.5 area %. In the case of antibody carrier groups, and based on experimental evidence to date, the leaving group byproduct species may comprise:

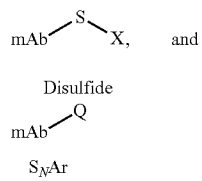

wherein X is as defined elsewhere herein and wherein Q refers to an X moiety not having a sulfur linking atom. Exemplary X and corresponding Q are illustrated below:

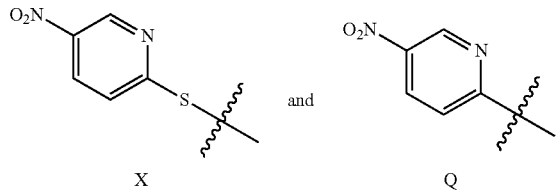

The reaction mixture may further comprise unconjugated carrier compounds comprising (i) unconjugated carrier monomer species comprising at least one disulfide bond formed by the reaction of two cysteine sulfhydryl moieties, (ii) unconjugated carrier dimer species comprising at least one disulfide bond formed by the reaction of two cysteine sulfhydryl moieties, and (iii) a combination of unconjugated carrier monomer species and unconjugated carrier dimer species. In some aspects, the total concentration of unconjugated carrier compounds compared to the area percentage of formed disulfide conjugate compounds as measured by MS/LC is less than 10 area %, less than 5 area %, less than 4 area %, less than 3 area %, less than 2 area %, less than 1 area %, less than 0.5 area %, less than 0.3 area %, less than 0.1 area %, or is not detectable.

Disulfide Conjugate Methods of Treatment

It is contemplated that the disulfide conjugate compounds of the present disclosure may be used to treat various diseases or disorders, e.g. characterized by the overexpression of a tumor antigen. Exemplary conditions or hyperproliferative disorders include benign or malignant solid tumors and hematological disorders such as leukemia and lymphoid malignancies. Others include neuronal, glial, astrocytal, hypothalamic, glandular, macrophagal, epithelial, stromal, blastocoelic, inflammatory, angiogenic and immunologic, including autoimmune, disorders.

In one aspect, a disulfide conjugate compound provided herein is used in a method of inhibiting proliferation of a cancer cell, the method comprising exposing the cell to the antibody-drug conjugate under conditions permissive for binding of the antibody or antibody-drug conjugates to a tumor-associated antigen on the surface of the cell, thereby inhibiting the proliferation of the cell. In certain embodiments, the method is an in vitro or an in vivo method. In further embodiments, the cell is a lymphocyte, lymphoblast, monocyte, or myelomonocyte cell.

Inhibition of cell proliferation in vitro may be assayed using the CellTiter-Glo™ Luminescent Cell Viability Assay, which is commercially available from Promega (Madison, Wis.). That assay determines the number of viable cells in culture based on quantitation of ATP present, which is an indication of metabolically active cells. See Crouch et al. (1993) *J. Immunol. Meth.* 160:81-88, U.S. Pat. No. 6,602,677. The assay may be conducted in 96- or 384-well format, making it amenable to automated high-throughput screening (HTS). See Cree et al. (1995) *AntiCancer Drugs* 6:398-404. The assay procedure involves adding a single reagent (CellTiter-Glo® Reagent) directly to cultured cells. This results in cell lysis and generation of a luminescent signal produced by a luciferase reaction. The luminescent signal is proportional to the amount of ATP present, which is directly proportional to the number of viable cells present in culture. Data can be recorded by luminometer or CCD camera imaging device. The luminescence output is expressed as relative light units (RLU).

In another aspect, a disulfide conjugate compound for use as a medicament is provided. In further aspects, a disulfide conjugate compound for use in a method of treatment is provided. In certain embodiments, a disulfide conjugate compound for use in treating cancer is provided. In certain embodiments, the disclosure provides a disulfide conjugate compound for use in a method of treating an individual comprising administering to the individual an effective amount of the disulfide conjugate compound.

Disulfide conjugate compounds of the disclosure can be used either alone or in combination with other agents in a therapy. For instance, an antibody or immunoconjugate of the disclosure may be co-administered with at least one additional therapeutic agent. In some embodiments, the additional therapeutic agent is an anthracycline. In some embodiments, the anthracycline is daunorubicin or idarubicin. In some embodiments, the additional therapeutic agent is cytarabine. In some embodiments, the additional therapeutic agent is cladribine. In some embodiments, the additional therapeutic agent is fludarabine or topotecan. In some embodiments, the additional therapeutic agent is 5-azacytidine or decitabine.

Such combination therapies noted herein encompass combined administration (where two or more therapeutic agents are included in the same or separate formulations), and separate administration, in which case, administration of the compositions of the disclosure can occur prior to, simultaneously, and/or following, administration of the additional therapeutic agent and/or adjuvant. Compositions of the disclosure can also be used in combination with radiation therapy.

Compositions of the disclosure (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Compositions of the disclosure would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. Compositions of the disclosure need not be, but are optionally formulated with one or more agents currently used to prevent or treat the disorder in question. The effective amount of such other agents depends on the amount of the composition of the disclosure present in the formulation, the type of disorder or treatment, and other factors discussed herein. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a composition of the disclosure (when used alone or in combination with one or more other additional therapeutic agents) will depend on the type of disease to be treated, the type of composition, the severity and course of the disease, whether the composition is administered for preventive or therapeutic purposes, previous therapy, the patient's clinical history and response to the composition, and the discretion of the attending physician. The composition is suitably administered to the patient at one time or over a series of treatments. Depending on the type and severity of the disease, about 1 µg/kg to 15 mg/kg (e.g. 0.1 mg/kg-10 mg/kg) of a composition of the disclosure can be an initial candidate dosage for administration to the patient, whether, for example, by one or more separate administrations, or by continuous infusion. One typical daily dosage might range from about 1 µg/kg to 100 mg/kg or more, depending on the factors mentioned herein. For repeated administrations over several days or longer, depending on the condition, the treatment would generally be sustained until a desired suppression of disease symptoms occurs. One exemplary dosage of the composition would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

Intracellular release of the drug from the disulfide conjugate compound in a target cell is believed to result from a combination of reductive cleavage of the disulfide bond by glutathione and linker immolation. Glutathione-mediated release provides for advantages as compared to certain linkers known in the prior art, such as acid-labile hydrazine linkers. More particularly, blood concentration of glutathione is known to be very low, such as in the micromolar range, whereas intracellular glutathione concentration is typically up to three orders of magnitude greater, such as in the millimolar range. It is further believed that glutathione concentration in cancer cells is even greater due to increased activity of reductive enzymes. It is yet further believed that steric hindrance at the linker carbon atom bearing a sulfur atom of certain conjugates of the present disclosure provides for improved blood stream stability and improved intracellular release (immolation). Therefore, it is believed that the disulfide conjugate compounds of the present disclosure provide for improved stability in the bloodstream and for improved intracellular release rates.

Articles of Manufacture

In another aspect of the disclosure, an article of manufacture containing materials useful for the treatment, prevention and/or diagnosis of the disorders described herein is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the disorder and may have a sterile access port (for example the container may be an intravenous solution bag or a vial having a stopper pierceable by a hypodermic injection needle). At least one active agent in the composition is a disulfide conjugate compound of the disclosure. The label or package insert indicates that the composition is used for treating the condition of choice. Moreover, the article of manufacture may comprise (a) a first container with a composition contained therein, wherein the composition comprises a disulfide conjugate compound of the disclosure; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

EXAMPLES

The following are examples of methods and compositions of the disclosure. It is understood that various other embodiments may be practiced, given the general description provided herein.

Example 1: General Method for ADC Preparation

Cysteine engineered antibodies, such as those listed in Tables A to D, were made reactive for conjugation with linker-drug intermediates of the present disclosure by treatment with a reducing agent such as DTT (Cleland's reagent, dithiothreitol) or TCEP (tris(2-carboxyethyl)phosphine hydrochloride; see Getz et al (1999) Anal. Biochem. Vol 273:73-80 (incorporated herein by reference); Soltec Ventures, Beverly, Mass.) followed by re-formation of the inter-chain disulfide bonds (re-oxidation) with a mild oxidant such as dehydroascorbic acid. Full length, cysteine engineered monoclonal antibodies (THIOMAB™ antibodies) expressed in CHO cells (see Gomez et al. (2010) Biotechnology and Bioeng. 105(4):748-760 (incorporated herein by reference); and Gomez et al (2010) Biotechnol. Prog. 26:1438-1445 (incorporated herein by reference)) were reduced, for example, with about a 50 fold excess of DTT overnight in 50 mM Tris, pH 8.0 with 2 mM EDTA at room temperature, which removes cysteine and glutathione adducts as well as reduces interchain disulfide bonds in the antibody. Removal of the adducts was monitored by reverse-phase liquid chromatography/mass spectrometric Analysis ("LC/MS") using a PLRP-S column. The reduced THIOMAB™ antibody was diluted and acidified by addition to at least four volumes of 10 mM sodium succinate, pH 5 buffer. Alternatively, the antibody was diluted and acidified by adding to at least four volumes of 10 mM succinate, pH 5 and titration with 10% acetic acid until pH was approximately five. The pH-lowered and diluted THIOMAB™ antibody was subsequently loaded onto a HiTrap S cation exchange column, washed with several column volumes of 10 mM sodium acetate, pH 5 and eluted with 50 mM Tris, pH 8.0, 150 mM sodium chloride.

Disulfide bonds were reestablished between cysteine residues present in the parent Mab by carrying out reoxidation. The eluted reduced THIOMAB™ antibody described above was treated with 15× dehydroascorbic acid (DHAA) for about 3 hours or, alternatively, with 200 nM to 2 mM aqueous copper sulfate (CuSO4) at room temperature overnight. Other oxidants, i.e. oxidizing agents, and oxidizing conditions, which are known in the art may be used. Ambient air oxidation may also be effective. This mild, partial reoxidation step formed intrachain disulfides efficiently with high fidelity. Reoxidation was monitored by reverse-phase LC/MS using a PLRP-S column. The reoxidized THIOMAB™ antibody was diluted with succinate buffer as described above to reach pH approximately 5 and purification on an S column was carried out as described above with the exception that elution was performed with a gradient of 10 mM succinate, pH 5, 300 mM sodium chloride (buffer B) in 10 mM succinate, pH 5 (buffer A). EDTA was added to the eluted THIOMAB™ antibody to a final concentration of 2 mM and concentrated, if necessary, to reach a final concentration of more than 5 mg/mL.

The resulting THIOMAB™ antibody, suitable for conjugation, was stored at −20° C. in aliquots. LC/MS Analysis was performed on a 6200 series TOF or QTOF Agilent LC/MS. Samples were chromatographed on a PRLP-S®, 1000 A, microbore column (50 mm×2.1 mm, Polymer Laboratories, Shropshire, UK) heated to 80° C. A linear gradient from 30-40% B (solvent A: 0.05% TFA in water, solvent B: 0.04% TFA in acetonitrile) was used and the eluent was directly ionized using the electrospray source. Data were collected and deconvoluted by the MassHunter software. Prior to LC/MS analysis, antibodies or drug conjugates (50 micrograms) were treated with PeptideN-Glucosidase F ("PNGase F") (2 units/ml; PROzyme, San Leandro, Calif.) for 2 hours at 37° C. to remove N-linked carbohydrates. Alternatively, antibodies or drug conjugates were partially digested with LysC (0.25 ug per 50 ug antibody or conjugate) for 15 minutes at 37 C to give a Fab and Fc fragment for analysis by LC/MS. Peaks in the deconvoluted LC/MS spectra were assigned and quantitated. Drug-to-antibody ratios (DAR) were calculated by calculating the ratio of intensities of the peak or peaks corresponding to drug-conjugated antibody relative to all peaks observed.

The THIOMAB™ antibody for conjugation, in 10 mM succinate, pH 5, 150 mM NaCl, 2 mM EDTA, was adjusted to pH 7.5-8.5 with 1M Tris. An excess, from about 3 molar to 20 equivalents of a linker-drug intermediate of the present disclosure with a thiol-reactive pyridyl disulfide group was dissolved in DMF or DMA and added to the reduced, reoxidized, and pH-adjusted antibody. The reaction was incubated at room temperature or 37° C. and monitored until completion (1 to about 24 hours), as determined by LC/MS analysis of the reaction mixture. When the reaction is complete, the conjugate may be purified by one or any combination of several methods to remove remaining unreacted linker-drug intermediate and aggregated protein (if present at significant levels). For example, the conjugate may be diluted with 10 mM histidine-acetate, pH 5.5 until final pH is approximately 5.5 and purified by S cation exchange chromatography using either HiTrap S columns connected to an Akta purification system (GE Healthcare) or S maxi spin columns (Pierce). Alternatively, the conjugate may be purified by gel filtration chromatography using an S200 column connected to an Akta purification system or Zeba spin columns. Alternatively, dialysis may be used. The THIOMAB™ antibody-drug conjugates were formulated into 20 mM His/acetate, pH 5, with 240 mM sucrose using either gel filtration or dialysis. The purified conjugate is concentrated by centrifugal ultrafiltration and filtered through a 0.2-μm filter under sterile conditions and frozen for storage. The antibody-drug conjugates were characterized by BCA assay to determine protein concentration, analytical SEC (size-exclusion chromatography) for aggregation analysis and LC/MS after treatment with Lysine C endopeptidase (LysC) to calculate DAR.

Size exclusion chromatography was performed on conjugates using a Shodex KW802.5 column in 0.2M potassium phosphate pH 6.2 with 0.25 mM potassium chloride and 15% IPA at a flow rate of 0.75 ml/min. The aggregation state of the conjugate was determined by integration of eluted peak area absorbance at 280 nm.

LC/MS analysis may be performed on conjugates using an Agilent QTOF 6520 ESI instrument. As an example, the antibody-drug conjugate was treated with 1:500 w/w Endoproteinase Lys C (Promega) in Tris, pH 7.5, for 30 min at 37° C. The resulting cleavage fragments were loaded onto a 1000 Å (Angstrom), 8 μm (micron) PLRP-S (highly cross-linked polystyrene) column heated to 80° C. and eluted with a gradient of 30% B to 40% B in 5 minutes. Mobile phase A was $H_2O$ with 0.05% TFA and mobile phase B was acetonitrile with 0.04% TFA. The flow rate was 0.5 ml/min. Protein elution was monitored by UV absorbance detection at 280 nm prior to electrospray ionization and MS analysis.

Chromatographic resolution of the unconjugated Fc fragment, residual unconjugated Fab and drugged Fab was usually achieved. The obtained m/z spectra were deconvoluted using Mass Hunter™ software (Agilent Technologies) to calculate the mass of the antibody fragments.

Example 2: Herceptin HC A118C Antibody-Probe Conjugates

Various probe compounds comprising a linker and a thiol leaving group were conjugated with Herceptin HC A118C. In each conjugation, 5 mg/mL antibody in a solvent system was contacted with a probe-linker-leaving group compound at an equivalent ratio of probe compound to antibody of 10:1 wherein the probe-linker is conjugated to the antibody via a disulfide bond. The solvent system comprised 75 mM Tris, pH 8.5 and 10 v/v % DMF. The conjugation reaction was run at room temperature for 24 hours. The reaction product mixture was analyzed by LC/MS to determine a drug to antibody ratio (DAR), an area percent of leaving group byproduct as compared to antibody-probe conjugate, an area percent of unconjugated dimer as compared to antibody-probe conjugate, and an area percent of unconjugated monomer as compared to antibody-probe conjugate.

The probe was of the formula below where the wavy line indicates the point of attachment to the linker:

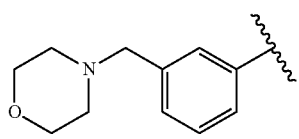 [SMILES: *c1cccc(CN2CCOCC2)c1]

Probe-linker-leaving group compounds evaluated included:

"Dimethyl/PDS"

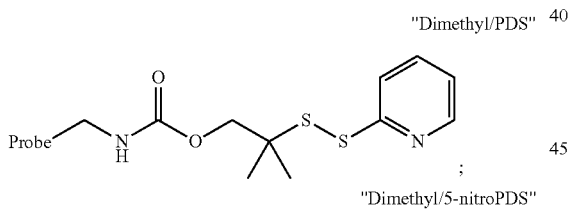

"Dimethyl/5-nitroPDS"

"Dimethyl/3-nitroPDS"

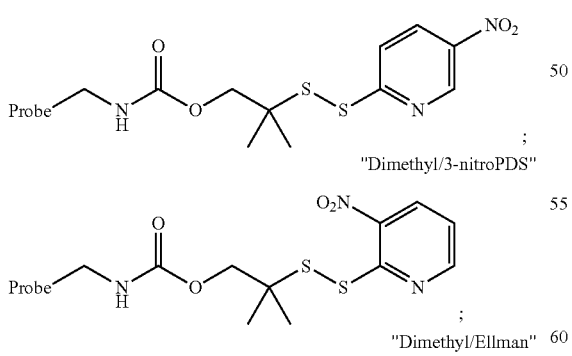

"Dimethyl/Ellman"

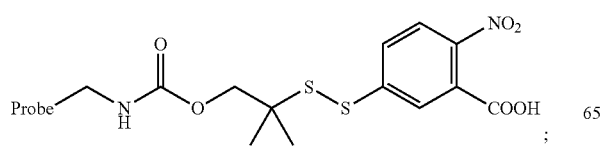

"Cyclopropyl/5-nitroDPS"

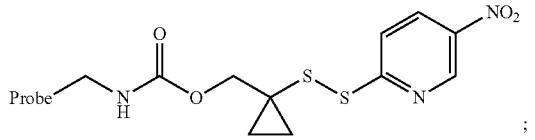

"Methyl/PDS"

"Methyl/5-nitroPDS"

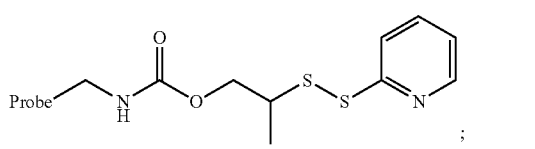

"Methyl/3-nitroPDS"

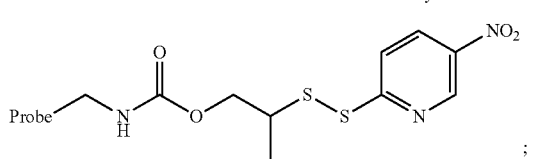

"Methyl/Ellman"

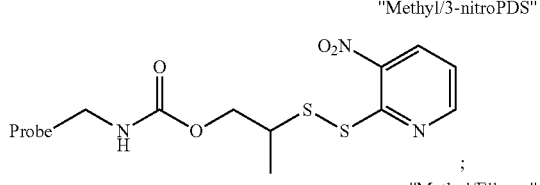

; and

"Ethyl/5-nitroPDS"

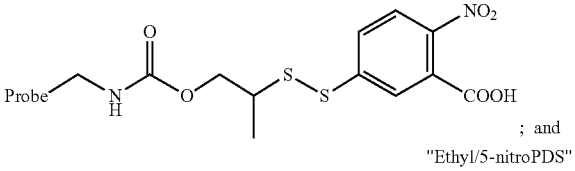

The results are reported in Table 1 below where "DAR" refers to drug-antibody ratio.

TABLE 1

| Linker-Leaving Group | DAR |
|---|---|
| Dimethyl/PDS | 0.6 |
| Dimethyl/5-nitroPDS | 0.7 |
| Dimethyl/3-nitroPDS | 0.2 |
| Dimethyl/Ellman | 0.2 |
| Cyclopropyl/5-nitroPDS | 2 |
| Ethyl/5-nitroPDS | 2 |
| Methyl/PDS | 1.1 |
| Methyl/5-nitroPDS | 1.4 |
| Methyl/3-nitroPDS | 2 |
| Methyl/Ellman | 1.7 |

Example 3: Herceptin LC K149C Antibody-Probe Conjugates

The probe compounds of Example 2 were evaluated for conjugation to Herceptin K149C via a disulfide bond under the reaction conditions of Example 2. The reaction product mixture was analyzed by LC/MS to determine a drug to antibody ratio (DAR). The results are reported in Table 2 below.

TABLE 2

| Linker-Leaving Group | DAR |
|---|---|
| Dimethyl/PDS | 0.3 |
| Dimethyl/5-nitroPDS | 0.6 |
| Dimethyl/3-nitroPDS | 0.2 |
| Dimethyl/Ellman | 0.2 |
| Cyclopropyl/5-nitroPDS | 2 |
| Ethyl/5-nitroPDS | 2 |
| Methyl/PDS | 0.7 |
| Methyl/5-nitroPDS | 1.6 |
| Methyl/3-nitroPDS | 1.8 |
| Methyl/Ellman | 1.8 |

Example 4: Herceptin HC A118C ADC

Various drug compounds comprising a linker and a 5-nitroPDS thiol leaving group were conjugated via a disulfide bond with Herceptin2 4D5 HC A118C antibody. In each conjugation, 5 mg/mL antibody in a solvent system was contacted with a drug-linker-leaving group compound at an equivalent ratio of drug-linker-leaving group compound to antibody of 3:1. The solvent system comprised 75 mM Tris, pH 8.5. The conjugation reaction was run at room temperature for 3 hours. The reaction product mixture was analyzed by LC/MS to determine a drug to antibody ratio (DAR) and an area percent of leaving group byproduct as compared to antibody-probe conjugate.

The drug was of the formula below where the wavy line indicates the point of attachment to the linker:

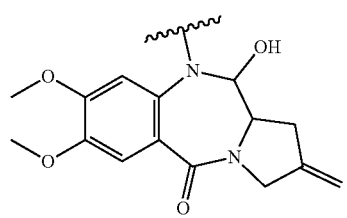

Drug-linker-leaving group compounds evaluated included:

"Unusbstituted"

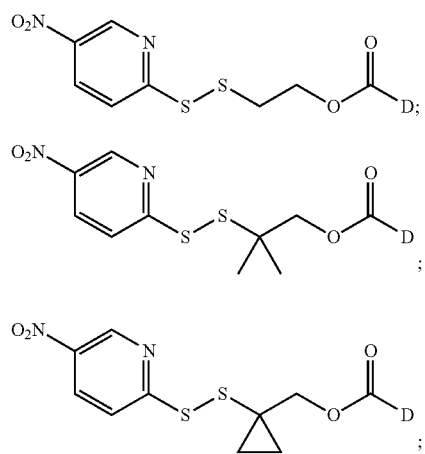

"Dimethyl"

"Cyclopropyl"

"Cyclobutyl"

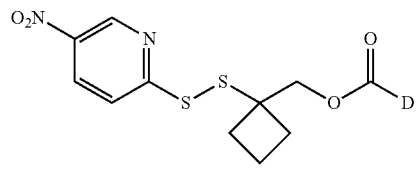

"Cyclopentyl"

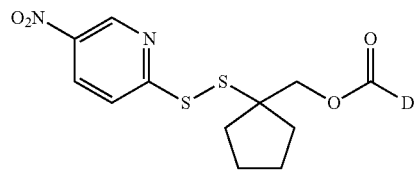

"Cyclohexyl"

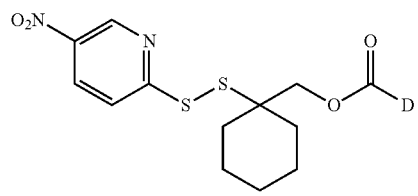

"THP"

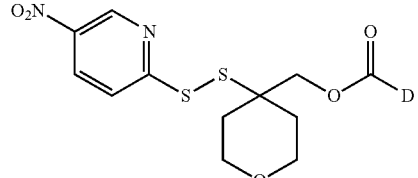

; and

"cyclohexyl-PAB"

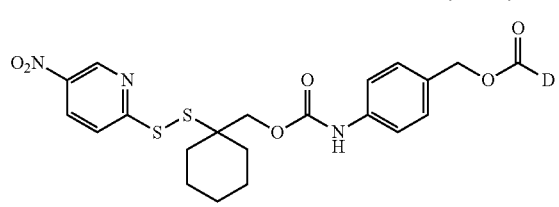

The results are reported in Table 3 below and the LC/MS results for cyclopropyl and cyclobutyl leaving groups are reproduced in FIGS. 1 and 2, respectively.

TABLE 3

| Linker-Leaving Group | DAR | % LG |
|---|---|---|
| Unsubstituted | 1.9 | 2.8 |
| Cyclopropyl | 1.9 | 4.8 |
| Cyclobutyl | 1.9 | 5 |
| Cyclopentyl | 0.8 | 48 |
| Dimethyl | 0.4 | 71 |
| Cyclohexyl | 0.3 | 54 |
| THP | 0 | 96 |
| Cyclohexyl-PAB | 0 | 10 with visible precipitate |

Example 5: CD22 LC K149C ADC

A linker-drug compound comprising a methylsulfonate leaving group (MTS) (Linker 1) was conjugated via a disulfide bond with CD22 LC K149C antibody in a first evaluation. In the second evaluation, a linker-drug compound comprising a MTS leaving group (Linker 2) was conjugated with antibody in a second evaluation. In each conjugation, 5 mg/mL antibody in a solvent system was contacted with a drug-linker-leaving group compound at an equivalent ratio of probe compound to antibody of 3:1. The solvent system comprised 75 mM Tris, pH 8.5. The conjugation reactions were run at room temperature for 3 hours. Linkers 1 and 2 are illustrated below:

Linker 1

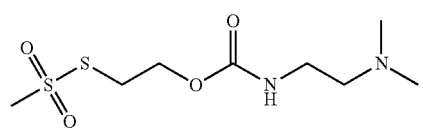

Linker 2

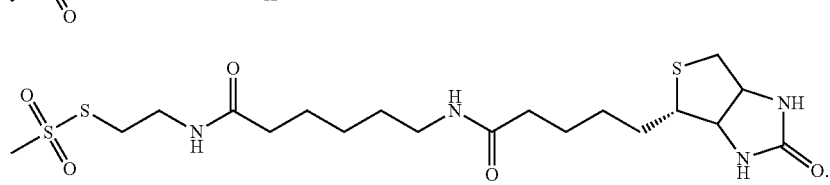

The reaction product mixture was analyzed by LC/MS to determine a drug to antibody ratio (DAR). The LC/MS results are reported in FIGS. 3A and 3B. For Linker 1, the drug to antibody ratio was 2.0. For Linker 2, the drug to antibody ratio was 1.5.

Example 6: CD22 LC K149C Antibody-Probe Conjugates Formed at Varying pH

The dimethyl/5-nitroPDS probe-linker-leaving group compound of Example 2 was evaluated for conjugation via a disulfide bond with CD22 LC K149C antibody in the following buffers: (1) 10 mM succinate, pH 5.0; (2) 75 mM Bis-Tris, pH 6.3; (3) 75 mM Tris, pH 7.5; and (4) 75 mM Tris, pH 8.5. In each evaluation, 5 mg/mL antibody was contacted with the probe-linker-leaving group at an equivalent ratio of probe compound to antibody of 10:1, and reacted over night at room temperature. The LC/MS results are depicted in FIGS. 4A to 4D. The LC/MS results show that lowering the pH does not improve dimethyl/nitro-PDS conjugation with the antibody.

Example 7: CD22 LC K149C Antibody-Probe Conjugates Formed at Varying pH

A probe-linker-dinitro PDS leaving group compound of the following structure

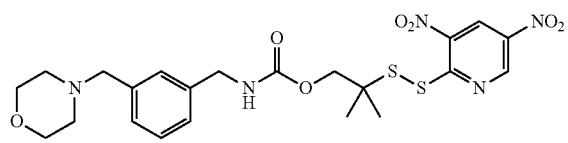 [SMILES: CC(C)(COC(=O)NCc1cccc(CN2CCOCC2)c1)SSc1ncc([N+](=O)[O-])cc1[N+](=O)[O-]]

was evaluated for conjugation via a disulfide bond with CD22 LC K149C antibody in pH 5.0, 6.3, 7.5 and 8.5 buffers in accordance with the method of Example 6. The LC/MS results are depicted in FIGS. 5A to 5D. The major byproducts are believed to comprise the following two species:

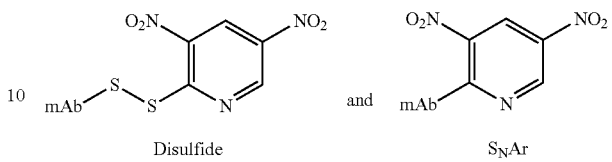

Disulfide     and     S$_N$Ar

Example 8: CD22 LC K149C Antibody-Probe Conjugates Formed at Varying pH

A probe-linker-2-mercapto-thiazole leaving group compound of the following structure

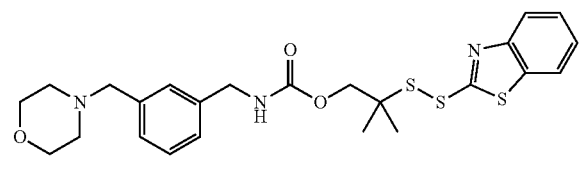 [SMILES: CC(C)(COC(=O)NCc1cccc(CN2CCOCC2)c1)SSc1nc2ccccc2s1]

was evaluated for conjugation via a disulfide bond with CD22 LC K149C antibody in pH 5.0, 6.3, 7.5 and 8.5 buffers in accordance with the method of Example 6. The LC/MS results are reported in Table 4 and are depicted in FIGS. 6A to 6D.

TABLE 4

| pH | DAR |
| --- | --- |
| 5.0 | 0.3 |
| 6.3 | 0.5 |
| 7.5 | 0.8 |
| 8.5 | 1.1 |

The LG byproduct is believed to predominantly comprise the following species:

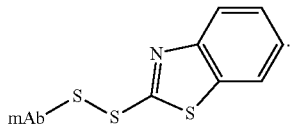

Example 9: CD22 LC K149C Antibody-Probe Conjugates Formed at Varying pH

A probe-linker-2-mercapto-oxazole PDS leaving group compound of the following structure

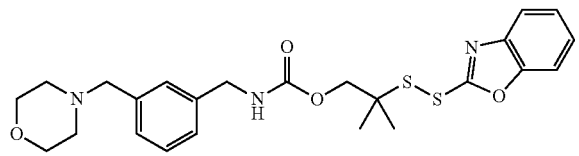 [SMILES: CC(C)(COC(=O)NCc1cccc(CN2CCOCC2)c1)SSc1nc2ccccc2o1]

was evaluated for conjugation via a disulfide bond with CD22 LC K149C antibody in pH 5.0, 6.3, 7.5 and 8.5 buffers in accordance with the method of Example 6. The LC/MS results are reported in Table 5 and are depicted in FIGS. 7A to 7D.

TABLE 5

| pH | DAR |
| --- | --- |
| 5.0 | 0.8 |
| 6.3 | 1.0 |
| 7.5 | 1.2 |
| 8.5 | 1.5 |

The LG byproduct is believed to predominantly comprise the following species:

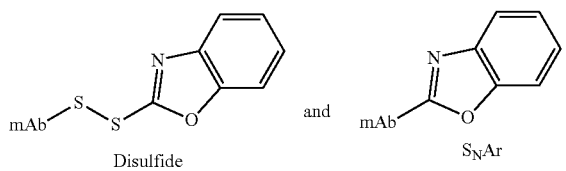

Disulfide and $S_NAr$ wherein the $S_NAr$ species is the major LG byproduct peak. It is further believed that the $S_NAr$ species predominantly forms at a pH of 6.3 or less.

Example 10: CD22 LC K149C Antibody-Probe Conjugates Formed at pH 8.5

Probe-linker-leaving group compounds of the following structures

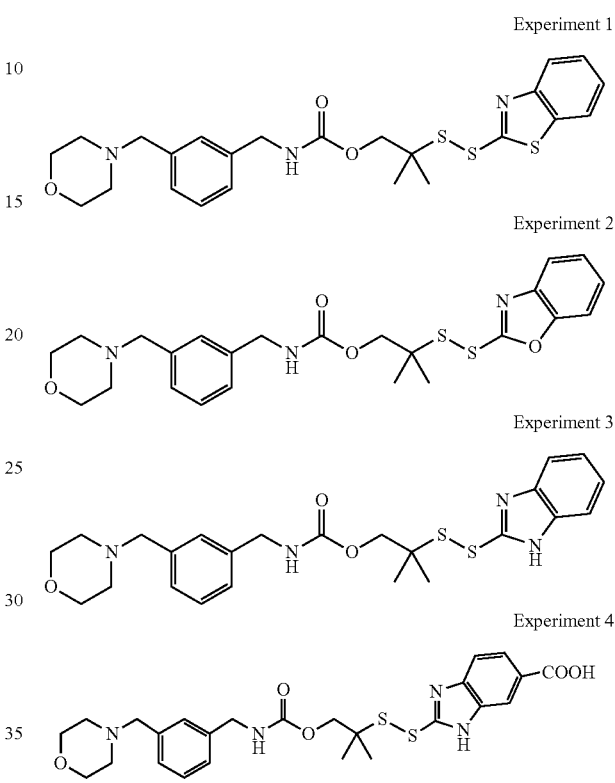

were evaluated for conjugation via a disulfide bond with CD22 LC K149C antibody in 75 mM Tris, pH 8.5 buffer in experiments 1 to 4, in accordance with the method of Example 6. The LC/MS results are depicted in FIGS. 8A to 8D and are summarized in Table 6 below.

TABLE 6

| Experiment | DAR |
| --- | --- |
| 1 | 1.2 |
| 2 | 1.6 |
| 3 | 1.7 |
| 4 | 1.8 |

Example 11: CD22 LC K149C ADC Formed at Varying pH

The leaving group-linker-drug compound below was evaluated for conjugation with CD22 LC K149C antibody in the following buffers: (1) 10 mM succinate, pH 5.0; (2) 75 mM Bis-Tris, pH 6.3; (3) 75 mM Tris, pH 7.5; and (4) 75 mM Tris, pH 8.5. In each evaluation, 5 mg/mL antibody was contacted the leaving group-linker-drug compound at an equivalent ratio of probe compound to antibody of 10:1, and reacted overnight at room temperature. The LC/MS results are depicted in FIGS. 9A to 9D and indicate that DAR for each conjugation reaction was 0.

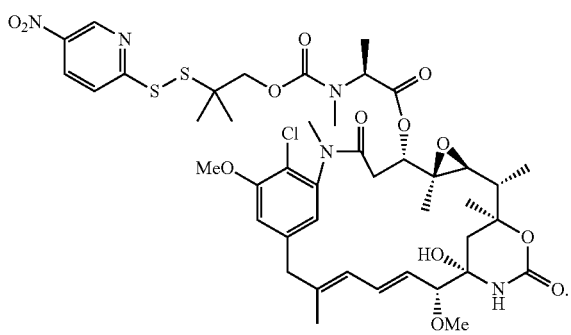

Example 12: THIOMAB™ Antibody-Drug and Antibody-Probe Conjugates

A THIOMAB™ antibody as described herein was conjugated with various activated linker-probe conjugates of the present disclosure by methods disclosed herein. The reaction product mixtures were evaluated for DAR by methods described herein.

In a first series of evaluations, the activated linker-probe compound

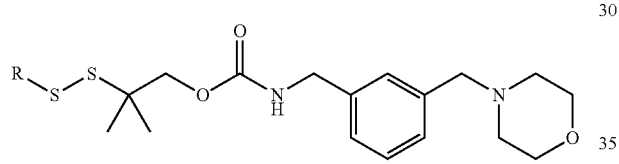

was conjugated with the antibody. Results are reported in Table 7 below wherein the wavy line indicates the point of attachment of R to the disulfide moiety.

TABLE 7

| R | DAR |
|---|---|
| pyridin-2-yl | 0 |
| pyrazin-2-yl | 0.1 |
| 5-nitropyridin-2-yl | 0.6 |

TABLE 7-continued

| R | DAR |
|---|---|
| pyrimidin-2-yl | 0.1 |
| 3-nitropyridin-2-yl | 0 |
| 5-(methylsulfonyl)pyridin-2-yl | 0.2 |
| 3,5-dinitropyridin-2-yl | 0 |
| benzothiazol-2-yl | 1.4 |
| 3-carboxy-5-nitropyridin-2-yl | 0.1 |
| benzoxazol-2-yl | 1.3 |
| 5-carboxy-3-nitropyridin-2-yl | 0.2 |

TABLE 7-continued

| R | DAR |
|---|---|
| (benzimidazole) | 1.5 |

In a second series of evaluations, the activated linker-MMAE drug compound illustrated below

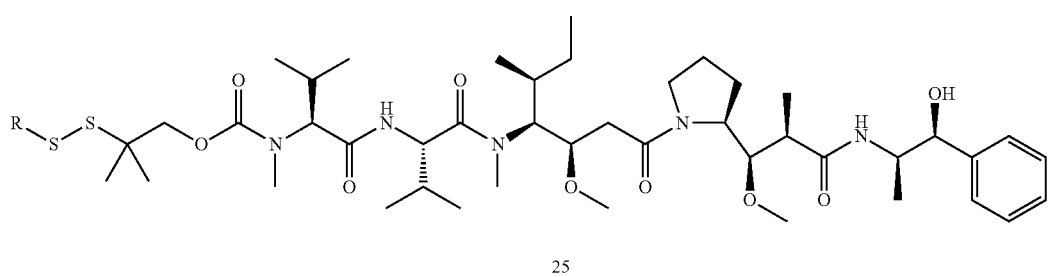

was conjugated with the following antibodies: a THIOMAB™ antibody with a LC K149C mutation (results are in Table 8A); a THIOMAB™ antibody with a HC A140C mutation (results are in Table 8B); a THIOMAB™ antibody with a LC S121C mutation (results are in Table 8B); a THIOMAB™ antibody with a LC V205C mutation (results are in Table 8B); and a THIOMAB™ antibody with a HC A118C mutation (results are in Table 8B). Each conjugation experiment was done at a 10× linker to drug ratio, in 75 mM Tris and 10% DMF for 15 to 17 hours at pH 8.5 and room temperature. In Tables 8A and 8B, the wavy line indicates the point of attachment of R to the disulfide moiety.

TABLE 8A

| R | DAR |
|---|---|
| $O_2N$-pyridine | 0.1 |
| imidazopyrazine | 0.8 |
| benzimidazole | 0.4 |
| benzimidazole-COOH | 0.4 |
| HOOC-benzimidazole | 0.5 |
| adenine ($NH_2$-purine) | 0.4 |
| $O_2N$-benzimidazole | 0.4 |
| imidazole | 0.1 |
| $O_2N$-benzimidazole | 0.5 |

TABLE 8A-continued
| R | DAR |
|---|---|
| 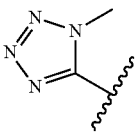 | 0.3 |
| 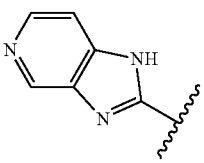 [SMILES: *c1nc2cnccc2[nH]1] | 0.6 |
| 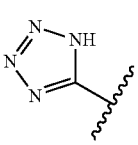 | 0 |
| 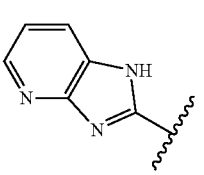 [SMILES: *c1nc2ncccc2[nH]1] | 0.7 |
| 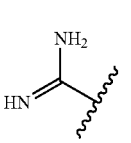 | 1.8 |
| 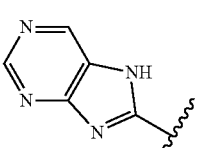 | 0.7 |
| 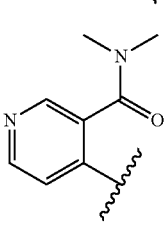 | 0.2 |
| 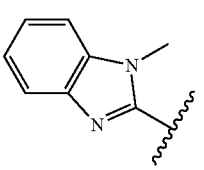 | 0.1 |
| 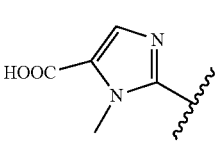 [SMILES: *c1ncc(C(=O)O)n1C] | 0.1 |
| 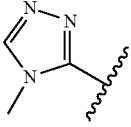 [SMILES: *c1nncn1C] | 0.1 |
| 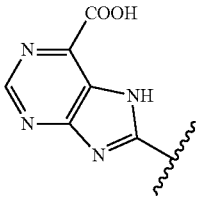 [SMILES: *c1nc2ncnc(C(=O)O)c2[nH]1] | 1.0 |
| 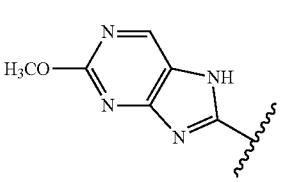 | 0.9 |
| 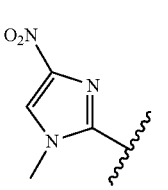 [SMILES: *c1nc([N+](=O)[O-])cn1C] | 0 |
| 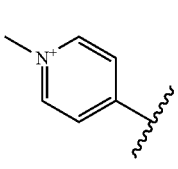 [SMILES: *c1cc[n+](C)cc1] | 0.8 |
| 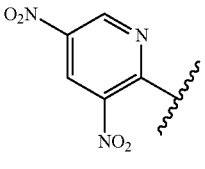 [SMILES: *c1ncc([N+](=O)[O-])cc1[N+](=O)[O-]] | 0 |
| 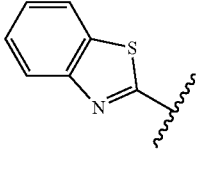 [SMILES: *c1nc2ccccc2s1] | 0.2 |
| 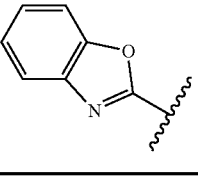 | 0.5 |
TABLE 8B
| R | LC S121C DAR | LC V205C DAR | HC A118C DAR |
|---|---|---|---|
| 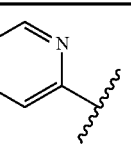 | 0 | 0.2 | 0.2 |

TABLE 8B-continued

| R | LC S121C DAR | LC V205C DAR | HC A118C DAR |
|---|---|---|---|
| benzimidazol-2-yl | 0.1 | 0.1 | 0.1 |
| 5-carboxy-benzimidazol-2-yl | 0.2 | 0.2 | 4 |
| 5-nitro-benzimidazol-2-yl | 0.1 | 0.3 | 0.2 |
| 4-nitro-benzimidazol-2-yl | 0.2 | 0.4 | 0.4 |
| imidazo[4,5-c]pyridin-2-yl | 0.2 | 0.5 | 0.4 |
| imidazo[4,5-b]pyridin-2-yl | 0.5 | 0.5 | 0.7 |
| imidazo[4,5-d]pyrimidin-2-yl | 0.1 | 0.5 | 0.7 |
| 1-methyl-benzimidazol-2-yl | 0.7 | 0.8 | 0.4 |
| 4-methyl-1,2,4-triazol-3-yl | 0.8 | 1.1 | 0.8 |

TABLE 8B-continued

| R | LC S121C DAR | LC V205C DAR | HC A118C DAR |
|---|---|---|---|
| imidazo[4,5-b]pyrazin-2-yl | 0.1 | 0.4 | 0.8 |
| 7-carboxy-benzimidazol-2-yl | 0.2 | 0.2 | 0.7 |
| 6-amino-purin-8-yl | 0.2 | 0.2 | 0.4 |
| imidazol-2-yl | 0.2 | 0.1 | 0.1 |
| 2-methyl-tetrazol-5-yl | 1.4 | 1.2 | 1.4 |
| tetrazol-5-yl | 0 | 0 | 0.2 |
| amidino | 1.2 | 1.4 | 1.5 |
| N,N-dimethyl-nicotinamide-4-yl | 0 | 0.2 | 0.8 |
| 5-carboxy-1-methyl-imidazol-2-yl | 0.1 | 0.2 | 0.2 |

TABLE 8B-continued

| R | LC S121C DAR | LC V205C DAR | HC A118C DAR |
|---|---|---|---|
| (COOH-purine) | 0.4 | 0.4 | 1.3 |
| (H3CO-methylpurine) | 0.2 | 0.4 | 0.6 |
| (HOOC-methylimidazole) | 0.2 | 1.1 | 0.3 |
| (N-methylpyridinium) | 0.4 | 0.7 | 1.2 |
| (dinitropyridine) | 0 | 0.1 | 0.2 |
| (benzothiazole) | 0.1 | 0.2 | 1.0 |
| (benzoxazole) | 0.5 | 0.7 | 0.9 |

TABLE 8C

| R | DAR Max | DAR Min | Max/Min |
|---|---|---|---|
| (HOOC-methylimidazole) | 1.1 (LC V205C) | 0 (LC K149C) | ∞ |
| (COOH-purine) | 1.3 (HC A118C) | 0.4 (LC S121C AND HC A118C) | 3.3 |
| (N-methylpyridinium) | 1.2 (HC A118C) | 0.4 (LC S121C) | 3.0 |
| (benzothiazole) | 1.0 (HC A118C) | 0.1 (LC S121C) | 10.0 |
| (methyltriazole) | 1.1 (LC V205C) | 0.1 (LC K149C) | 11 |
| (methyltetrazole) | 1.4 (LC S121C and HC A118C) | 0.3 (LC K149C) | 4.7 |

In a second series of evaluations, the activated linker-pyrrolobenzodiazepine dimer compound illustrated below

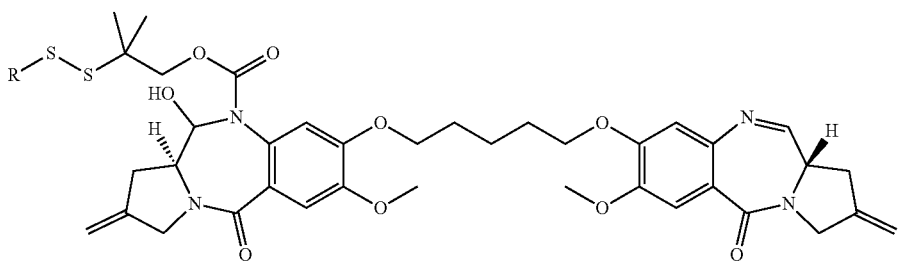

was conjugated with a THIOMAB™ antibody with a LC K149C mutation. Results are reported in Table 9 below wherein the wavy line indicates the point of attachment of R to the disulfide moiety.

TABLE 9

| R | DAR |
|---|---|
| 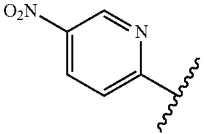 [SMILES: *c1ccc([N+](=O)[O-])cn1] | 0.1 |
| 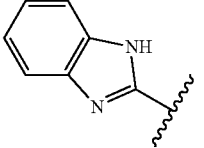 [SMILES: *c1nc2ccccc2[nH]1] | 0.2 |
| 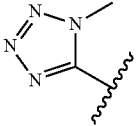 | 0.2 |

TABLE 9-continued

| R | DAR |
|---|---|
| 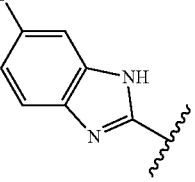 | 0.2 |
| 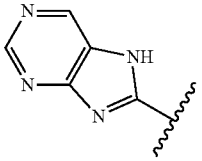 [SMILES: *c1nc2ncncc2[nH]1] | 0.6 |

Example 13: THIOMAB™ Antibody-Drug Conjugation Evaluation for Activated PBD Dimers, Activate CBI-PBD Dimers and Activated MMAE Each of the following activated drug compounds were conjugated with each of a THIOMAB™ antibody with a LC K149C mutation, a THIOMAB™ antibody with an HC A140C mutation, a THIOMAB™ antibody with a LC S121C mutation, a THIOMAB™ antibody with a LC V205C mutation, and a THIOMAB™ antibody with an HC A118C mutation:

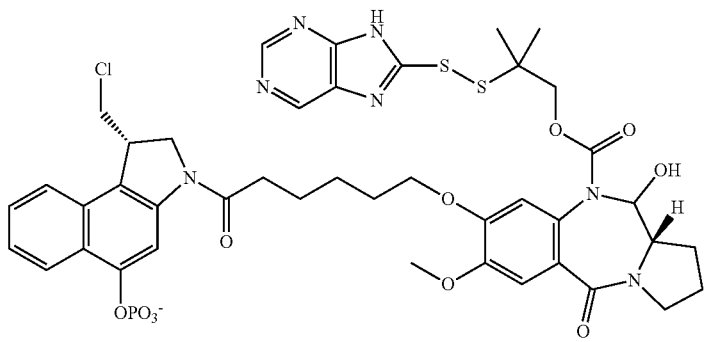

CBI-PBD Dimer

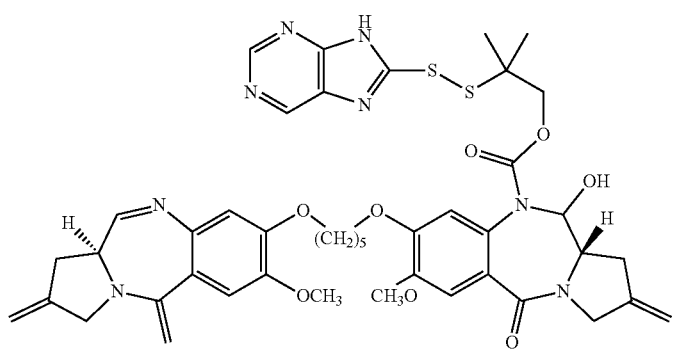

PBD-Dimer

-continued

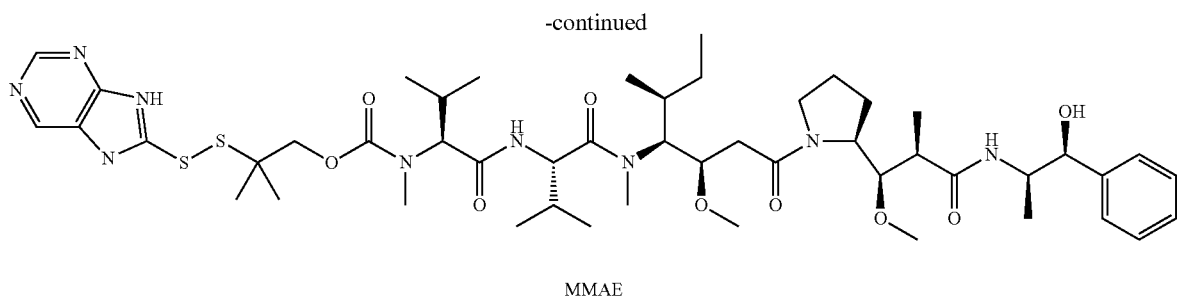

MMAE

Each conjugation experiment was done at a 10× linker to drug ratio, in 75 mM Tris and 10% DMF for 15 to 17 hours at pH 8.5 and room temperature. The results are presented in Table 10 below.

TABLE 10

| Antibody | MMAE | CBI-PBD Dimer | PBD Dimer |
|---|---|---|---|
| K149C | 1.5 | 1.2 | 0.5 |
| A140C | 0.4 | 0.3 | 0.1 |
| S121C | 0.2 | 0.7 | 0.1 |
| V205C | 1.4 | 1.5 | 0.9 |
| A118C | 1.3 | 0.9 | 0.4 |

The Table 10 values were normalized to LC K149C, where the LC K149C results for each antibody normalized to 100. The normalized results are reported in Table 11 below.

TABLE 11

| Antibody | MMAE | CBI-PBD Dimer | PBD Dimer |
|---|---|---|---|
| K149C | 100 | 100 | 100 |
| A140C | 27 | 24 | 20 |
| S121C | 13 | 59 | 20 |
| V205C | 93 | 124 | 180 |
| A118C | 87 | 76 | 80 |

The Table 10 results show, for a given leaving group and Cys mutation site, conjugation of activated MMAE is greater than the conjugation of activated CBI-PBD Dimer is greater than the conjugation of activated PBD Dimer for the evaluated leaving group. These differences may be due to differential solubility among MMAE, PBD dimer and CBI-PBD dimer linker-drugs. The normalized data results in Table 11 indicate that the DAR trends are comparable across the Cys mutation sites for MMAE, CBI-PBD Dimer and PBD Dimer with the same leaving group, suggesting that Cys site selectivity is predominantly governed by the leaving group.

Example 14: Conjugation Evaluation of Activated Drugs to THIOMAB™ Anti-CD22 LC K149C and to THIOMAB™ Anti-Her2 4D5 LC K149C According to the method of Example 13, the CBI-PBD Dimer and the PBD Dimer of Example 13 and the following activated MMAE drug were conjugated with each of THIOMAB™ antibody anti-CD22 LC K149C and to THIOMAB™ anti-Her2 4D5 LC K149C:

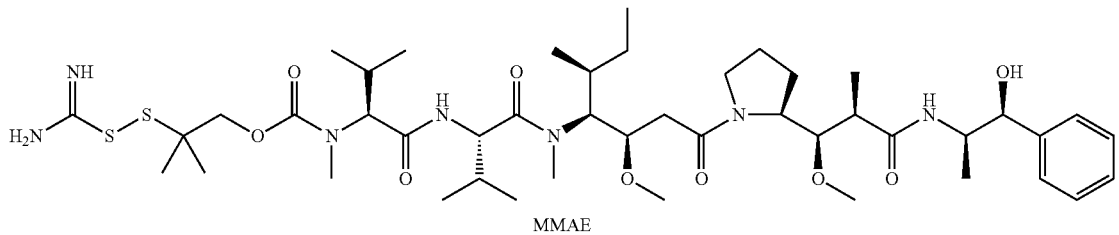 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCC(C)(C)SSC(=N)N)C(C)C]

MMAE

The DAR results are presented in Table 12 below.

TABLE 12

| Antibody | MMAE | CBI-PBD Dimer | PBD Dimer |
|---|---|---|---|
| Thio anti-CD22 LC K149C | 1.9 | Not Determined | Not Determined |
| Thio anti-Her2 4D5 LC K149C | 1.9 | 1.1 | 0.6 |

Example 15: THIOMAB™ Antibody Conjugates Comprising a Maytansinoid or a MMAE

Maytansinoid and MMAE as depicted below were conjugated with Her2 4D5 LC K149C with various linker-leaving group compounds:

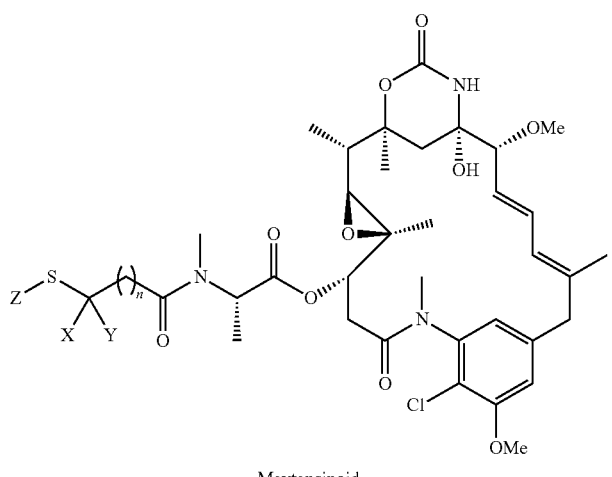
Maytansinoid

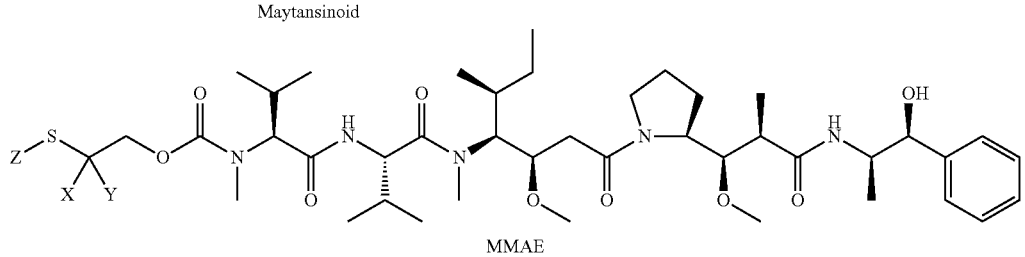
MMAE

The conjugations were done at a 10× linker to drug stoichiometric ratio for 15-17 hours at room temperature in 75 mM Tris at pH 8.5 in 10% DMF. The results are reported in Table 13 below where "DAR" refers to drug to antibody ratio, "May" refers to maytansinoid compound and "MMAE" refers to auristatin compound.

TABLE 13

| Drug Compound | n | X | Y | Z | DAR |
|---|---|---|---|---|---|
| May 1 | 1 | H | H | 2-pyridyl-S- | 1.7 |
| May 2 | 2 | Me | H | 2-pyridyl-S- | 1.3 |
| May 1 | 1 | H | H | 5-nitro-2-pyridyl-S- | 1.9 |
| May 2 | 2 | Me | H | 5-nitro-2-pyridyl-S- | 1.9 |
| May 3 | 2 | Me | Me | 5-nitro-2-pyridyl-S- | 0.1 |
| May 4 | 2 | Me | H | methylsulfonyl- | 2.0 |
| May 5 | 2 | Me | Me | methylsulfonyl- | 1.8 |
| MMAE 1 | — | H | H | 2-pyridyl-S- | 1.7 |
| MMAE 2 | — | Me | H | 2-pyridyl-S- | 1.6 |
| MMAE 1 | — | H | H | 5-nitro-2-pyridyl-S- | 1.9 |
| MMAE 2 | — | Me | H | 5-nitro-2-pyridyl-S- | 1.9 |

TABLE 13-continued

| Drug Compound | n | X | Y | Z | DAR |
|---|---|---|---|---|---|
| MMAE 3 | — | Me | Me | 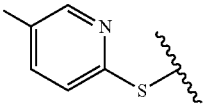 | 0.1 |

Example 16: Synthesis of Activated Linker

A linker was activated with 5-nitropyridine-2-thiol as follows: Sulfuryl chloride (2.35 mL of a 1.0M solution in DCM, 2.35 mmol) was added drop-wise to a stirred suspension of 5-nitropyridine-2-thiol (334 mg, 2.14 mmol) in dry DCM (7.5 mL) at 0° C. (ice/acetone) under an argon atmosphere. The reaction mixture turned from a yellow suspension to a yellow solution and was allowed to warm to room temperature then stirred for 2 hours after which time the solvent was removed by evaporation in vacuo to provide a yellow solid. The solid was re-dissolved in DCM (15 mL) and treated drop-wise with a solution of (R)-2-mercapto-propan-1-ol (213 mg, 2.31 mmol) in dry DCM (7.5 mL) at 0° C. under an argon atmosphere. The reaction mixture was allowed to warm to room temperature and stirred for 20 hours at which point analysis by LC/MS revealed substantial product formation at retention time 1.41 minutes (ES+) m/z 247 ([M+H]$^+$, ~100% relative intensity). The precipitate was removed by filtration and the filtrate evaporated in vacuo to give an orange solid which was treated with H$_2$O (20 mL) and basified with ammonium hydroxide solution. The mixture was extracted with DCM (3×25 mL) and the combined extracts washed with H$_2$O (20 mL), brine (20 mL), dried (MgSO$_4$), filtered and evaporated in vacuo to give the crude product. Purification by flash chromatography (gradient elution in 1% increments: 100% DCM to 98:2 v/v DCM/MeOH) gave (R)-2-((5-nitropyridin-2-yl)disulfanyl)propan-1-ol as an oil (111 mg, 21% yield).

Triphosgene (48 mg, 0.16 mmol) was added to a stirred solution of (R)-2-((5-nitropyridin-2-yl)disulfanyl)propan-1-ol (111 mg, 0.45 mmol) and pyridine (34 μL, 33.5 mg, 0.42 mmol) in dry DCM (5 mL). The reaction mixture was allowed to stir under an argon atmosphere for 45 minutes after which time the solvent was removed by evaporation in vacuo to provide (R)-2-((5-nitropyridin-2-yl)disulfanyl)propyl carbonochloridate as a yellow film.

Example 17: Tumor Growth Inhibition in Her2 Model

The in vivo efficacy of two antibody-drug conjugates (ADC) of the invention was measured by a high expressing HER2 transgenic explant mouse model. Anti-Her2 antibody-drug conjugates were tested with the Fo5 model, a transgenic mouse model in which the human HER2 gene is over-expressed in mammary epithelium under transcriptional regulation of the murine mammary tumor virus promoter (MMTV-HER2). The HER2 over-expression causes spontaneous development of a mammary tumor. The mammary tumor of one of these founder animals (founder #5 [Fo5]) was propagated in subsequent generations of FVB mice by serial transplantation of tumor fragments (~2×2 mm in size). All studies were conducted in accordance with the Guide for the Care and Use of Laboratory Animals.

Tumors were established and allowed to grow to 150-200 mm$^3$ in volume (as measured using calipers) before a single treatment on day 0. Initial tumor size was about 200 mm$^3$ volume. Subjects were treated once intravenously with 1 milligram per kilogram ("mpk") ADC1, 3 mpk ADC1, 6 mpk ADC1 or 1 mpk ADC2, or a placebo buffer control (Vehicle) and monitored over 3 weeks to measure tumor volume. Tumor volume was measured using calipers according to the formula: V (mm$^3$)=0.5A×B$^2$, where A and B are the long and short diameters, respectively. ADC1 and ADC2 are illustrated below and differ with respect to a methyl substituent on the linker carbon atom bearing the S atom forming a disulfide bond with the antibody. The antibody for both ADC1 and ADC2 was THIOMAB with a LC K149C mutation.

ADC1

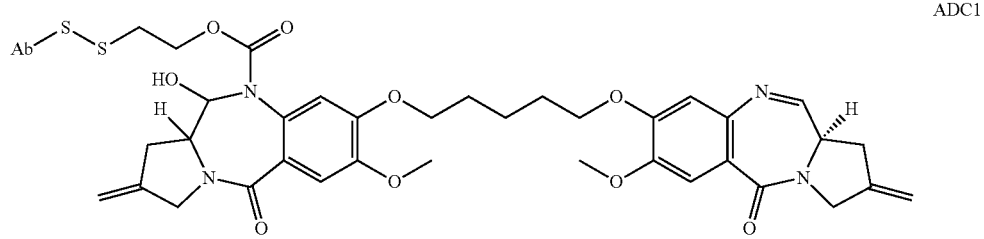

ADC2

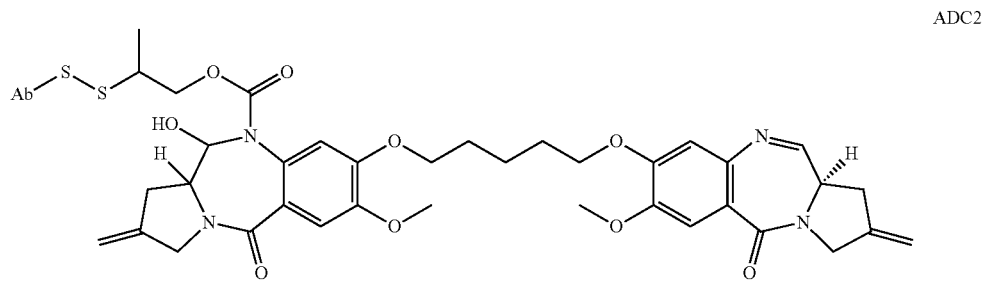

The results are reported in Table 14 below.

TABLE 14

Tumor volume versus time and ADC

| Day | Vehicle | 1 mpk ADC1 | 3 mpk ADC1 | 6 mpk ADC1 | 1 mpk ADC2 |
|---|---|---|---|---|---|
| 0 | 150 mm$^3$ | 150 mm$^3$ | 150 mm$^3$ | 150 mm$^3$ | 150 mm$^3$ |
| 7 | 560 mm$^3$ | 560 mm$^3$ | 510 mm$^3$ | 370 mm$^3$ | 240 mm$^3$ |
| 10 | 910 mm$^3$ | 800 mm$^3$ | 690 mm$^3$ | 510 mm$^3$ | 230 mm$^3$ |
| 14 | 1410 mm$^3$ | 1330 mm$^3$ | 990 mm$^3$ | 720 mm$^3$ | 190 mm$^3$ |
| 18 | — | — | 1280 mm$^3$ | 1200 mm$^3$ | 170 mm$^3$ |
| 21 | — | — | — | 1710 mm$^3$ | 160 mm$^3$ |

Example 18: Preparation of PBD Dimers Comprising an Activated Hindered Disulfide As an example representative of other activated PBD dimers described herein, PBD dimer compound 1 comprising an activated disulfide linker hindered with a methyl moiety was synthesized according to the following overall reaction scheme 1:

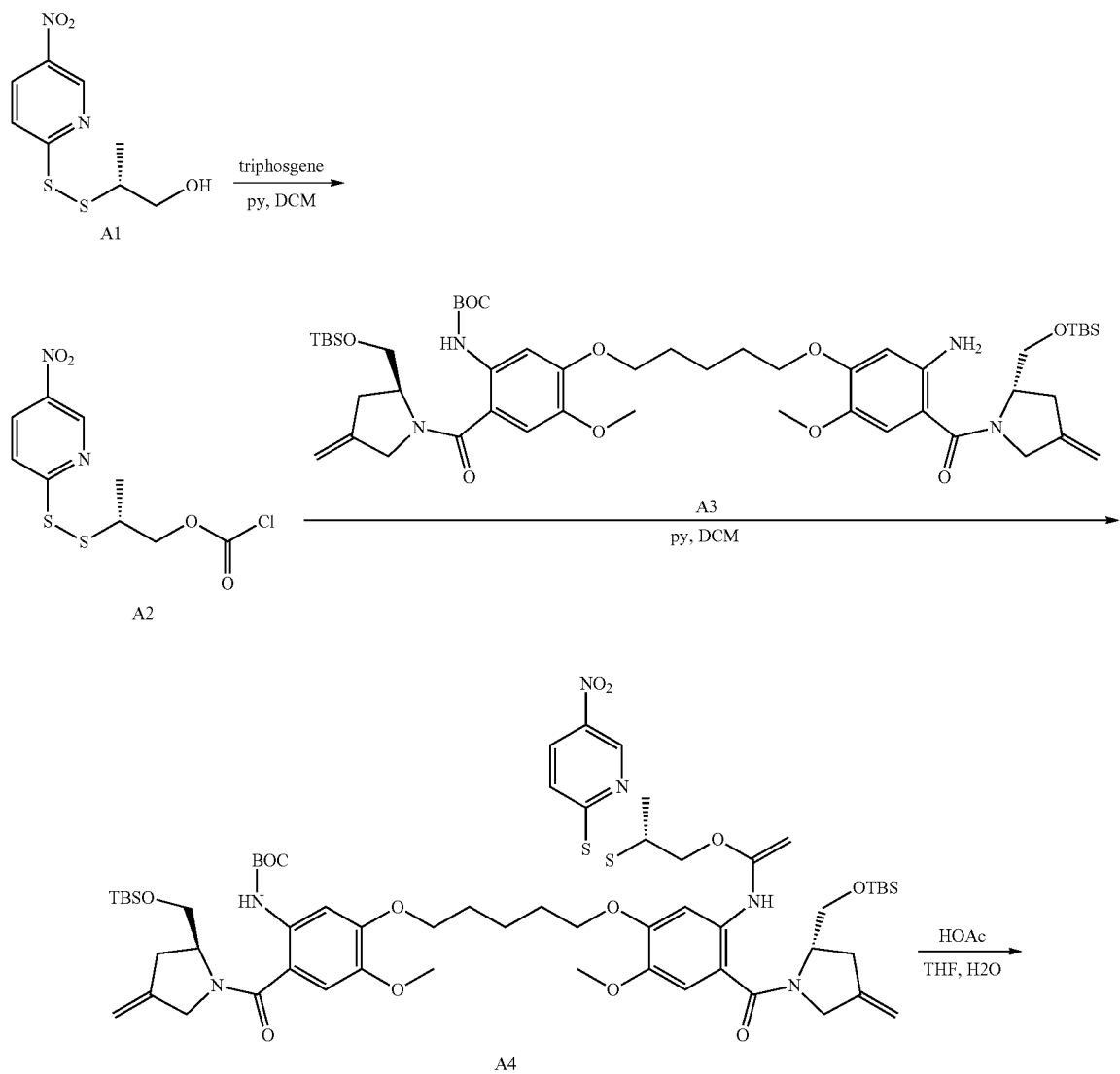

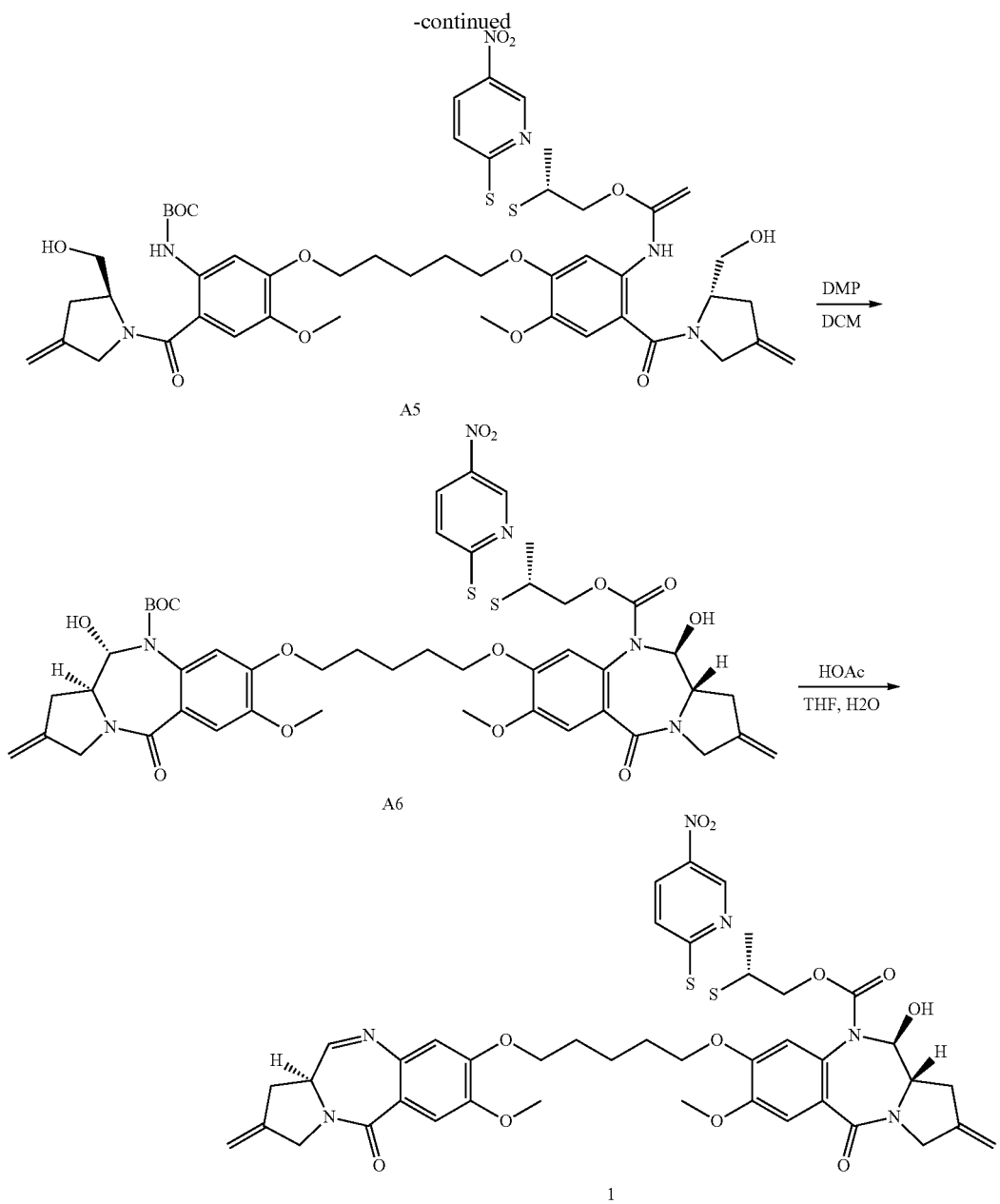

To a solution of triphosgene (241 mg, 0.812 mmol) in DCM (10 mL) was added dropwise to a solution of compound A1 (prepared using procedures analogous to those described in WO2013055987, 500 mg, 2.03 mmol) and pyridine (153 mg, 1.93 mmol) in DCM (10 mL) at 20° C. The reaction mixture was stirred at 20° C. for 30 min then was concentrated. The residue was used directly in the next step without further purification.

A solution of compound A2 (627 mg, 2.03 mmol) in DCM (10 mL) was added dropwise to a solution of compound A3 (prepared as described in WO2013055987, 1.50 g, 1.57 mmol) and pyridine (161.79 mg, 2.05 mmol) at 20° C. The reaction mixture was stirred at 20° C. for 3 h. The solvent was removed and the residue was purified by flash column chromatography (0 to 30% EtOAc in petroleum ether) to give the product (1.6 g, 83%) as yellow foam. LCMS (Condition A, 5-95AB, 1.5 min): RT=1.22 min, m/z=1225.4 [M+H]$^+$.

Glacial HOAc (15 mL) was added to a solution of compound A4 (900 mg, 0.734 mmol) in a mixture of THF and H$_2$O (10 mL/10 mL) at 20° C. The reaction mixture was stirred at 20° C. for 24 h. The reaction mixture was diluted with EtOAc (50 mL) and was washed with water (2×20 mL), sat. aq. NaHCO$_3$ (30 mL) and brine (30 mL). The organic layer was dried over Na$_2$SO$_4$, filtered, and was concentrated to give the crude product. This material was purified by flash column chromatography (1 to 5% CH$_3$OH in DCM) to give the product (700 mg, 96%) as a yellow foam. LCMS (Condition A, 5-95AB, 1.5 min): RT=0.83 min, m/z=997.4 [M+23]$^+$.

DMP (255 mg, 0.601 mmol) was added to a solution of compound A5 (200 mg, 0.200 mmol) in DCM (10 mL) at 0° C. After the reaction mixture was stirred at 20° C. for 2 h, it was quenched with a saturated solution of NaHCO$_3$/Na$_2$SO$_3$ (5 mL/5 mL), and extracted with DCM (3×10 mL).

The combined organic layers were washed with NaHCO$_3$/Na$_2$SO$_3$ (5 mL/5 mL) and brine (10 mL), then were dried over Na$_2$SO$_4$, filtered and were concentrated. The residue was purified by prep-TLC (DCM:MeOH=15:1) to give the product (130 mg, 65%) as a yellow foam. LCMS (Condition A, 5-95AB, 1.5 min): RT=0.77 min, m/z=1015.4 [M+23]$^+$.

Cold TFA (10 mL) was added to compound A6 (650 mg, 0.655 mmol) at 0° C. The reaction mixture was stirred at 0° C. for 30 min then was added dropwise to sat. aq. NaHCO$_3$ (150 mL) at 0° C. The resulting mixture was extracted with DCM (4×40 mL) and the combined organic layers were washed with brine (50 mL), dried over Na$_2$SO$_4$, filtered, and were concentrated to give the crude product. This material was purified by prep-TLC (DCM:MeOH=15:1) to give compound 1 (300 mg, 52%) as a yellow foam. LCMS (Condition A, 5-95AB, 1.5 min): RT=0.87 min, m/z=875.5 [M+H]$^+$; $^1$H NMR (400 MHz, CDCl3) δ 9.14 (s, 1H), 8.23 (d, J=7.6 Hz, 1H), 7.62 (d, J=3.6 Hz, 1H), 7.56 (d, J=8.4 Hz, 1H), 7.41 (s, 1H), 7.18 (s, 1H), 6.71 (s, 1H), 6.68 (s, 1H), 5.52 (d, J=6.8 Hz, 1H), 5.13-5.06 (m, 4H), 4.51 (s, 1H), 4.23-4.12 (m, 4H), 4.08-3.90 (m, 5H), 3.85-3.75 (s, 6H), 3.75-3.70 (m, 2H), 3.62-3.52 (m, 1H), 3.12-3.02 (m, 2H), 2.88-2.78 (m, 2H), 2.67-2.63 (m, 1H), 1.84-1.56 (m, 6H), 1.19 (d, J=6.0 Hz, 3H).

PBD dimer compound 2 comprising an activated disulfide linker hindered with a cyclopropyl moiety was synthesized according to the following overall reaction scheme 2:

Scheme 2:

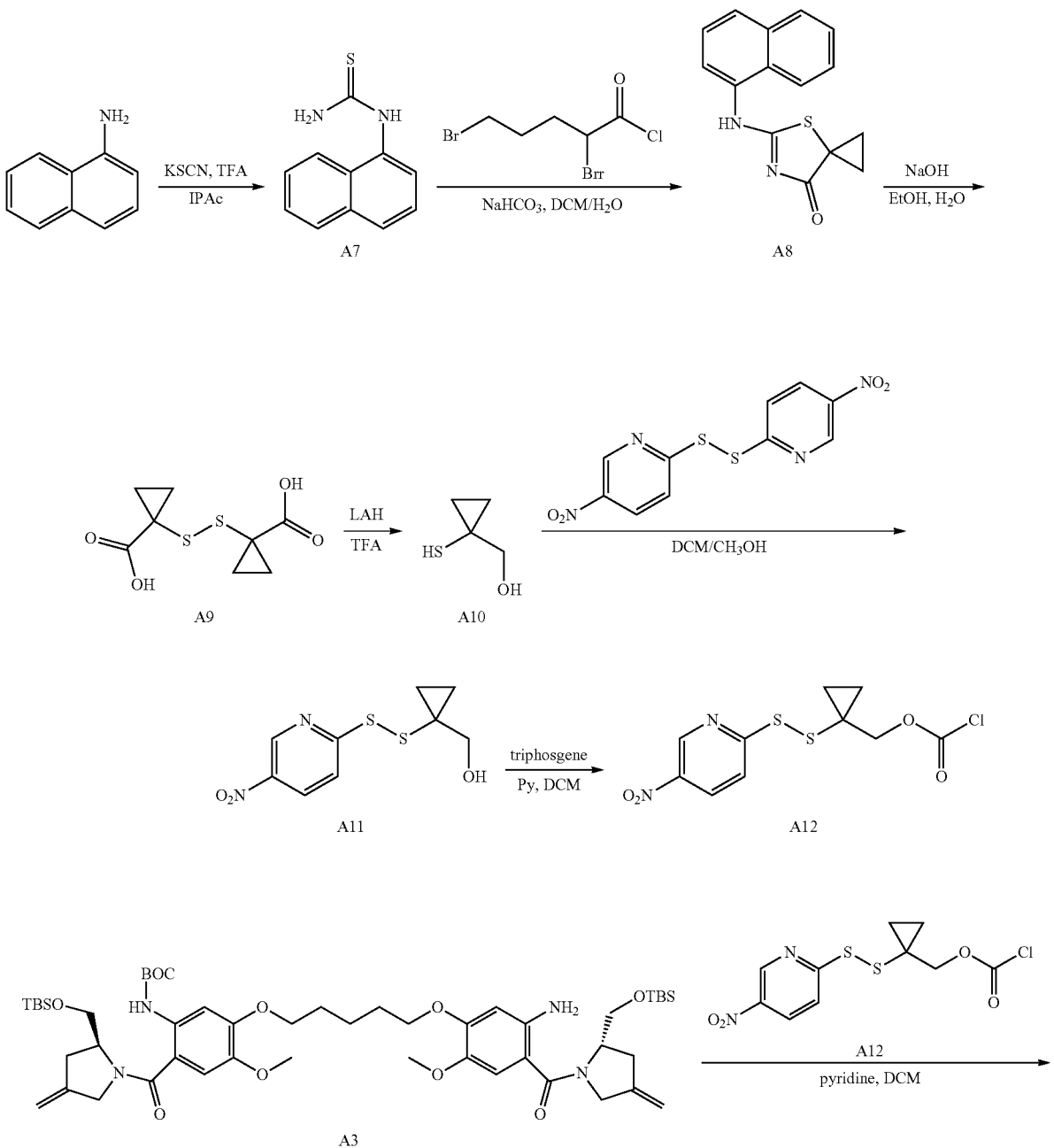

-continued

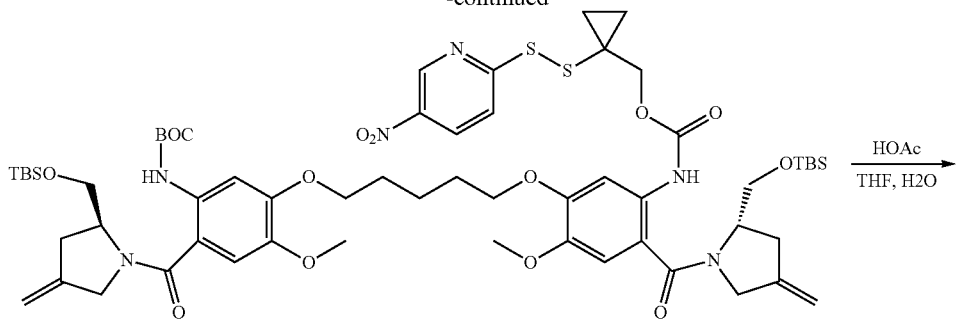

A13

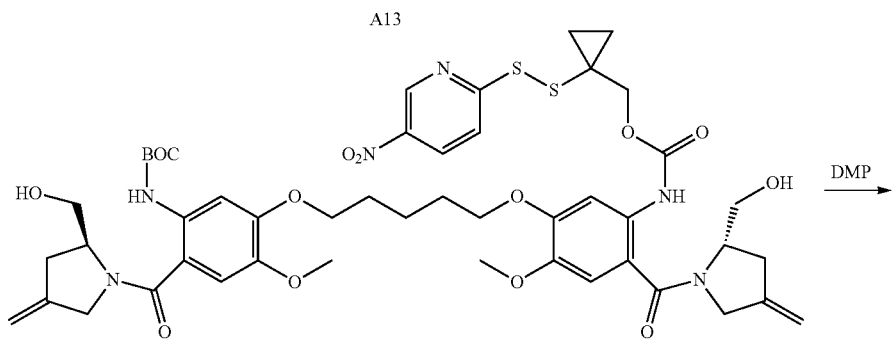

A14

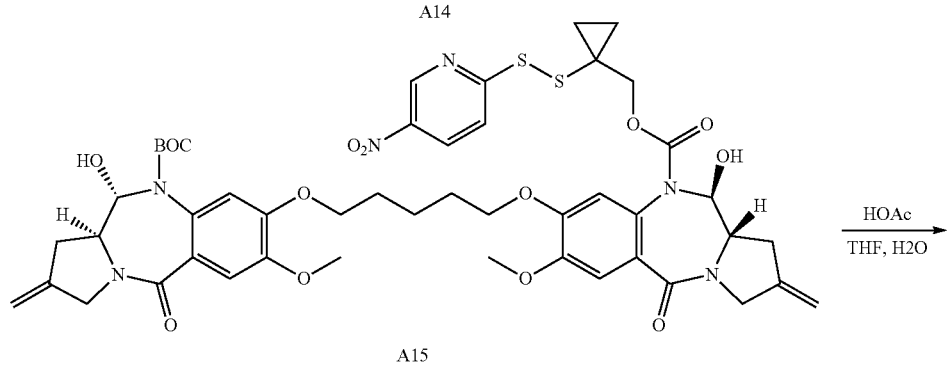

A15

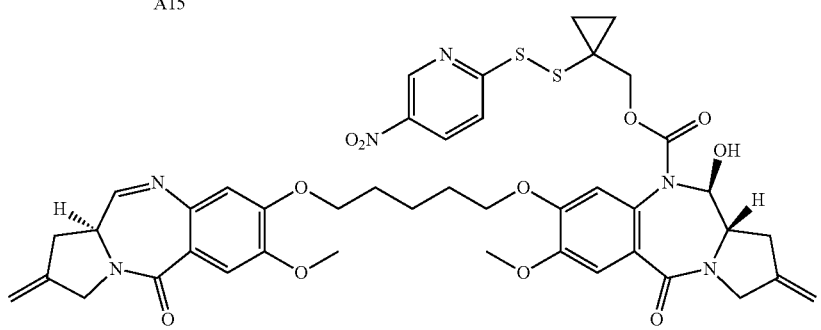

2

TFA (16.3 g, 167.6 mmol) and KSCN (8.14 g, 83.8 mmol) were added sequentially to a sulaphthalene naphthalen-1-amine (12.0 g, 83.8 mmol) in isopropyl acetate (100 mL) at 20° C. The reaction mixture was stirred under reflux overnight, then was cooled to room temperature and filtered. The filter cake was washed with IPOAc (100 mL) then was dried under vacuum to afford compound 2 (12.0 g, 71%) as colorless solid. $^1$H NMR (400 MHz, DMSO-d6) δ 9.76 (s, 1H), 7.96 (d, J=7.6 Hz, 1H), 7.90-7.85 (m, 2H), 7.60-7.45 (m, 4H), 6.96 (br, 2H). For related preparations see: O. R. Thiel, et al. J. Org. Chem. 2008, 73, 3508.

2,4-Dibromobutanoyl chloride (13.5 g, 51.07 mmol) was added to a mixture of compound A7 (10.33 g, 51.07 mmol) in saturated NaHCO₃ solution (80 mL) and DCM (150 mL) slowly at 0° C. The mixture was stirred at 0° C. for 30 min, then 15% aq. NaOH solution (50 mL) and benzyltriethylammonium chloride (200 mg) were added sequentially. After stirring overnight at room temperature, H₂O (100 mL) was added and the mixture was extracted with DCM (200 mL×3). The combined organic layers were dried over Na₂SO₄, filtered, and were concentrated. The residue was purified by flash column chromatography (20% EtOAc in petroleum ether) to give compound A8 (9.0 g, 44%) as a yellow solid. $^1$H NMR (400 MHz, CDCl3) δ 7.99 (d, J=8.0 Hz, 1H), 7.95-7.92 (m, 1H), 7.61-7.55 (m, 4H), 7.46 (d, J=7.2 Hz, 1H), 1.90-1.84 (m, 2H), 1.47-1.41 (m, 2H).

The mixture of compound A8 (5.0 g, 18.63 mmol) in 15% aq. NaOH solution (50 mL) and EtOH (50 mL) was stirred under reflux for 6 h. After the EtOH was removed under vacuum, the aqueous phase was extracted with EtOAc (70 mL×4) to remove unwanted byproducts. The aqueous phase was acidified to pH 3 by the slow addition of an aq. HCl solution, and then was extracted with EtOAc (70 mL×4). The combined organic layers were dried over Na$_2$SO$_4$ and MnO$_2$ (3.2 g, 36.8 mmol) was subsequently added.

The mixture was stirred at room temperature for 0.5 h then was filtered and concentrated. The residue was purified by flash column chromatography (5% CH$_3$OH in DCM) to give compound A9 (1.3 g, 60%) as a yellow solid. $^1$H NMR (400 MHz, CDCl3) δ 1.92 (s, 4H), 1.62 (s, 4H).

A solution of compound A9 (400 mg, 1.71 mmol) in anhydrous THF (10 mL) was added to a suspension of LAH (389 mg, 10.2 mmol) in anhydrous THF (10 mL) at 25° C. The reaction mixture was stirred under reflux for 1 h then was cooled to 0° C. and carefully quenched with 2 N aqueous HCl solution. The resulting mixture was diluted with DCM/MeOH (see below) and used directly in next step without further purification.

A mixture of crude compound A10 (356 mg, 3.42 mmol) and 1,2-bis(5-nitropyridin-2-yl)disulfane (2.12 g, 6.84 mmol) in DCM/MeOH (60 mL/60 mL) was stirred at room temperature overnight. MnO$_2$ (3.0 g, 34.5 mmol) was then added and the mixture was stirred for another 0.5 h at room temperature. The mixture was filtered, and the filter cake was washed with DCM (100 mL). The combined filtrate and washings were concentrated under vacuum and the residue was purified by flash column chromatography (0 to 1% DCM in MeOH) to give the desired product. This material was further purified by prep-TLC (DCM/MeOH=20/1) to afford A11 (400 mg, 46% over 2 steps) as brown oil. LCMS (5-95AB, 1.5 min): RT=0.80 min, m/z=258.8 [M+H]+; $^1$H NMR (400 MHz, CDCl3) δ 9.35 (s, 1H), 8.36 (dd, J=8.8, 2.4 Hz, 1H), 7.65 (d, J=8.8 Hz, 1H), 4.41 (s, 1H), 3.47 (s, 2H), 1.15-1.12 (m, 2H), 1.01-0.98 (m, 2H).

A solution of compound A11 (85.0 mg, 0.33 mmol) and pyridine (25.0 mg, 0.32 mmol) in DCM (3 mL) was added dropwise to a solution of triphosgene (39.0 mg, 0.13 mmol) in DCM (3.0 mL) at 0° C. The reaction mixture was stirred at 0° C. for 15 min then was used directly in the next step.

The solution of crude compound A12 prepared above (96.0 mg, 0.30 mmol) was added dropwise to a solution of compound A3 (220.0 mg, 0.23 mmol) and pyridine (24.0 mg, 0.30 mmol) in DCM (6.0 mL) at 26° C. The reaction mixture was stirred at 26° C. for 2 h whereupon TLC analysis showed appearance of desired product (50% EtOAc in petroleum ether, Rf=0.30) and consumption of the starting material (Rf=0.25). The solvent was removed under reduced pressure and the residue was purified by prep-TLC (30% EtOAc in petroleum ether) to afford compound A13 (150 mg, 53%) as a yellow foam. LCMS (Condition A, 5-95AB, 1.5 min): RT=1.25 min, m/z=1237.4 [M+H]+.

Glacial HOAc (3.0 mL, 52 mmol) was added to a solution of compound A13 (150.0 mg, 0.12 mmol) in H2O (2.0 mL) and THF (2.0 mL) at 20° C. The reaction mixture was stirred at 20° C. for 24 h whereupon TLC analysis showed appearance of the desired product (3.3% MeOH in DCM, Rf=0.5) and consumption of the starting material (Rf=0.65). The reaction mixture was diluted with EtOAc (10 mL) and was washed with water (2×4 mL), saturated aq. NaHCO$_3$ (6 mL) and brine (6 mL). The organic layer was dried over Na$_2$SO$_4$, filtered, and was concentrated. The residue was purified by prep-TLC (5% MeOH in DCM, Rf=0.5) to afford compound A14 (70 mg, 57%) as a yellow foam. LCMS (Condition A, 5-95AB, 1.5 min): RT=0.87 min, m/z=1009.4 [M+H]+.

Dess-Martin periodinane (88.0 mg, 0.210 mmol) was added to a solution of compound A14 (70.0 mg, 0.070 mmol) in DCM (4.0 mL) at 0° C. The reaction mixture was warmed to 20° C. and was stirred for 2 h. A saturated solution of NaHCO$_3$/Na$_2$SO$_3$ (3.0 mL/3.0 mL) was then added and the mixture was extracted with DCM (3×20 mL). The combined organic layers were washed with NaHCO$_3$/Na$_2$SO$_3$ (3.0 mL/3.0 mL), brine (5 mL), dried over Na$_2$SO$_4$, filtered, and were concentrated. The residue was purified by prep-TLC (6.25% MeOH in DCM, Rf=0.5) to give compound A15 (45 mg, 65%) as a yellow foam. LCMS (Condition B, 10-80AB, 7.0 min): RT=2.70 min, m/z=887.5 [M-100-18]+.

Cold TFA (95% in water, 2.0 mL) was added to compound A15 (45 mg, 0.045 mmol) at 0° C. After the reaction mixture was stirred at 0° C. for 30 min, it was added dropwise to a solution of saturated aq. NaHCO$_3$ (4.0 mL) at 0° C. The resulting mixture was extracted with DCM (4×8.0 mL), and the combined organic layers were washed with brine (20 mL), dried over Na$_2$SO$_4$, filtered, and were concentrated to give the crude product. This material was purified by prep-TLC (6.25% MeOH in DCM, Rf=0.5) to afford compound 2 (22 mg, 55%) as a yellow solid. LCMS (Condition A, 5-95AB, 1.5 min): RT=0.75 min, m/z=887.5 [M+H]+; $^1$H NMR (400 MHz, CDCl3) δ 9.18 (s, 1H), 8.22-8.20 (m, 1H), 7.66 (d, J=4.4 Hz, 1H), 7.51 (d, J=8.8 Hz, 1H), 7.47 (s, 1H), 7.25 (s, 1H), 6.89 (s, 1H), 6.76 (s, 1H), 5.56 (d, J=9.6 Hz, 1H), 7.19-5.13 (m, 4H), 4.48 (br, 1H), 4.32-4.23 (m, 4H), 4.16-4.02 (m, 5H), 3.93-3.86 (m, 6H), 3.81-3.79 (m, 1H), 3.70-3.68 (m, 2H), 3.14-3.08 (m, 1H), 2.95-2.91 (m, 2H), 2.26 (d, J=16.0 Hz, 1H), 1.93-1.89 (m, 4H), 1.63-1.59 (m, 2H), 1.06-1.02 (m, 2H), 0.94-0.84 (m, 2H).

PBD dimer compound 11 comprising an activated disulfide linker hindered with a cyclobutyl moiety was synthesized according to the following overall reaction scheme 3:

Scheme 3:

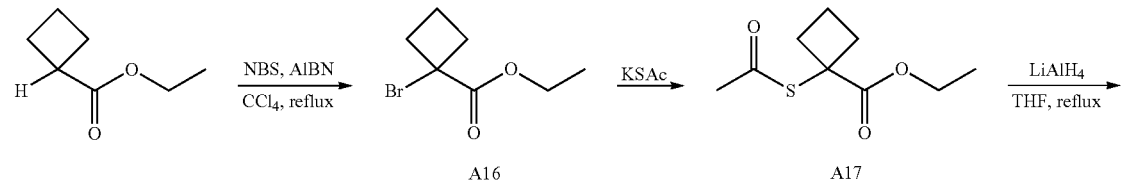

119 120
-continued
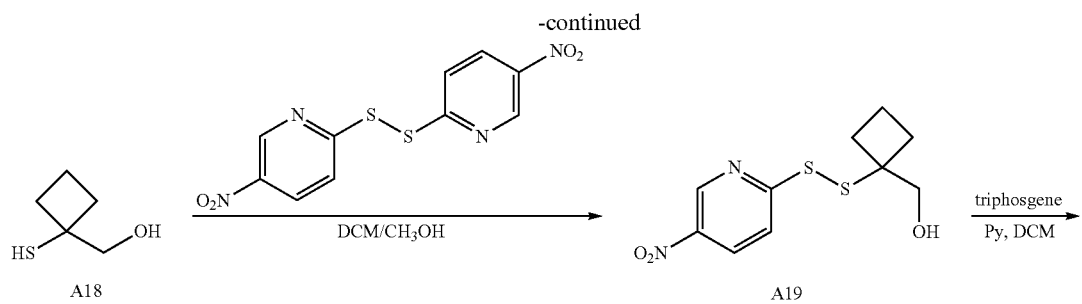
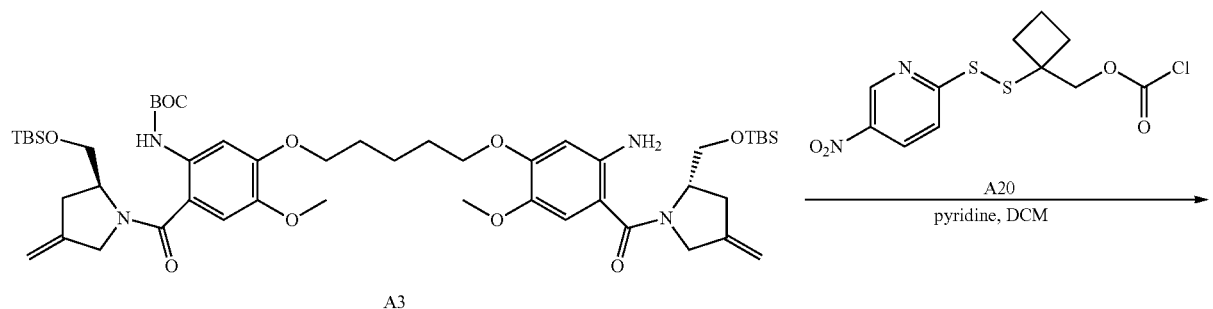
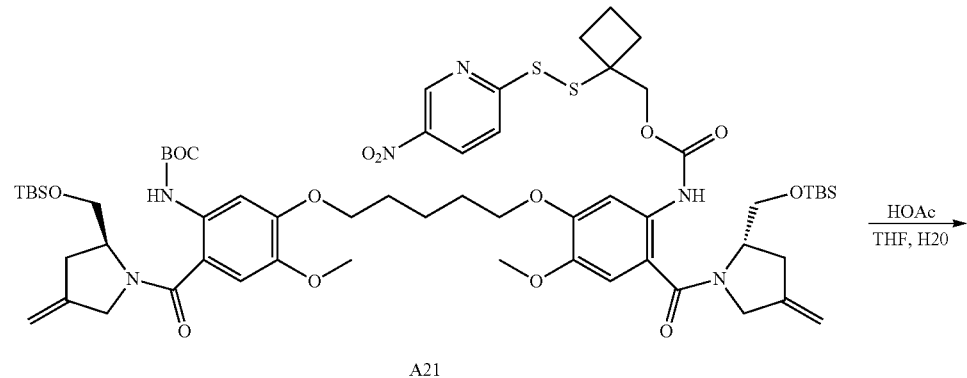
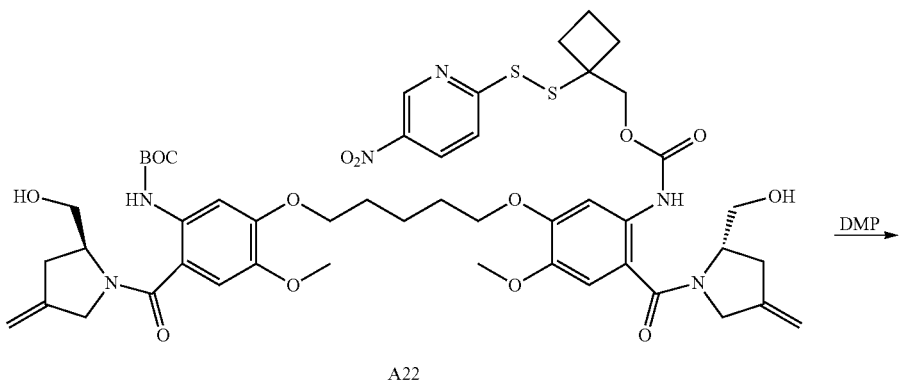

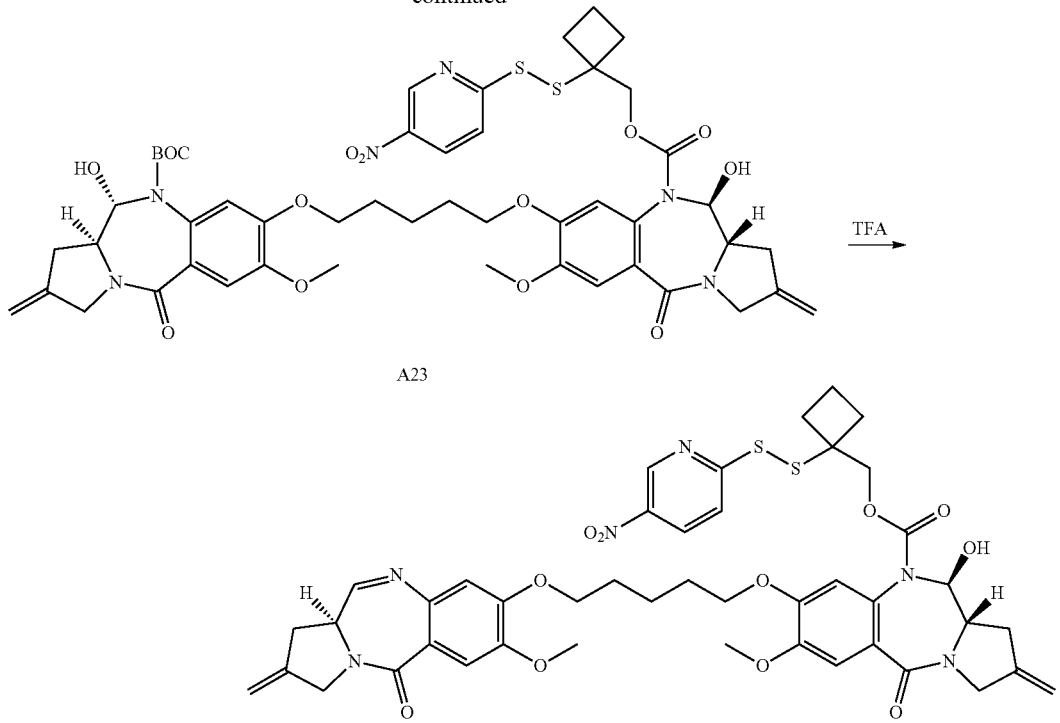

A23

11

N-Bromosuccinimide (17.2 g, 96.6 mmol) and AIBN (1.28 g, 7.8 mmol) were added sequentially to a solution of ethyl cyclobutanecarboxylate (10.0 g, 78.0 mmol) in CCl$_4$ (140 mL) at 25° C. The reaction mixture was heated to 80° C. and was maintained at that temperature for 16 h whereupon TLC analysis showed that the desired product was formed (3% EtOAc in petroleum ether, Rf=0.4). The mixture was cooled to room temperature then was diluted with DCM (100 mL) and washed with water (100 mL×2) and brine (100 mL). The organic layer was dried over Na$_2$SO$_4$, filtered, and was concentrated. The residue was purified by flash column chromatography (1-3% EtOAc in petroleum ether) to afford compound A16 (6.4 g, 40%) as colorless oil, which was used without additional characterization.

KSAc (3.88 g, 34.0 mmol) was added to a mixture of compound A16 (6.4 g, 30.9 mmol) in acetone (100 mL) at 25° C. The reaction mixture was stirred at 80° C. for 30 h whereupon TLC analysis showed that the desired product was formed (10% EtOAc in petroleum ether, Rf=0.6). The mixture was cooled to room temperature then was poured into H$_2$O (200 mL) and extracted with EtOAc (100 mL×3). The combined organic layers were washed with brine (100 mL), dried over Na$_2$SO$_4$, filtered, and were concentrated. The residue was purified by flash column chromatography (0-5% EtOAc in petroleum ether) to afford compound A17 (2.5 g, 40%) as yellow oil. $^1$H NMR (400 MHz, CDCl3) δ 4.22-4.17 (m, 2H), 2.89-2.83 (m, 2H), 2.27 (s, 3H), 2.22-2.03 (m, 4H), 1.26 (t, J=6.8 Hz, 3H).

A solution of compound A17 (2.5 g, 12.36 mmol) in THF (20 mL) was added to a mixture of LAH (1.88 g, 49.4 mmol) in THF (50 mL) at 0° C. After completing the addition, the mixture was heated to reflux at 80° C. for 2 h whereupon TLC analysis showed formation of the desired product (10% EtOAc in petroleum ether, Rf=0.2). The reaction mixture was cooled to 0° C. and was carefully quenched by the slow addition of aqueous HCl (6 mL, 2.0 M). The mixture was diluted with DCM/MeOH (see below) and was used directly in the next step.

The reaction mixture prepared in the previous step was added to a suspension of 1,2-bis(5-nitropyridin-2-yl)disulfane (7.67 g, 24.7 mmol) in DCM (60 mL) and MeOH (60 mL) at 15° C. The reaction mixture was then stirred at 15° C. for 16 h whereupon TLC analysis showed that the desired product was formed (100% DCM, Rf=0.3). MnO$_2$ (5.0 g) was added and the mixture was stirred at room temperature for 30 min then filtered. The filtrate was concentrated to give a yellow solid which was triturated with 50 mL of MeOH and filtered a second time. The filtrate was once again concentrated and the residue was purified by flash column chromatography (0-1% MeOH in DCM) to afford compound A19 (1.46 g, 43% over two steps) as yellow solid. LCMS (Condition A, 5-95AB, 1.5 min): RT=0.70 min, m/z=272.9 [M+H]$^+$.

A solution of compound A19 (200.0 mg, 0.73 mmol) and pyridine (58.0 mg, 0.73 mmol) in DCM (3.0 mL) was added dropwise to a solution of triphosgene (87.0 mg, 0.29 mmol) in DCM (2.0 mL) at 0° C. The mixture was stirred at 0° C. for 1 h then was used directly in the next step.

The crude solution of compound A20 prepared above (245.0 mg, 0.50 mmol) in DCM (5.0 mL) was added dropwise to a stirred mixture of Compound A3 (500.0 mg, 0.52 mmol) and pyridine (0.06 mL, 0.74 mmol) in DCM (5.0 mL) at 25° C. After the addition was complete, the mixture was stirred at 25° C. for 2 h and was subsequently concentrated. The residue was purified by flash column chromatography (0-33% EtOAc in petroleum ether) to afford compound A21 (510 mg, 76%) as a yellow solid. LCMS (Condition A, 5-95AB, 1.5 min): RT=1.25 min, m/z=1273.7 [M+Na]$^+$.

Glacial HOAc (11.76 mL, 205 mmol) was added to a mixture of compound A21 (510.0 mg, 0.40 mmol) in THF (8.0 mL) and water (8.0 mL) at 25° C. The reaction mixture was stirred at 25° C. for 16 h then was diluted with EtOAc (70 mL) and was washed sequentially with water (25 mL×3), saturated aq. NaHCO$_3$ (20 mL×3), and brine (30 mL). The organic phase was dried over Na$_2$SO$_4$, filtered, and was concentrated. The residue was purified by flash column chromatography (0-5% MeOH in DCM) to afford compound A22 (350 mg, 84%) as a yellow solid. LCMS (Condition A, 5-95AB, 1.5 min): RT=0.86 min, m/z=1023.5 [M+H]$^+$.

Dess-Martin periodinane (185 mg, 0.44 mmol) was added to a stirred mixture of compound A22 (154.0 mg, 0.15 mmol) in DCM (10 mL) at 0° C. After the reaction was stirred at 25° C. for 20 h, it was poured into aqueous Na$_2$S$_2$O$_3$ solution (10%, 30 mL) and the resulting mixture was extracted with EtOAc (20 mL×3). The combined organic layers were washed with sat. aq. NaHCO$_3$ (30 mL) and brine (30 mL), then were dried over Na$_2$SO$_4$, filtered, and concentrated. The residue was purified by prep-TLC (6.25% MeOH in DCM, Rf=0.5) to give compound A23 (80 mg, 52%) as a white solid. LCMS (Condition A, 5-95AB, 1.5 min): RT=0.82 min, m/z=1041.5 [M+Na]$^+$.

Cold TFA (1.9 mL, 25 mmol) and water (0.10 mL) were added sequentially to compound A23 (100.0 mg, 0.10 mmol) at 0° C. The reaction mixture was stirred at 0° C. for 1 h, then was added dropwise to a sat. aq. solution of NaHCO$_3$ (150 mL) at 0° C. The resulting mixture was extracted with DCM (40 mL×4), and the combined organic layers were washed with brine (50 mL), dried over Na$_2$SO$_4$, filtered, and concentrated to give the crude product. This material was purified by prep-TLC (10% MeOH in DCM, Rf=0.4) to give compound 11 (20 mg, 23%) as a yellow solid. LCMS (Condition A, 5-95AB, 1.5 min): RT=0.77 min, m/z=901.4 [M+H]$^+$; $^1$H NMR (400 MHz, CDCl$_3$) δ9.21 (d, J=1.98 Hz, 1H) 8.36 (dd, J=8.8, 2.4 Hz, 1H) 7.70 (d, J=4.4 Hz, 1H) 7.56-7.51 (m, 2H), 7.49 (s, 1H), 6.80 (s, 1H), 6.74 (s, 1H), 5.59 (d, J=10.0 Hz, 1H), 5.20 (d, J=11.2 Hz, 2H), 5.16 (br., 2H), 4.64-4.48 (m, 1H), 4.40-4.25 (m, 5H), 4.21-3.98 (m, 6H), 3.91-3.73 (m, 2H), 3.65 (t, J=8.80 Hz, 1H) 3.50 (s, 1H) 3.22-3.08 (m, 1H) 2.99-2.87 (m, 2H) 2.73 (m, 1H) 2.04-1.86 (m, 8H) 1.38-1.15 (m, 1H).

Example 19: Preparation of MMAE Compounds Comprising an Activated Hindered Disulfide Activated MMAE compound A was synthesized according to the following overall reaction scheme 1.

Scheme 1:

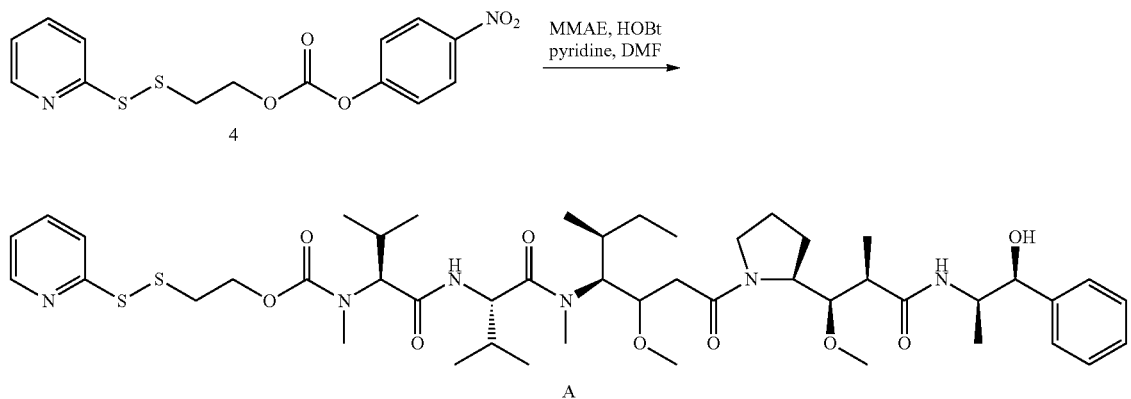

To a solution of compound 1 (60 mg, 0.17 mmol), MMAE (110 mg, 0.123 mmol), HOBt (4.6 mg, 0.034 mmol) in dry DMF (3.0 mL) was added pyridine (134 mg, 1.7 mmol) at 20° C., and the mixture was allowed to stir at 16° C. for 16 h under $N_2$. The mixture was filtered and purified by prep-HPLC (FA conditions), to give compound A (99.7 mg, yield: 64%) as a white solid. LCMS: (10-80, AB, 2 min), 1.331 min, MS=932.5[M+2]; $^1$H NMR (400 MHz, DMSO-$d_6$) δ 8.46 (d, J=4.4 Hz, 1H), 7.80-7.76 (m, 2H), 7.56 (s, 1H), 7.34-7.18 (m, 7H), 5.10 (s, 1H), 4.56-4.51 (m, 2H), 4.29-4.16 (m, 3H), 4.03 (s, 2H), 3.77 (d, J=11.6 Hz, 2H), 3.37 (d, J=9.6 Hz, 2H), 3.28-3.23 (m, 8H), 3.15 (s, 3H), 2.84 (s, 3H), 2.40 (s, 2H), 2.18 (s, 2H), 2.00 (s, 1H), 1.81 (s, 3H), 1.62-1.56 (m, 2H), 1.34 (d, J=6.4 Hz, 1H), 1.05-1.01 (m, 8H), 0.88-0.80 (m, 18H). The molecular weight determined by NMR was 930.50.

Activated MMAE compound B was synthesized according to the following overall reaction scheme 2.

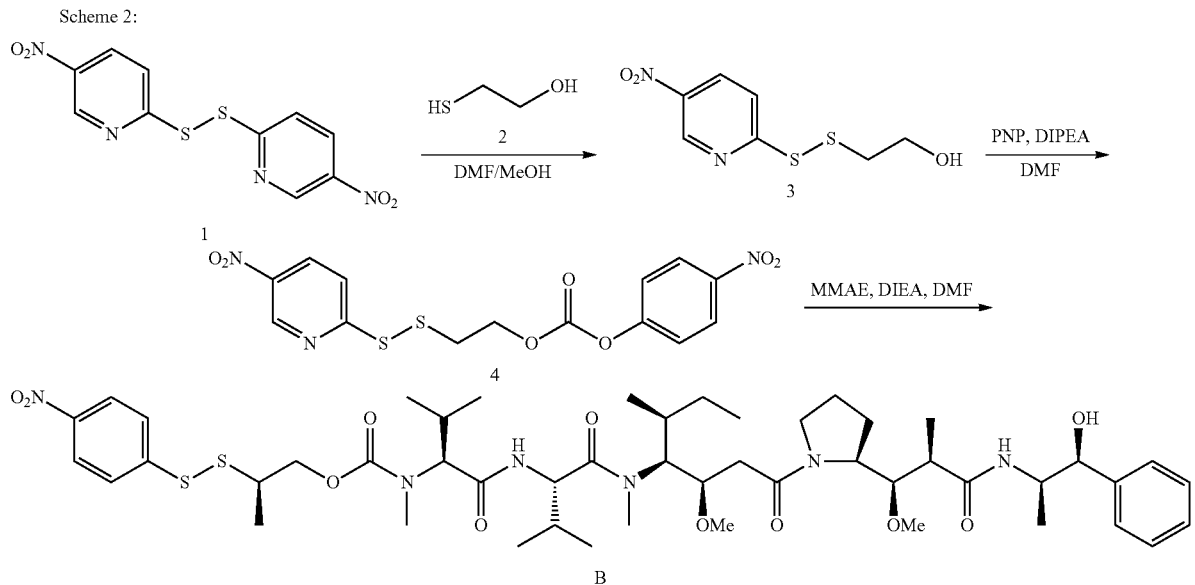

To a stirred solution of compound 1 (3.00 g, 9.68 mmol) in MeOH/DMF (1:1, 10.0 mL), a solution of compound 2 (380 mg, 4.84 mmol) in MeOH/DMF (1.0 mL) was added dropwise over 5 min under $N_2$ at 15° C. After the mixture was stirred at 15° C. for 16 h under $N_2$, it was concentrated and purified by prep-TLC (DCM/MeOH=30/1) to give compound 3 (500 mg, yield: 45%).

To a stirred solution of Compound 3 (50.0 mg, 0.215 mmol), PNP (131 mg, 0.43 mmol) in DMF (3.0 mL) and DIPEA (56 mg, 0.43 mmol) were added at 15° C. The mixture was stirred at 15° C. for 16 h under $N_2$. The mixture was concentrated and purified by prep-TLC (DCM/MeOH=30/1) to give compound 4 (60 mg, yield: 74%).

To a stirred solution of compound 4 (30 mg, 0.0756 mmol), were added MMAE (49 mg, 0.068 mmol), HOBt (2.0 mg, 0.015 mmol) in DMF (3.0 mL) and pyridine (60 mg, 0.756 mmol) at 22° C. After the mixture was stirred at 20° C. for 16 h, it was purified by prep-HPLC (FA) to give compound B (60.0 mg, yield: 80%). LCMS: (5-95, AB, 1.5 min), 1.007 min, MS=998.6[M+23]$^+$; $^1$H NMR (400 MHz, DMSO-$d_6$) δ 9.23 (s, 1H), 8.53 (d, J=7.6 Hz, 1H), 7.44-8.02 (d, J=8.0 Hz, 1H), 7.58 (s, 1H), 7.35-7.18 (m, 7H), 5.10 (s, 1H), 4.70-4.45 (m, 2H), 4.31 (s, 2H), 4.18 (s, 1H), 4.03 (s, 2H), 3.80 (s, 1H), 3.46 (s, 1H), 3.40-3.18 (m, 12H), 2.84 (d, J=6.0 Hz, 3H), 2.41 (s, 2H), 2.18 (s, 2H), 1.81 (s, 3H), 1.74-1.50 (m, 2H), 1.37 (s, 1H), 1.04-0.78 (m, 28H). The molecular weight determined by NMR was 975.48.

Activated MMAE compound C was synthesized according to the following overall reaction scheme 3.

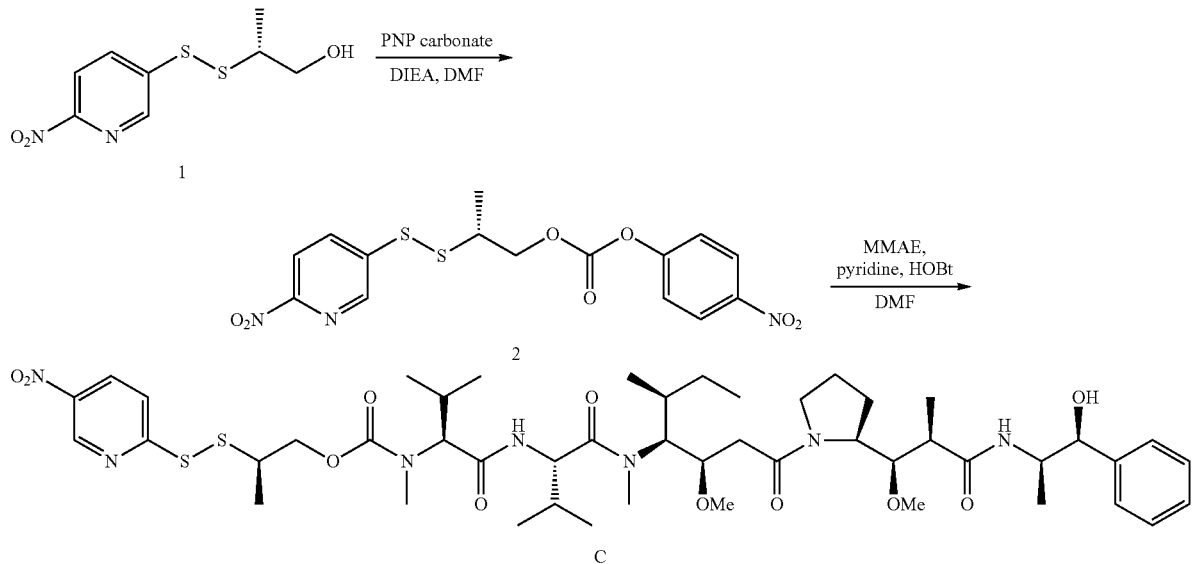

To a stirred solution of compound 1 (50 mg, 0.203 mmol) and PNP carbonate (123 mg, 0.406 mmol) in DMF (2.0 mL) was added DIEA (78 mg, 0.609 mmol). The reaction mixture was stirred at 27° C. for 2 h. Solvent was removed under reduced pressure, and the residue was partitioned between DCM (50 mL×2) and H$_2$O (40 mL). The combined organic phase was dried over Na$_2$SO$_4$, concentrated and purified by prep-TLC (PE/EtOAc=3/1) to give compound 2 (60 mg, yield: 72%) as a yellow solid. LCMS: (5-95, AB, 1.5 min), 0.857 min, MS=411.8[M+1]$^+$.

To a stirred solution of MMAE (30 mg, 0.042 mmol) and compound 2 (34 mg, 0.084 mmol) in dry DMF (2.0 mL) was added HOBt (1.0 mg, 0.0042 mmol) and pyridine (33 mg, 0.42 mmol). The mixture was stirred at 27° C. for 12 h and purified by prep-HPLC (FA) to give compound C (23 mg, yield: 55%) as a white solid. $^1$H NMR (400 MHz, MeOH-d$_4$) δ ppm 9.24 (br. s., 1H), 8.54 (dd, J=8.9, 2.6 Hz, 1H), 8.07 (dd, J=9.0, 2.0 Hz, 1H), 7.53-7.09 (m, 5H), 4.73-4.56 (m, 5H), 4.36-4.15 (m, 5H), 3.92-3.51 (m, 1H), 3.49-3.37 (m, 2H), 3.35 (s, 5H), 3.25-3.09 (m, 2H), 3.02-2.86 (m, 3H), 2.56-2.39 (m, 2H), 2.32-1.51 (m, 2H), 1.38 (dd, J=6.8, 2.8 Hz, 4H), 1.23-1.09 (m, 6H), 1.06-0.77 (m, 19H). The molecular weight determined by NMR was 989.50.

Activated MMAE compounds E, F and G were synthesized according to the following overall reaction scheme 4.

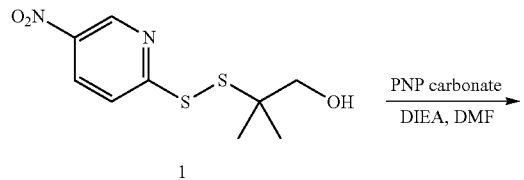

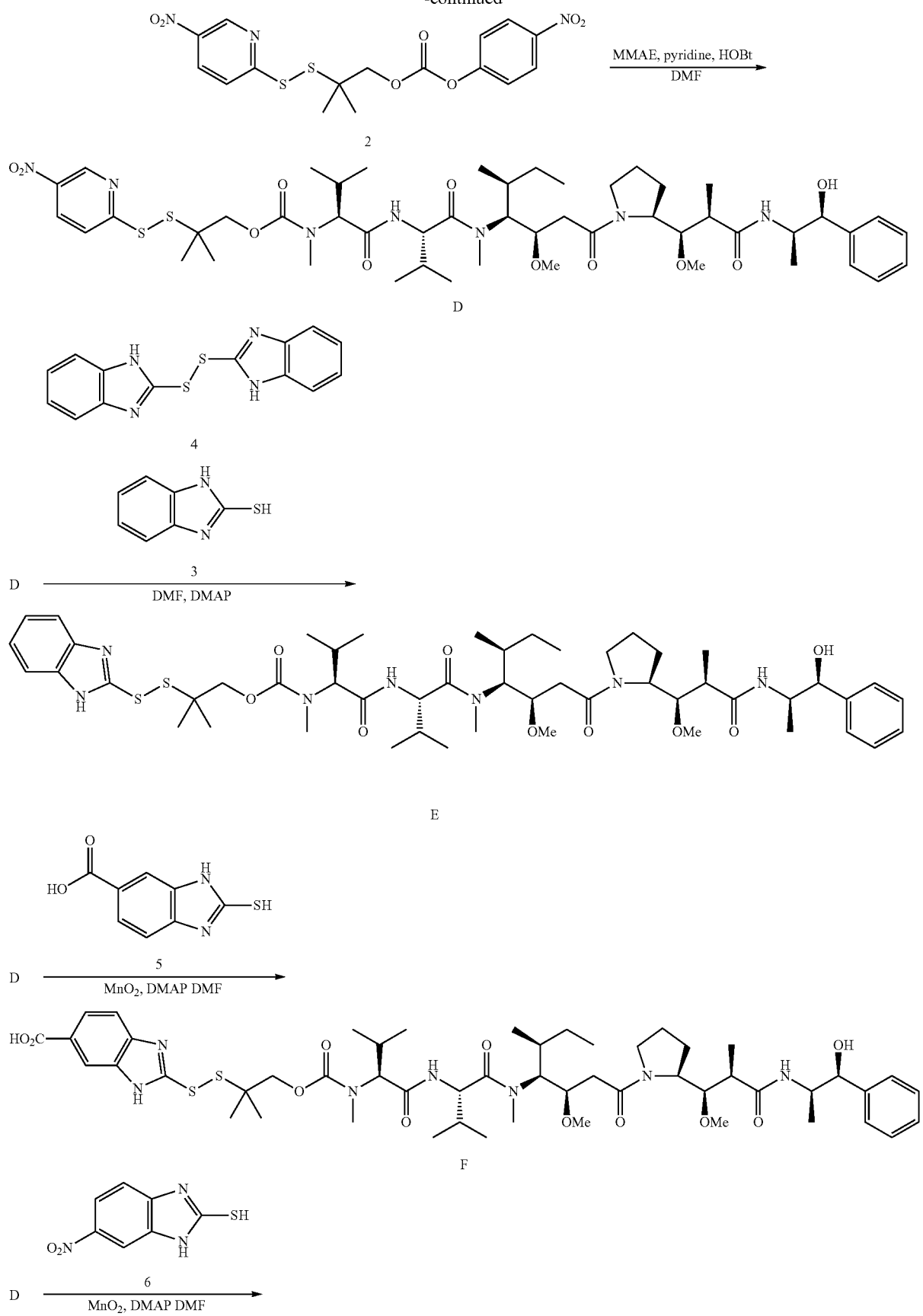

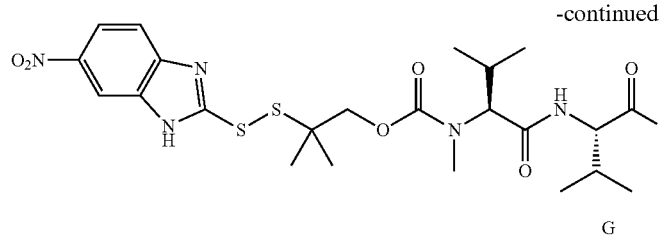

G

A mixture of compound 1 (500.0 mg, 1.92 mmol) and PNP carbonate (1169 mg, 3.84 mmol) in DMF (2.0 mL) was added DIEA (744.7 mg, 5.76 mmol). The reaction mixture was stirred at 14° C. for 8 h under N$_2$. The reaction mixture was concentrated in vacuo and purified by column chromatography (100% DCM) to give compound 2 (300 mg, 34% yield) as a yellow oil. LCMS (5-95AB/1.5 min): RT=0.850 min, [M+H]$^+$ 425.8.

To a mixture of compound 2 (100.0 mg, 0.240 mmol) and pyridine (186 mg, 2.35 mmol) in DMF (10 mL) was added MMAE (107 mg, 0.210 mmol) and HOBt (3.18 mg, 0.020 mmol). The reaction mixture was stirred at 30° C. for 8 h. The mixture was concentrated in vacuo and purified prep-TLC (5% MeOH in DCM) to give compound D (110 mg, 46%) as a white solid. LCMS (5-95AB/1.5 min): RT=0.899 min, [M+Na]$^+$1026.3. $^1$H NMR (400 MHz, CDCl$_3$) δ 9.18 (s, 1H), 8.30 (d, J=8.4 Hz, 1H), 7.88 (d, J=12.8 Hz, 1H), 7.32-7.19 (m, 4H), 6.42 (d, J=9.2 Hz, 1H), 4.88 (s, 1H), 4.72-4.60 (m, 1H), 4.25-4.20 (m, 1H), 4.14-3.94 (m, 5H), 3.78 (d, J=5.6 Hz, 1H), 3.44 (m, 1H), 3.35-3.31 (m, 4H), 3.24 (s, 3H), 3.04 (s, 1H), 2.84-3.00 (m, 2H), 2.44-2.34 (m, 3H), 2.34-2.30 (m, 1H), 1.88-2.05 (m, 3), 1.84-1.75 (m, 3H), 1.30 (s, 7H), 1.20 (m, 3H) 1.00-0.75 (m, 24H). The molecular weight determined by NMR was 1003.51.

A mixture of compound D (20.0 mg, 0.020 mmol), compound 3 (14.96 mg, 0.1000 mmol), compound 4 (29.71 mg, 0.100 mmol), and DMAP (7.3 mg, 0.060 mmol) in DMF (2.0 mL) was stirred at 30° C. for 8 h. The mixture was purified by prep-HPLC to give compound E (4.1 mg, 20.2%) as a white solid. LCMS (5-95AB/1.5 min): RT=0.758 min, [M/2+H]$^+$ 500.1.

A solution of compound 5 (58.02 mg, 0.30 mmol) in DMF (5.0 mL) was added MnO$_2$ (51.99 mg, 0.600 mmol). After the reaction mixture was stirred at 15° C. for 30 min, it was filtered and the filtrate was added to compound D (30.0 mg, 0.030 mmol), compound 5 (29 mg, 0.15 mmol) and DMAP (10.96 mg, 0.090 mmol). The mixture was stirred at 30° C. for 8 h. The mixture was purified by prep-HPLC to give compound F (4.8 mg, 0.0047 mmol, 15.8% yield) as a white solid. LCMS (5-95AB/1.5 min): RT=0.767 min, [M/2+Na]$^+$ 522.1.

To a solution of compound 6 (25 mg, 0.167 mmol) in DMF (5.0 mL) was added MnO$_2$ (58.68 mg, 0.670 mmol). After the reaction mixture was stirred at 18° C. for 30 min, it was filtered, and the filtrates was added to compound D (30.0 mg, 0.0300 mmol), compound 6 (51 mg, 0.339 mmol) and DMAP (12.37 mg, 0.100 mmol). The reaction mixture was stirred at 40° C. for 8 h. The reaction mixture was purified by prep-HPLC to give compound G (9.8 mg, 27%) as a white solid. LCMS (5-95AB/1.5 min): RT=0.849 min, [M+H]$^+$ 1043.5.

Activated MMAE compound H was synthesized according to the following overall reaction scheme 5.

Scheme 6:

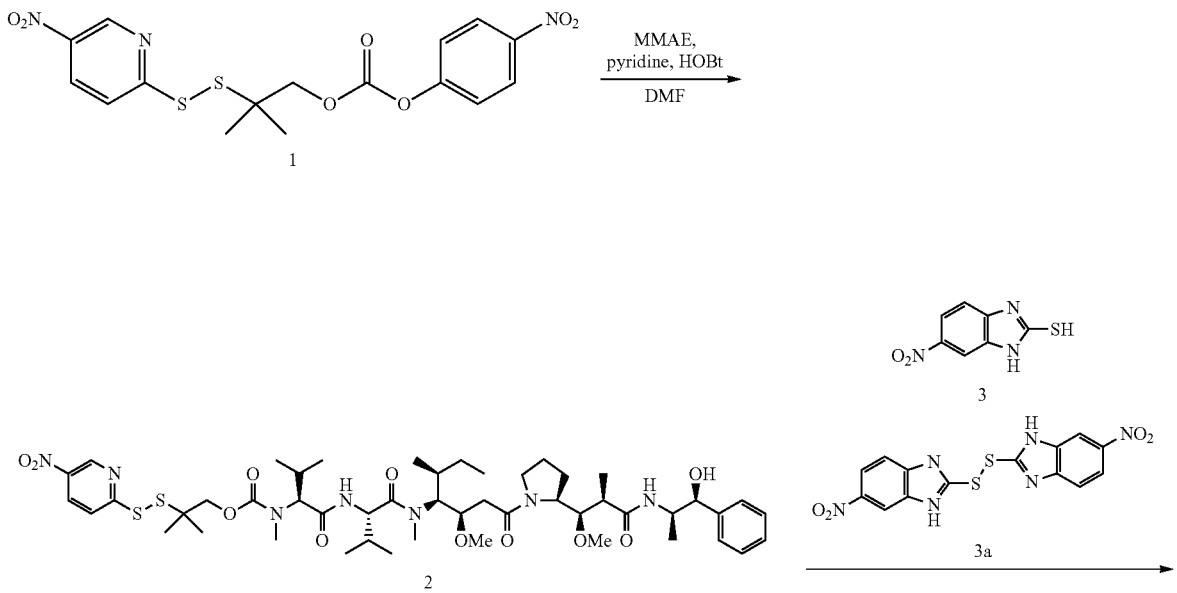

-continued

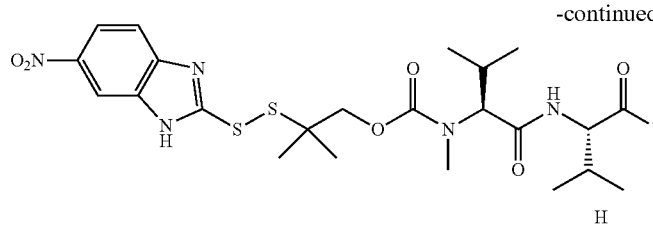

H

To a mixture of compound 1 (150.0 mg, 0.350 mmol) and pyridine (278.9 mg, 3.53 mmol) in DMF (10.0 mL) was added MMAE (160.5 mg, 0.320 mmol) and HOBt (4.76 mg, 0.040 mmol). After the reaction mixture was stirred at 20° C. for 8 h, it was concentrated in vacuo and purified by prep-TLC (9% MeOH in DCM) to give compound 2 (110 mg, 0.110 mmol, 31.1% yield) as a white solid. LCMS (5-95AB/1.5 min): RT=0.897 min, [M+H]+ 1004.5.

A solution of compound 3 (51.0 mg, 0.339 mmol) in DMF (5.0 mL) was added MnO$_2$ (58.68 mg, 0.670 mmol), and the reaction mixture was stirred at 18° C. for 30 min. The mixture was filtered, and to the filtrates was added to compound 2 (30.0 mg, 0.030 mmol), compound 3 (25.0 mg, 0.167 mmol) and DMAP (12.37 mg, 0.100 mmol). The reaction mixture was stirred at 40° C. for 8 h. The reaction mixture was purified by prep-HPLC (column: waters Xbridge Prep OBD C18 150*30 5u, condition: 0.225% FA-ACN) to give compound H (9.8 mg, 0.0091 mmol, 27% yield) as a white solid. LCMS (5-95AB/1.5 min): RT=0.849 min, [M+H]+ 1043.5.

Activated MMAE compound I was synthesized according to the following overall reaction scheme 6.

Carbon disulfide (192 mg, 2.52 mmol) was added to a mixture of KOH (141 mg, 2.52 mmol) in EtOH (4.0 mL) and water (1.0 mL). The reaction mixture was stirred at 20° C. for 15 min. Then compound 3 (250.0 mg, 2.29 mmol) was added. The reaction mixture was stirred under microwave irradiation at 120° C. for 15 min and then cooled to r.t. The reaction mixture was adjusted to pH=5 with HOAc, then the solvent was removed. The solid was washed with water (5.0 mL), dried under reduced pressure to give compound 2 (220 mg, 63.5%) as a black solid. $^1$H NMR (400 MHz, DMSO-d6) δ 8.08 (d, J=4.0 Hz, 1H), 7.45 (d, J=8.0 Hz, 1H), 7.12-7.09 (m, 1H).

To the mixture of compound 2 (45.0 mg, 0.300 mmol) in DMF (2.0 mL) was added MnO$_2$ (129 mg, 1.49 mmol). The mixture was stirred at 25° C. for 15 min. The mixture was filtered and the filtrate was used directly in the next step.

To the mixture of compound 1 (30.0 mg, 0.030 mmol), compound 2a (44.0 mg, 0.150 mmol) and compound 2 (45.2 mg, 0.300 mmol) in DMF (3.0 mL) was added DMAP (18.3 mg, 0.150 mmol). The mixture was stirred at 40° C. for 2 h. The mixture was purified by prep-HPLC (acetonitrile 45-75%/10 mM NH$_4$HCO$_3$-ACN) to afford compound I (7.8

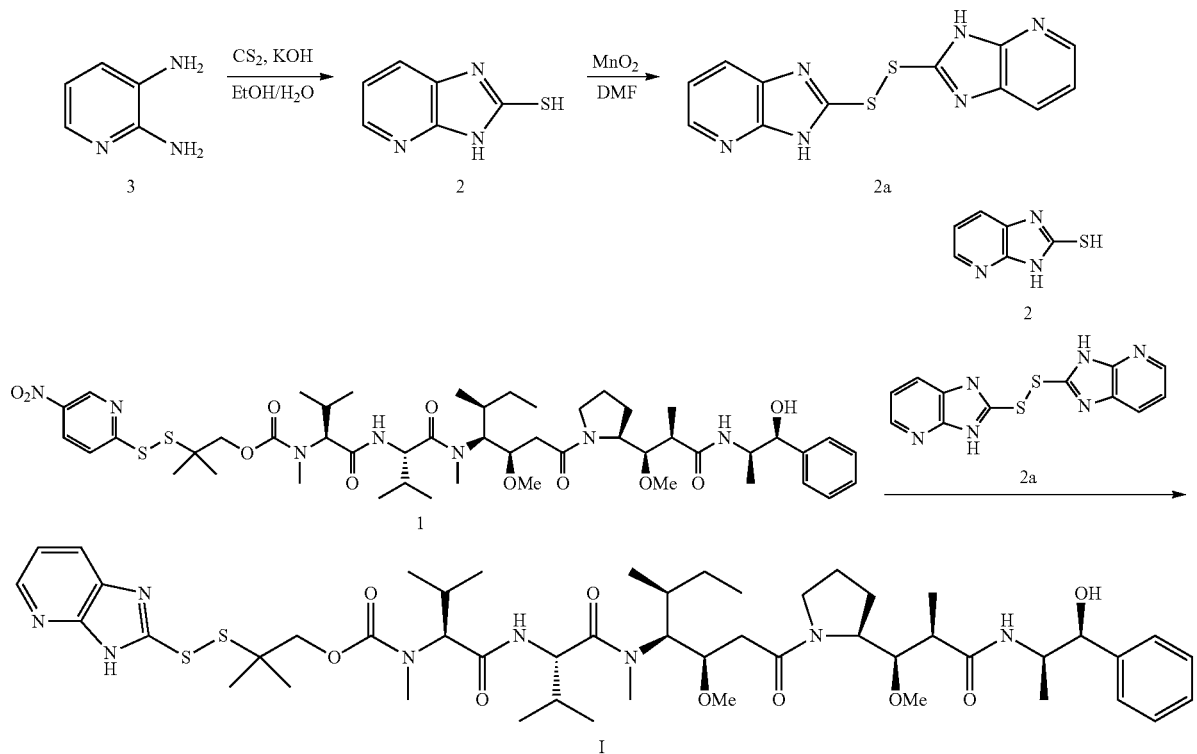

mg, 25.8%) as a white solid. LCMS (5-95AB/1.5 min): RT=0.735 min, [M+H]$^+$ 999.6.

Activated MMAE compound J was synthesized according to the following overall reaction scheme 7.

Scheme 7:

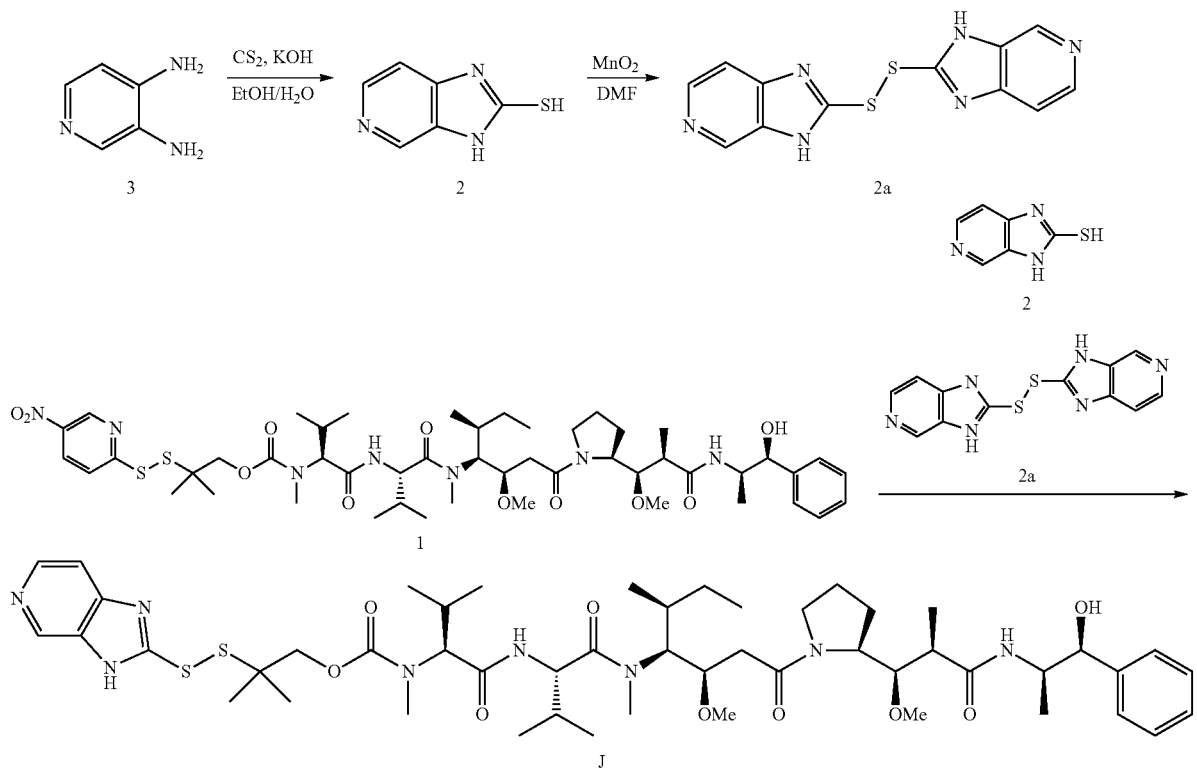

Carbon disulfide (191 mg, 2.52 mmol) was added to a mixture of KOH (141 mg, 2.52 mmol) in EtOH (4.0 mL) and water (1.0 mL). The reaction mixture was stirred at 20° C. for 15 min. Then compound 3 (250 mg, 2.29 mmol) was added. The reaction mixture was heated under microwave irradiation at 130° C. for 15 min and cooled to r.t. The reaction mixture was diluted with H$_2$O (10 mL), adjusted to pH=5 with HOAc, and cooled to 0° C. The solid was filtered and dried under reduced pressure to give compound 2 (230 mg, 66.4%) as a white solid. $^1$H NMR (400 MHz, DMSO-d6) δ 12.87-12.84 (m, 2H), 8.36 (s, 1H), 8.23 (d, J=5.2 Hz, 1H), 7.15 (d, J=5.2 Hz, 1H).

To the mixture of compound 2 (45.0 mg, 0.300 mmol) in DMF (2.0 mL) was added MnO$_2$ (129 mg, 1.49 mmol) and the mixture was stirred at 25° C. for 15 min. The mixture was filtrated and the filtrate was used directly to the next step.

To a mixture of compound 1 (30.0 mg, 0.030 mmol), compound 2a (44.0 mg, 0.150 mmol) and compound 2 (45.16 mg, 0.300 mmol) in DMF (3.0 mL) was added DMAP (18.25 mg, 0.150 mmol). The mixture was stirred at 40° C. for 15 h. The mixture was purified by prep-HPLC (acetonitrile 35-65%/0.225% FA-ACN) to afford compound J (8.8 mg, 29.5%) as a white solid. LCMS (5-95AB/1.5 min): RT=0.717 min, [M+H]$^+$ 999.5.

Activated MMAE compound K was synthesized according to the following overall reaction scheme 8.

Scheme 8:

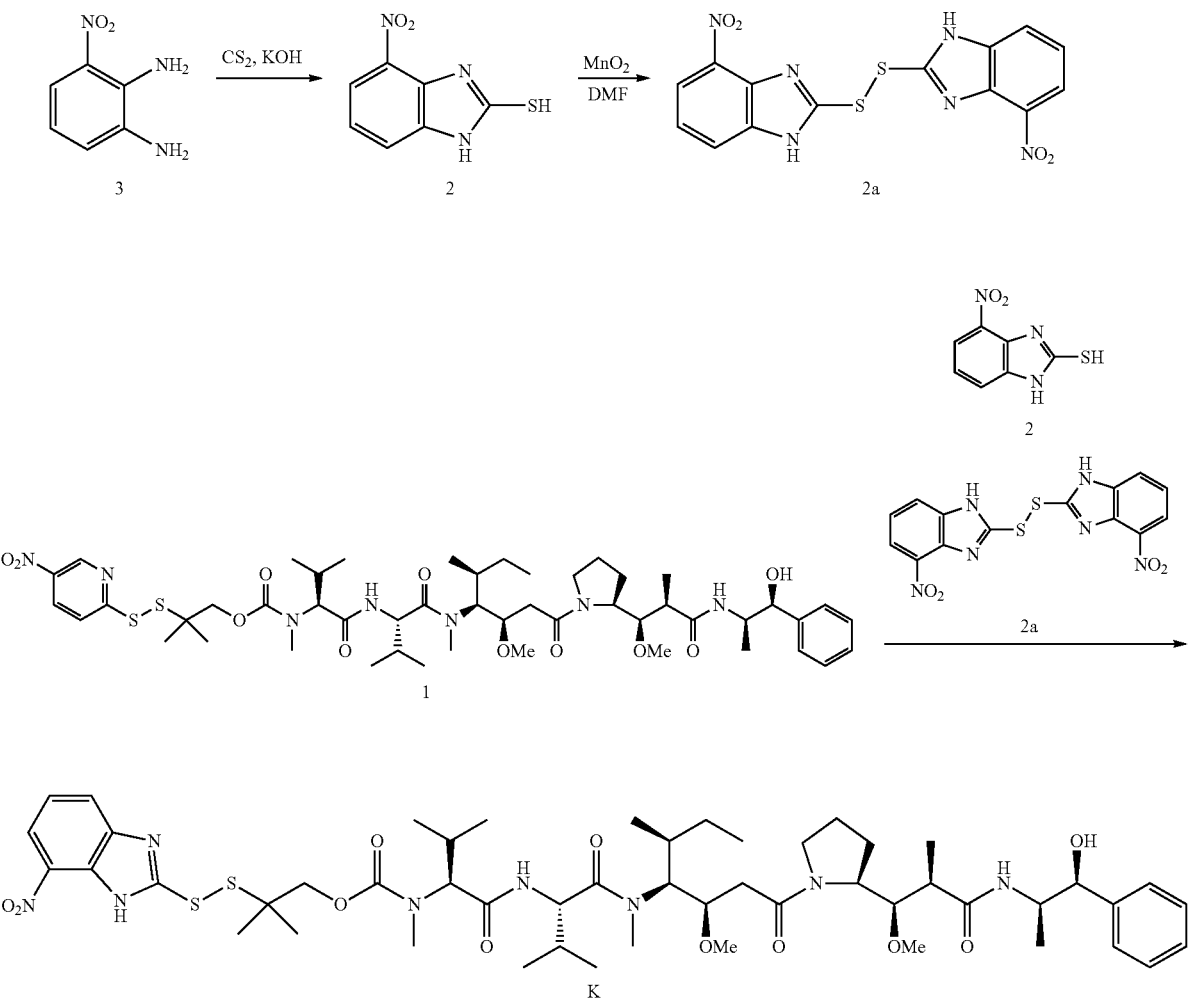

To a solution of compound 3 (250.0 mg, 1.63 mmol) in DMF (1.0 mL) was added carbon disulfide (174 mg, 2.29 mmol). The mixture was stirred at 25° C. for 72 h. The reaction mixture was diluted with H₂O (10.0 mL), adjusted to pH=5.0 with HOAc, and filtered under reduced pressure to give compound 2 (200 mg, 62.8%) as a yellow solid, which was used in the next step directly. ¹H NMR (400 MHz, DMSO-d6) δ 13.18-13.07 (m, 2H), 7.91 (d, J=8.0 Hz, 1H), 7.49 (d, J=8.0 Hz, 1H), 7.29 (t, J=8.4 Hz, 1H).

To the mixture of compound 2 (60.0 mg, 0.310 mmol) in DMF (2.0 mL) was added MnO₂ (134 mg, 1.54 mmol). The mixture was stirred at 25° C. for 15 min, then filtered. The filtrate was used directly in the next step.

To a mixture of compound 1 (30.0 mg, 0.030 mmol), compound 2a (58.0 mg, 0.150 mmol) and compound 2 (58.3 mg, 0.300 mmol) in DMF (3.0 mL) was added DMAP (18.25 mg, 0.150 mmol). The mixture was stirred at 40° C. for 2 h. The mixture was purified by prep-HPLC (acetonitrile 50-80%/0.225% FA-ACN) to afford compound K (7.7 mg, 0.0072 mmol, 23.9% yield) as a yellow solid. LCMS (5-95AB/1.5 min): RT=0.863 min, [M+H]⁺ 1043.7.

Activated MMAE compound L was synthesized according to the following overall reaction scheme 9.

Scheme 9:

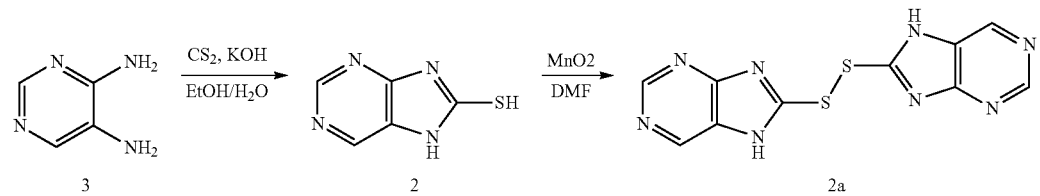

-continued

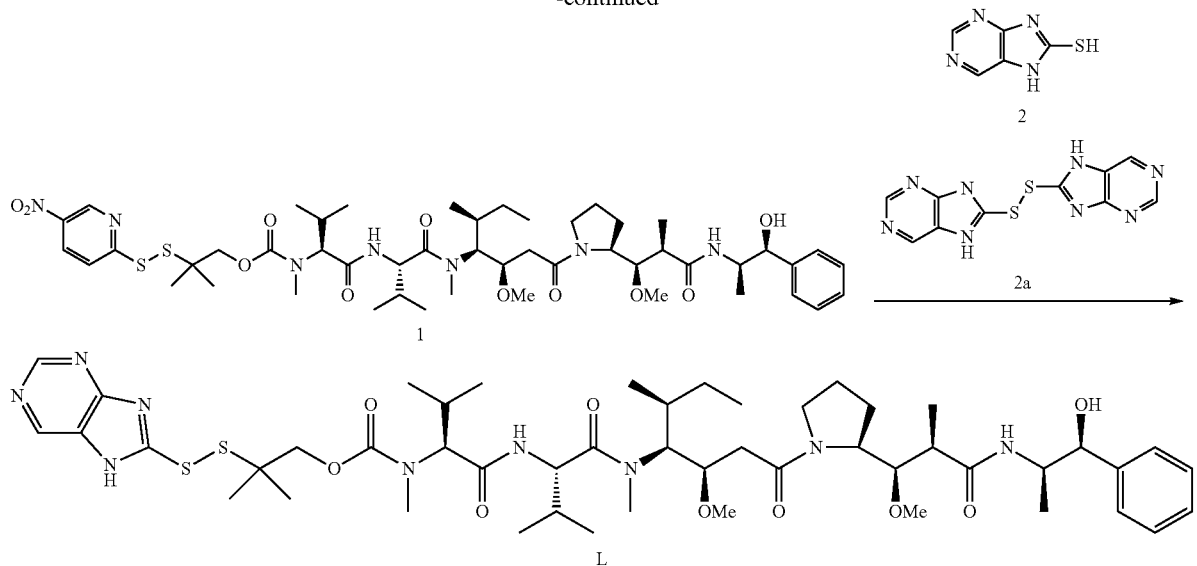

Carbon disulfide (207.4 mg, 2.72 mmol) was added to a mixture of KOH (153 mg, 2.72 mmol) in EtOH (2.0 mL) and water (0.50 mL). The reaction mixture was stirred at 120° C. for 15 min. Then compound 3 (250 mg, 2.27 mmol) was added. The reaction mixture was stirred under microwave irradiation at 130° C. for 15 min and then cooled to r.t. The reaction mixture was diluted with H$_2$O (10.0 mL), adjusted to pH=5 with HOAc, and cooled to 0° C. The solid was collected by filtration and dried under reduced pressure to give compound 2 (220 mg, 63.7%) as a yellow solid. $^1$H NMR (400 MHz, DMSO-d6) δ 13.50 (s, 1H), 13.01 (s, 1H), 8.67 (s, 1H), 8.42 (s, 1H).

To the mixture of compound 2 (45.0 mg, 0.300 mmol) in DMF (3.0 mL) was added MnO$_2$ (128.5 mg, 1.48 mmol).

The mixture was stirred at 25° C. for 15 min and filtered. The filtrate was used directly used in the next step without further purification.

To a mixture of compound 1 (30.0 mg, 0.030 mmol), compound 2a (44.0 mg, 0.150 mmol) and compound 2 (45.5 mg, 0.300 mmol) in DMF (3.0 mL) was added DMAP (18.26 mg, 0.150 mmol). The mixture was stirred at 40° C. for 15 h. The mixture was purified by prep-HPLC (acetonitrile 30-60%/0.1% NH$_4$OH in water) to afford compound L (9.2 mg, 30.1%) as a white solid. LCMS (5-95AB/1.5 min): RT=0.873 min, [M+H]$^+$ 1001.0.

Activated MMAE compound M was synthesized according to the following overall reaction scheme 10.

Scheme 10:

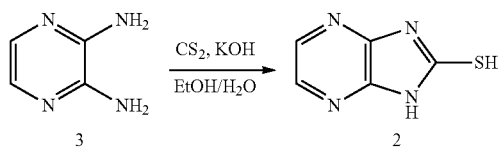

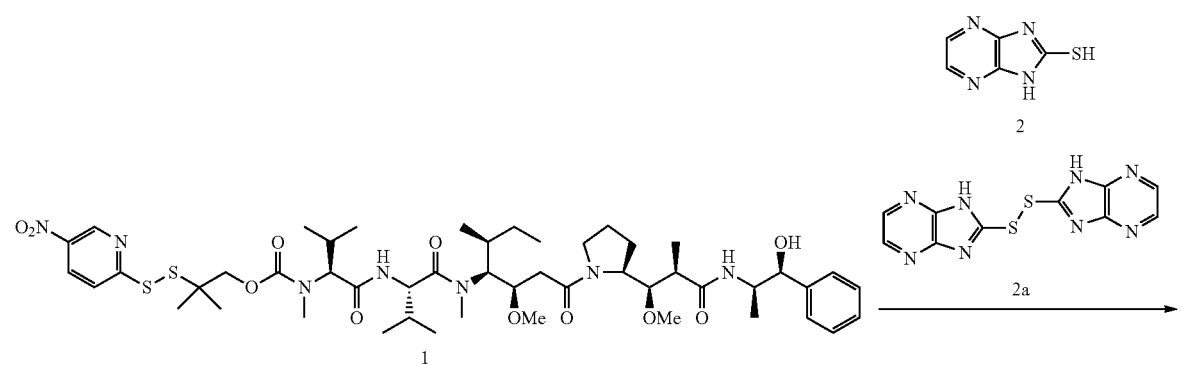

-continued

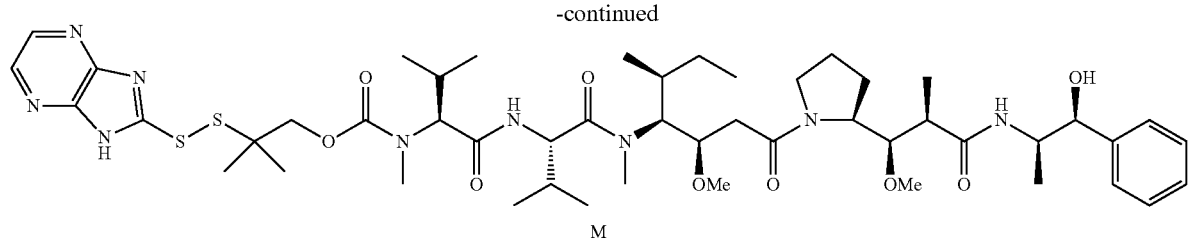

M

To a solution of pyrazine-2,3-diamine (3) (250.0 mg, 2.27 mmol) and carbon disulfide (242.0 mg, 3.18 mmol) in DMF (2.0 mL). The reaction mixture was stirred at 25° C. for 16 h. The reaction mixture was concentrated under reduced pressure, and filtered to give compound 2 (200 mg, 1.31 mmol, 57.9% yield) as a yellow solid, which was used directly in the next step. $^1$H NMR (400 MHz, CDCl$_3$) δ 13.45 (s, 2H), 8.08 (s, 2H).

A mixture of compound 1 (30.0 mg, 0.030 mmol) and compound 2a (101.9 mg, 0.340 mmol), DMAP (12.35 mg, 0.100 mmol) in DMF (1.0 mL) was added compound 2 (51.3 mg, 0.340 mmol). After the reaction mixture was stirred at 40° C. for 8 h, it was purified by prep-HPLC (Condition: water (0.225% FA)-CAN) to give the compound M (6.0 mg, 0.0059 mmol, 17.6% yield) as a white solid. LCMS (5-95AB/1.5 min): RT=0.788 min, [M+H]$^+$ 1000.5.

Activated MMAE compound N was synthesized according to the following overall reaction scheme 11.

Scheme 11:

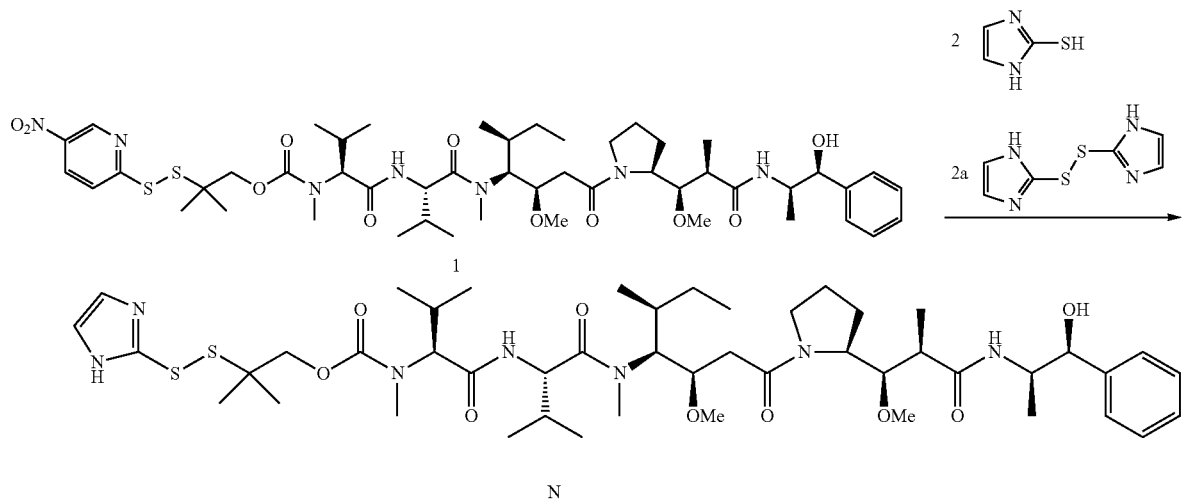

To a solution of compound 2 (16.87 mg, 0.170 mmol) in DMF (5.0 mL) was added MnO$_2$ (29.3 mg, 0.340 mmol). After the reaction mixture was stirred at 15° C. for 30 min, it was filtered, and to the filtrate was added compound 1 (30.0 mg, 0.030 mmol), DMAP (12.35 mg, 0.100 mmol) and compound 2 (16.87 mg, 0.170 mmol). The reaction mixture was stirred at 40° C. for 8 h. The reaction mixture was purified by prep-HPLC (Column: Waters Xbridge 150*25 5u, Condition: water (0.225% FA)-CAN) to give compound N (7.1 mg, 21.6%) as a white solid. LCMS (5-95AB/1.5 min): RT=0.683 min, [M+Na]$^+$ 971.0.

Activated MMAE compound O was synthesized according to the following overall reaction scheme 12.

Scheme 12:
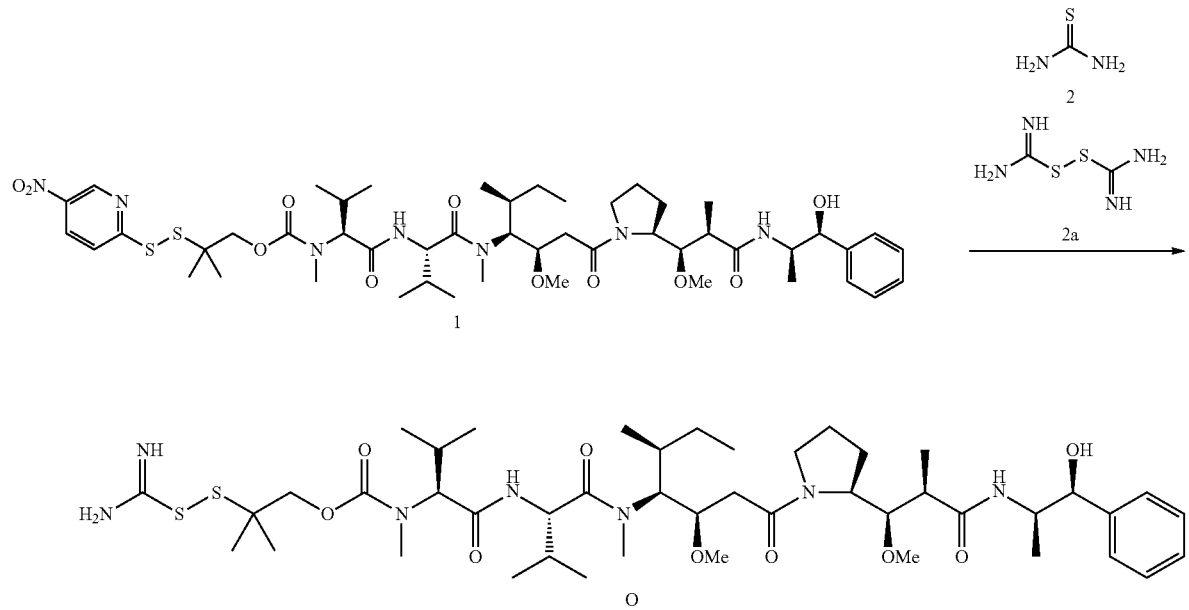
To a solution of compound 1 (80.0 mg, 0.080 mmol) in DMF (4.0 mL) was added compound 2 (60.64 mg, 0.800 mmol), compound 2a (119.67 mg, 0.800 mmol) and DMAP (29.2 mg, 0.240 mmol). The mixture was stirred at 38° C. for 12 h. The mixture was purified by prep-HPLC (HCl) to give compound O (31 mg, 41.7%) as a white solid. LCMS (5-95AB/1.5 min): RT=0.706 min, [M+H]$^+$ 924.5.
Activated MMAE compound P was synthesized according to the following overall reaction scheme 13.
Scheme 13:
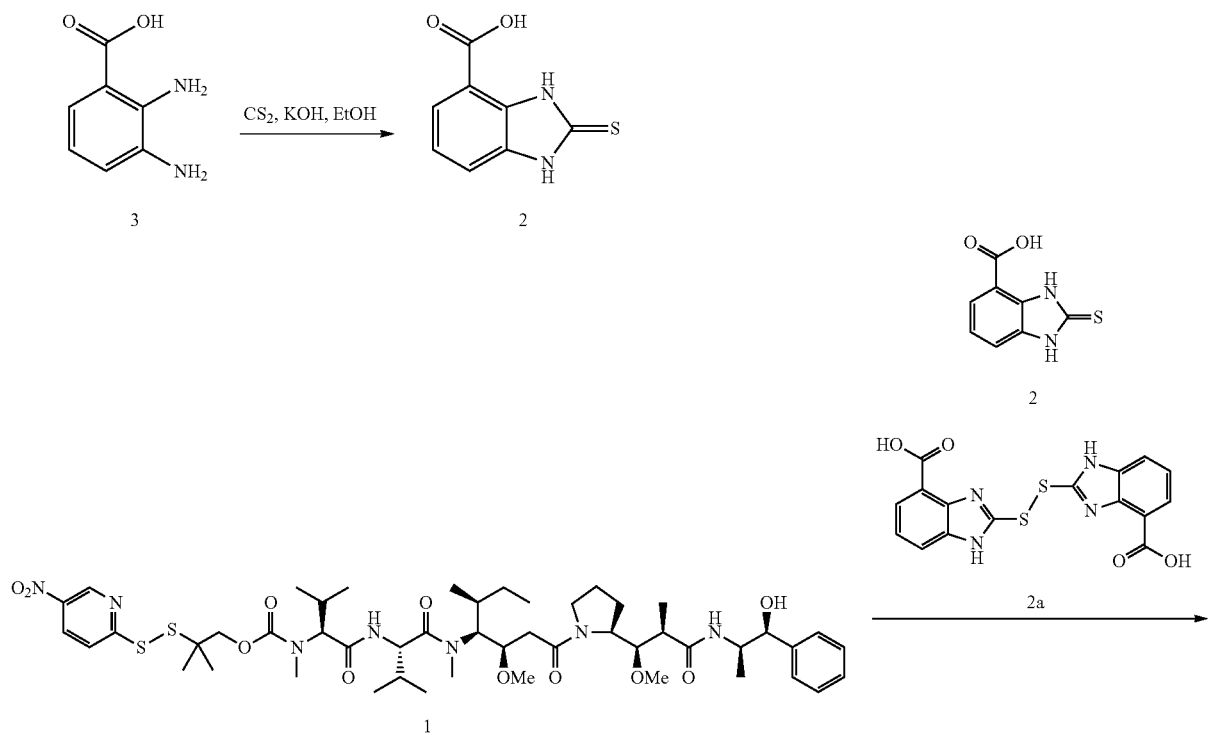

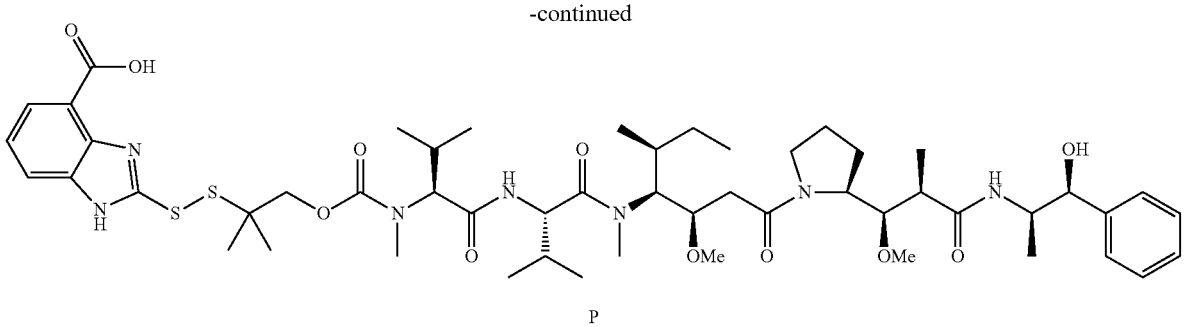

P

Compound 3 (200.0 mg, 1.31 mmol) and KOH (110.6 mg, 1.97 mmol) in EtOH (4.0 mL) and water (1.0 mL) was added CS$_2$ (150.1 mg, 1.97 mmol). The reaction mixture was stirred at 130° C. for 1.0 h under microwave irradiation. The mixture was poured into ice water, adjusted pH=5 with HOAc, and extracted with DCM (10 mL×3). The organic layer was concentrated to afford compound 2 (150 mg, 0.772 mmol, 58.8% yield) as a black oil.

A mixture of compound 2 (100.0 mg, 0.510 mmol) and MnO$_2$ (259.5 mg, 2.99 mmol) in DMF (10.0 mL) was stirred at 26° C. for 20 min. The reaction mixture was filtered, and the filtrate was add to a solution of compound 1 (20 mg, 0.02 mmol) and compound 2 (50 mg, 0.26 mmol) and DMAP (0.24 mg, 0.002 mmol) in DMF (2.0 mL) at 26° C. The mixture was stirred at 26° C. for 12 h. The mixture was concentrated in vacuo, and purified by prep-HPLC (acetonitrile 55-85%/0.225% FA in water) to give compound P (5.6 mg, 24.1%) as a white solid. LCMS (5-95AB/1.5 min): RT=0.810 min, [M+H]$^+$ 1043.6.

Activated MMAE compound Q was synthesized according to the following overall reaction scheme 14.

Scheme 14:

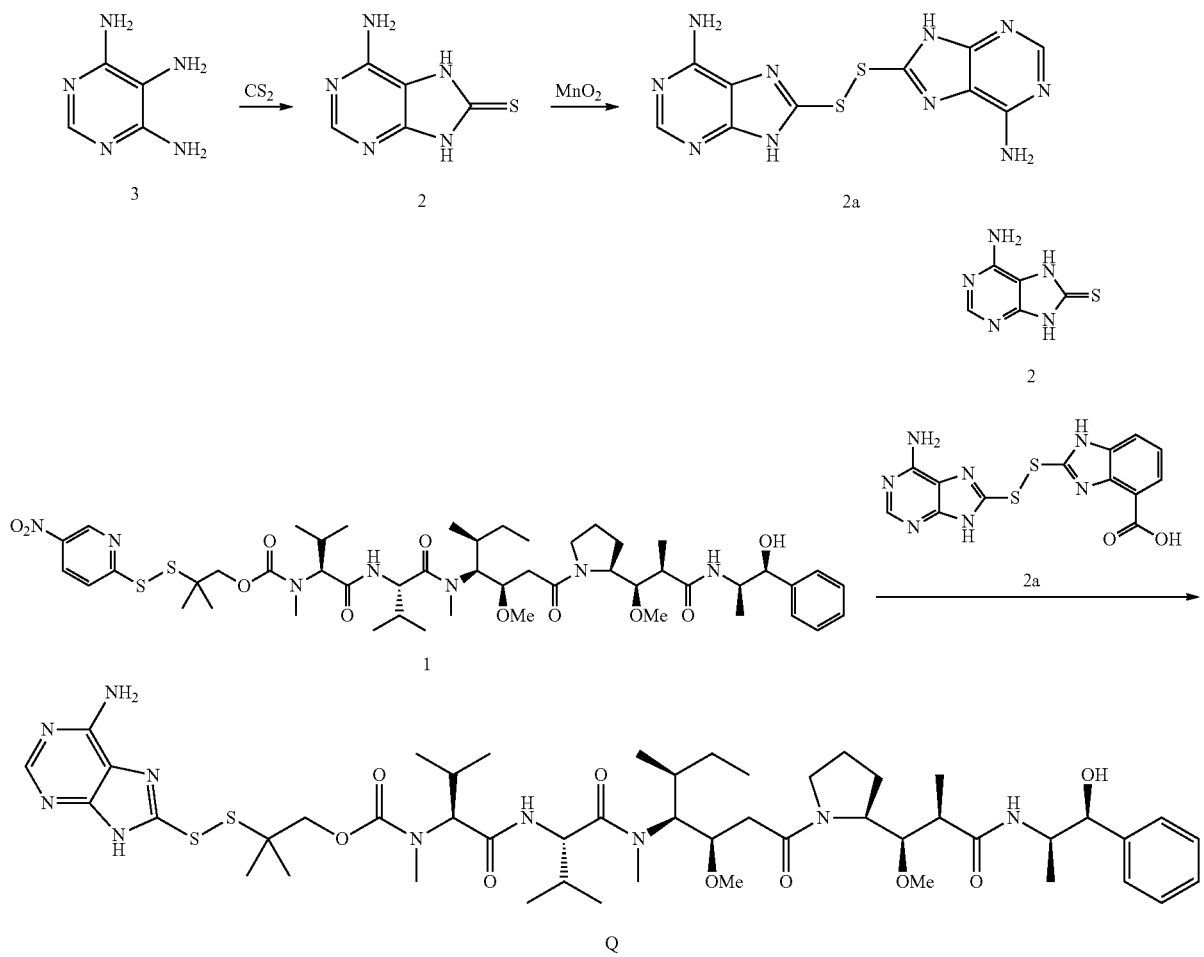

Q

To a solution of compound 3 (300.0 mg, 2.40 mmol) in DMF (12.0 mL) was added carbon disulfide (365 mg, 4.80 mmol). After the mixture was stirred at 20° C. for 24 h, it was concentrated and washed with water (15 mL×2), and solid was collected to give compound 2 (120 mg, 29.9% yield) as a gray solid which was used directly in next step.

To a solution of compound 3 (300.0 mg, 2.40 mmol) in DMF (12.0 mL) was added carbon disulfide (365 mg, 4.80 mmol). After the mixture was stirred at 20° C. for 24 h, it was concentrated and washed with water (15 mL×2), and solid was collected to give compound 2 (120 mg, 29.9% yield) as a gray solid which was used directly in next step.

The solution of compound 1 (30.0 mg, 0.030 mmol), compound 2 (24.9 mg, 0.150 mmol) and compound 2a (49.64 mg, 0.150 mmol) was stirred at 20° C. for 2.0 h. The reaction mixture was purified by prep-HPLC (acetonitrile 20-50/water (0.225FA)-ACN) to give compound Q (2.6 mg, 8.6%) as a white solid. LCMS (5-95AB/1.5 min): RT=0.722 min, [M+H]$^+$ 1015.5.

Activated MMAE compound R was synthesized according to the following overall reaction scheme 15.

(2.9 mL, 47.91 mmol) was added and the mixture was stirred for 1 h. To the reaction mixture was added iodomethane (3.33 mL, 53.47 mmol). The reaction mixture was warmed to 26° C. and stirred for 16 h. The mixture was concentrated, the residue was diluted with EtOAc (120 mL), washed successively with an aqueous solution of citric acid (60 mL×2), sat. $Na_2CO_3$ (60 mL), and brine (60 mL). The organic layer was dried over $Na_2SO_4$, filtered, and concentrated in vacuo to compound 4 (9.00 g, 90.5%) as a colorless oil.

To a solution of compound 4 (10.00 g, 43.99 mmol) in EtOH (100 mL)/water (20 mL) was added sodium azide (5.05 g, 77.68 mmol). The reaction mixture was stirred at 80° C. for 16 h. The solution was concentrated in vacuo to remove most of EtOH. The remaining solution was diluted with EtOAc (60 mL), adjusted to pH=3 with 1.0 M HCl solution, and extracted with EtOAc (60 mL×3). The combined organic layers were dried over $Na_2SO_4$, filtered, and concentrated in vacuo. The residue was purified by column chromatography (0-10% MeOH in DCM) to afford compound 5 (7.00 g, 71.6%) as a white solid.

Scheme 15:

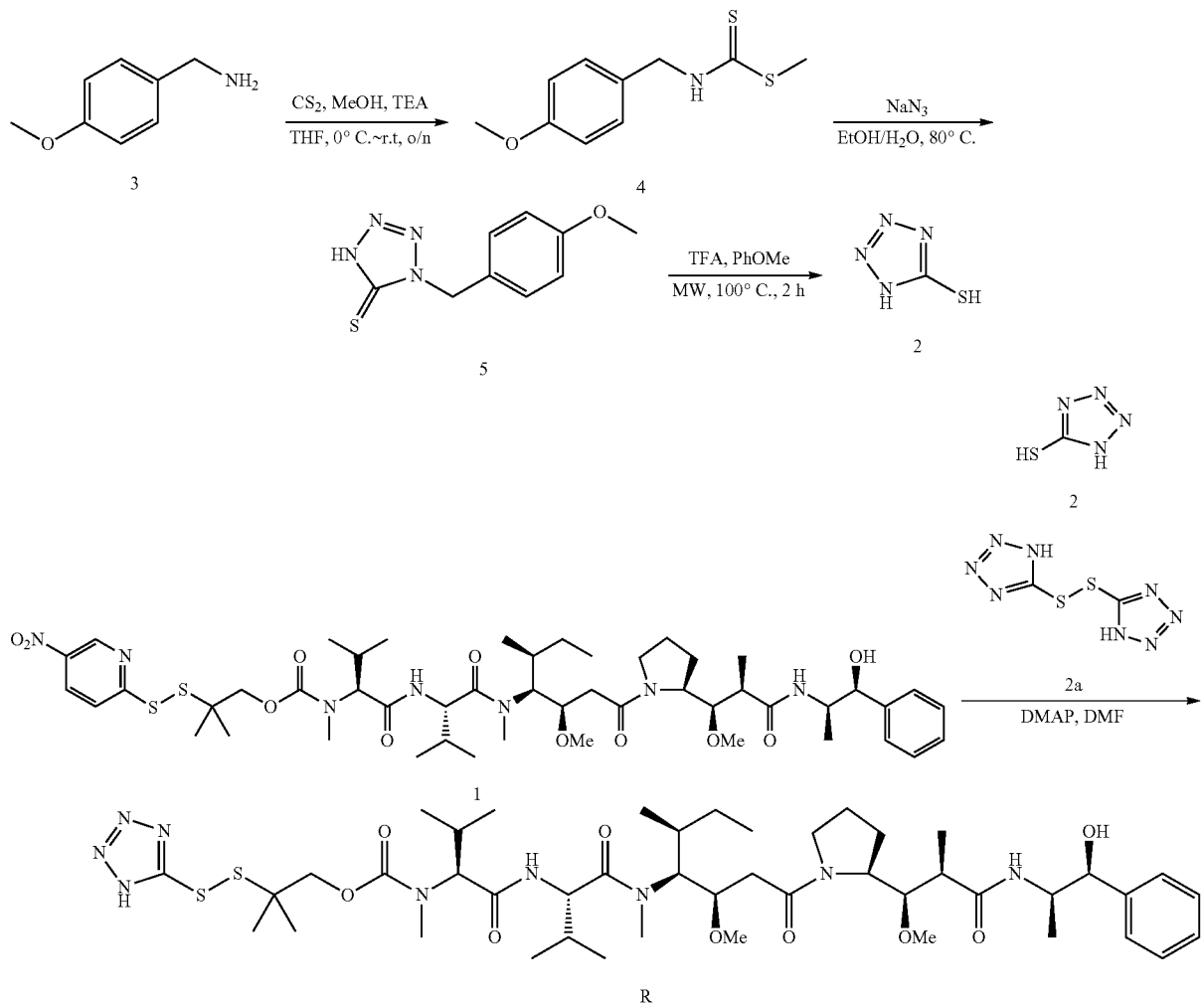

4-Methoxybenzylamine (3) (6.00 g, 43.74 mmol) was dissolved in anhydrous THF (120 mL). Under ice cooling, triethylamine (7.32 mL, 52.81 mmol) and carbon disulfide A solution of compound 5 (444.0 mg, 2.0 mmol), anisole (0.70 mL, 6.44 mmol) and TFA (3.3 mL, 44.43 mmol) was heated at 100° C. under microwave irradiation for 2 h. After the reaction mixture was cooled to r.t., the resulting precipitates were re-dissolved in EtOAc (4.0 mL). The solvent was removed under reduced pressure to afford a yellow solid, which was dissolved in EtOAc (10 mL) and water (5 mL). To the mixture was added NaOH (1.12 g, 28 mmol). After the mixture was stirred for 30 min, the aqueous layer was separated. And the pH was adjusted to 1-2 with concentrated HCl. The solution was extracted with EtOAc (20 mL×2) dried over $Na_2SO_4$, concentrated in vacuo to afford 1H-tetrazole-5-thiol (180 mg, 88.2%) as a white solid.

To a solution of compound 2 (50.2 mg, 0.500 mmol) in anhydrous DMF (1.0 mL) was added $MnO_2$ (216 mg, 2.49 mmol). The mixture was stirred at 24° C. for 20 min. Then the mixture was filtered, the filtrate was added to a solution of compound 1 (50.0 mg, 0.050 mmol), compound 2 (26 mg, 0.500 mmol), and DMAP (18.3 mg, 0.150 mmol) in anhydrous DMF (3.0 mL). The reaction solution was stirred at 40° C. for 16 h. The solution was purified by prep-HPLC (acetonitrile 50-80/0.225% FA in water) to afford compound R (14.1 mg, 27.7%) as a white solid. LCMS (5-95AB/1.5 min): $R_T$=0.916 min, $[M+H]^+$ 950.7.

Activated MMAE compound S was synthesized according to the following overall reaction scheme 16.

Scheme 16:
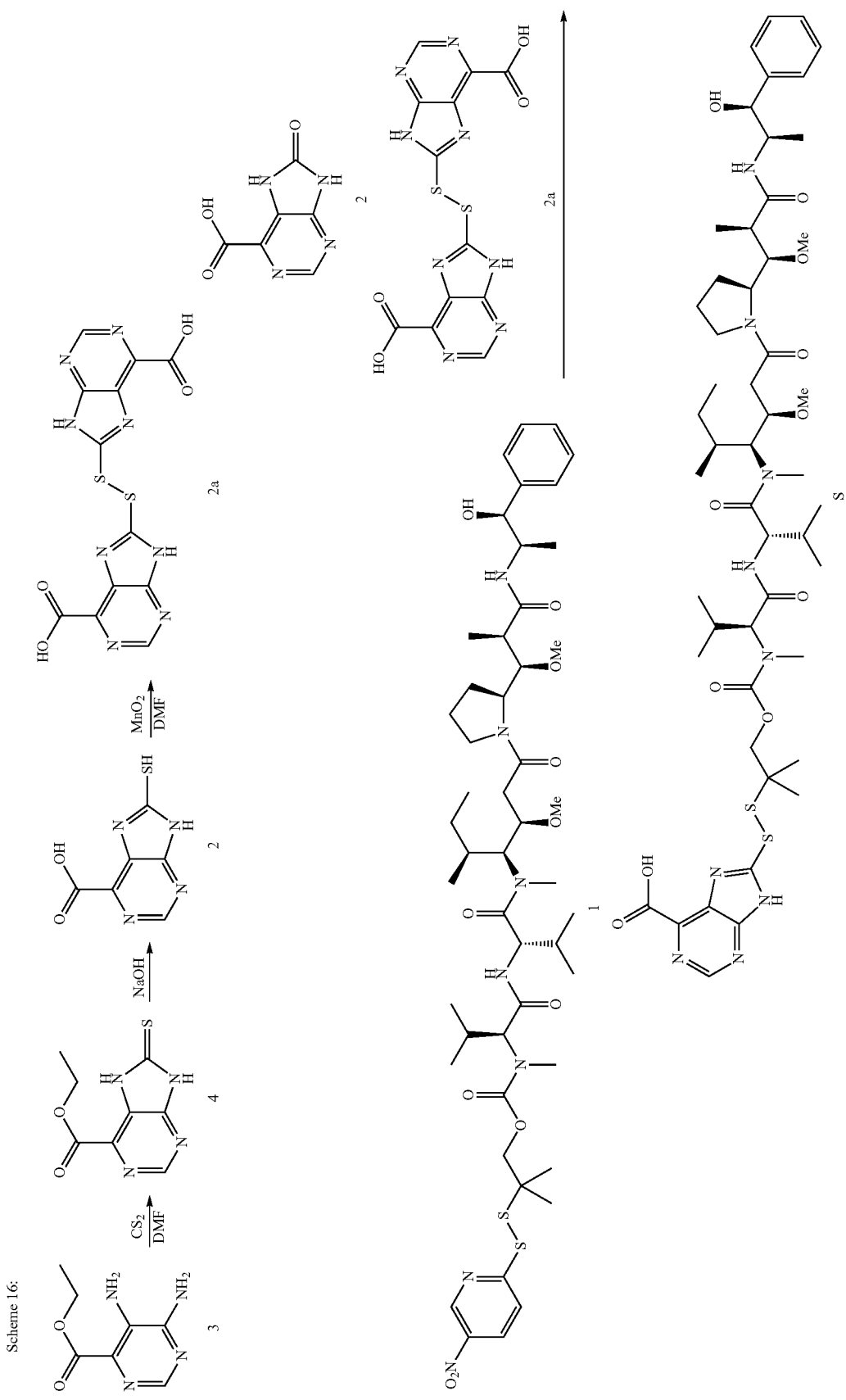

To a solution of compound 3 (100.0 mg, 0.550 mmol) in DMF (3.0 mL) was added carbon disulfide (2.089 g, 27.45 mmol). The mixture was stirred at 80° C. for 48 h. The mixture was concentrated to give the crude product compound 4 (100 mg, 81.2%) as a red solid. $^1$H NMR (400 MHz, DMSO-d6) δ 8.74 (s, 1H), 4.45 (m, 2H), 1.35 (t, J=7.2 Hz, 3H).

A solution of compound 4 (80.0 mg, 0.360 mmol) in a 5:3:1 mixture of THF/EtOH/H$_2$O (4.5 mL) was cooled to 0° C. in an ice-water bath, LiOH H$_2$O (75 mg, 1.78 mmol) was added, the reaction mixture was allowed to warm to 10° C. and it was stirred for 1 h. It was cooled to 0° C., diluted with H$_2$O (3.0 mL), and the pH was adjusted to 6 with HOAc. The solvent was concentrated to give compound 2 (68 mg, 0.347 mmol, 97.2% yield) as a yellow solid, which was used in the next step without further purification.

A mixture of compound 1 (30.0 mg, 0.030 mmol), compound 2a, (58.3 mg, 0.150 mmol), compound 2 (29.3 mg, 0.150 mmol) and DMAP (7.3 mg, 0.060 mmol) in DMF (2.0 mL) was stirred for 12 h at 38° C. The mixture was purified by prep-HPLC (acetonitrile 35-60%/0.225% FA in water) to give compound S (9.0 mg, 28.9%) as a white solid. LCMS (5-95AB/1.5 min): RT=0.746 min, [M+H]$^+$ 1044.4. HPLC (10-80AB/15 min): RT=8.55 min.

Activated MMAE compound T was synthesized according to the following overall reaction scheme 17.

Scheme 17:
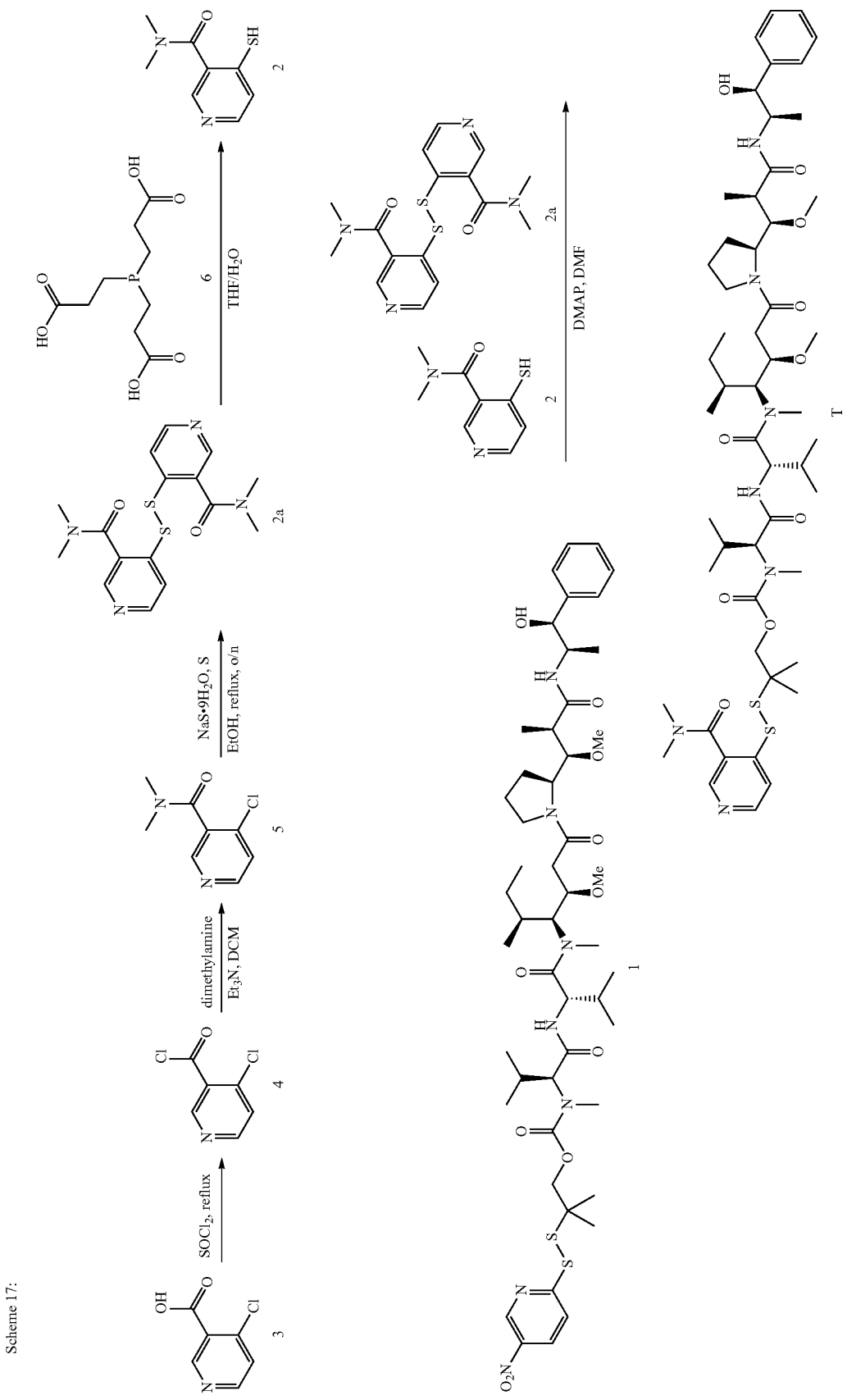

A mixture of 4-chloronicotinic acid 3 (5.00 g, 31.74 mmol) in thionyl chloride (100.0 mL, 31.74 mmol) was stirred at 80° C. for 1.5 h. The mixture was concentrated in vacuo, the residue was diluted with toluene, and concentrated again to afford compound 4 (5.50 g, 98.5% yield) as a yellow solid which was used directly for next step.

To a solution of compound 4 (5.50 mg, 31.25 mmol) in anhydrous DCM (150 mL) was added triethylamine (9.49 g, 93.75 mmol) at 0° C. A solution of N,N-dimethylamine (15.63 mL, 31.25 mmol) in anhydrous THF (15.6 mL) was added dropwise at 0° C. The reaction mixture was stirred at 0° C. for 1 h. The mixture was concentrated in vacuo and the residue was purified by column chromatography (0-12% MeOH in DCM) to afford compound 5 (4.10 g, 71.1%) as a brown oil.

Sodium sulfide nonahydrate (4.94 g, 20.58 mmol) and sulfur (659 mg, 20.58 mmol) in anhydrous EtOH (80 mL) was stirred at 80° C. for 15 min. The mixture was filtered while hot and the filtrate was added to compound 5 (3.80 g, 20.58 mmol). The mixture was stirred at 80° C. under $N_2$ for another 16 h. The mixture was cooled to r.t., and $MnO_2$ (8.70 g) was added, the mixture was stirred at r.t. for another 2 h. The mixture was filtered, the filtrate was concentrated in vacuo, the residue was purified by column chromatography (0-15% MeOH in DCM) to afford compound 2a (1500 mg, 27.7%) as pale brown oil. LCMS (0-60AB/2 min): $R_T$=0.923 min, $[M+H]^+$ 362.9.

To a solution of compound 2a (200.0 mg, 0.550 mmol) in THF (5 mL)/Water (5.0 mL) was added 3-[bis(2-carboxyethyl)phosphanyl]propanoic acid (6) (414 mg, 1.66 mmol). The reaction solution was stirred at 26° C. for 1 h. The solution was adjusted to pH 7 with aq. $NaHCO_3$ solution, and extracted with DCM/MeOH (10:1, 30 mL×3). The combined organic layers were dried over $Na_2SO_4$, filtered, and concentrated in vacuo to afford compound 2 (50 mg, 24.9%) as crude brown oil.

A solution of compound 1 (50.0 mg, 0.050 mmol), compound 2 (45.38 mg, 0.250 mmol), compound 2a (144 mg, 0.400 mmol), and DMAP (18.25 mg, 0.1500 mmol) in anhydrous DMF (4.0 mL) was stirred at 40° C. for 16 h. The solution was purified by prep-HPLC (acetonitrile 45-75/ 0.225% FA in water) to afford compound T (34.1 mg, 65.8%) as a white solid. LCMS (5-95AB/1.5 min): $R_T$=0.878 min, $[M+H]^+$ 1030.9.

Activated MMAE compound U was synthesized according to the following overall reaction scheme 18.

Scheme 18:

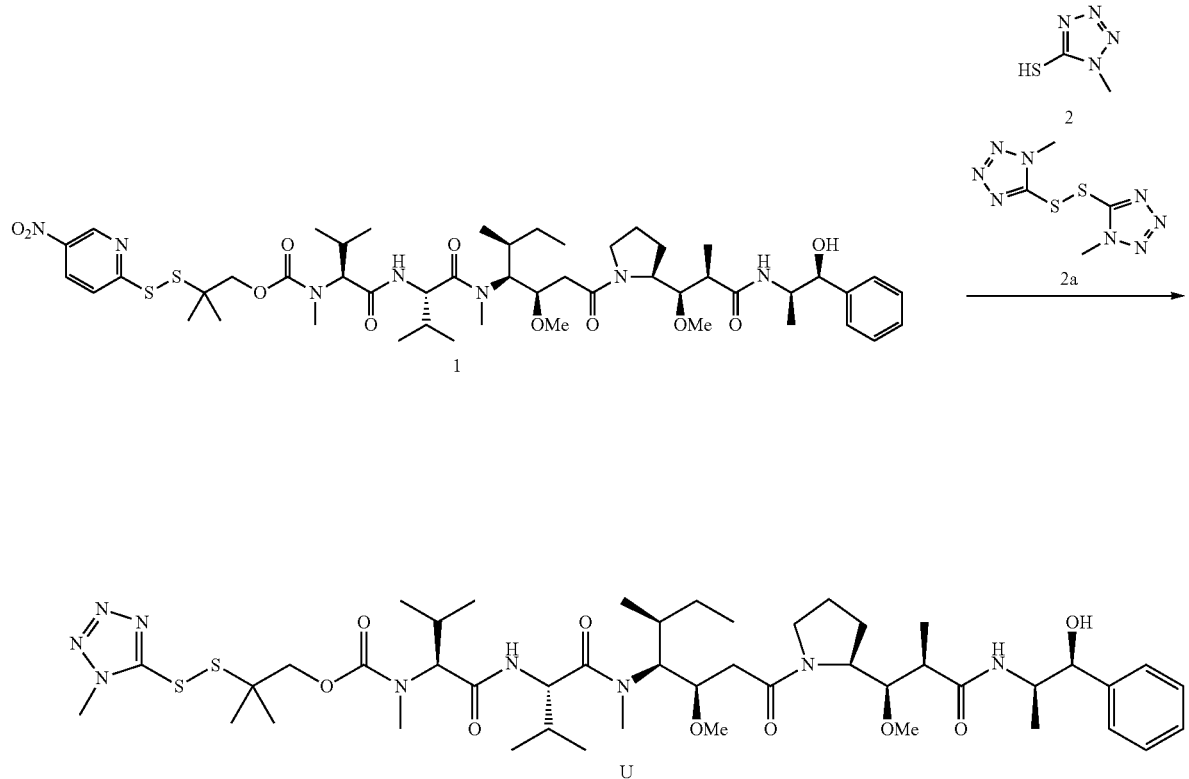

To a solution of compound 2 (28.9 mg, 0.250 mmol) in DMF (2.0 mL) was added $MnO_2$ (10.8 mg, 0.120 mmol). After the reaction mixture was stirred at 15° C. for 30 min, it was filtered, and to the filtrate were added compound 1 (25.0 mg, 0.020 mmol), DMAP (9.1 mg, 0.070 mmol) and compound 2 (28.9 mg, 0.250 mmol). The reaction mixture was stirred at 40° C. for 3 h. The reaction mixture was purified by prep-HPLC (Column: Waters Xbridge Prep OBD C18 150*30 5u, Condition: water (0.225% FA)-CAN to give compound U (11.1 mg, 43.5%) as a white solid. LCMS (5-95AB/1.5 min): RT=0.831 min, $[M+H]^+$ 964.6. $^1H$ NMR (400 MHz, DMSO-d6) δ 8.05 (m, 1H), 7.88-7.60 (m, 1H), 7.29-7.22 (m, 4H), 7.15 (d, J=4.0 Hz, 1H), 5.40-5.32 (m, 1H), 4.47-4.39 (m, 1H), 4.23-4.05 (m, 5H), 3.98-3.93 (m, 2H), 3.60-3.51 (m, 2H), 3.21 (d, J=8.0 Hz, 5H), 3.16 (d, J=8.0 Hz, 3H), 3.10 (s, 2H), 3.03-2.95 (m, 2H), 2.85-2.79 (m, 3H), 2.65 (s, 1H), 2.38 (d, J=12.0 Hz, 1H), 2.31-2.25 (m, 1H), 1.21-1.99 (m, 3H), 1.78-1.69 (m, 3H), 1.51-1.44 (m, 2H), 1.33-1.27 (m, 7H), 1.03-0.95 (m, 7H), 0.86-0.71 (m, 19H). The molecular weight determined by NMR was 963.53.

Activated MMAE compound V was synthesized according to the following overall reaction scheme 19

Scheme 19:
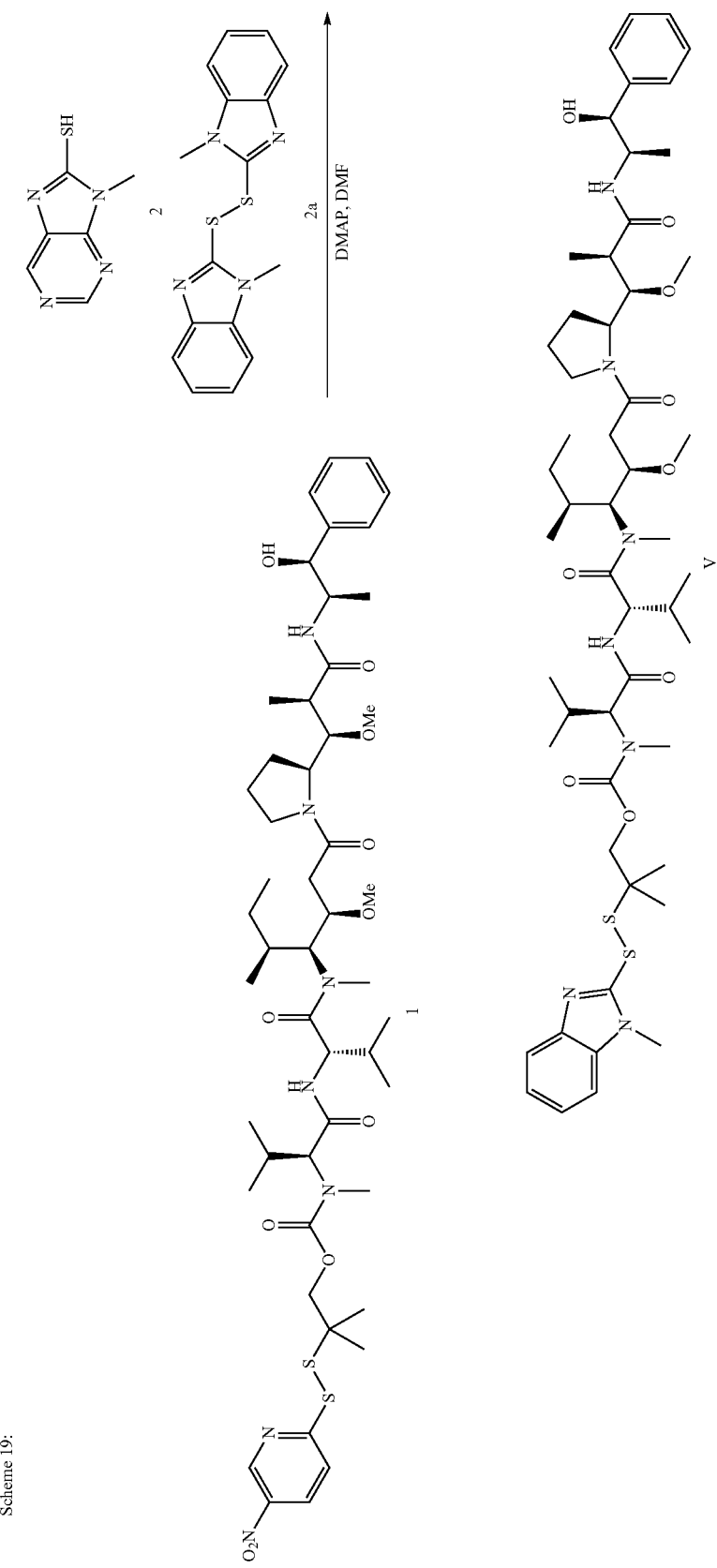

To a solution of compound 2 (36.0 mg, 0.220 mmol) in anhydrous DMF (3.0 mL) was added manganese dioxide (86.57 mg, 1.00 mmol). The mixture was stirred at 24° C. for 0.5 h. Then the mixture was filtered, the filtrated was added to a solution of compound 1 (20.0 mg, 0.020 mmol), compound 2 (13.0 mg, 0.08 mmol), and DMAP (7.3 mg, 0.060 mmol) in anhydrous DMF (1.0 mL). The reaction solution was stirred at 40° C. for 16 h. The solution was purified by prep-HPLC (Waters Xbridge Prep OBD C18 100*19 mm*5 um, acetonitrile 45-75/0.225% FA in water) to afford compound V (1.0 mg, 0.0010 mmol, 4.8% yield) as a white solid. LCMS (5-95AB/1.5 min): RT=0.910 min, [M+Na]$^+$1034.8.

Activated MMAE compound W was synthesized according to the following overall reaction scheme 20.

Scheme 20:

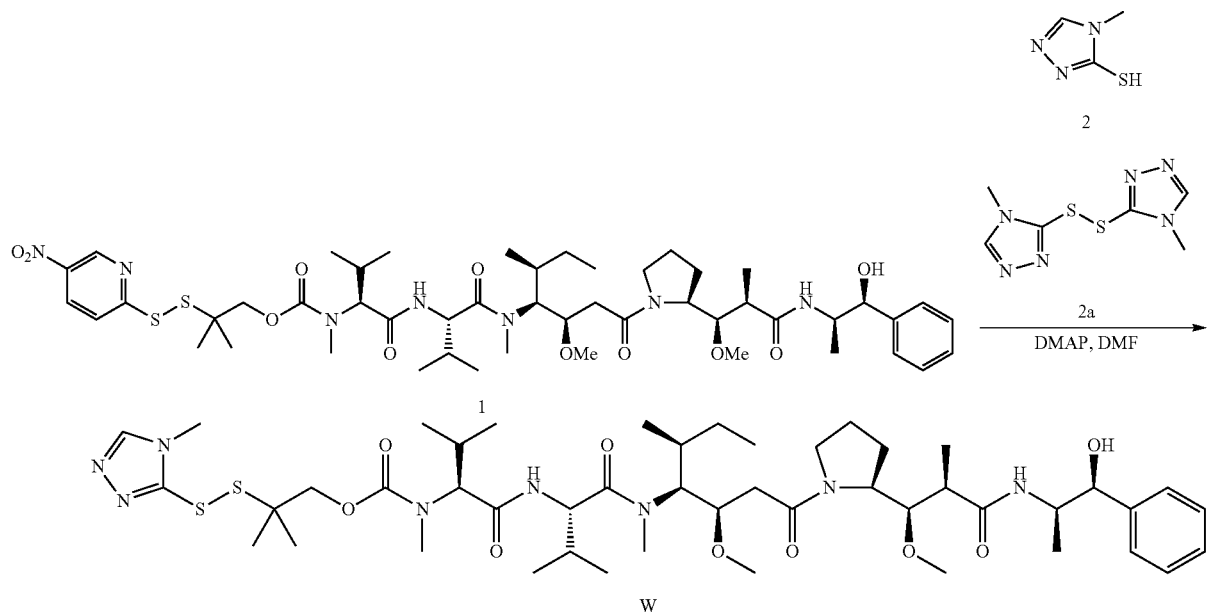

To a solution of compound 2 (34 mg, 0.300 mmol) in anhydrous DMF (4.0 mL) was added manganese dioxide (130 mg, 1.49 mmol). After the mixture was stirred at 24° C. for 0.5 h, it was filtered, the filtrated was added to a mixture of compound 1 (30.0 mg, 0.030 mmol), compound 2 (17 mg, 0.150 mmol) and DMAP (10.95 mg, 0.090 mmol). The reaction solution was stirred at 40° C. for 16 h. The solution was purified by prep-HPLC (Waters Xbridge Prep OBD C18 100*19 mm*5 um, acetonitrile 45-75/0.225% FA in water) to afford compound W (8.0 mg, 0.0079 mmol, 26.4% yield) as a white solid. LCMS (5-95AB/1.5 min): $R_T$=0.770 min, [M+H]$^+$ 963.6.

Activated MMAE compound X was synthesized according to the following overall reaction scheme 21.

Scheme 21:

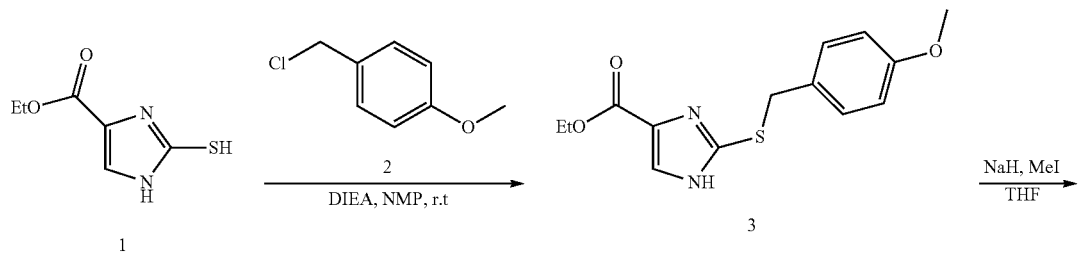

-continued

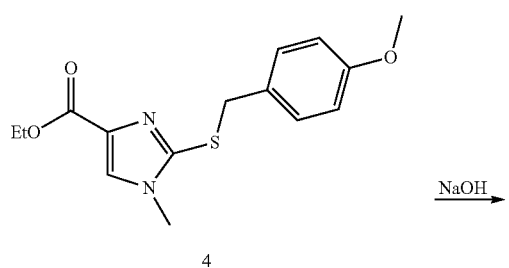

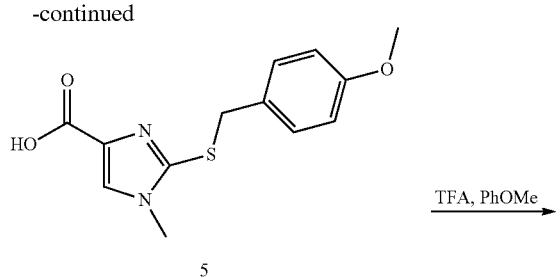

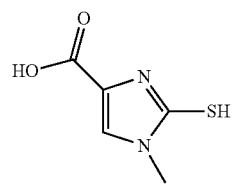

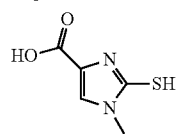

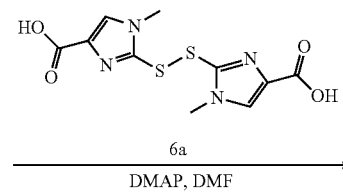

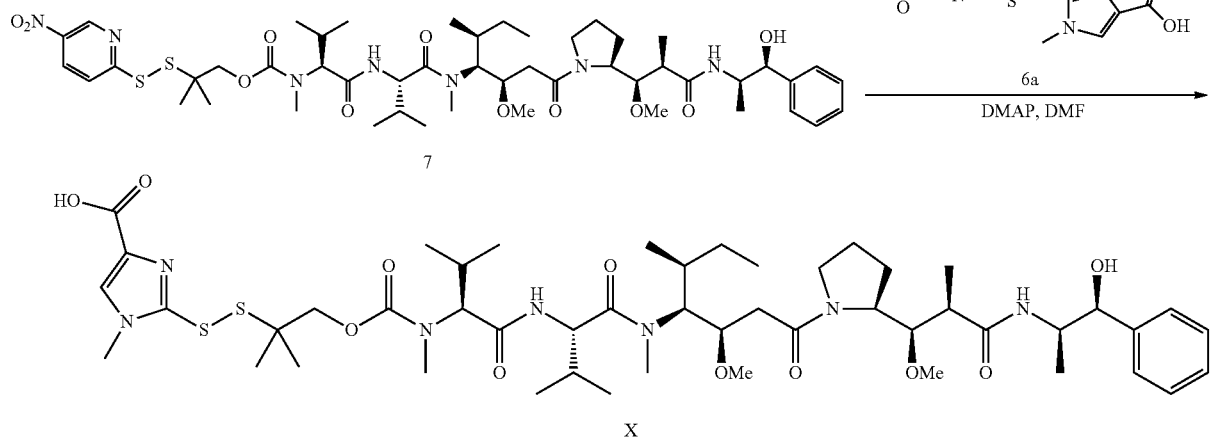

To a solution of compound 1 (300.0 mg, 1.74 mmol) in NMP (10.0 mL) was added DIEA (675 mg, 5.23 mmol), followed by compound 2 (409 mg, 2.61 mmol). After the reaction solution was stirred at 20° C. for 16 h, it was diluted with EtOAc (60 mL), washed with brine (30 mL×5), dried over $Na_2SO_4$, filtered, and concentrated. The residue was purified by prep-TLC (5% MeOH in DCM, Rf=0.6) to afford compound 3 (500 mg, 1.71 mmol, 98.2% yield) as a white solid.

To a solution of compound 1 (300.0 mg, 1.74 mmol) in NMP (10.0 mL) was added DIEA (675 mg, 5.23 mmol), followed by compound 2 (409 mg, 2.61 mmol). After the reaction solution was stirred at 20° C. for 16 h, it was diluted with EtOAc (60 mL), washed with brine (30 mL×5), dried over $Na_2SO_4$, filtered, and concentrated. The residue was purified by prep-TLC (5% MeOH in DCM, Rf=0.6) to afford compound 3 (500 mg, 1.71 mmol, 98.2% yield) as a white solid.

To a mixture of compound 4 (500 mg, 1.63 mmol) in MeOH (6.0 mL)/water (3.0 mL) was added NaOH (196 mg, 4.90 mmol). The reaction mixture was stirred at 40° C. for 2 h. The solution was concentrated in vacuo to remove most of MeOH, and the water slurry was diluted with $H_2O$ (20 mL), washed with DCM (20 mL×3). The water phase was adjusted to pH=2 with HCl solution, and extracted with DCM/MeOH (10:1, 30 mL×3). The combined organic layers were dried over $Na_2SO_4$, filtered, and concentrated in vacuo to afford compound 5 (300 mg, 0.830 mmol, 50.9% yield) as a brown solid. LCMS (0-60AB/7 min): $R_T$=2.66 min, $[M+H]^+$278.9. $^1$H NMR (400 MHz, DMSO-$d_6$) δ 7.86 (s, 1H), 7.18 (d, J=8.4 Hz, 2H), 6.84 (d, J=8.4 Hz, 2H), 4.22 (s, 2H), 3.72 (s, 3H), 3.41 (s, 3H).

A solution of compound 5 (300 mg, 1.08 mmol) in TFA (6.0 mL)/anisole (1.0 mL) was stirred at 40° C. for 24 h. The solution was concentrated in vacuo to remove the solvent, the residue was washed with DCM (20 mL) to afford compound 6 (100 mg, 0.632 mmol, 58.7% yield) as a white solid. $^1$H NMR (400 MHz, DMSO-$d_6$) δ 12.77 (s, 1H), 7.80 (s, 1H), 3.45 (s, 3H).

To a solution of compound 6 (48 mg, 0.300 mmol) in anhydrous DMF (5.0 mL) was added manganese dioxide (130 mg, 1.50 mmol). After the mixture was stirred at 24° C. for 1 h, it was filtered, the filtrated was added to a mixture of compound 7 (30.0 mg, 0.030 mmol), compound 6 (24 mg, 0.150 mmol) and DMAP (18.3 mg, 0.150 mmol). The reaction solution was stirred at 40° C. for 2 days. The solution was purified by prep-HPLC (Waters Xbridge Prep OBD C18 150*30 mm*5 um, acetonitrile 42-88/0.225% FA in water) to afford Compound X (3.80 mg, 0.0038 mmol, 12.7% yield) as a white solid. LCMS (5-95AB/1.5 min): $R_T$=0.888 min, [M+Na]$^+$1028.8.

Activated MMAE compound Y was synthesized according to the following overall reaction scheme 22.

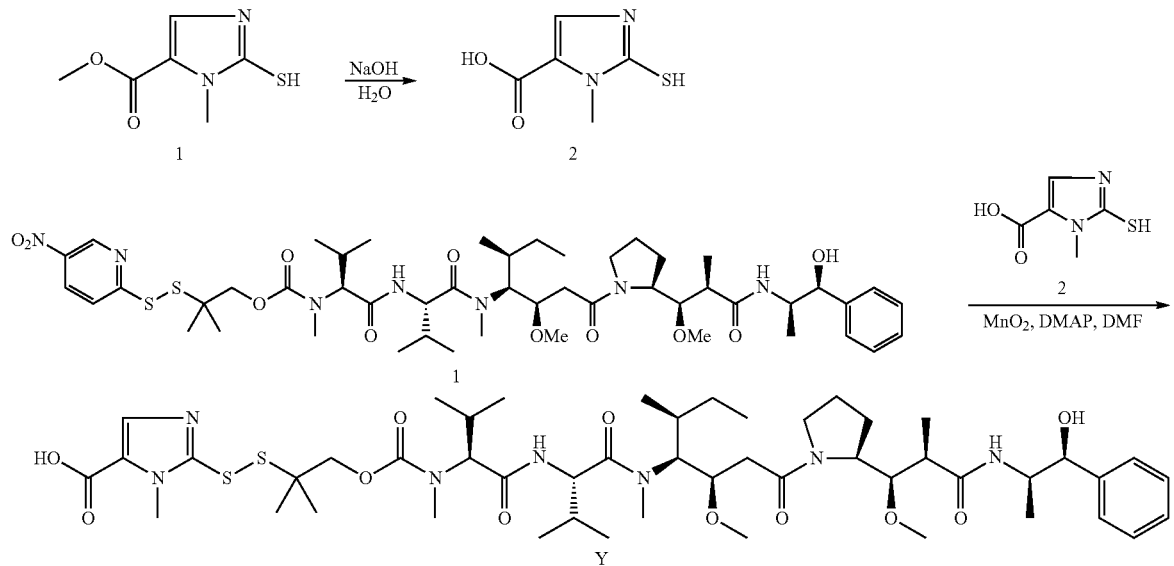

A solution of compound 1 (300.0 mg, 1.74 mmol) in a NaOH solution (2.0 M, 4.0 mL, 8.0 mmol) in water (4.0 mL) was stirred at 20° C. for 4 h. The solution was adjusted to pH=2.0 with conc. HCl solution. The precipitate formed was collected by filtration, and dried in vacuo to afford Compound 2 (200 mg, 1.264 mmol, 72.6% yield) as a white solid. $^1$H NMR (400 MHz, DMSO-$d_6$) δ 12.76 (s, 1H), 7.69 (d, J=2.4 Hz, 1H), 3.68 (s, 3H). LCMS showed most product was dimer. LCMS (5-95AB/1.5 min): $R_T$=0.807 min, [M+H]$^+$ 158.7, dimer: [M+1]$^+$314.9.

To a solution of Compound 2 (47.0 mg, 0.300 mmol) in anhydrous DMF (4.0 mL) was added MnO$_2$ (129.85 mg, 1.49 mmol). After the mixture was stirred at 24° C. for 0.5 h, it was filtered, and the filtrated was added to a mixture of Compound 3 (30.0 mg, 0.030 mmol), compound 2 (23 mg, 0.150 mmol), and DMAP (10.95 mg, 0.090 mmol). After the reaction solution was stirred at 40° C. for 2 days, it was purified by prep-HPLC to afford compound Y (4.8 mg, 0.0047 mmol, 15.8% yield) as a white solid. LCMS (5-95AB/1.5 min): $R_T$=0.886 min, [M+Na]$^+$1028.8.

Activated MMAE compound Z was synthesized according to the following overall reaction scheme 23.

Scheme 23:

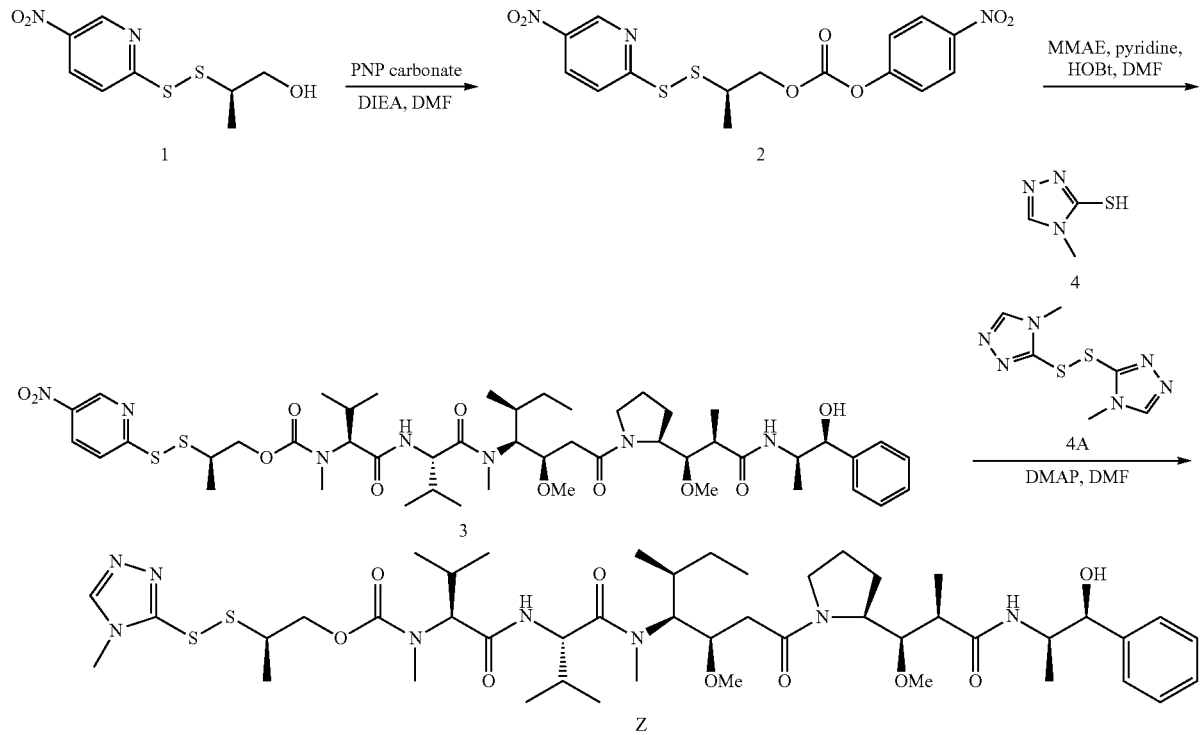

A mixture of compound 1 (500.0 mg, 2.03 mmol) and N,N-Diisopropylethylamine (787.06 mg, 6.09 mmol) in N,N-Dimethylformamide (10 mL) was added PNP carbonate (1235.1 mg, 4.06 mmol), the reaction mixture was stirred at 20° C. for 12 h under $N_2$. The reaction mixture was purified by chromatography on silica (solvent gradient:0-50% EtOAC in petroleum ether) to give compound 2 (300 mg, 0.5834 mmol, 28.7% yield) as colorless oil. LCMS (5-95AB/1.5 min): RT=0.845 min, [M+H]+ 411.9.

To a solution of MMAE (100.0 mg, 0.140 mmol) in anhydrous DMF (5.0 mL) was added compound 2 (68.76 mg, 0.170 mmol), 1-HOBt (3.76 mg, 0.030 mmol), and pyridine (110.17 mg, 1.39 mmol). The solution was stirred at 15° C. for 2 days. The solution was concentrated in vacuo, and the residue was purified by prep-TLC (5% MeOH in DCM, $R_f$=0.5) to afford compound 3 (100 mg, 0.098 mmol, 70.3% yield) as a white solid. LCMS (5-95AB/1.5 min): $R_T$=0.996 min, [M+H]+ 990.6.

To a solution of compound 4 (47 mg, 0.410 mmol) in anhydrous DMF (5.0 mL) was added $MnO_2$ (175.59 mg, 2.02 mmol). The mixture was stirred at 24° C. for 1 h. Then the mixture was filtered, the filtrated was added to a mixture of compound 3 (40.0 mg, 0.040 mmol), compound 4A (22 mg, 0.200 mmol) and DMAP (14.8 mg, 0.120 mmol). The reaction solution was stirred at 40° C. for 16 h. The solution was purified by prep-HPLC (Diamonsil 150*20 mm*5 um, acetonitrile 35-65/0.225% FA in water). It was further purified by prep-TLC (10% MeOH in DCM, Rf=0.5) to afford GNT_B343_837-1 (28.2 mg, 0.0282 mmol, 69.9% yield) as a white solid. LCMS (5-95AB/1.5 min): $R_T$=0.866 min, [M+H]+ 949.5.

Activated MMAE compound AA was synthesized according to the following overall reaction scheme 24.

Scheme 24:

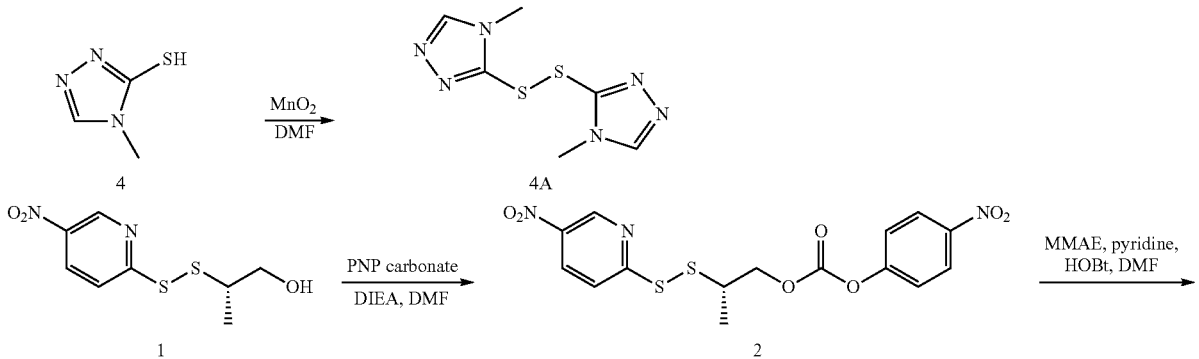

-continued

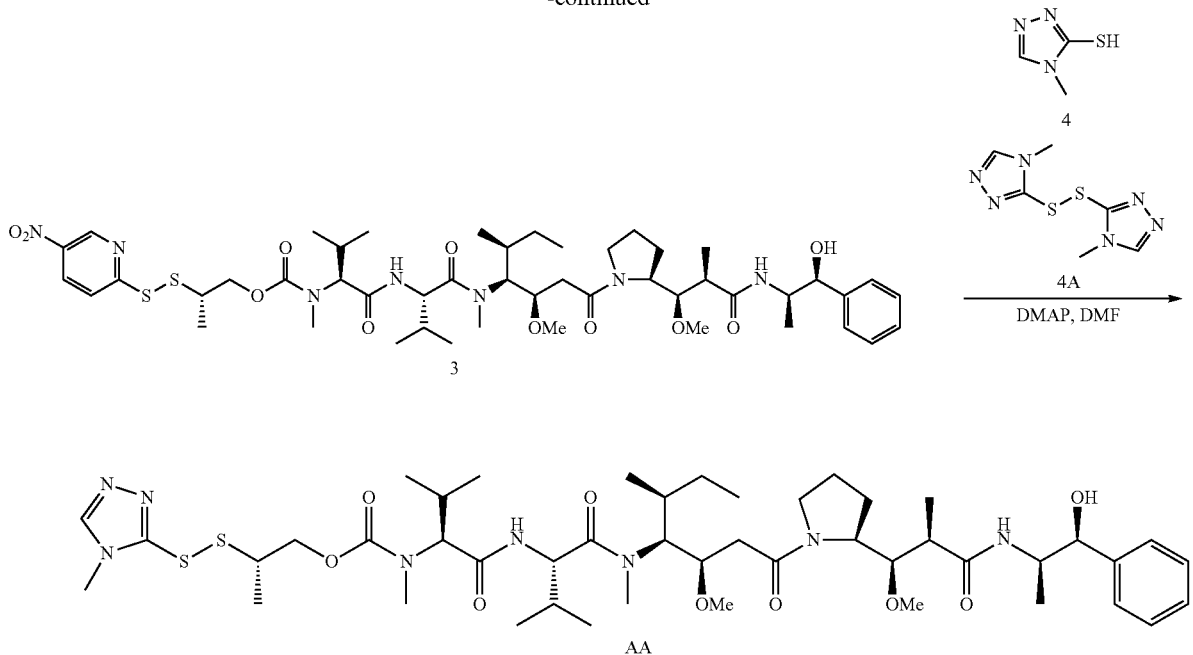

To a solution of compound 1 (50.0 mg, 0.20 mmol) and PNP carbonate (92.63 mg, 0.30 mmol) in DMF (8.0 mL) was added DIEA (78.71 mg, 0.61 mmol). The mixture was stirred at 15° C. for 3 h. The mixture was concentrated in vacuo and purified by prep-TLC (DCM) to afford compound 2 (80 mg, 0.19 mmol, 95.8% yield) as a white solid.

A mixture of MMAE (30.0 mg, 0.04 mmol) and compound 2 (60.0 mg, 0.15 mmol) in DMF (3.0 mL) was added pyridine (33.05 mg, 0.42 mmol) and HOBt (0.56 mg, 0.01 mmol). The reaction mixture was stirred at 30° C. for 8 h. The mixture was concentrated in vacuo and purified by prep-TLC (5% MeOH in DCM) to give Compound 3 (35 mg, 0.035 mmol, 83.7% yield) as a white solid. LCMS (5-95AB/1.5 min): RT=0.994 min, [M+H]+ 990.5.

To a solution Compound 4 (200.0 mg, 1.74 mmol) in DMF (10.0 mL) was added MnO$_2$ (754.9 mg, 8.68 mmol). The mixture was stirred at 15° C. for 2 h. The mixture was filtered and concentrated to give Compound 4A (150 mg, 0.66 mmol, 75.7% yield) as a red solid.

To a solution of Compound 3 (40.0 mg, 0.04 mmol) in DMF (4.0 mL) was added Compound 4 (46.52 mg, 0.40 mmol), Compound 4A (92.22 mg, 0.40 mmol) and DMAP (14.8 mg, 0.12 mmol). The mixture was stirred at 38° C. for 12 h. The mixture was purified by prep-HPLC (acetonitrile 30-60%/0.1% NH$_4$HCO$_3$ in water) to give compound AA (20 mg, 0.02 mmol, 50.1% yield) as a white solid. LCMS (5-95AB/1.5 min): RT=0.875 min, [M+H]+ 949.5. HPLC (10-80AB/15 min): RT=4.79 min.

Activated MMAE compound BB was synthesized according to the following overall reaction scheme 25.

Scheme 25:

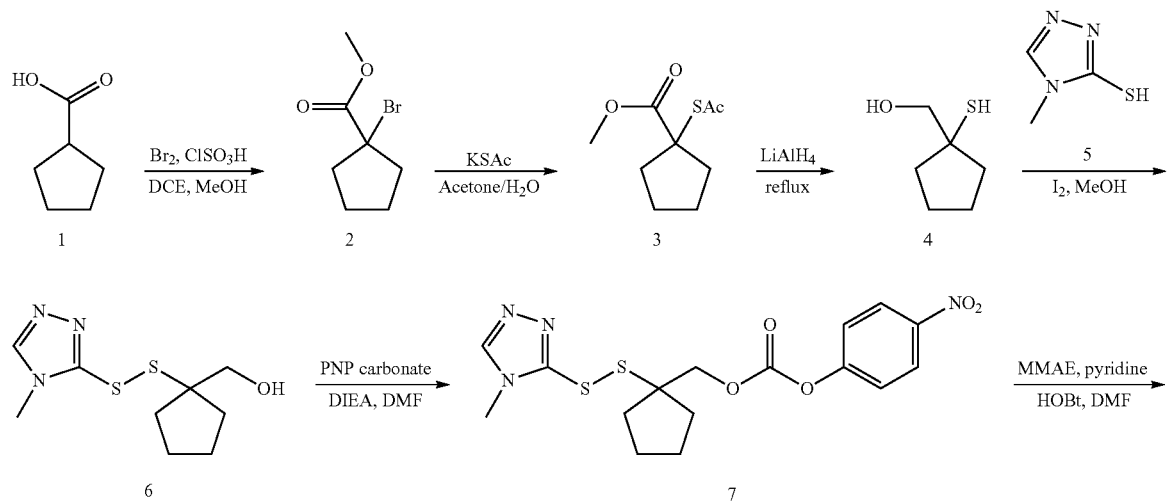

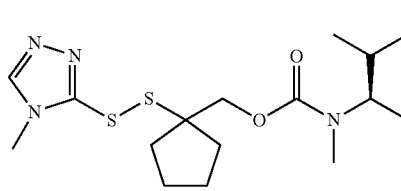
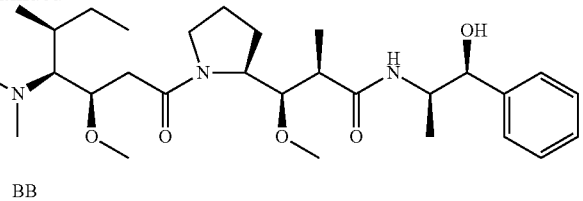

BB

To a solution of cyclopentanecarboxylic acid (8.0 g, 70.09 mmol) in 1,2-Dichloroethane (100 mL) was added Br$_2$ (11.27 g, 70.09 mmol) and chlorosulfonic acid (8.17 g, 70.09 mmol). The mixture was stirred at 85° C. for 2 h and concentrated. The residue was dissolved in METHANOL (70 mL) and the mixture was stirred at 77° C. for 12 h. TLC (3% EtOAc in petroleum ether, Rf=0.4) showed most STM was consumed and a new spot. The mixture was concentrated and diluted with MTBE (100 ml), washed with water (80 ml*3) and brine (80 ml). The organic layer was concentrated to give the product methyl 1-bromocyclopentanecarboxylate (12.4 g, 59.883 mmol, 85.4% yield) as a yellow oil.

To the mixture of potassium ethanethioate (7.28 g, 63.75 mmol) in acetone (80.0 mL) was added a solution of compound 2 (11.0 g, 53.12 mmol) in water (50.0 mL). The reaction mixture was stirred at 80° C. for 3 h. The mixture was concentrated, diluted with MTBE (150 mL) and washed with water (150 mL×3). The combined organic phase was concentrated and purified by column chromatography (0-5% EtOAc in PE) to afford compound 3 (4.60 g, 22.74 mmol, 42.8% yield) as a yellow oil.

To the mixture of LAH (4.32 g, 113.0 mmol) in THF (70 mL) at 0° C. was added a solution of compound 3 (4.60 g, 22.74 mmol) in THF (20 mL). After addition, the mixture was heated to reflux at 80° C. for 3 h under N$_2$. The mixture was quenched with an aq. HCl solution (2.0 M, 20.0 mL) at 0° C. It was filtered, and the filtrate was concentrated and dissolved in EtOAc (150 mL). The organic phase was washed with water (150 mL×3) and concentrated to give the crude compound 4 (2.5 g, 18.91 mmol, 83.1% yield) as a yellow oil, which was used in the next reaction directly without further purification. $^1$H NMR (400 MHz, CDCl$_3$) δ 3.51 (s, 2H), 2.25 (s, 1H), 1.91-1.67 (m, 8H).

Iodine (2.879 g, 11.34 mmol) was added slowly to a solution of compound 4 (500 mg, 3.78 mmol) and compound 5 (4.355 g, 37.82 mmol) in MeOH (30.0 mL). The mixture was stirred at 10° C. for 2 h. The mixture was concentrated and dissolved in DCM (80 mL), washed withe sat.Na$_2$S$_2$O$_3$ solution (80 mL×3). The organic layer was concentrated and purified by prep-TLC (20% EtOAc in PE, Rf=0.4) to give compound 6 (350 mg, 1.355 mmol, 35.8% yield) as a colorless oil. LCMS (0-60AB_2 min): RT (220/254 nm)=1.043 min, [M+H]$^+$ 245.8.

A mixture of bis(4-nitrophenyl)carbonate (372 mg, 1.22 mmol) and DIEA (0.320 mL, 1.83 mmol) in DMF (15.0 mL) was added compound 6 (150.0 mg, 0.610 mmol). The reaction mixture was stirred at 20° C. for 12 h under N$_2$. The reaction mixture was concentrated in vacuo and purified by column chromatography (50%-100% EtOAc in PE, Rf=0.5) to give compound 7 (200 mg, 0.468 mmol, 76.5% yield) as a white solid. LCMS (5-95AB/1.5 min): RT=0.723 min, [M+H]$^+$ 411.0.

A mixture of HOBt (1.65 mg, 0.010 mmol) and MMAE (78.6 mg, 0.110 mmol) in DMF (5.0 mL) was added pyridine (0.10 mL, 1.22 mmol) and compound 7 (50.0 mg, 0.120 mmol). After the reaction mixture was stirred at 20° C. for 18 h, it was concentrated in vacuo and purified prep-HPLC (acetonitrile 50-75/0.225% FA in water) to give compound BB (50 mg, 0.050 mmol, 41.1% yield) as a white solid. LCMS (5-95AB/1.5 min): RT=0.795 min, [M+H]$^+$ 989.4. HPLC (10-80AB/8 min): RT=5.11 min.

Activated MMAE compound CC was synthesized according to the following overall reaction scheme 26.

Scheme 26:

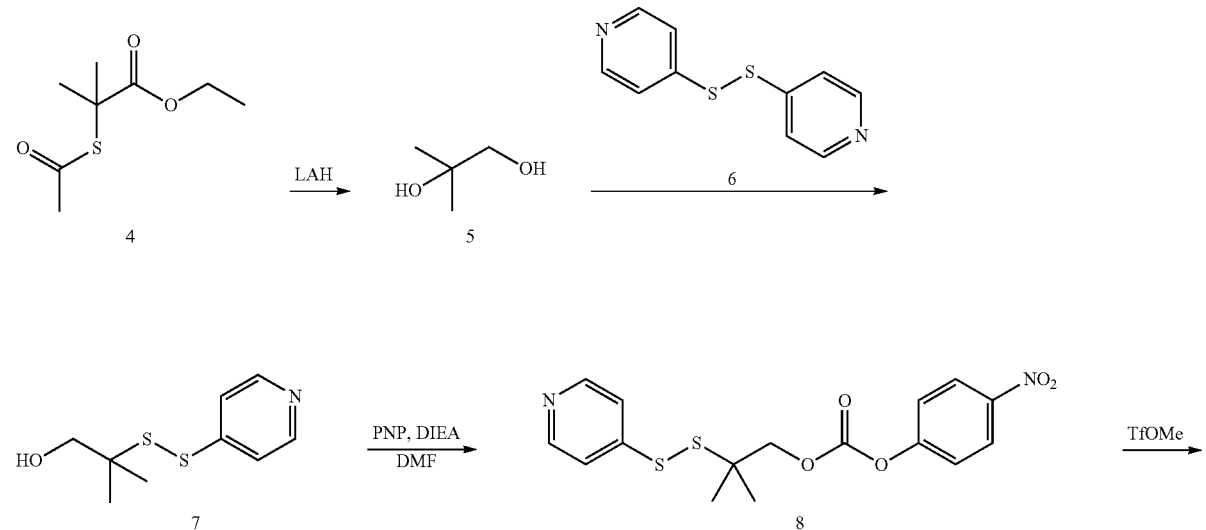

-continued

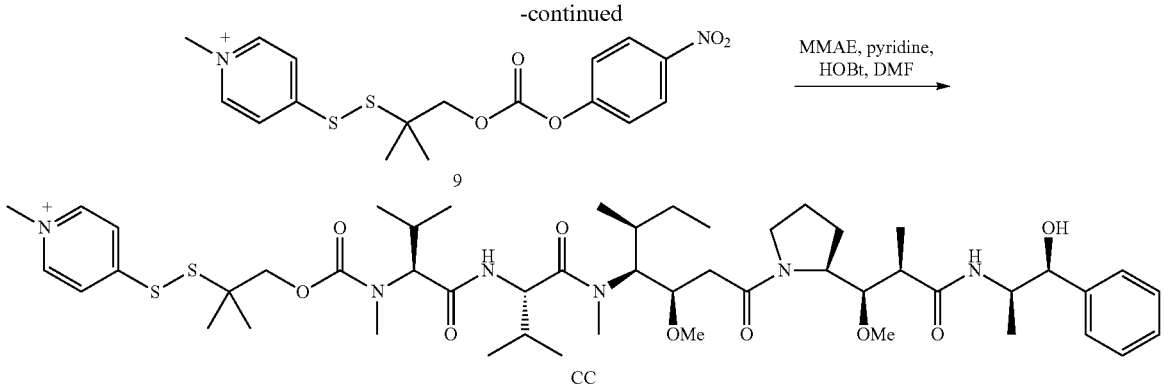

A solution of LAH (1.02 mL, 42.05 mmol) in THF (20 mL) was added a solution of compound 4 (2.00 g, 10.51 mmol) in THF (20 mL) at 0° C. The reaction mixture was stirred at 80° C. for 2 h. The solution was quenched with EtOAc (6.0 mL) and aq. HCl solution (2.0 M, 8 mL), then the crude mixture was used directly.

A solution of compound 5 (1.10 g, 10.36 mmol) in DCM (20 mL) and MeOH (20 mL) was added compound 6 (2.28 g, 10.36 mmol). The reaction mixture was stirred at 20° C. for 16 h. $MnO_2$ (10.0 g) was added to the mixture and stirred at r.t. for 2 h. The reaction mixture was filtered, the filtrate was concentrated in vacuo, and purified by chromatography on silica (0-50% EtOAC in PE) to give compound 7 (320 mg, 1.486 mmol, 14.3% yield) as a yellow solid. LCMS (5-95AB/7 min): RT=1.546 min, $[M+H]^+$ 215.7.

A solution of compound 7 (100.0 mg, 0.460 mmol) in DMF (10.0 mL) and was added PNP carbonate (282 mg, 0.930 mmol) and DIEA (180 mg, 1.39 mmol). The reaction mixture was stirred at 18° C. for 16 h. The mixture was concentrated in vacuo and purified by column chromatography (0-50% EtOAC in PE, Rf=0.5) to give compound 8 (85 mg, 0.217 mmol, 46.7% yield) as a yellow solid. LCMS (5-95_1.5 min): RT (220/254 nm)=0.780 min, $[M+H]^+$ 380.9.

A solution of compound 7 (100.0 mg, 0.460 mmol) in DMF (10.0 mL) and was added PNP carbonate (282 mg, 0.930 mmol) and DIEA (180 mg, 1.39 mmol). The reaction mixture was stirred at 18° C. for 16 h. The mixture was concentrated in vacuo and purified by column chromatography (0-50% EtOAC in PE, Rf=0.5) to give compound 8 (85 mg, 0.217 mmol, 46.7% yield) as a yellow solid. LCMS (5-95_1.5 min): RT (220/254 nm)=0.780 min, $[M+H]^+$ 380.9.

To a mixture of compound 9 (24.79 mg, 0.060 mmol) in DMF (5.0 mL) was added MMAE (15.0 mg, 0.020 mmol), pyridine (16.53 mg, 0.210 mmol) and HOBt (1.41 mg, 0.010 mmol). The mixture was stirred at 35° C. for 12 h under $N_2$. The mixture was filtered and purified by prep-HPLC (Column: Phenomenex Synergi C18 250*21.2 mm*4 um, Condition: water (0.05% HCl)-ACN) to give compound CC (10.3 mg, 0.0101 mmol, 48.6% yield) as a white solid. LCMS (5-95_1.5 min): RT (220/254 nm)=0.708 min, $[M+H]^+$ 974.0.

Activated MMAE compound DD was synthesized according to the following overall reaction scheme 27.

Scheme 27:
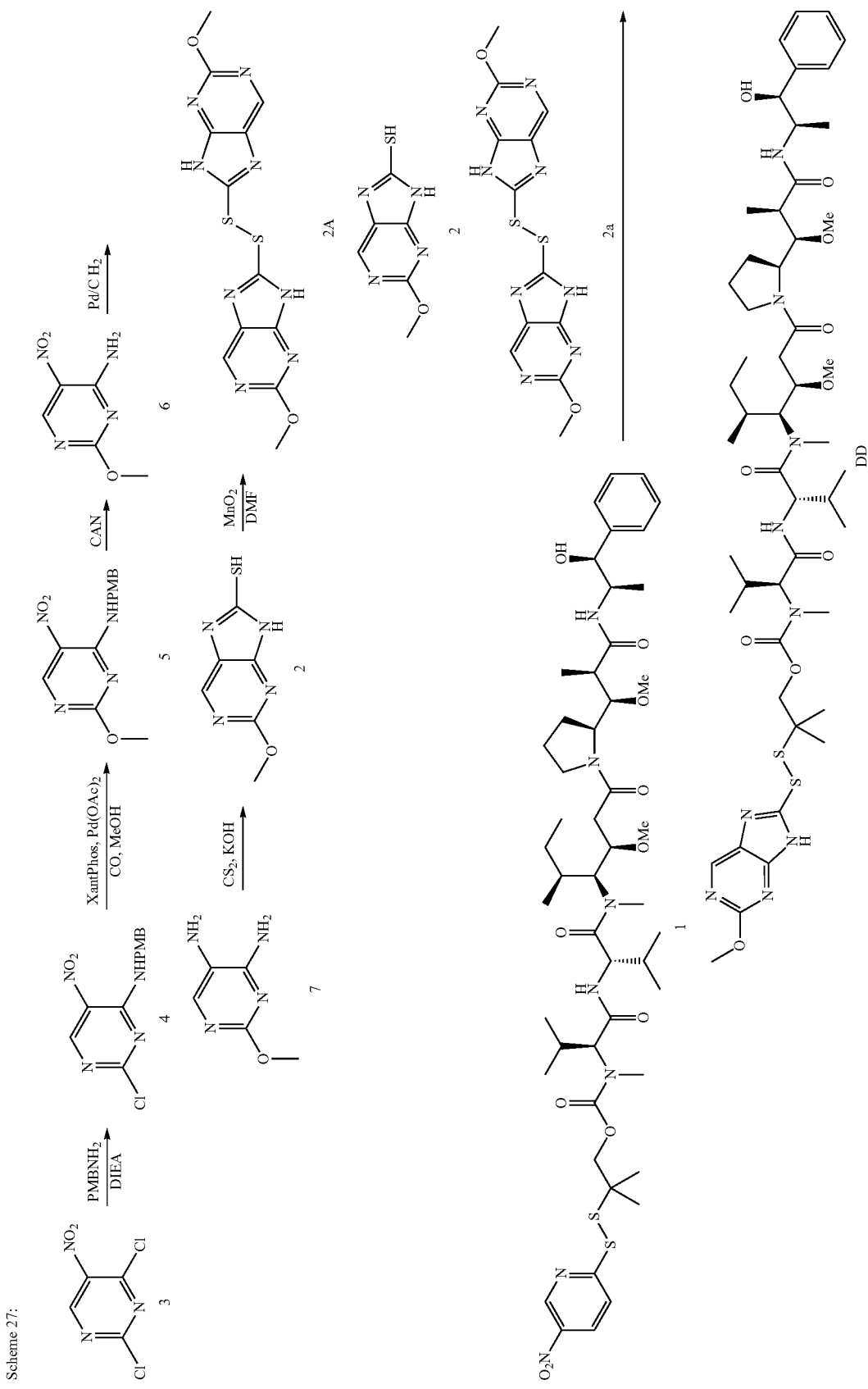

To a solution of 2,4-dichloro-5-nitropyrimidine (3) (7.80 g, 40.2 mmol) and DIEA (10.39 g, 80.4 mmol) in THF (200 mL) was added 4-methoxybenzylamine (4.96 g, 36.2 mmol) dropwise at 0° C. After the mixture was stirred at 20° C. for 12 h, it was concentrated and purified on column chromatography (0-33.3% EtOAc in PE, Rf=0.6) to give compound 4 (6.80 g, 23.1 mmol, 57.4% yield) as a yellow oil. LCMS (5-95AB_1.5 min): RT (220/254 nm)=0.788 min, [M+H]+ 294.9.

To a solution of triethylamine (4.58 mL, 32.6 mmol), XantPhos (251.33 mg, 0.430 mmol), MeOH (4.4 mL, 108 mmol) and compound 4 (3.20 g, 10.86 mmol) in toluene (30 mL) was added palladium(II) acetate (97.5 mg, 0.430 mmol). The mixture was stirred under CO (15 psi) at 70° C. for 16 h. The mixture was filtrated and the filtrate was concentrated and purified by column chromatography on silica (20% EtOAc in PE, Rf=0.4) to give compound (1.71 g, 5.89 mmol, 54.3% yield) as a brown solid.

A mixture of ceric ammonium nitrate (9.09 g, 16.59 mmol) in acetonitrile (60 mL) and water (15 mL) was added compound 5 (1.70 g, 5.86 mmol). The mixture was stirred at 20° C. for 12 h. The reaction was quenched with a.q. NaHCO3 (80 mL) and extracted with EtOAc (70 mL×3), washed with brine. The organic layer was concentrated and purified by column chromatography (40% EtOAc in PE, Rf=0.4) to compound 6 (610 mg, 2.87 mmol, 44.5% yield) as a brown solid.

A mixture of compound 6 (560 mg, 3.29 mmol) in MeOH (30 mL) was added 10% Pd on carbon (56.4 mg). After the mixture was stirred at 20° C. under H2 (15 psi) for 1 h, it was filtered and the filtrate was concentrated to give compound 7 (310 mg, 2.21 mmol, 67.2% yield) as a brown solid.

To a mixture of KOH (192 mg, 3.43 mmol) in EtOH (8.0 mL) and water (2.0 mL) was added compound 7 (160.0 mg, 1.14 mmol) and carbon disulfide (261 mg, 3.43 mmol). The mixture was stirred at 130° C. under microwave for 1 h. The mixture was concentrated to remove EtOH, and adjusted pH=5 with HOAc. The mixture was filtrated, the solid was washed with water (2.0 mL×2) to give 2 as a brown solid (140 mg, 0.768 mmol, 67.3% yield). $^1$H NMR (400 MHz, DMSO-$d_6$) δ 13.30 (br. s., 1H), 12.81 (br. s., 1H), 8.18 (s, 1H), 3.34 (s, 3H).

To a solution of compound 2 (60.0 mg, 0.330 mmol) in DMF (5.0 mL) was added MnO2 (143.2 mg, 1.65 mmol). After the mixture was stirred at 15° C. for 1 h, it was filtrated, and the filtrate was concentrated to give compound 2A (45.0 mg, 0.124 mmol, 37.7% yield) as a brown solid, which was used in next step without further purification. LCMS (5-95_1.5 min): RT (220/254 nm)=0.653 min, [M+H]+ 363.0.

To a solution of DMAP (12.16 mg, 0.100 mmol) in DMF (5.0 mL) was added compound 1 (20.0 mg, 0.020 mmol), 2 (18.14 mg, 0.100 mmol) and 2A (36.08 mg, 0.1000 mmol). After the mixture was stirred at 40° C. for 12 h, it was filtered and the filtrate was purified by prep-HPLC (Acetonitrile 45-75%/0.225% FA in water) to give compound DD (5.7 mg, 0.0055 mmol, 27.8% yield) as an off white solid. LCMS (5-95AB/1.5 min): R$_T$=0.905 min, [M+1]+1030.6.

Example 20: Preparation of Maytansinoid Compounds Comprising an Activated Hindered Disulfide Activated maytansinoid compound A was synthesized according to the following overall reaction scheme 1.

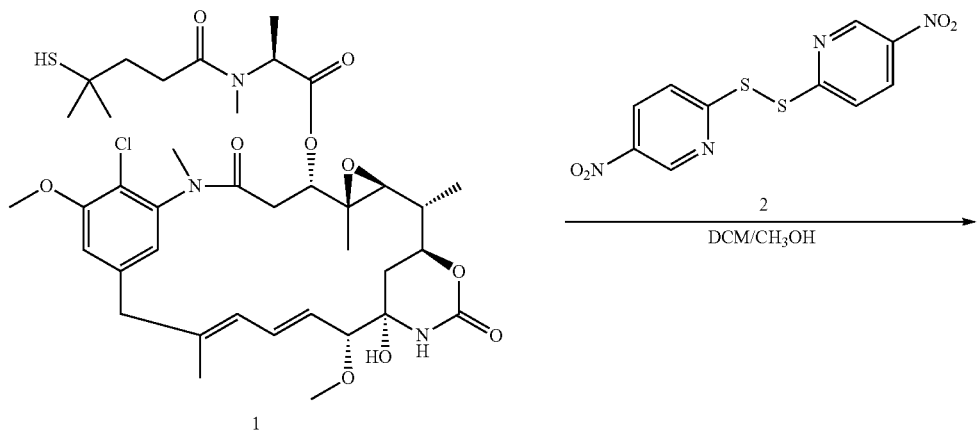

-continued

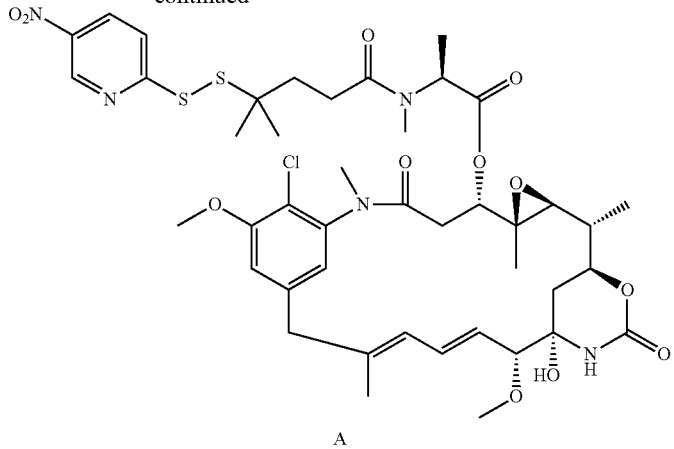

A

To a solution of compound 1 (40.0 mg, 0.050 mmol) in DCM (6.0 mL)/MeOH (3.0 mL) was added compound 2 (31.81 mg, 0.100 mmol), the mixture was stirred at 23° C. for 18 h. Then additional compound 2 (31.81 mg, 0.100 mmol) was added and the mixture was stirred at 23° C. for 18 h. The reaction mixture was concentrated and purified by prep-TLC (10% MeOH in DCM, Rf=0.5) to afford compound A (23 mg, 0.0224 mmol, 43.7% yield) as a yellow solid. LCMS (5-95AB/1.5 min): RT=0.978 min, MS=[M-18+H]$^+$ 916.3; $^1$HNMR (400 MHz, DMSO-d$_6$) δ 9.17-9.16 (d, J=3.2 Hz, 1H), 8.50-8.47 (m, 1H), 7.96-7.94 (d, J=8.8 Hz, 1H), 7.20-7.17 (d, J=12.0 Hz, 1H), 6.97 (s, 1H), 6.54-6.48 (m, 3H), 5.90 (s, 1H), 5.55-5.48 (m, 1H), 5.28-5.26 (m, 1H), 4.51-4.47 (m, 1H), 4.03 (s, 1H), 3.90 (s, 3H), 3.46-3.34 (m, 2H), 3.22-3.16 (m, 4H), 2.77-2.75 (d, J=8.8 Hz, 1H), 2.69 (s, 3H), 2.53-2.50 (m, 2H), 2.4-1.6 (m, 4H), 1.55 (s, 3H), 1.50-1.08 (m, 18H), 0.75 (s, 3H). The molecular weight determined by NMR was 933.31.

Activated maytansinoid compound B was synthesized according to the following overall reaction scheme 2.

Scheme 2:

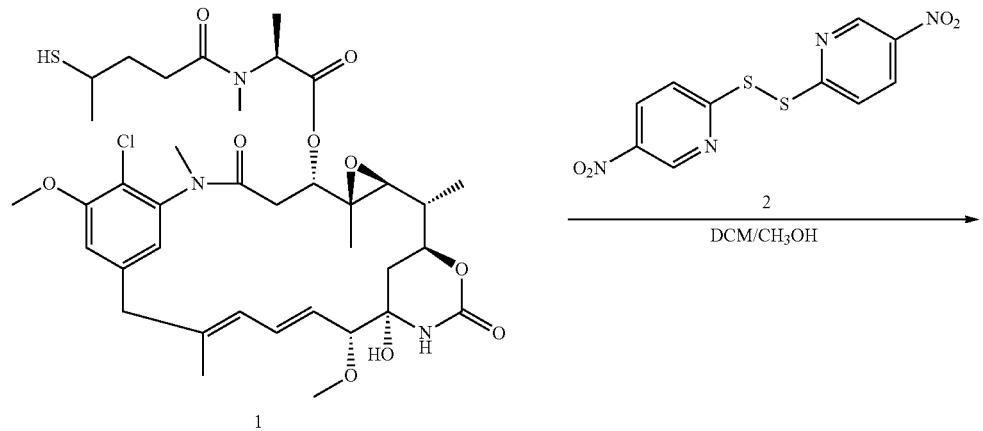

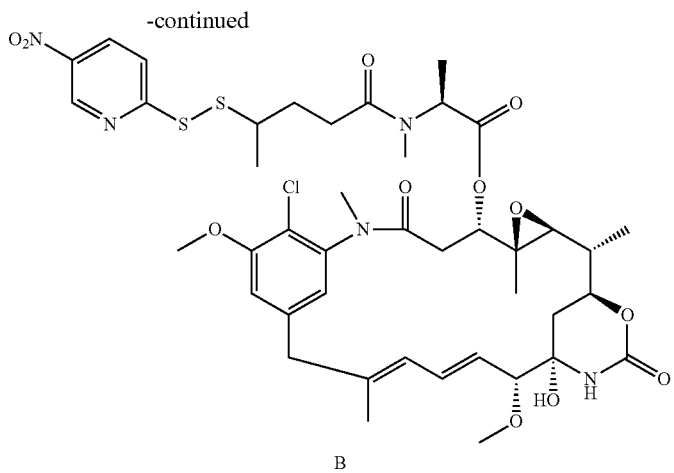

B

To a solution of compound 1 (15.0 mg, 0.020 mmol) in DCM (2.0 mL) was added compound 2 (18.22 mg, 0.060 mmol). After the mixture was stirred at 18° C. for 72 h, it was purified by prep-TLC (10% MeOH in DCM, Rf=0.5) to afford compound B (3.0 mg, 17% yield) as a white solid. LCMS (5-95AB/1.5 min): RT=0.982 min, [M-18+H]$^+$902.3. $^1$H NMR (400 MHz, DMSO-d6) δ 9.21-9.20 (m, 1H), 8.54-8.50 (m, 1H), 8.0-7.93 (m, 1H), 7.19-7.17 (d, J=8.0 Hz, 1H), 6.89 (s, 1H), 6.56-6.51 (m, 3H), 5.93 (s, 1H), 5.57-5.52 (m, 1H), 5.34-5.29 (m, 1H), 4.52 (d, J=8.0 Hz, 1H), 4.07-4.04 (m, 1H), 3.94 (s, 3H), 3.49-3.40 (m, 2H), 3.26 (s, 3H), 3.19-3.08 (m, 5H), 2.81-2.71 (m, 4H), 2.50-2.30 (m, 1H), 2.19-1.75 (m, 4H), 1.59-1.58 (m, 3H) 1.46-1.40 (m, 2H), 1.24-1.11 (m, 12H), 0.78-0.77 (d, J=3.6 Hz, 3H). The molecular weight determined by NMR was 919.29.

Activated maytansinoid compound C was synthesized according to the following overall reaction scheme 3.

Scheme 3:

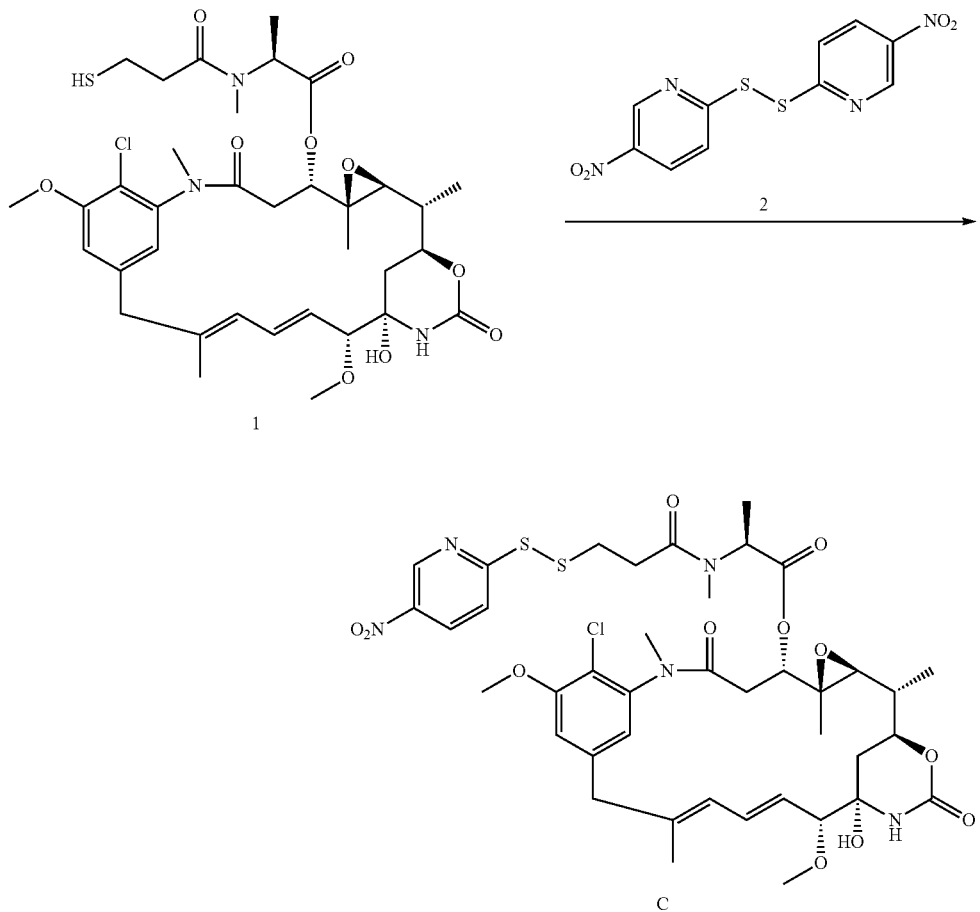

C

To a solution of compound 2 (67.25 mg, 0.22 mmol) in DCM (5.0 mL) was added compound 1 (80.0 mg, 0.11 mmol). After the mixture was stirred at 40° C. for 1 h it was concentrated and purified by prep-TLC (15% MeOH in DCM, Rf=0.5) to give compound C (80.0 mg, 0.11 mmol) as a white solid. LCMS (5-95AB/1.5 min): RT=0.929 min, [M-18+H]⁺874.1.

Activated maytansinoid compound D was synthesized according to the following overall reaction scheme 4.

Scheme 4:

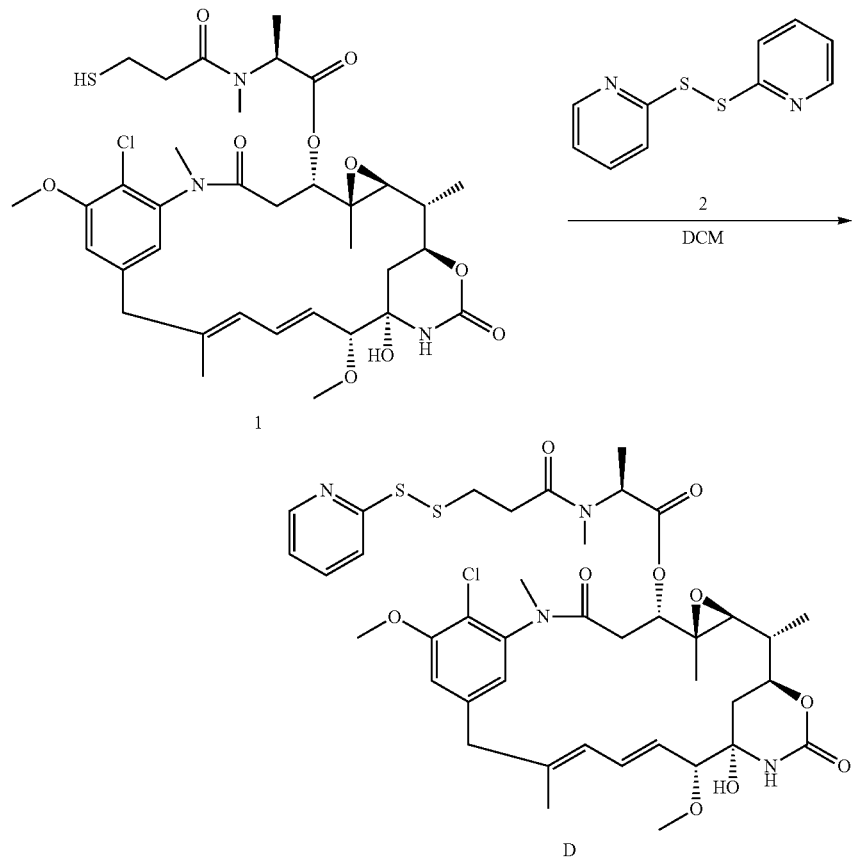

A solution of compound 1 (20.0 mg, 0.030 mmol) in DCM (2.0 mL) was added compound 2 (29.84 mg, 0.140 mmol). The reaction mixture was stirred at 20° C. for 1 h. The reaction mixture was purified by prep-HPLC (Column: Waters Xbridge Prep OBD C18 150*30 5u, Condition: water (0.225% FA)-CAN to give compound D (15.6 mg, 66.6%) as a white solid. LCMS (5-95AB/1.5 min): RT=0.768 min, [M-18+H]⁺847.3. $^1$H NMR (400 MHz, CDCl$_3$) δ 8.33-8.32 (d, J=4.8 Hz, 1H), 7.50 (s, 2H), 7.01-6.98 (m, 1H), 6.61-6.72 (m, 2H), 6.50 (s, 1H), 6.35 (m, 1H), 6.16 (s, 1H), 5.58 (m, 1H), 5.33 (m, 1H), 4.65-4.75 (m, 1H), 4.20 (m, 1H), 3.91 (s, 3H), 3.51-3.59 (m, 1H), 3.43 (d, J=8.8 Hz, 1H), 3.29 (s, 3H), 3.18 (br, 1H), 3.11 (s, 3H), 2.88-3.06 (m, 4H), 2.60-2.83 (m, 5H), 2.46-2.55 (m, 1H), 2.04-2.14 (m, 1H), 1.34-1.52 (m, 5H), 1.12-1.25 (m, 7H), 0.72 (s, 3H). The molecular weight determined by NMR was 846.27.

Activated maytansinoid compound E was synthesized according to the following overall reaction scheme 5.

Scheme 5:

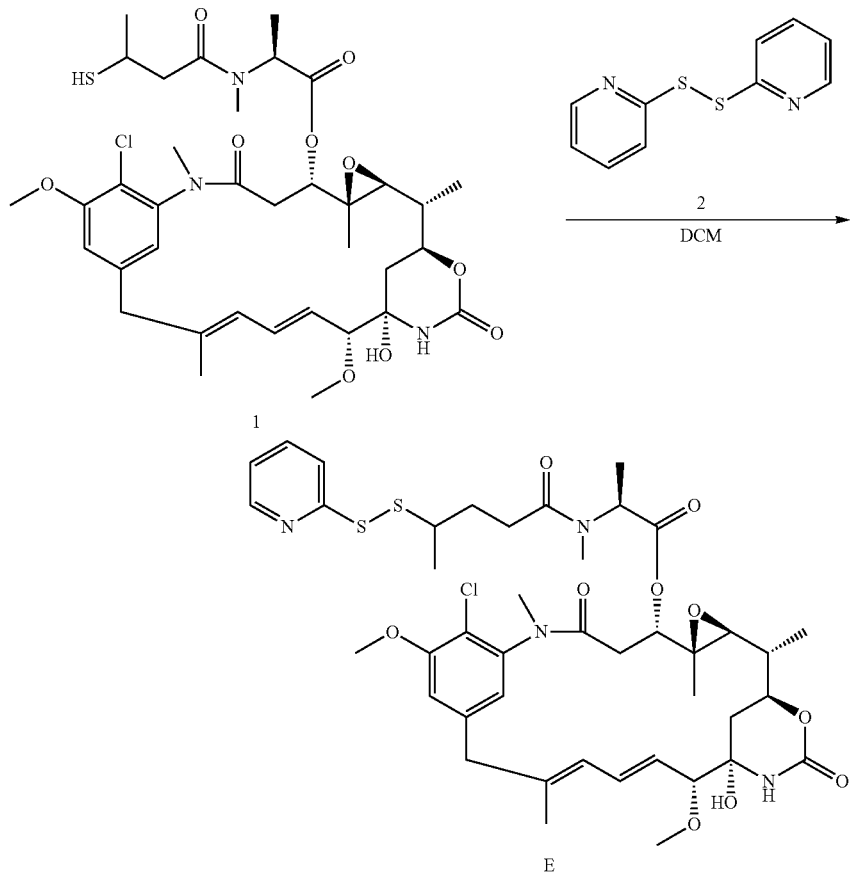

A solution of 1 (10.0 mg, 0.010 mmol) in DCM (2.0 mL) was added compound 2 (5.86 mg, 0.030 mmol). The reaction mixture was stirred at 20° C. for 24 h. The reaction mixture was concentrated in vacuo and purified by prep-TLC (5% MeOH in DCM, Rf=0.4), to give compound E (9.3 mg, 0.010 mmol, 75.1% yield) as a white solid. LCMS (5-95AB/ 1.5 min): RT=0.788 min, [M+H]$^+$ 875.4.

Example 21: Linker Immolation and Cell Killing Activity of Disulfide-Linked PBD ADCs The in vitro linker immolation and release parameters associated with PBD dimers containing 3-mercaptoethyl-carbamate disulfide linkers with methyl-, cyclopropyl-, and cyclobutyl-substitutions were investigated. The cell killing activity of related ADSs were also investigated.

In a first phase of the experiment, disulfide cleavage and immolation by incubation with cysteine and glutathione—with the thiol concentrations mimic those in plasma and cancer cells—was investigated using unconjugated small molecule model systems with para-nitro-pyridyl disulfide-containing linker drug analogs 1, 2 and 11 below. In particular, cleavage and immolation was evaluated in vitro by incubation at 15 M with cysteine (30 M or 200 μM) or glutathione (GSH, 4 mM) in 100 mM Tris buffer pH 7.0 containing 5% methanol at 37° C. Aliquots were taken at specified time points and the samples were analyzed by LC/MS on Sciex TripleTOF 5600 on a Hypersil Gold C18 column (100×2.1, 1.9 M, Thermo Scientific). The column was eluted by a gradient of buffer A (0.1% formic acid in 10 mM ammonium acetate) to buffer B (0.1% formic acid in 10 mM ammonium acetate in 90% acetonitrile), 5% B 0-0.5 min, 5-25% B 0.5-8 min, 25-75% B 8-13 min, and 75-95% B 13-13.5 min, 95% B 13.5-14.5 min, 95-5% B 14.5-15 min at 0.4 mL/min. Under these conditions, para-nitropyridyl thiol was eluted at 5.3 min. All products (compounds 1, 2, 11, 3a, 3b, 4a, 4b, 12a, 12 b, 6, 7, 13 and 8) were separated and characterized by LC/MS/MS in a positive ESI ion mode. All analytes had the protonated molecular MH$^+$ as the major species with little source fragmentation. Full scan accurate mass peak areas were used to estimate relative abundance of each component and the disappearance of 1, 2, and 11 estimated relative full scan peak areas was consistent with that estimated based on the relative abundance compared to time 0 by MS or UV. The results are reported in Table 15 below and the analytical results are presented in Table 16 below where "Cmpd" refers to compound, "RT" refers to retention time in minutes, and "Calc. Mass" refers to calculated mass. The relative abundance of disulfide cleavage and immolation products over time were evaluated and are disclosed in FIGS. 12A to 12C, 13A to 13C, 14A to 14C and 15A to 15C where the products were monitored by LC/MS from incubations of linker drugs 1, 2, and 11 at pH 7.0 and 37° C. in the presence of: 0.2 mM cysteine (FIGS. 12A, 12B and 12C); 0.03 mM cysteine (FIGS. 13A, 13B and 13C); 4 mM glutathione (FIGS. 14A, 14B and 14C); and 0.03 mM glutathione (FIGS. 15A, 15B and 15C). In FIGS. 12A to 12C, 13A to 13C, 14A to 14C and 15A to 15C, compound reference numbers 1, 2, 3a, 3b, 4a, 4b, 6, 7, 8, 11, 12a, 12b and 13 correspond to the structures below.

The structures of drug analogs 1, 2 and 11 are depicted below:

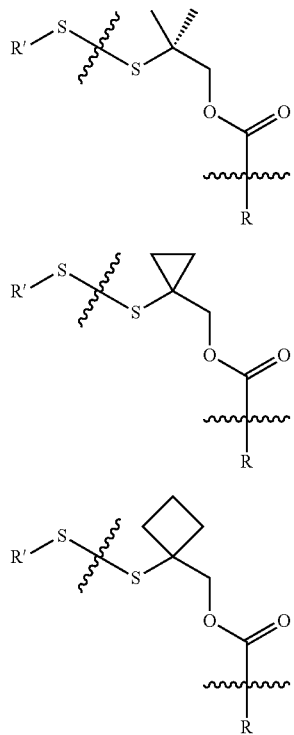

pound 12a was prepared by disulfide exchange between compound 11 and cysteine. Compound 12b was prepared by disulfide exchange between compound 11 and GSH.

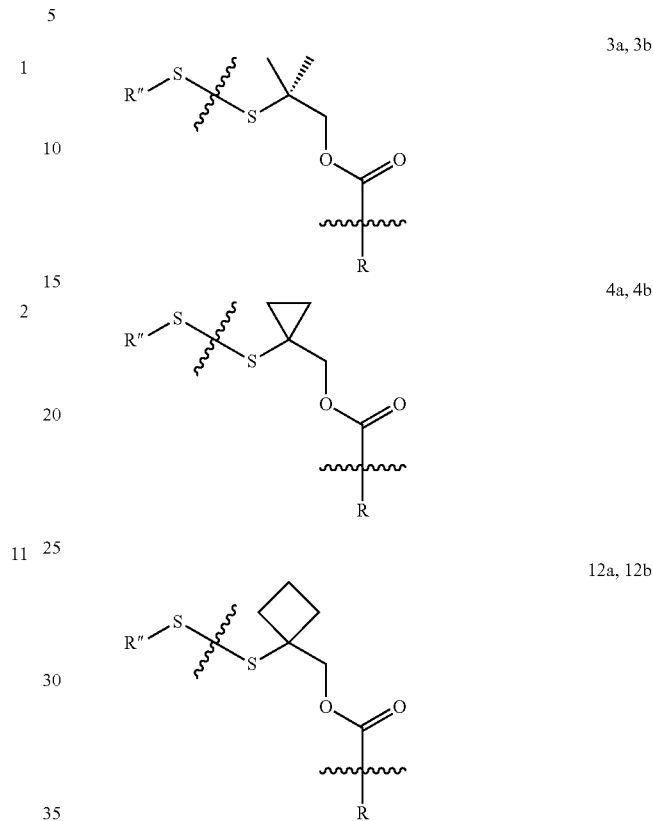

where R' and R (PBD dimer) are:

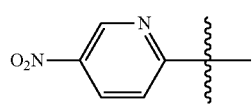

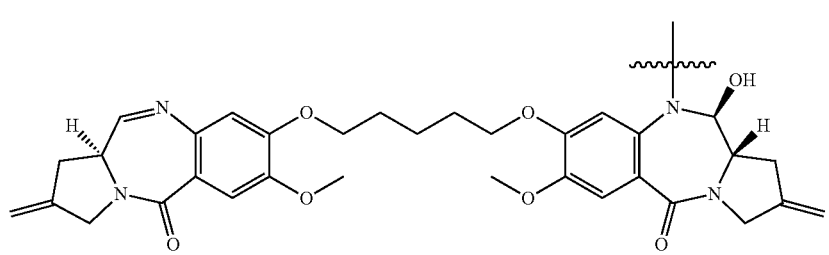

The structure of compounds 3a, 3b, 4a, 4b, 12a and 12 b are depicted below where R" refers to cysteine or GSH. Compound 3a was prepared by disulfide exchange between compound 1 and cysteine. Compound 3b was prepared by disulfide exchange between compound 1 and GSH. Compound 4a was prepared by disulfide exchange between compound 2 and cysteine. Compound 4b was prepared by disulfide exchange between compound 2 and GSH. Com- Disulfide reduction/immolation of compounds 3a and 3b is believed to generate compound 6 and PBD dimer 8 below; disulfide reduction/immolation of compounds 4a and 4b is believed to generate compound 7 and PBD dimer 8 below; and disulfide reduction/immolation of compounds 12a and 12b is believed to generate compound 13 and PBD dimer 8 below.

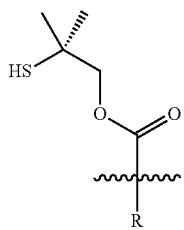

6

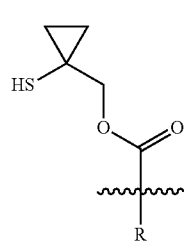

7

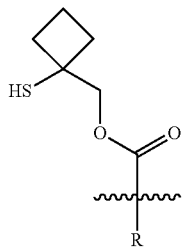

13

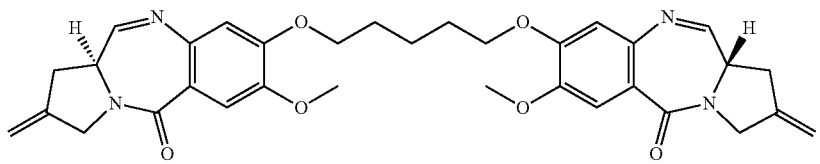

8

TABLE 15

Characterization of disulfide cleavage products of linker drugs 1, 2, and 11 in the presence of cysteine and glutathione.

| Treatment | | Compound | 1 h | 4 h | 24 h |
|---|---|---|---|---|---|
| 30 µM cysteine | Starting Material | 1 | 10.6 | 7.9 | 4.5 |
| | | 2 | 21.1 | 19.1 | 12.0 |
| | | 11 | 21.2 | 15.5 | 4.8 |
| | Thiol-Cys | 3a | 80.1 | 79.9 | 75.0 |
| | | 4a | 73.7 | 71.1 | 75.9 |
| | | 12a | 73.5 | 74.8 | 66.7 |
| | Thiol | 6 | 2.5 | 1.7 | 0.5 |
| | | 7 | 5.1 | 9.7 | 11.6 |
| | | 13 | 1.3 | 1.1 | 0.1 |
| | Drug Payload | 1 to 8 | 6.8 | 10.5 | 20.5 |
| | | 2 to 8 | 0.1 | 0.1 | 0.5 |
| | | 11 to 8 | 3.6 | 8.7 | 27.6 |
| 200 µM cysteine | Starting Material | 1 | 2.8 | 1.0 | 0 |
| | | 2 | 16.1 | 10.8 | 7.0 |
| | | 11 | 6.5 | 3.6 | 1.5 |
| | Thiol-Cys | 3a | 5.6 | 1.9 | 0 |
| | | 4a | 39.1 | 15.2 | 3.2 |
| | | 12a | 21.5 | 11.6 | 0.8 |

TABLE 15-continued

Characterization of disulfide cleavage products of linker drugs 1, 2, and 11 in the presence of cysteine and glutathione.

| Treatment | | Compound | 1 h | 4 h | 24 h |
|---|---|---|---|---|---|
| | Thiol | 6 | 7.8 | 2.8 | 0.1 |
| | | 7 | 44.7 | 73.6 | 87.3 |
| | | 13 | 3.2 | 1.6 | 0 |
| | Drug Payload | 1 to 8 | 83.7 | 94.4 | 99.9 |
| | | 2 to 8 | 0.1 | 0.3 | 2.5 |
| | | 11 to 8 | 68.8 | 83.2 | 97.7 |
| 4 mM GSH | Starting Material | 1 | 9.1 | 0.9 | 0.1 |
| | | 2 | 17.9 | 9.0 | 4.3 |
| | | 11 | 9.1 | 4.5 | 0.7 |
| | Thiol-Cys | 3b | 0.3 | 0 | 0 |
| | | 4b | 1.1 | 0.4 | 1.0 |
| | | 12b | 1.6 | 0.2 | 0 |
| | Thiol | 6 | 2.6 | 0 | 0 |
| | | 7 | 80.8 | 89.7 | 92.3 |
| | | 13 | 2.3 | 0 | 0 |
| | Payload | 1 to 8 | 88.0 | 98.5 | 99.9 |
| | | 2 to 8 | 0.2 | 0.4 | 2.3 |
| | | 11 to 8 | 86.7 | 94.9 | 99.3 |

TABLE 16

LC/MS characterization of disulfide cleavage products of linker drugs 1, 2, and 11 in the presence of cysteine and glutathione (in a positive ESI mode)

| Cmpd. | Formula | RT | Calc. Mass | Found Mass | Major Fragments |
|---|---|---|---|---|---|
| 1 | $C_{42}H_{46}N_6O_{11}S_2$ | 12.4 | 875.2739 | 875.2757 | 857.2663, 585.2729, 504.2146, 229.0110 |

TABLE 16-continued

LC/MS characterization of disulfide cleavage products of linker drugs 1, 2, and 11 in the presence of cysteine and glutathione (in a positive ESI mode)

| Cmpd. | Formula | RT | Calc. Mass | Found Mass | Major Fragments |
|---|---|---|---|---|---|
| 2 | $C_{43}H_{46}N_6O_{11}S_2$ | 12.4 | 887.2739 | 887.2741 | 869.2656, 585.2715, 504.2138, 492.2140, 241.0110 |
| 11 | $C_{44}H_{48}N_6O_{11}S_2$ | 12.7 | 901.2895 | 901.2879 | 883.2802, 585.2711, 504.2130, 492.2123, 255.0262 |
| 3a | $C_{40}H_{49}N_5O_{11}S_2$ | 10.3 | 840.2943 | 840.2958 | 822.2861, 778.2964, 585.2722, 536.2043, 504.2144, 492.2142, 213.0694 |
| 4a | $C_{41}H_{49}N_6O_{11}S_2$ | 10.3 | 852.2943 | 852.2948 | 834.2866, 790.2968, 585.2724, 536.2046, 504.2147, 492.2124, 213.0700 |
| 12a | $C_{42}H_{51}N_5O_{11}S_2$ | 10.5 | 866.3099 | 866.3087 | 848.2992, 804.3102, 585.2708, 536.2031, 504.2135, 492.2136, 220.0465 |
| 5 | $C_5H_4N_2O_2S$ | 5.3 | 721.2902 | 721.2882 | 703.2798, 585.2708, 504.2129, 492.2123 |
| 6 | $C_{37}H_{44}N_4O_9S$ | 11.5 | 721.2902 | 721.2882 | 703.2798, 585.2708, 504.2129, 492.2123 |
| 7 | $C_{38}H_{44}N_4O_9S$ | 11.9 | 733.2902 | 733.2901 | 715.2814, 585.2716, 536.2040, 504.2140, 492.2140 |
| 13 | $C_{39}H_{46}N_4O_9S$ | 12.2 | 747.3058 | 747.3041 | 729.2967, 629.2612, 585.2717, 504.2138, 492.2132, 411.1546, 259.1083 |
| 8 | $C_{33}H_{36}N_4O_6$ | 10.7 | 585.2708 | 585.2711 | 504.2144, 492.2144, 411.1570, 327.1724, 259.1096, 246.1139 |
| 3b | $C_{47}H_{59}N_7O_{15}S_2$ | 10.3 | 1026.3583 | 1026.3538 | 964.3623, 933.3183, 879.3053, 852.2518, 585.2713, 536.1980, 504.2154 |
| 4b | $C_{48}H_{59}N_7O_{15}S_2$ | 10.3 | 1038.3583 | 1038.3590 | 945.3183, 891.3074, 585.2712, 536.2030, 504.2156, 485.1522, 392.0955 |
| 12b | $C_{49}H_{61}N_7O_{15}S_2$ | 10.4 | 1052.3740 | 1052.3714 | 957.3185, 585.2715, 504.2157 |

The data show that the para-nitropyridyl disulfide moieties in these molecules underwent rapid disulfide cleavage with a half-life of minutes (FIGS. 12A to 12C, 13A to 13C, 14A to 14C and 15A to 15C, Table 15). Analysis by LC/MS/UV showed that reduction of compounds 1 and 2 gave different products: PBD-dimer compound 8 was obtained as a major product from methyl-containing compound 1 while the thiol compound 7 was formed from cyclopropyl-containing compound 2 (Tables 15 and 16 and FIGS. 12A, 12B, 14A and 14B) when an excess level of a reducing thiol was present (0.2 mM cysteine or 4 mM GSH). In contrast, when a relatively low concentration of cysteine (0.03 mM) was used (FIGS. 13A and 13B), thiol-cysteine adduct compounds 3a and 4a were the major and stable products in the 24-h incubations due to consumption of the reducing thiol. Similarly, thiol-GSH adduct compounds 3b and 4b were observed as the major products when compounds 1 and 2 were exposed to a low concentration of GSH (0.03 mM) for the same time period (FIGS. 15A and 15B). These cleavage reactions also formed the para-nitropyridyl thiol compound 5 as a depicted in the proposed mechanism below). Reversible disulfide exchange was observed between para-nitropyridyl thiol compound 5 and cyclopropyl-containing thiol compound 7 with a comparable pKa value (4.7-4.8) at 0.03 mM GSH concentration (FIG. 15B). The observation of intermediate compounds 3a and 6 (albeit at low levels) was consistent with a proposed mechanism—without being bound to any particular mechanism—for formation of PBD-dimer compound 8 from compound 1 that involves (1) cysteine attack on the 2-mercaptoethyl-derived disulfide sulfur atom to form compound 3a, (2) 2nd cysteine attack on the less hindered sulfur atom of the resulting thiol-cysteine disulfide to afford a thiolate intermediate, and (3) the thiolate immolation to liberate PBD-dimer compound 8 or capture of a proton to form the corresponding thiol compound 6 (See the proposed mechanism below). The depicted regiochemistry of initial cysteine attack on compound 1 is believed to be influenced by both disulfide electronics and the acidic nitropyridyl thiolate pKa (i.e., this fragment is a good leaving group) (See Singh, R.; Whitesides, G. M. *Suppl. S Chem. sulfur-containing Funct. groups* 1993, 633. See also Freter, Rolf; Pohl, Eric R.; Wilson, Janet M.; Hupe, D. J. *J Organ Chem* 1979, 44 (11), 1771). The thiol-cysteine disulfide compound 3a is identical to the proposed intermediate produced by intracellular catabolism of the corresponding ADC following internalization and lysosomal proteolysis in cells (See Erickson, H. K.; Widdison, W. C.; Mayo, M. F.; Whiteman, K.; Audette, C.; Wilhelm, S. D.; Singh, R. *Bioconjug Chem* 2013, 21 (1), 84).

One mechanism, without being bound to any particular mechanism, for PBD dimer-linker immolation and release is depicted below:

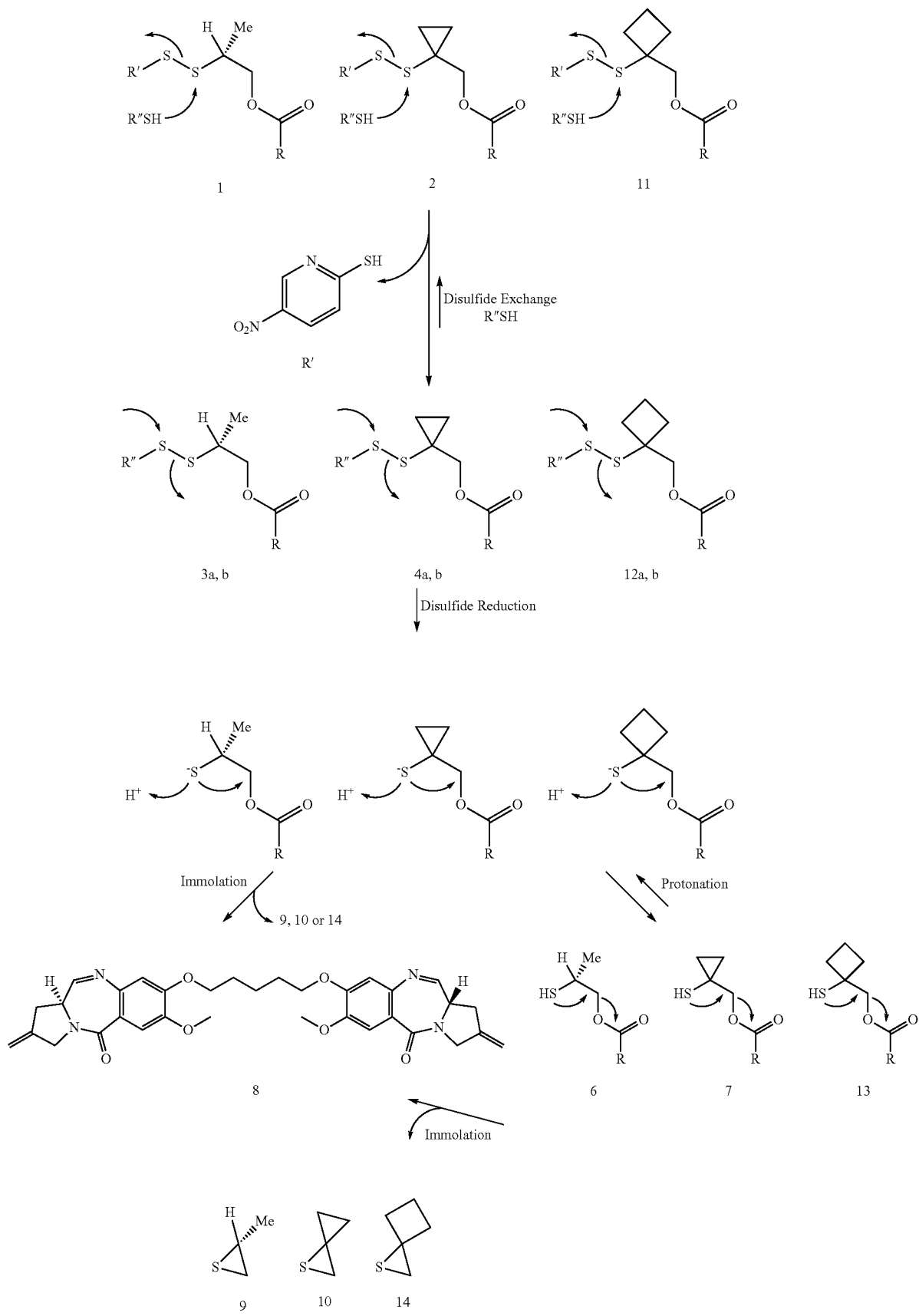

where R is:

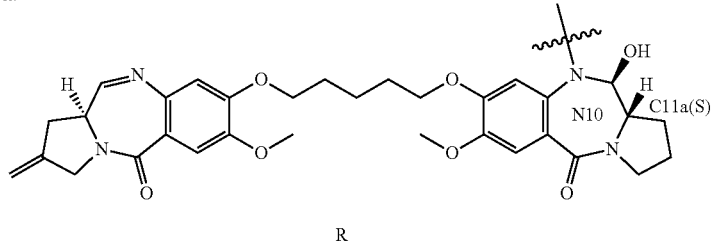

-continued

R and where R" is cysteine (the compounds designated "a", e.g., 3a) or GSH (the compounds designated "b", e.g., 3b).

Figure 12A:
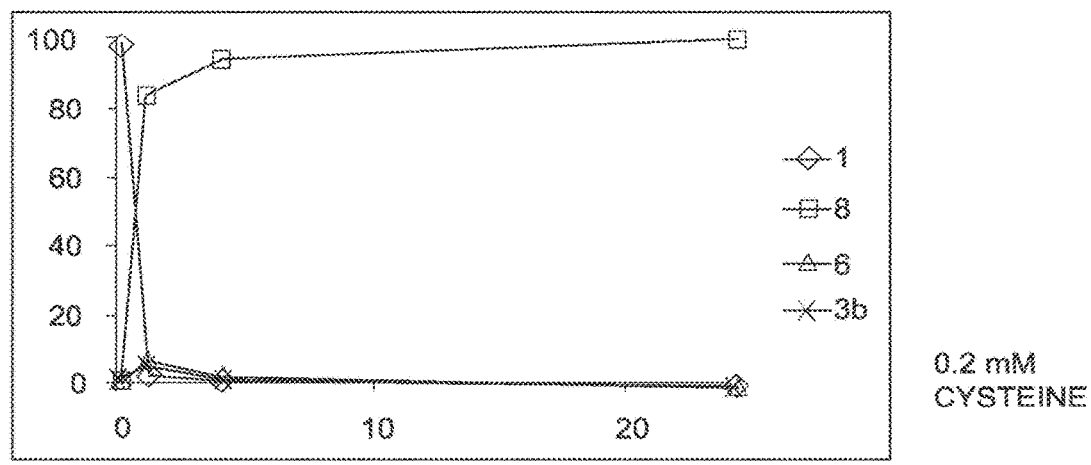
Figure 12B:
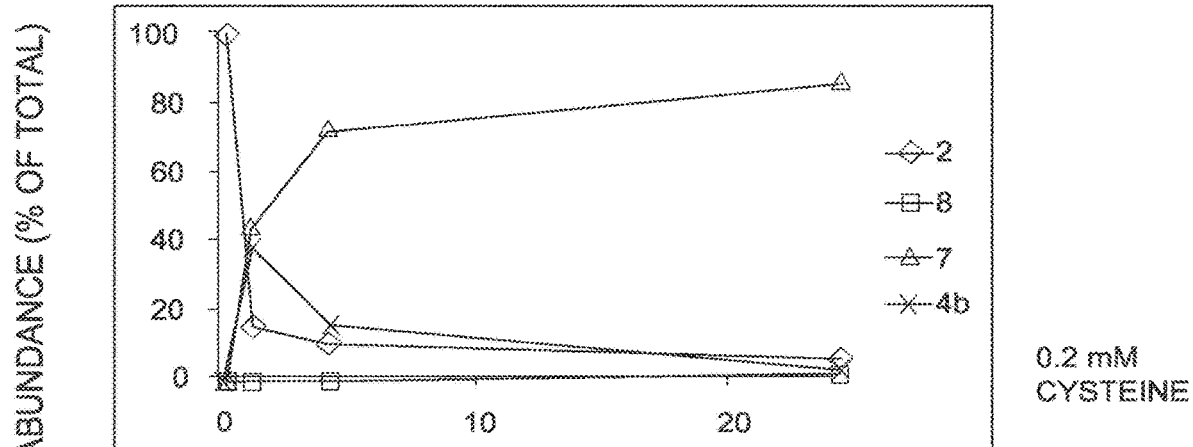
Figure 12C:
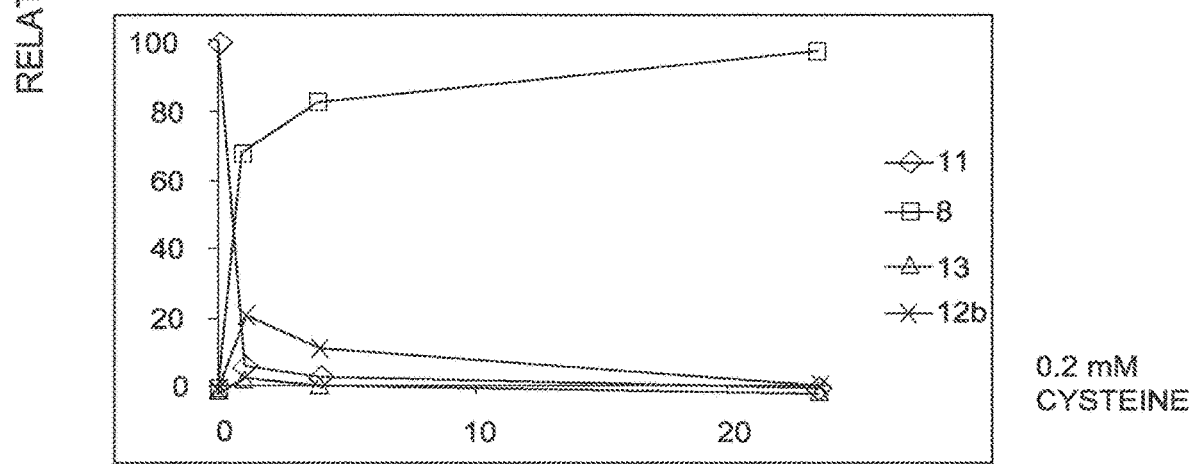

As shown in FIGS. 12A and 14A and Table 15, the methyl-containing thiol intermediate compound 6 could be detected by LC/MS at low levels in the initial phase of the incubations but immolated quickly to afford the PBD-dimer compound 8. However, the corresponding cyclopropyl-containing thiol compound 7 produced from disulfide compound 2 did not appreciably immolate and appeared to be stable. Furthermore, the thiirane compound 9 was detected via LC/MS in the cleavage experiment utilizing compound 1 while the corresponding thiirane compound 10 was not identified from studies employing compound 2 (See above proposed mechanism). Subsequently, the cyclobutyl analog compound 11 was prepared. Both compound 11 and its thiol-cysteine adduct compound 12a underwent rapid disulfide cleavage followed by efficient immolation of its thiolate and thiol 13 to form thiirane compound 14 and PBD-dimer compound 8 (FIGS. 12C, 13C and 14C). The cyclobutyl-substituted disulfide in compound 11 is more stable than the methyl analog compound 1 since greater amounts of starting material compound 11 were observed relative to compound 1 in the incubation with a lower concentration of glutathione (0.03 mM) (FIGS. 15A and 15C). Immolation of cyclobutyl-containing thiol compound 13 may also be slightly more efficient than the methyl-containing thiol compound 6, as less compound 13 was detected than compound 6 under all incubation conditions (Table 15). Non-immolation of the cyclopropyl linker compared to efficient immolation of the cyclobutyl or methyl-containing linkers is believed to be due to multiple factors. For example, the bond angles associated with the cyclopropyl ring are believed to result in increased ring strain in the fused di-cyclopropyl thiirane compound 10 relative to thiolate compounds 9 and 14 and thereby impede the desired immolation reaction (See Jung, M. E.; Piizzi, G. Chem. Rev. 2005, 105 (5), 1735). The cyclopropyl ring may also exert an electronic effect (p-orbital character) on the thiolate intermediate which reduces its nucleophilicity and therefore its ability to cyclize. Consistent with this possibility, a significantly lower pKa value (more acidic) was measured for the cyclopropyl-containing thiol compound 15 relative to that measured for the cyclobutyl-containing thiol compound 16 (4.8 versus 9.6, respectively). Collectively, these results demonstrate that minor structural modifications to the disulfide linker can lead to differences in the corresponding immolation and release efficiencies.

The effects of immolation on cell-killing activities of related ADCs were evaluated. Anti-CD22 conjugates (LC-K149C-anti-CD22-PBD) 19-1 (methyl-), 20-1 (cyclopropyl-), and 21-1 (cyclobutyl-) and the corresponding control conjugates (LC-K149C-anti-NaPi2b-PBD) 19-2, 20-2, and 21-2 were prepared from compounds 1, 2, and 11. The CD22 antigen was chosen because of its high expression on cancers of B-cell origin and relatively low prevalence on non-B cell-related normal cells and tissues (See Polson, a G.; Williams, M.; Gray, a M.; Fuji, R. N.; Poon, K. a; McBride, J.; Raab, H.; Januario, T.; Go, M.; Lau, J.; Yu, S.-F.; Du, C.; Fuh, F.; Tan, C.; Wu, Y.; Liang, W.-C.; Prabhu, S.; Stephan, J.-P.; Hongo, J.; Dere, R. C.; Deng, R.; Cullen, M.; de Tute, R.; Bennett, F.; Rawstron, a; Jack, a; Ebens, a. Leukemia 2010, 24 (9), 1566). FIG. 20 shows LC-K149C-anti-CD22-PBD and LC-K149C-anti-NaPi2b-PBD ADCs were prepared where PBD-N10 corresponds to PBD compound designated as "R" above.

Full length, cysteine-engineered monoclonal antibodies (THIOMAB™) expressed in CHO cells were exposed to a 50-fold excess of DTT overnight at room temperature to reduce disulfide bonds which may form between the engineered cysteine residues and the cysteine or glutathione present in the culture media. The reduced THIOMAB™ antibodies were diluted and loaded onto a HiTrap SP column in 10 mM sodium succinate, pH 5, washed with sodium succinate buffer, and eluted with 50 mM Tris, pH 8 containing 150 mM sodium chloride. The reduced antibodies without small molecule reductant present were treated with 15 equivalents of dehydroascorbic acid (DHAA), previously dissolved as a stock in N,N-dimethylacetamide, for ~3 hours to reform the interchain disulfides while leaving the engineered cysteines free for conjugation. The DHAA was removed in the same manner used for removal of reductant with the exception that the final conjugatable THIOMAB™ antibodies were eluted with a gradient of 10 mM succinate, pH 5.0, 300 mM NaCl in 10 mM succinate, pH 5.0. EDTA was then added to the final protein pools at a final concentration of 2 mM.

For conjugation of THIOMAB™ antibody, the antibodies were first pH-adjusted to pH 8.5 with 1 M Tris, pH 8.5. To these solutions was added an excess of the appropriate nitropyridyl disulfides (compound 1, 2, or 11 depicted above, about 6 to 15 molar equivalents), dissolved in N,N-dimethylformamide such that the final amount of DMF in the reaction volumes were 10%.

The conjugation reactions were allowed to proceed overnight at room temperature. The conjugation mixtures were purified to remove unconjugated 1, 2, or 11 and conjugation byproducts using a combination of standard cation exchange (S maxi spin column, Pierce) and gel filtration (Zeba spin columns or S200 column) methods. The final conjugates were formulated into a buffer of 20 mM histidine-acetate, pH 5.5, 240 mM sucrose, and 0.02% Tween-20.

During and after the THIOMAB™ antibody preparations (reduction/reoxidation) and subsequent conjugations, the reactions were monitored for both aggregation and drug-to-antibody ratio (DAR). For aggregation measurements, analytical SEC was used (Shodex KW-802.5 column; 0.2 M potassium phosphate, pH 6.2, 0.25 M potassium chloride buffer). To measure DAR, we analyzed conjugates either intact or partially digested by the protease Lys-C (separating Fab and Fc domains) by reverse-phase LCMS (PLRP-S column, 1000 angstrom, 50 mm×2.1 mm, Polymer Laboratories) using an Agilent 1100 series TOF mass spectrometer (Agilent Technologies). Data were collected by Agilent Chemstation acquisition software and deconvolution was performed using Agilent MassHunter software (Novatia, LLC, New Jersey). DAR values were calculated by comparing peaks corresponding to drug-modified antibody with those corresponding to antibody without drug. Protein concentrations were determined using a BCA assay (Pierce). All conjugates had aggregation levels <5%, amounts of remaining unconjugated linker drug <5%, concentrations >2 mg/mL and endotoxin levels <0.5 EU/mg. DAR values for the various conjugates are provided in Table 17 below.

TABLE 17

| | Conjugate | | | | | |
|---|---|---|---|---|---|---|
| | 19-1 | 19-2 | 20-1 | 20-2 | 21-1 | 21-2 |
| DAR | 1.8 | 1.9 | 1.9 | 1.9 | 1.5 | 1.5 |

BJAB, and WSU-DLCL2, and Jurkat2 cell lines were seeded at 4-7,000 cells/well and grown on Corning® 384 well Flat Clear Bottom White Polystyrene TC-Treated Microplates in cysteine-free RPMI or DMEM_Ham's F-12 media containing 10% FBS, 2 mM L-Glutamine and 0.015 g/L methionine supplemented with 50 M fresh cystine to confluence. ADC conjugates (19, 20, and 21) at 10 concentrations (1 to 3 dilutions) were incubated for 4 days before the cell viability was determined using Promega CellTiter-Glo luminescent reagent, which measures ATP level (an indirect measure of cell number). The luminescent intensity was measured on PerkinElmer Envision reader. The relative cell viability was calculated by normalizing to non-drug treatment control and was graphed using KleidaGraph software package. $IC_{50}$ value was determined as the concentrations to obtain 50% of the maximum cell killing (N=4). The $IC_{50}$ results are presented in Table 18 and the cell viability results are presented in FIGS. 11A to 11F.

TABLE 18

Cell-killing activities of methyl-, cyclopropyl, and cyclobutyl-containing conjugates 19-1, 20-1, and 21-1 in CD22-expressing BJAB and WSU-DLCL2 cell cultures

| | $IC_{50}$ (nM) | |
|---|---|---|
| Compound | BJAB | WSU-DLCL2 |
| 19-1, methyl-CD22 | 1.16 ± 0.04 | 1.19 ± 0.11 |
| 19-2, methyl-NaPi | 6.13 ± 0.03 | 13.9 ± 0.02 |
| 20-1, cyclopropyl-CD22 | 85.0 ± 0.06 | 95.7 ± 0.06 |
| 20-2, cyclopropyl-NaPi | 87.8 ± 0.14 | 125 ± 0.04 |
| 21-1, cyclobutyl-CD22 | 0.47 ± 0.04 | 1.50 ± 0.08 |
| 21-2, cyclobutyl-NaPi | 3.84 ± 0.04 | 8.95 ± 0.05 |

The methyl- and cyclobutyl-containing conjugates 19-1 and 21-1 showed potent, target-dependent cell-killing activities in two CD22-expressing cell lines (WSU-DLCL2 and BJAB, Table 18). However, the cyclopropyl-containing conjugate 20-1 was significantly (>50-fold) weaker than 19-1 and 21-1 in these experiments and also exhibited almost no potency differences from the corresponding non-target control conjugate (20-2). These results were consistent with the in vitro data depicted in FIG. 11 and Table 15 which illustrate the inability of the cyclopropyl-containing thiol compound 7 to both efficiently alkylate DNA Oligos and to release PBD-dimer compound 8 via immolation. The ADC cell data was also consistent with the efficient release of a potent DNA alkylating agent (di-imine compound 8) from in vitro model systems related to conjugates 19-1 and 21-1 (See Table 15 and the proposed immolation and release mechanism above).

Example 22: In Vivo Tumor Killing Activity of Disulfide-Linked PBD ADCs

The efficacy of the anti-CD22 antibody-drug conjugate ADCs of the structures 1-1, 2-1 and 3-1 (corresponding to structures 19-1, 20-1 and 21-1 depicted above in Example 21) was investigated in a mouse xenograft model of human diffuse large B-cell lymphoma WSU-DLCL2 (German Collection of Microorganisms and Cell Cultures; Braunschweig, Germany) versus non-target control anti-NaPi antibody-drug conjugate ADCs of the structures 1-2, 2-2, and 3-2 (corresponding to structures 19-2, 20-2 and 21-2 depicted above in Example 22). PBD cyclopropyl thiol compound 7 of the following structure was also evaluated:

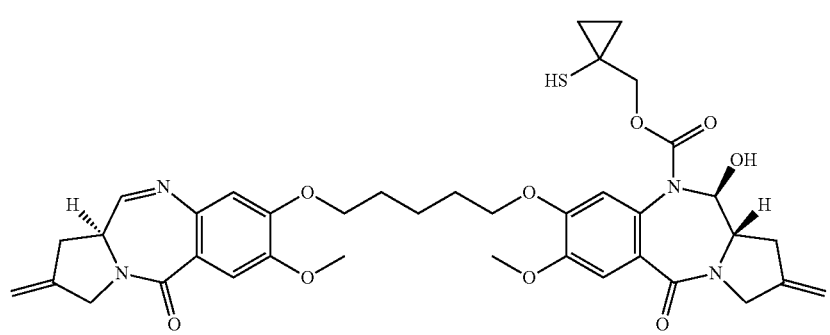

7

Ammonium formate, formic acid, and calf DNA were purchased from Sigma-Aldrich. Human CD22 and Napi antibodies with two engineered cysteine residues were generated as described previously (Bhakta et al., 2013; Polson et al., 2010). Anti-CD22 conjugates (Light chain-K149C-anti-CD22-PBD) compound 1-1 (methyl-), compound 2-1 (cyclopropyl-), and compound 3-1 (cyclobutyl-) as well as the corresponding control conjugates (Light chain-K149C-anti-NaPi-PBD) compounds 1-2, 2-2, and 3-2, PBD-dimer 8 and cyclopropyl thiol 7 were prepared. Mice (CB-17 SCID, Nude, and Balb/C strains) were purchased from Charles Rivers Laboratories. All animal studies were carried out in compliance with National Institutes of Health guidelines for the care and use of laboratory animals and were approved by the Institutional Animal Care and Use Committee at Genentech, Inc.

To establish subcutaneous xenograft model, the tumor cells (20 million cells in 0.2 mL Hank's Balanced Salt Solution; Hyclone) were inoculated subcutaneously into the flanks of female CB17 SCID mice (Charles Rivers Laboratories). When tumor size reached the desired volume, animals were divided into groups of 8 mice each and received a single intravenous injection of anti-Napi (non-target control), LC-K149C-anti-CD22-methyl-PBD compound 1-1, cyclopropyl-PBD compound 2-1, or cyclobutyl-PBD compound 3-1 at 0.5 or 1 mg/kg through the tail vein (Day 0 of the study). Tumors and body weights of mice were measured 1-2 times a week throughout the study. Mice were promptly euthanized when body weight loss was >20% of their starting weight. All animals were euthanized before tumors reached 3000 mm$^3$ or showed signs of impending ulceration. Tumor volume was measured in two dimensions (length and width) using calipers and the tumor volume was calculated using the formula: Tumor size (mm$^3$)=(longer measurement×shorter measurement$^2$)×0.5.

Selected tissues including tumor, liver, and plasma were collected at 24 and 96 h post-dose of single IV 5 m/kg of compound 2-1 (cyclopropyl-) and compound 3-1 (cyclobutyl-) and kept frozen at −80 C until being analyzed for exposure assessment on total antibody and payloads. Selected plasma samples were collected at 1, 4, and 7 days post-dose of single IV 1 m/kg of compound 1-1 (methyl-), compound 2-1 (cyclopropyl-) and compound 3-1 (cyclobutyl-) and kept frozen at −80 C until analysis for DAR values.

Total mAb and catabolites were characterized in tumors and other tissues after xenograft mice were dosed with cyclopropyl-containing compound 2-1 or cyclobutyl-containing compound 3-1 with a single IV 5 mg/kg. The plasma, liver and tumor were collected at 24 and 96 h, and homogenized in control mouse plasma and analyzed by LC/MS/MS for catabolites following extraction with an organic solvent. Another portion of the tissues were homogenized in PBS buffer containing protease inhibitor cocktail (Sigma-Aldrich) and analyzed by affinity-capture LC/MS for total antibody following Protein A capture and trypsin digestion.

To quantitate the concentrations of catabolites in the mouse plasma and tissues, 50 µL plasma or approximately 50 mg tissues (liver or tumor) were mixed with ice-cooled 150 µL blank mouse plasma. The samples were thoroughly homogenized 2 cycles of 30 seconds each by pre-cooled beads (10 beads, −80° C.) and then extracted by ice-cooled 400 µL acetonitrile containing 10 nM internal standard (589.2/261.0). After 6,500×g centrifuge for 15 min, 10 µL supernatant was injected to an AB Sciex Triple Quad 6500 mass spectrometer (MS) coupled with a Shimadzu liquid chromatography (LC). The LC conditions use Phenomenex Kinetex C18, 1.7 jam, 100 Å, 100×2.1 mm with mobile phase A (0.1% formic acid) and B (100% acetonitrile) and a gradient of 0-0.5 min 5% B, 0.5-3.5 min 5-90% B, 3.5-4.0 min 90% B, 4.0-4.5 min 90-5% B, 4.5-5.0 min 5% B at a flow rate of 0.5 mL/min (column temperature of 35° C.). The retention times of PBD-dimer 8, catabolite thiol 5 and IS were 2.6, 3.1 and 2.9 min, respectively. The multiple reaction monitor (MRM) transitions in MS were PBD 4 (585.1/504.2) and catabolite thiol compound 5 (732.2/504.2). The compound-dependent MS parameters were 61, 10, 29-41, 14 for DP, EP, CE, and CXP, respectively. The MS instrument-dependent parameters were CAD (−3), CUR (10), GS1 (90), GS2 (50), IS (5500), and TEM (500). The standard curve samples for quantitation were 0.24, 0.49, 0.98, 1.96, and 3.91 and 0.24, 0.49, 0.98, 1.96, and 3.91, and 7.81 nM for PBD-dimer compound 8 and thiol compound 7, respectively. The lower limits of quantification (LLOQs) of compounds 7 and 8 were both 0.24 nM. The matrix effects of the tissue samples were minimized by homogenizing the tissues in blank mouse plasma.

The samples were analyzed by LC/MS on Sciex TripleTOF 5600 on a Hypersil Gold C18 column (100×2.1, 1.9 µM, Thermo Scientific). The column was eluted by a gradient of 0.1% formic acid in 10 mM ammonium formate to acetonitrile containing 0.1% formic acid in 10 mM ammonium formate. PBD-dimer compound 8 was identified by LC/MS at M/Z found: 585.2708 and calculated: 585.2711, C33H36N4O6 and major fragments at M/Z: 504.2144, 492.2144, 411.1570, 327.1724, 259.1096, and 246.1139. Cyclopropyl-containing thiol compound 7 was identified by LC/MS at M/Z found: 733.2901 and calculated: 733.2902, C38H44N4O9S and major fragments at M/Z: 715.2814, 585.2716, 536.2040, 504.2140, and 492.2140.

An affinity capture approach using protein A magnetic beads was used to enrich the cyclobutyl- or cyclopropyl-containing compounds 2-1 and 3-1 from the mouse tissue homogenate in PBS buffer, pH 7.4. The bound ADCs were subjected to "on-bead" proteolysis with trypsin, following standard protein denaturation, reduction, and alkylation processing steps. Briefly, quantification of the total antibody concentration was achieved by using LC-MS/MS measurement of its surrogate peptide(s) produced by proteolytic digestion. A surrogate peptide, TTPPVLDSDGSFFLYSK, generated from the human Fc region unique to allow the differentiation of cyclobutyl- or cyclopropyl-containing compounds 2-1 and 3-1 from the endogenous matrix components, was quantified by the MRM transition of 938.0/836.7. In addition, several other peptides characteristic to the human Fc region were monitored for the conformational and troubleshooting purposes as described previously (Xu et al., "A multiplexed hybrid LC-MS/MS pharmacokinetic assay to measure two co-administered monoclonal antibodies in a clinical study" *Bioanalysis* 6:1781-94 (2014)).

The DAR was determined as described previously (Xu et al., Characterization of intact antibody-drug conjugates from plasma/serum in vivo by affinity capture capillary liquid chromatography-mass spectrometry. *Anal Biochem* 412:56-66 (2011)). Briefly, an appropriate volume of plasma of mice after IV administration of ADCs was incubated at room temperature with the biotinylated CD22 target antigen, which was coupled to the streptavidin paramagnetic beads (Invitrogen). The bead captured ADC analytes were washed and deglycosylated at 37° C. overnight. The ADC was eluted by 30% acetonitrile in water with 1% formic acid and injected onto a Triple TOF 5600 mass spectrometer (AB Sciex) coupled with a reversed phase HPLC column. A gradient condition with a flow rate at 15 µL/min was applied. Mobile phase A was water with 0.1% formic acid and mobile phase B was acetonitrile with 0.1% formic acid. Positive time-of-flight (TOF) MS scan was acquired and processed. Peak deconvolution was performed to obtain the distribution profile of DAR0, DAR1 and DAR2 species (FIG. 21), and the corresponding peak areas were measured. Subsequently, the relative ratio of each DAR and the average DAR value at each time point could be calculated.

For DNA binding analysis, compounds 7 and 8 were incubated at 1 NM with 1 mg/mL calf DNA for 1 hour in 0.5 mL of 10 mM Bis-Tris, pH 7.1 at 37° C. Ethyl acetate (1 mL) was used to extract the reaction mixture twice by vortex (20 seconds) and centrifugation (4 min at 5,000×g). The combined organic extracts were concentrated under vacuum and reconstituted in 0.15 mL of 1:1 water/methanol before injection on LC/MS. The samples were analyzed by LC/MS/UV on Sciex TripleTOF 5600 on a Hypersil Gold C18 column (100×2.1, 1.9 M, Thermo Scientific) in a positive ESI ion mode. The column was eluted by a gradient of buffer A (0.1% formic acid) to buffer B (0.1% formic acid in acetonitrile), 5% B 0-0.5 min, 5-25% B 0.5-8 min, 25-75% B 8-13 min, and 75-95% B 13-13.5 min, 95% B 13.5-14.5 min, 95-5% B 14.5-15 min at 0.4 mL/min.

The efficacy of conjugates 1-1 (methyl-), 2-1 (cyclopropyl-), and 3-1 (cyclobutyl-) was studied in vivo in a CD22-expressing WSU-DLCL2 xenograft mouse model. When dosed once IV at both 0.5 and 1 mg/kg, conjugates containing disulfide linkers bearing methyl (1-1) and cyclobutyl (2-1) substituents exhibited strong efficacy with partial responses observed beginning in week 1 and lasting for 35 days (FIG. 16). These entities were well-tolerated in mice as the corresponding body weight losses were within 5% in all treatment groups (FIG. 17). The related non-target NaPi (Lin et al., 2015) control conjugates (3-2, and 2-2) displayed minimal efficacy in the same mouse model. A 1.0 mg/kg IV administration of the cyclopropyl-containing anti-CD22 conjugate (2-1) afforded almost no anti-tumor activity and all animals in this group together with the NaPi control group were euthanized due to tumor growth within two weeks of ADC dosing (FIGS. 16 and 17).

A study was done to evaluate whether the systemic pharmacokinetics could be a possibility for the weak efficacy exhibited by the cyclopropyl-containing conjugate 2-1 in the experiment described above. To explore this possibility, total mAb and catabolite concentrations were measured in plasma, liver, and tumors of WSU-DLCL2 xenograft mice after animals were administered a single IV 5 mg/kg dose of both cyclopropyl-containing 2-1 and cyclobutyl-containing 3-1. The tissue sampling was performed at relatively early time points (24 and 96 h) to ensure sufficient tumor quantities were available for analysis. As shown in Table 19, the measured tumor and plasma exposures of total antibody for both entities were similar at both 24 and 96 h after dosing with much higher total mAb concentrations in plasma (216-370 nM) than in tumors (16-59 nM). In a separate experiment employing 1 mg/kg IV doses, the drug-antibody ratios of the two conjugates determined from plasma samples were similar and relatively stable over a 7-day period (FIG. 18). Consequently, the conjugated antibody should also have similar concentrations between the cyclopropyl- and cyclobutyl-containing conjugates in mice. These results indicated that there was no significant PK and/or in vivo stability difference that could be responsible for the drastically different efficacy outcomes observed for cyclopropyl-containing 2-1 and cyclobutyl-containing 3-1 ADCs.

TABLE 19

Total antibody (mAb) and catabolite concentrations in tissues of WSU-DLCL2 xenograft mice following a single 5 mg/kg IV dose of PBD-containing ADCs 2-1 (cyclopropyl-) and 3-1 (cyclobutyl) (n = 2)

| ADC | Time | PBD-Dimer 8 (nM) | | | Cyclopropyl-thiol 7 (nM) | | | mAb (nM) | | |
|-----|------|--------|-------|-------|--------|-------|-------|--------|-------|-------|
|     |      | Plasma | Liver | Tumor | Plasma | Liver | Tumor | Plasma | Liver | Tumor |
| 3-1 | 24 h | 0.43 | 0.26 | 1.03 | NA | NA | NA | 370 | 24.8 | 43.5 |
|     |      | 0.55 | 0.55 | 2.09 | NA | NA | NA | 342 | 19.5 | 25.0 |
|     | 96 h | <LLOQ | <LLOQ | 1.93 | NA | NA | NA | 285 | 20.9 | 25.3 |
|     |      | <LLOQ | <LLOQ | 2.05 | NA | NA | NA | 272 | 21.1 | 56.0 |
| 2-1 | 24 h | ND | ND | ND | 0.74 | 1.42 | 7.58 | 294 | 28.4 | 59.4 |
|     |      | ND | ND | ND | 0.57 | 0.63 | 6.76 | 216 | 18.6 | 27.4 |
|     | 96 h | ND | ND | ND | <LLOQ | <LLOQ | 4.33 | 349 | 23.4 | 23.5 |
|     |      | ND | <LLOQ | ND | 0.30 | 0.34 | 4.69 | 331 | 16.6 | 16.6 |

In the results of Table 19: Catabolites PBD-dimer 8 and cyclopropyl-thiol 7 and were not detected in tissues of mice dosed with vehicle; ND=not detected; NA=not applicable; LLOQ=0.244 nM for both 7 and 8 in homogenates; and the concentration in tumor and liver in nM was estimated based on an assumption of tissue density of 1 g/mL.

Examination of the associated catabolites present in tumors helped to explain the disparate efficacy results. In experiments employing cyclobutyl-containing 3-1, the PBD-dimer 8 was detected in marked quantities in tumors (1.0-2.0 nM) at both 24 and 96 h after dosing (Table 19). As expected for an ADC-mediated delivery, the tumor concentrations of PBD-dimer 8 were significantly higher than those detected in plasma and liver at both time points. In addition, the concentration of PBD-dimer 8 was maintained or slightly increased in tumors from 24 to 96 h but decreased to a very low level in plasma. In contrast, PBD dimer 8 was not detected at appreciable levels in tumors or plasma in experiments which utilized the cyclopropyl-containing 2-1 conjugate. Instead, measurable levels of the thiol-containing catabolite 7 were observed in tumor (4.3-7.5 nM) as well as plasma and liver (0.5-1.4 nM at 24 h) that were much higher than the corresponding concentrations of PBD-dimer 8 from the cyclobutyl-containing ADC 3-1.

The DNA binding potential of the catabolites PBD-dimer 8 and cyclopropyl thiol 7 was evaluated in vitro. As shown in FIG. 19D, after 1-hour incubation of PBD-dimer 8 in a DNA solution approximately 94% of PBD-dimer 8 became unextractable (<10% recovery). In contrast the cyclopropyl thiol 7 was quantitatively recovered from similar incubations (FIG. 19B). These results suggest that cyclopropyl thiol 7 does not bind to DNA while PBD-dimer 8 quickly binds to DNA, which supports their distinct efficacy profiles. Therefore, the lower PBD-dimer 8 concentrations in the tumor and liver relative to 7 (approximately 2.5-4-fold) are consistent with loss of PBD-dimer 8 due to efficient DNA alkylation in tissues (FIG. 18, cyclopropyl thiol 7 does not appreciably bind DNA). Based on these tissue analysis results, an IV dose of 0.5 mg/kg of 3-1 (cyclobutyl-) is predicted to generate PBD-dimer 8 at a concentration range of 0.10-0.20 nM in tumors (representing <5% of total mAb measured in tumor) assuming linear PK, uptake, and catabolism in mice. Such PBD-dimer 8 concentrations are consistent with the strong tumor killing observed in the corresponding efficacy experiments performed with cyclobutyl-containing 3-1 given the high potency of PBD-dimer 8 ($IC_{50}$=~50 pM) in target-expressing cell lines (Hartley, J A "The development of pyrrolobenzodiazepines as antitumour agents" *Expert Opin Investig Drugs* 20:733-744 (2011)) and the likely underestimation of actual intra-tumor quantities due to DNA alkylation. The similar concentrations of total antibody for cyclopropyl-containing 2-1 and cyclobutyl-containing 3-1 in plasma as well as in tumor would predict a similar efficacy between the two ADCs in vivo. However, under one theory and without being bound to any particular theory, drug catabolites in tumors and associated DNA binding properties helps to explain the efficacy differences exhibited by these two conjugates. Thus, the measurement of ADC-delivered payload in tumors, which is responsible for DNA binding/alkylation and ultimate efficacy, is a factor in understanding the efficacy of a given ADC. These results demonstrate that tumor catabolite analysis may be used to predict in vivo efficacy outcomes of ADCs.

Example 23: In Vitro Stability and Cell Killing Activity of Maytansinoid and MMAE ADCs As disclosed in Table 20 below, activated maytansinoid and MMAE drugs depicted in Example 15 with substitutions indicated below were conjugated with human THIOMAB™ antibodies according to methods described elsewhere herein.

TABLE 20

Maytansinoid and MMAE ADCs

| Drug | n | X | Y | Z | Antibody | DAR |
| --- | --- | --- | --- | --- | --- | --- |
| May 1 | 2 | H | $CH_3$ | 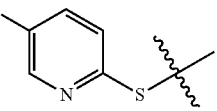 | Anti-CD22 10F4v3 Fc: S400C | 2 |
| May 2 | 2 | $CH_3$ | $CH_3$ | H | Anti-CD22 10F4v3 Fc: S400C | 2 |
| May 3 | 2 | $CH_3$ | $CH_3$ | H | Anti-CD22 10F4v3 LC K149C | 1.9 |
| MMAE 1 | NA | H | $CH_3$ | 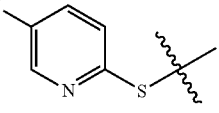 | Anti-CD22 10F4v3 HC: A118C | 2 |
| MMAE 2 | NA | $CH_3$ | $CH_3$ | 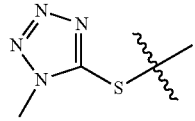 [SMILES: *Sc1nnnn1C] | Anti-CD22 10F4v3 HC: A118C | 1.5 |
| MMAE 3 | NA | $CH_3$ | $CH_3$ | 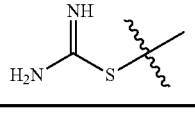 | Anti-CD22 10F4v3 LC: K149C | 1.8 |

The 24-hour stability, as measured by DAR loss due to disulfide exchange, of May 1 to May 3 and MMAE 1 to MMAE 3 in cynomolgus monkey whole blood, human whole blood, mouse whole blood and rat whole, blood was determined. The results are presented in Table 21 below.

TABLE 21

24-hour whole blood stability

| Drug | Cynomolgus WB | Human WB | Mouse WB | Rat WB |
| --- | --- | --- | --- | --- |
| May 1 | DAR loss | DAR loss | DAR loss | DAR loss |
| May 2 | Stable | Stable | Stable | Not tested |
| May 3 | Stable | Stable | Stable | Stable |
| MMAE 1 | DAR loss | DAR loss | DAR loss | DAR loss |
| MMAE 2 | Slight DAR loss | Slight DAR loss | Stable | Stable |
| MMAE 3 | Slight DAR loss | Slight DAR loss | Stable | Stable |

As disclosed in Table 22 below, activated maytansinoid and MMAE drugs depicted in Example 15 with substitutions indicated below were conjugated with human THIOMAB™ antibodies according to methods described elsewhere herein.

TABLE 22

Maytansinoid and MMAE ADCs

| Drug | n | X | Y | Z |
|---|---|---|---|---|
| May 4 | 2 | CH₃ | CH₃ | H |
| | Antibody: Anti-CD22 10F4v3 LC K149C | | | |
| May 5 | 2 | CH₃ | CH₃ | H |
| | Antibody: Anti-CD22 10F4v3 LC V205C | | | |
| May 6 | 2 | CH₃ | CH₃ | H |
| | Antibody: Anti-Her2 4D5 LC K149C | | | |
| May 7 | 2 | CH₃ | CH₃ | H |
| | Antibody: Anti-CD22 10F4v3 Fc S400C | | | |
| May 8 | 2 | H | H | 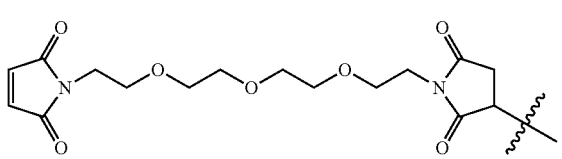 [SMILES: *C1CC(=O)N(CCOCCOCCOCCN2C(=O)C=CC2=O)C1=O] |
| | Antibody: Anti-CD22 10F4v3 LC K149C | | | |
| May 9 | 2 | CH₃ | CH₃ | 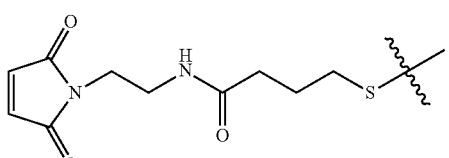 |
| | Antibody: Anti-CD22 10F4v3 LC K149C | | | |
| May 10 | 2 | H | CH₃ | 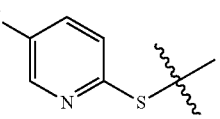 |
| | Antibody: Anti-CD22 10F4v3 Fc S400C | | | |
| MMAE 1 | NA | CH₃ | CH₃ | 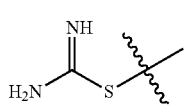 |
| | Antibody: Anti-CD22 10F4v3 LC K149C | | | |
| MMAE 2 | NA | CH₃ | CH₃ | 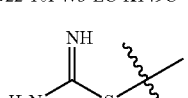 |
| | Antibody: Anti-Her2 4D5 10F4v3 LC K149C | | | |
| MMAE 3 | NA | CH₃ | CH₃ | 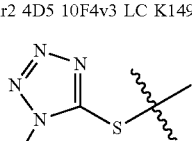 |
| | Antibody: Anti-CD22 10F4v3 HC A118C | | | |
| MMAE 4 | NA | H | CH₃ | 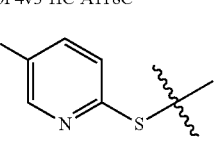 |
| | Antibody: Anti-CD22 10F4v3 HC A118C | | | |
| MMAE 5 | NA | H | CH₃ | |
| | Antibody: Anti-Her2 4D5 10F4v3 LC K149C | | | |

MMAE 6 ADC was prepared from the following MMAE (where X was H, Y was CH₃ and Z was para nitro pyridine depicted in Table 22)

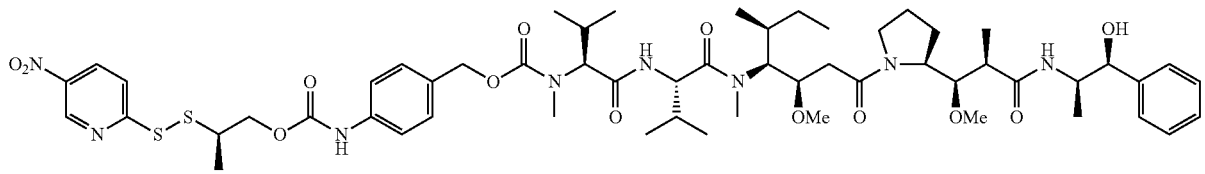 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)OC[C@@H](C)SSc2ccc([N+](=O)[O-])cn2)cc1)C(C)C]

and the antibody: Anti-Her2 7C2 LC K149C.

The in vitro $IC_{50}$ of ADC compounds May 4 to May 10 and MMAE 1 to MMAE 4 of Table 22 against BJAB, WSU-DLCL2 and Jurkat cells was evaluated. The cells were plated in 96-well plates (100,000 cells per mL). The media was cysteine free RPMI+10% FBS+20 mM glutamine+50 M cysteine. Media was then removed and was replaced with fresh media containing different ADC concentrations. Cell viability was measured 4 days after drug administration using Cell Titer-Glo. The results are presented in Table 23 below.

TABLE 23

$IC_{50}$ of maytansinoid and MMAE ADCs against BJAB, WSU-DLCL2 and Jurkat cells

| ADC | DAR | BJAB $IC_{50}$ mM | ng/mL | WSU-DLCL2 $IC_{50}$ mM | ng/mL | Jurkat $IC_{50}$ mM | ng/mL |
|---|---|---|---|---|---|---|---|
| MAY 4 | 1.9 | 3.03 | 454.4 | 0.42 | 62.79 | 6.85 | 1026.8 |
| MAY 5 | 1.8 | 8.34 | 1250.2 | 0.46 | 68.82 | 7.94 | 1191.0 |
| MAY 6 | 1.9 | 3.08 | 462.2 | 2.69 | 403.9 | 3.46 | 518.5 |
| MAY 7 | 2 | 1.62 | 243.2 | 0.34 | 51.48 | 6.51 | 976.1 |
| MAY 8 | 2 | 8.94 | 1340.0 | 5.18 | 776.9 | 30.8 | 4619.3 |
| MAY 9 | 2 | 3.16 | 473.9 | 0.48 | 71.87 | 10.61 | 1590.9 |
| MAY 10 | 2 | 6.20 | 929.4 | 0.50 | 74.98 | 27.52 | 4126.2 |
| MMAE 1 | 1.8 | 32.30 | 4842.0 | 24.94 | 3738.8 | 22.95 | 3440.2 |
| MMAE 2 | 1.8 | 53.19 | 7974.0 | 38.31 | 5744.0 | 28.23 | 4232.7 |
| MMAE 3 | 1.5 | 15.0 | 2248.7 | 7.15 | 1071.4 | 7.58 | 1136.3 |
| MMAE 4 | 2 | 22.69 | 3401.4 | 15.14 | 2269.8 | 14.74 | 2209.8 |

The in vitro $IC_{50}$ of ADC compounds MMAE 1, MMAE 2, MMAE 5 and MMAE 6 against SK-BR-3 and KPL-4 cells was evaluated. The cells were plated in 96-well plates (SK-BR-3 at 5000 cell per well; KPL-4 at 1500 cells per mL) in cysteine free RPMI+10% FBS+20 mM glutamine+ 50 pM cysteine media and allowed to adhere overnight. Media was then removed and was replaced with fresh media containing different ADC concentrations. Cell viability was measured 5 days after drug administration using Cell Titer-Glo. The results are presented in Table 24 below.

TABLE 24

$IC_{50}$ of MMAE ADCs against SK-BR-3 and KPL-4 cells

| ADC | DAR | SK-BR-3 $IC_{50}$ (ng/mL) | KPL-4 $IC_{50}$ (ng/mL) |
|---|---|---|---|
| MMAE 1 | 1.8 | >10,000 | 1643 |
| MMAE 2 | 1.8 | 139 | 85.6 |
| MMAE 5 | 2.0 | 497 | 388 |
| MMAE 6 | 1.99 | 780 | 411 |

Example 24: MMAE ADC and Maytansinoid ADC In Vivo Testing

MMAE and maytansinoid ADCs were evaluated in vivo in mouse xenograph BJAB-luciniferase tumor models to study efficacy and catabolism.

The efficacy of anti-CD22 antibody-MMAE conjugates anti-CD22 antibody-maytansinoid conjugates and was investigated in a mouse xenograft model of BJAB-luc (human Burkitt's lymphoma). The BJAB cell line was obtained from DSMZ (German Collection of Microorganisms and Cell Cultures; Braunschweig, Germany), and a sub-line BJAB-luc was generated at Genentech to stably express the luciferase gene.

Female SCID mice (Charles River Laboratories; Hollister, Calif.) were each inoculated subcutaneously in the flank area with about 20 million cells of BJAB-luc. When the xenograft tumors reached an average tumor volume of about 200 mm³ (referred to as Day 0), the mice were randomized into groups and animal received a single intravenous injection of the ADC or vehicle. Tumors and body weights of mice were measured at various times. Mice were promptly euthanized when body weight loss was >20% of their starting weight, before tumors reached about 1500 mm³ or showed signs of impending ulceration.

Plasma drug to antibody ratios were measured according to the method disclosed in Zhang, D., et al., Chemical Structure and Concentration of Intratumor Catabolites Determine Efficacy of Antibody Drug Conjugates, Drug Meta Dispos. 44:1517-1523, September 2016. In general, an appropriate volume of mouse plasma after intravenous administration of ADCs was incubated at room temperature with the biotinylated CD22 target antigen, which was coupled to the streptavidin paramagnetic beads (Invitrogen/ Thermo Fisher Scientific). The bead-captured ADC analytes were washed and deglycosylated at 37° C. overnight. The resulting samples in 30% acetonitrile in water containing 1% formic acid were injected onto a Triple TOF 5600 mass spectrometer (AB Sciex) coupled with HPLC using a reversed-phase HPLC column. The compounds were eluted by a gradient of mobile phase A (water with 0.1% formic acid) and mobile phase B (acetonitrile with 0.1% formic acid) at a flow rate of 5 ml/min. Positive time-of-flight (TOF) MS scan was acquired and processed. Peak deconvolution was performed to obtain the distribution profiles of DAR0, DAR1, and DAR2 species, and the corresponding peak areas were measured. Subsequently, the relative ratio of each DAR and the average DAR value at each time point were calculated.

In a first evaluation, as disclosed in Table 25 below, activated maytansinoid drugs depicted in Example 15 with substitutions indicated below were conjugated with human THIOMAB™ antibodies according to methods described elsewhere herein. The mice were randomized into groups. The mice described above received a single IV dose of the vehicle, May 1 to 4, or the control at day 0. The May 1 does was 3.1 mg/kg (100 μg/m²) and the dose for the remaining ADCs was 2.8 mg/kg (100 μg/m²). Tumor volume and body weights of the mice were measured at 0, 4, 7, 11, 14, 18 and 21 days, or was terminated when tumor volume reached about 1000 mm³. Plasma from mice dosed with an ADC was collected at days 1, 4 and 7 and evaluated for DAR.

TABLE 25

Maytansinoid ADCs

| Drug | N | X | Y | Z | Antibody | DAR |
|---|---|---|---|---|---|---|
| May 1 | 1 | H | H | O$_2$N-pyridine-S- | Anti-CD22 10F4v3 LC-V205C | 1.8 |
| May 2 | 2 | H | CH$_3$ | O$_2$N-pyridine-S- | Anti-CD22 10F4v3 LC-V205C | 2 |
| May 3 | 1 | H | H | O$_2$N-pyridine-S- | Anti-CD22 10F4v3 LC-K149C | 2 |
| May 4 | 2 | H | CH$_3$ | O$_2$N-pyridine-S- | Anti-CD22 10F4v3 LC-K149C | 2 |
| Control | 2 | H | CH$_3$ | O$_2$N-pyridine-S- | Anti-Her2 4D5 LC-K149C | 2 |

The tumor volume results (in mm$^3$) and normalized DAR results are reported in Table 26 below.

TABLE 26

Tumor volume and DAR results for the ADC compounds of table 25

|  | Vehicle | Control | May 1 | May 2 | May 3 | May 4 |
|---|---|---|---|---|---|---|
| Tumor volume (mm$^3$) | | | | | | |
| Day 0 | 190 | 190 | 190 | 190 | 190 | 190 |
| Day 4 | 270 | 330 | 220 | 110 | 150 | 150 |
| Day 7 | 520 | 590 | 320 | 80 | 100 | 100 |
| Day 11 | 1040 | 1090 | 570 | 40 | 30 | 30 |
| Day 14 | — | — | 820 | 30 | 10 | 10 |
| Day 18 | — | — | — | 20 | 10 | 10 |
| Day 21 | — | — | — | 10 | 10 | 10 |
| DAR (in %) | | | | | | |
| Day 0 | 100 | 100 | 100 | 100 | 100 | 100 |
| Day 1 | — | 95 | 45 | 90 | 90 | 95 |
| Day 4 | — | 90 | 5 | 80 | 75 | 90 |
| Day 7 | — | 90 | 0 | 65 | 60 | 85 |

In a second evaluation, as disclosed in Table 27 below, activated maytansinoid drugs depicted in Example 15 with substitutions indicated below were conjugated with human THIOMAB™ antibodies according to methods described elsewhere herein. The mice were randomized into groups. The mice described above received a single IV dose of the vehicle and May 5 to 12 at day 0. The dose for each ADC was 50 μg/m$^2$. Tumor volume and body weights of the mice were measured at 0, 3, 7, 10, 14, 17 and 21 days, or was terminated when tumor volume exceeded about 1000 mm$^3$. Plasma from mice dosed with an ADC was collected at days 1, 3 and 7 and evaluated for DAR.

TABLE 27

Maytansinoid ADCs

| Drug | n | X | Y | Z |
|---|---|---|---|---|
| May 5 | 1 | H | H | 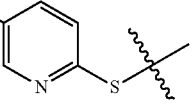 |

Antibody: anti-CD22 10F4v3 LC-K149C; DAR = 2; Dose = 1.61 mg/kg

TABLE 27-continued

Maytansinoid ADCs

| Drug | n | X | Y | Z |
|---|---|---|---|---|
| May 6 | 2 | H | CH$_3$ | 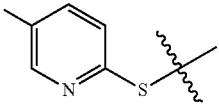 |

Antibody: anti-CD22 10F4v3 LC-K149C; DAR = 2; Dose = 1.55 mg/kg

| | | | | |
|---|---|---|---|---|
| May 7 (noncleavable) | 1 | H | H | 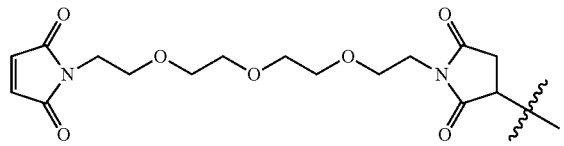 [SMILES: *C1CC(=O)N(CCOCCOCCOCCN2C(=O)C=CC2=O)C1=O] |

Antibody: anti-CD22 10F4v3 LC-K149C; DAR = 2; Dose = 1.62 mg/kg

| | | | | |
|---|---|---|---|---|
| May 8 (conjugation through lysine) | 2 | CH$_3$ | CH$_3$ | 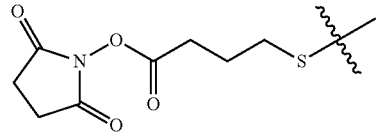 [SMILES: *SCCCC(=O)ON1C(=O)CCC1=O] |

Antibody: anti-CD22 10F4v3 LC-K149C; DAR = 3.27; Dose = 0.93 mg/kg

| | | | | |
|---|---|---|---|---|
| May 9 (conjugation through cysteine) | 2 | CH$_3$ | CH$_3$ | 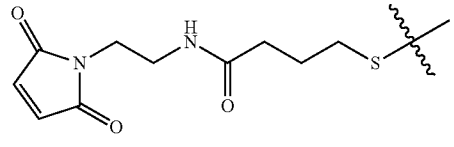 [SMILES: *SCCCC(=O)NCCN1C(=O)C=CC1=O] |

Antibody: anti-CD22 10F4v3 LC-K149C; DAR = 2; Dose = 1.52 mg/kg

| | | | | |
|---|---|---|---|---|
| May 10 | 2 | CH$_3$ | CH$_3$ | H |

Antibody: anti-CD22 10F4v3 LC-K149C; DAR = 1.9; Dose = 1.6 mg/kg

| | | | | |
|---|---|---|---|---|
| May 11 | 2 | CH$_3$ | CH$_3$ | H |

Antibody: anti-CD22 10F4v3 Fc-S400C; DAR = 2; Dose = 1.52 mg/kg

| | | | | |
|---|---|---|---|---|
| May 12 | 2 | H | CH$_3$ | 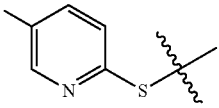 |

Antibody: anti-CD22 10F4v3 Fc-S400C; DAR = 2; Dose = 1.55 mg/kg

The tumor volume results (in mm$^3$) and normalized DAR results are reported in Table 28 below.

TABLE 28

Tumor volume and DAR results for the ADC compounds of table 27

| | Vehicle | May 5 | May 6 | May 7 | May 8 | May 9 | May 10 | May 11 | May 12 |
|---|---|---|---|---|---|---|---|---|---|
| Tumor volume (mm$^3$) | | | | | | | | | |
| Day 0 | 190 | 190 | 190 | 190 | 190 | 190 | 190 | 190 | 190 |
| Day 3 | 270 | 180 | 180 | 270 | 230 | 220 | 170 | 190 | 220 |
| Day 7 | 470 | 140 | 105 | 420 | 290 | 280 | 100 | 140 | 280 |
| Day 10 | 760 | 100 | 55 | 605 | 480 | 380 | 55 | 90 | 340 |
| Day 14 | 1350 | 80 | 20 | 1020 | 520 | 520 | 20 | 50 | 430 |
| Day 17 | — | 80 | 20 | — | 660 | 680 | 20 | 40 | 505 |
| Day 21 | — | 100 | 20 | — | 820 | 920 | 25 | 45 | 620 |
| DAR (in %) | | | | | | | | | |
| Day 0 | — | — | — | 100 | 100 | 100 | 100 | 100 | 100 |
| Day 1 | — | — | — | 100 | 82 | 98 | 100 | 98 | 80 |
| Day 3 | — | — | — | 100 | 67 | 73 | 100 | 90 | 33 |
| Day 7 | — | — | — | 100 | — | 0 | 100 | 63 | 0 |

In a third evaluation, activated MMAE drugs depicted below and in corresponding Table 29 below were conjugated with human THIOMAB™ antibodies according to methods described elsewhere herein. The mice were randomized into groups. The mice described above received a single IV dose of the vehicle, MMAE 1 to 4, or control 1 or 2 at day 0. For tumor efficacy studies, the dose for MMAE 1 was 1 mg/kg and the dose for MMAE 2 to 4 and controls 1 and 2 was 20 mg/kg. For DAR studies, the dose for MMAE 1 was 1 mg/kg, and the dose for MMAE 2 to 4 was 20 mg/kg. Tumor volume and body weights of the mice were measured at 0, 4, 7, 11, 14, 18, 21, 25 and 32 days, or was terminated when tumor volume exceeded about 1000 mm³. Plasma from mice dosed with an ADC was collected at days 1, 4 and 7 and evaluated for DAR.

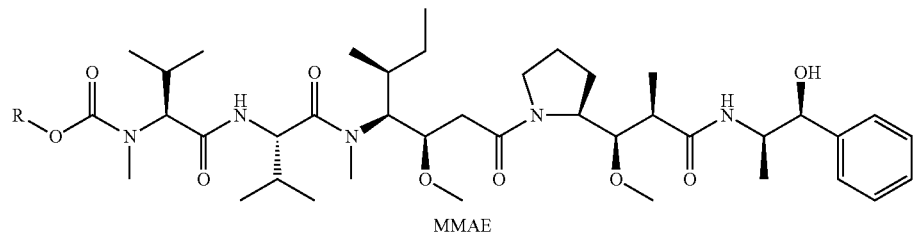

MMAE

20

TABLE 29

MMAE ADCs

| Drug | R |
|---|---|
| MMAE 1 | Antibody: anti-CD22 LC-K149C; DAR: 1.9 |
| MMAE 2 | Antibody: anti-CD22 LC-K149C; DAR: 2 |
| MMAE 3 | Antibody: anti-CD22 LC-K149C; DAR: 1.99 |
| Control 1 | Antibody: anti-Her2 (7C2) LC-K149C; DAR: 1.99 |

TABLE 29-continued

MMAE ADCs

| Drug | R |
|---|---|
| MMAE 4 | 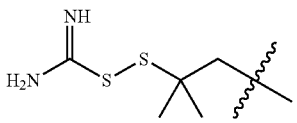<br>Antibody: anti-CD22 LC-K149C; DAR: 1.9 |
| Control 2 | 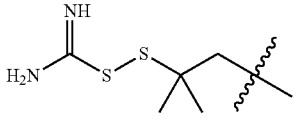 [SMILES: *CC(C)(C)SSC(=N)N]<br>Antibody: anti-Her2 (4D5) LC-K149C; DAR: 1.9 |

TABLE 30

Tumor volume and DAR results for the ADC compounds of table 29

| | Vehicle | Control 1 | Control 2 | MMAE 1 | MMAE 2 | MMAE 3 | MMAE 4 |
|---|---|---|---|---|---|---|---|
| Tumor volume (mm$^3$) | | | | | | | |
| Day 0 | 190 | 190 | 190 | 190 | 190 | 190 | 190 |
| Day 4 | 300 | 290 | 300 | 130 | 300 | 130 | 260 |
| Day 7 | 530 | 360 | 430 | 100 | 360 | 100 | 300 |
| Day 11 | 1000 | 440 | 770 | 60 | 500 | 60 | 280 |
| Day 14 | — | 790 | 1120 | 40 | 740 | 50 | 240 |
| Day 18 | — | — | — | 20 | 1440 | 50 | 190 |
| Day 21 | — | — | — | 10 | — | 60 | 170 |
| Day 25 | — | — | — | 10 | — | 100 | 190 |
| Day 28 | — | — | — | 15 | — | 120 | 270 |
| Day 32 | — | — | — | 20 | — | 170 | 470 |
| DAR (in %) | | | | | | | |
| Day 0 | — | — | — | 100 | 100 | 100 | 100 |
| Day 1 | — | — | — | 100 | 98 | 95 | 90 |
| Day 4 | — | — | — | 98 | 91 | 90 | 90 |
| Day 7 | — | — | — | 96 | 88 | 85 | 90 |

Example 25: Conjugation of Activated Disulfide-MMAE Molecules to Albumin and Penetratin In a first evaluation, MMAE was conjugated to human serum albumin (HSA). Human serum albumin bears a single free endogenous cysteine residue, Cys-34, to which Cys-reactive molecules can ultimately be conjugated (e.g., Bioconj Chem, 2015, 26(5), 941-949). This Cys residue is blocked as a mixed disulfide with Cys or glutathione, preventing complete conjugation of other molecules to this residue. In a manner analogous to removing such blocking groups from THIOMAB™ antibodies, the blocking group on Cys-34 of HSA was removed through a reduction-reoxidation procedure and the protein was stored in a buffer of 10 mM succinate, pH 5, 150 mM NaCl, 2 mM EDTA. Disulfide-MMAE molecules with varying leaving groups were conjugated to HSA by mixing the protein at 2.2 mg/mL with 1M Tris, pH 8.5 (final buffer concentration of 75 mM Tris, pH 8.5) and with the disulfide MMAE compound at 10 molar equivalents relative to HSA for ~16 hours at room temperature. Conjugate reactions were analyzed by LC/MS. The extent of the expected MMAE-HSA conjugate formed during the reaction is represented by the "Conjugate Ratio", measured by dividing the abundance of the MS peak for the MMAE-HSA conjugate by the sum total abundance of all peaks observed. The ideal value for the Conjugate Ratio is 1.0. The results are reported in table 31 below wherein the wavy line for the leaving group represents the point of attachment to the disulfide bond, and "HSA CR" refers to human serum albumin conjugate ratio.

In a second evaluation, MMAE was conjugated to penetratin (AntP) peptide. The AntP peptide, with sequence H$_2$N-RQIKIWFQNRRMKWKKC-CONH$_2$ (SEQ ID NO:1) bearing a free Cys thiol at the C-terminus, was synthesized via standard Fmoc solid-phase peptide synthesis methods. This peptide was conjugated at a concentration of 25 uM to disulfide MMAE molecules with varying leaving groups (5 equivalents) in a buffered solution composed of 75 mM Tris, pH 8.5 and 10% DMF for ~16 hours at room temperature. Extent of the reaction was measured by dividing the integrated area for the UV peak of the MMAE-AntP conjugate by the sum of all peaks ("% Product"). The ideal value for % Product is 100%. The results are reported in table 31 below wherein the wavy line for the leaving group represent the point of attachment to the disulfide bond, and "AntP % P" refers to penetratin (AntP) peptide % product.

TABLE 31
HSA Conjugation Ratio and AntP % Product
| Leaving Group | HAS CR | AntP % P |
|---|---|---|
| 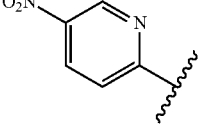 | 0.11 | 14 |
| 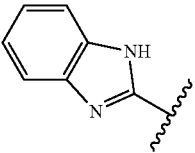 | 0.52 | 18 |
| 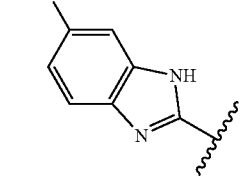 | 0.64 | 20 |
| 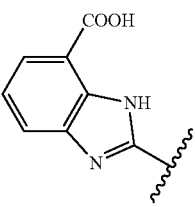 [SMILES: *c1nc2cccc(C(=O)O)c2[nH]1] | 0.34 | 25 |
| 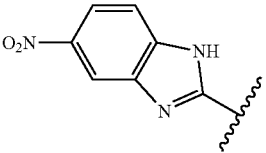 [SMILES: *c1nc2cc([N+](=O)[O-])ccc2[nH]1] | 0.69 | 26 |
| 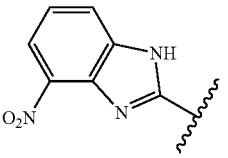 [SMILES: *c1nc2c([N+](=O)[O-])cccc2[nH]1] | 0.65 | 26 |
| 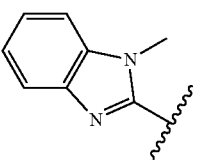 [SMILES: *c1nc2ccccc2n1C] | 0.87 | 7.5 |
| 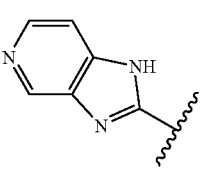 [SMILES: *c1nc2cnccc2[nH]1] | 0.86 | 26 |
| 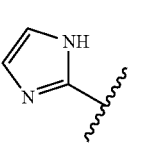 | 0.99 | 1.7 |
| 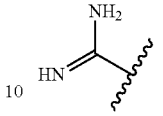 | 0.98 | 90 |
| 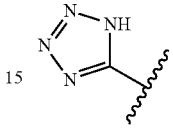 | 0.09 | 1.9 |
| 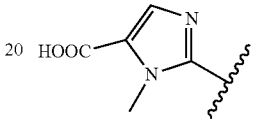 | 0.55 | 4 |
| 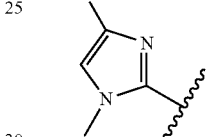 | 0.38 | 4.9 |
| 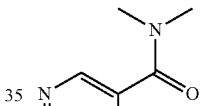 | 0.22 | 51 |
|  | 0.86 | 32 |
| 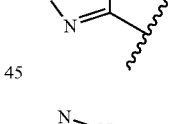 | 0.66 | 17 |
| 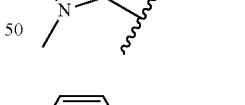 | 0.84 | 12 |
| 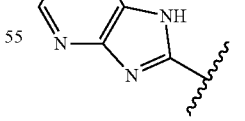 | 0.6 | 34 |

TABLE 31-continued

HSA Conjugation Ratio and AntP % Product

| Leaving Group | HAS CR | AntP % P |
|---|---|---|
| (imidazopyrazine structure) | 0.63 | 36 |
| (6-aminopurine structure) | 0.23 | 21 |

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A linker-drug compound of structure (I):

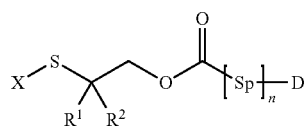

(I)

wherein:

X is a leaving group selected from the group consisting of;

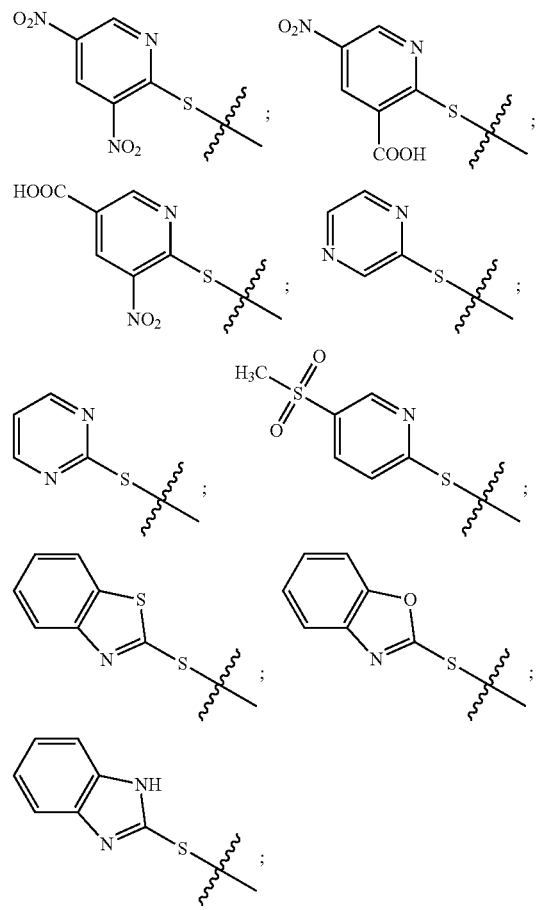

-continued

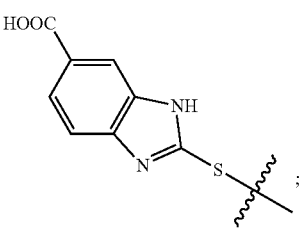

-continued

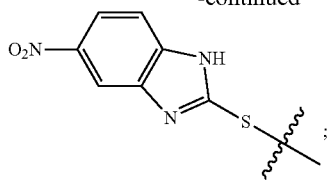

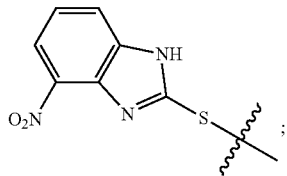

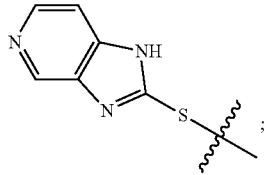

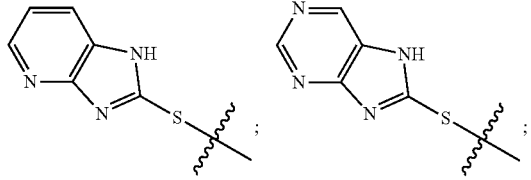

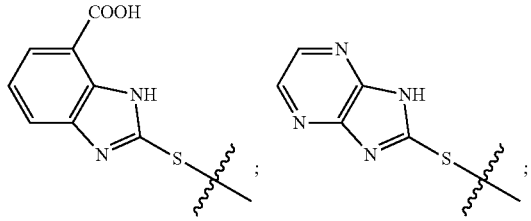

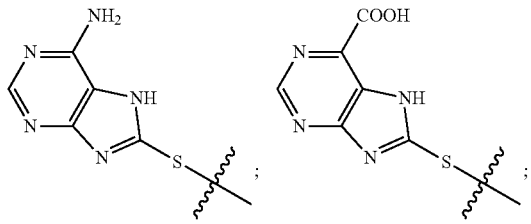

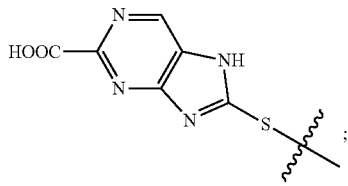

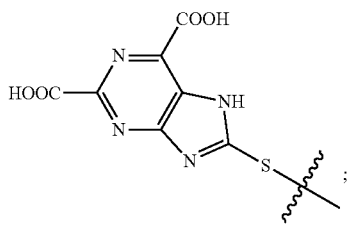

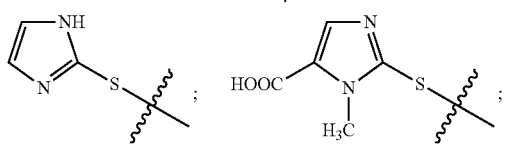

-continued

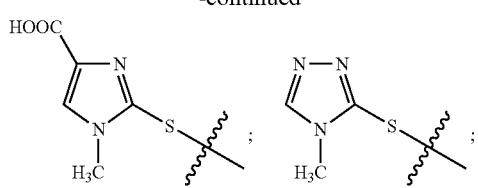

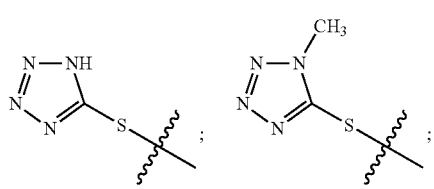

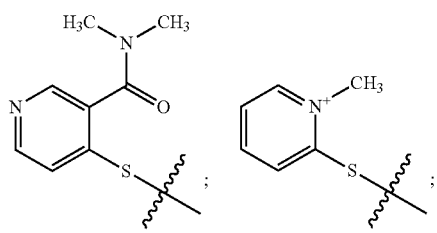

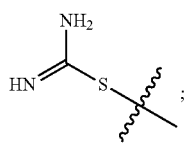

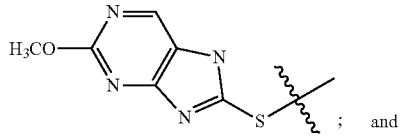

; and

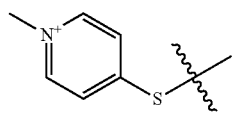

wherein the sulfur atom of leaving group, X, and the sulfur atom, S, of Structure (I) are bound via a sulfur-sulfur bond;

$R^1$ and $R^2$ are independently selected from —CH$_3$ and —CH$_2$CH$_3$, or $R^1$ and $R^2$ together with the carbon atom to which they are bound form a ring selected from cyclobutyl, cyclopentyl, cyclohexyl, oxetane, tetrahydrofuran and tetrahydropyran;

Sp is a spacer wherein n is 0 or 1; and

D is a drug moiety selected from a maytansine, an auristatin, a dolastatin, a pyrrolobenzodiazepine (PBD) monomer or dimer having the structure:

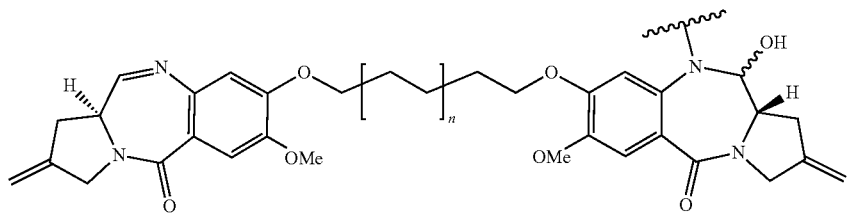

wherein n in the structure of the pyrrolobenzodiazepine (PBD) dimer is 0 or 1, a 1-(chloromethyl)-2,3-dihydro-1H-benzo[e]indole (CBI) monomer or dimer, and a CBI-PBD dimer.

2. The linker-drug compound of claim 1 wherein X is selected from the group consisting of:

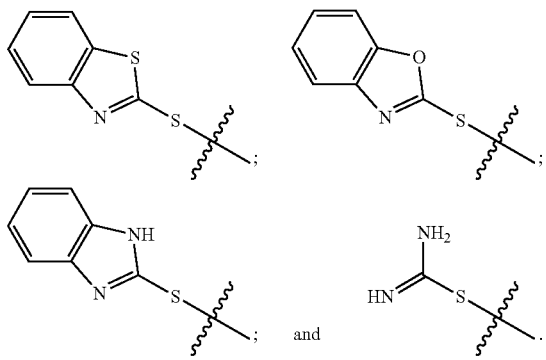

3. The linker-drug compound of claim 1 wherein $R^1$ and $R^2$ are each —$CH_3$.

4. The linker-drug compound of claim 1 wherein $R^1$ and $R^2$ form a ring selected from cyclobutyl, cyclopentyl, cyclohexyl, oxetane, tetrahydrofuran and tetrahydropyran.

5. The linker-drug compound of claim 1 wherein n of Sp is 0.

6. The linker-drug compound of claim 1 wherein n of Sp is 1, and Sp-D is of the structure:

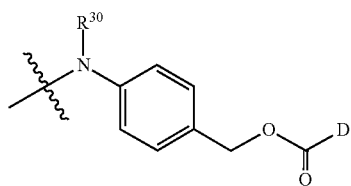

wherein the wavy line indicates the point of attachment of the spacer to the linker carbonyl carbon atom, and $R^{30}$ is selected from H and —$CH_3$.

7. A disulfide conjugate compound of structure (II):

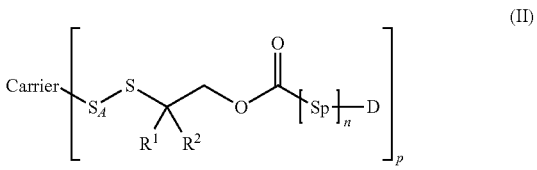

(II)

wherein
the carrier comprises a cysteine sulfur atom $S_A$;
p is 1, 2, 3, 4, 5, 6, 7 or 8;
$R^1$ and $R^2$ together with the carbon atom to which they are bound form a ring selected from cyclobutyl, cyclopentyl, cyclohexyl, oxetane, tetrahydrofuran and tetrahydropyran;
Sp is a spacer wherein n is 0 or 1; and
D is a drug moiety selected from a maytansine, an auristatin, a dolastatin, a pyrrolobenzodiazepine (PBD) monomer or dimer having the structure:

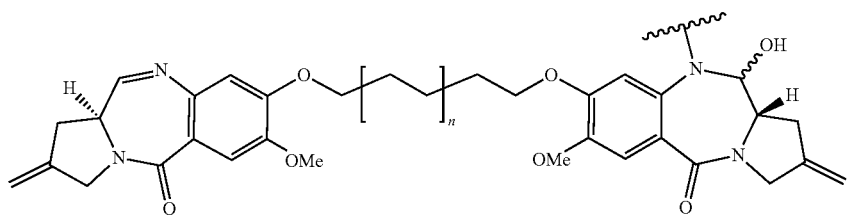

wherein n in the structure of the pyrrolobenzodiazepine (PBD) dimer is 0 or 1, a 1-(chloromethyl)-2,3-dihydro-1H-benzo[e]indole (CBI) monomer or dimer, and a CBI-PBD dimer.

8. The disulfide conjugate compound of claim 7 wherein the carrier is an antibody which binds to one or more tumor-associated antigens or cell-surface receptors.

9. The disulfide conjugate compound of claim 8 wherein the antibody is a cysteine-engineered antibody.

10. The disulfide conjugate compound of claim 9 wherein the cysteine-engineered antibody comprises LC K149C, HC A118C, LC S121C or LC V205C as the site of linker conjugation.

11. The disulfide conjugate compound of claim 8 wherein the antibody is selected from anti-HER2, anti-CD22, anti-CD33, anti-Napi2b, and anti-CLL-1.

12. The disulfide conjugate compound of claim 7 wherein p is 1, 2, 3, or 4.

13. The disulfide conjugate compound of claim 7 comprising a mixture of the antibody-drug conjugate compounds, wherein the average drug loading per antibody in the mixture of antibody-drug conjugate compounds is about 2 to about 5.

14. The disulfide conjugate compound of claim 7 wherein the carrier is a protein.

15. The disulfide conjugate compound of claim 7 wherein the carrier is a peptide.

16. The disulfide conjugate compound of claim 7 wherein $R^1$ and $R^2$ form a cyclobutyl ring.

17. The disulfide conjugate compound of claim 7 wherein n of Sp is 0.

18. The disulfide conjugate compound of claim 7 wherein n of Sp is 1, and Sp-D is of the structure:

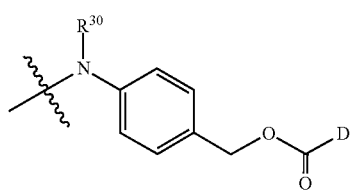

wherein the wavy line indicates the point of attachment of the spacer to the linker carbonyl carbon atom, and $R^{30}$ is selected from H and —$CH_3$.

19. A pharmaceutical composition comprising the disulfide conjugate compound according to claim 7 and a pharmaceutically acceptable diluent, carrier or excipient.

20. A method of treating cancer comprising administering to a patient the pharmaceutical composition of claim 19.

21. An article of manufacture comprising a pharmaceutical composition of claim 19, a container, and a package insert or label indicating that the pharmaceutical composition can be used to treat cancer.

22. A method of preparing a disulfide conjugate compound of structure (II):

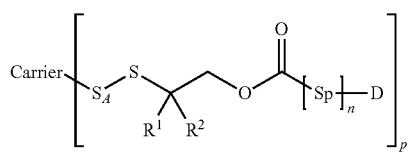

(II)

the method comprising:

(A) forming a reaction mixture comprising
(i) a solvent system comprising water,
(ii) a carrier comprising at least one cysteine having a sulfhydryl moiety having a sulfur atom $S_A$ capable of bonding to a linker sulfur atom to form the disulfide bond, and
(iii) a stoichiometric excess of a linker-drug conjugate compound of structure (I):

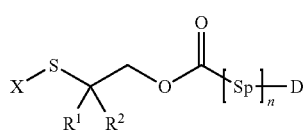

(I)

wherein:

X is a leaving group selected from the group consisting of;

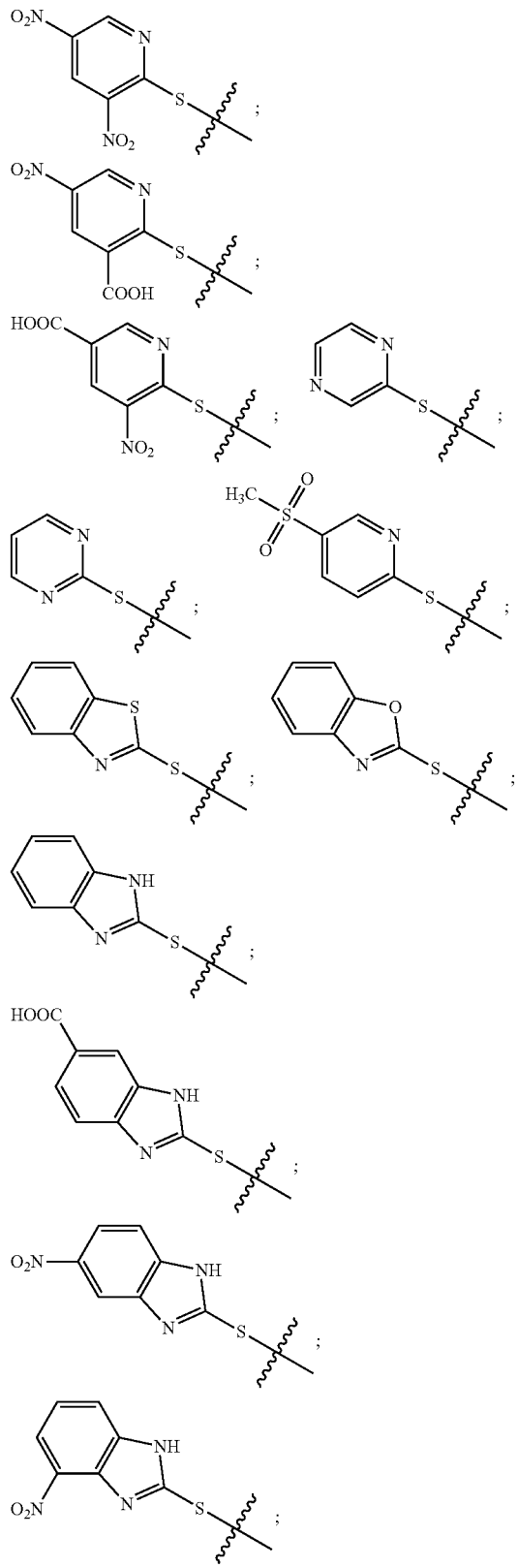

-continued

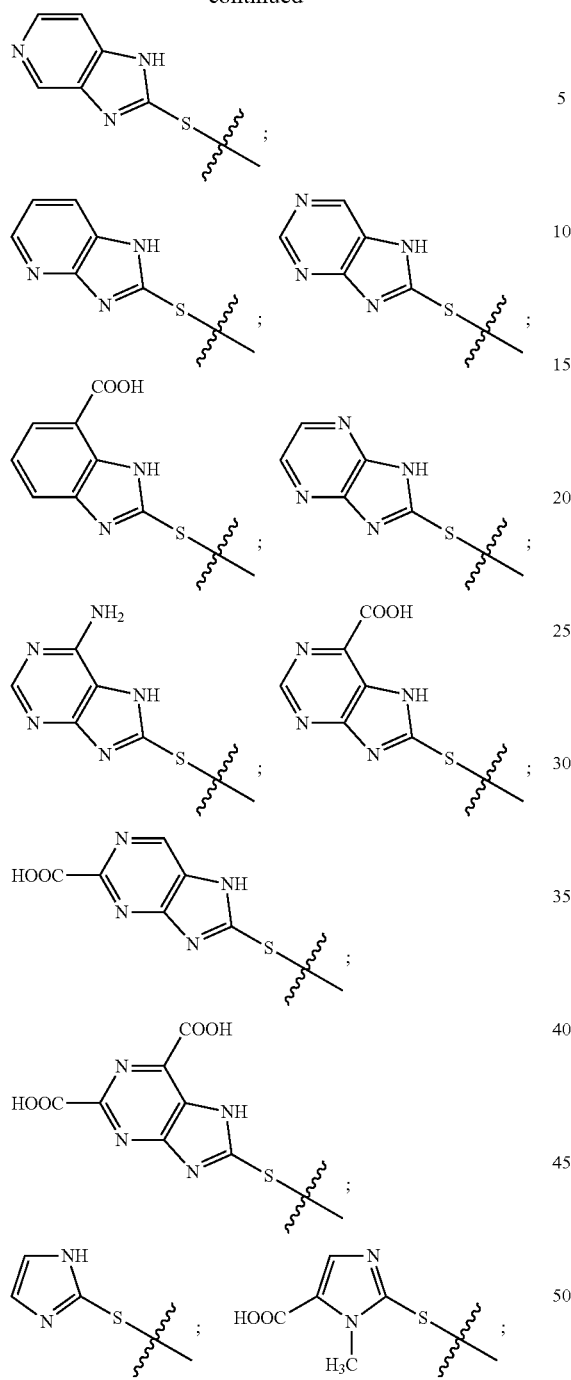

-continued

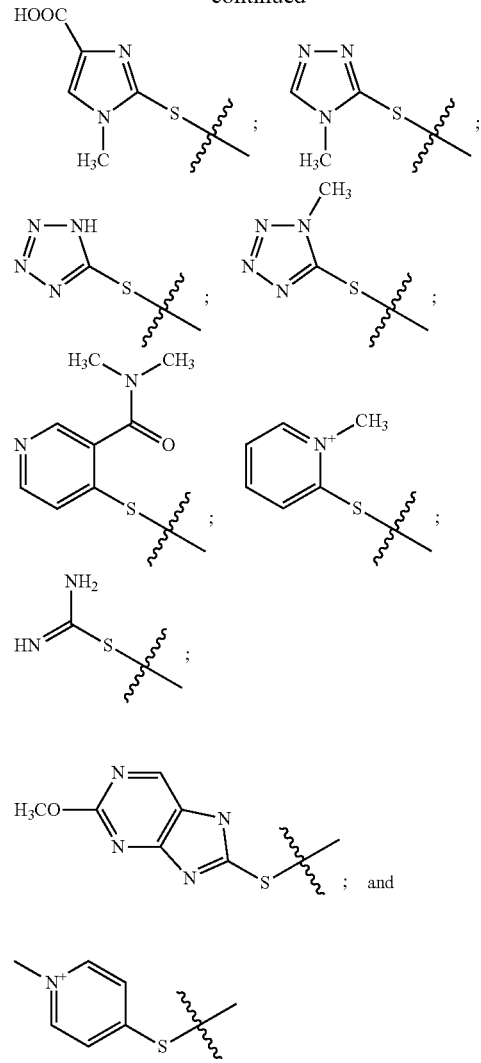

wherein the sulfur atom of leaving group, X, and the sulfur atom, S, of Structure (I) are bound via a sulfur-sulfur bond;

R$^1$ and R$^2$ are independently selected from —CH$_3$ and —CH$_2$CH$_3$, or R$^1$ and R$^2$ together with the carbon atom to which they are bound form a ring selected from cyclobutyl, cyclopentyl, cyclohexyl, oxetane, tetrahydrofuran and tetrahydropyran;

Sp is a spacer wherein n is 0 or 1; and

D is a drug moiety selected from a maytansine, an auristatin, a dolastatin, a pyrrolobenzodiazepine (PBD) dimer having the structure:

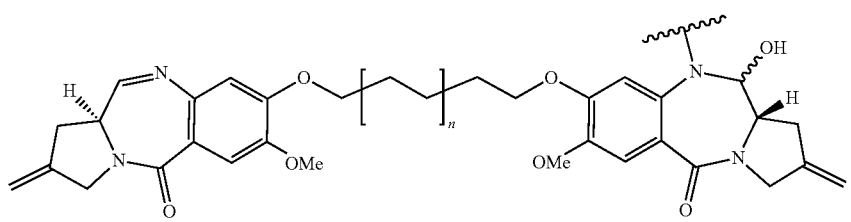

wherein n in the structure of the pyrrolobenzodiazepine (PBD) dimer is 0 or 1, a 1-(chloromethyl)-2,3-dihydro-1H-benzo[e]indole (CBI) monomer or dimer, and a CBI-PBD dimer; and (B) reacting the reaction mixture to form a product mixture comprising the disulfide conjugate compound of structure (II) wherein p is 1, 2, 3, 4, 5, 6, 7 or 8, and wherein the average value of p for a plurality of formed disulfide conjugate compounds in the product mixture is from about 1 to about 5, from about 1.5 to about 3, from about 1.5 to about 2.5, from about 1.7 to about 2.3, from about 1.8 to about 2.2, or about 2.

* * * * *

SEQUENCE LISTING

<160> NUMBER OF SEQ ID NOS: 1

<210> SEQ ID NO 1
<211> LENGTH: 16
<212> TYPE: PRT
<213> ORGANISM: Drosophila melanogaster

<400> SEQUENCE: 1

Arg Gln Ile Lys Ile Trp Phe Gln Asn Arg Arg Met Lys Trp Lys Lys
1               5                   10                  15